United States Patent
Ludlam et al.

(10) Patent No.: US 12,258,551 B2
(45) Date of Patent: Mar. 25, 2025

(54) METHODS FOR DYNAMIC EVOLUTION AND MONITORING OF CHARACTERISTICS IN LIVING CELLS USING A MICROFLUIDIC-ENABLED MULTI-WELL CELL CULTURE DEVICES AND SYSTEMS

(71) Applicant: Cairn Biosciences, Inc., San Francisco, CA (US)

(72) Inventors: Mary J. C. Ludlam, San Francisco, CA (US); David Wartmann, Berkeley, CA (US); Ciara Gallagher, Redwood City, CA (US)

(73) Assignee: Cairn Biosciences, Inc., San Francisco, CA (US)

( * ) Notice: Subject to any disclaimer, the term of this patent is extended or adjusted under 35 U.S.C. 154(b) by 762 days.

(21) Appl. No.: 17/293,407

(22) PCT Filed: Nov. 14, 2019

(86) PCT No.: PCT/US2019/061514
§ 371 (c)(1),
(2) Date: May 12, 2021

(87) PCT Pub. No.: WO2020/102562
PCT Pub. Date: May 22, 2020

(65) Prior Publication Data
US 2021/0403853 A1 Dec. 30, 2021

Related U.S. Application Data

(60) Provisional application No. 62/768,493, filed on Nov. 16, 2018.

(51) Int. Cl.
| | | |
|---|---|---|
| *C12M 1/34* | (2006.01) |
| *C12M 1/00* | (2006.01) |
| *C12M 1/42* | (2006.01) |
| *C12M 3/06* | (2006.01) |
| *C12N 5/09* | (2010.01) |
| *G01N 21/64* | (2006.01) |

(52) U.S. Cl.
CPC ............ *C12M 41/36* (2013.01); *C12M 23/16* (2013.01); *C12M 23/20* (2013.01); *C12M 29/00* (2013.01); *C12M 35/04* (2013.01); *C12M 35/08* (2013.01); *C12M 41/46* (2013.01); *C12M 47/04* (2013.01); *C12N 5/0693* (2013.01); *G01N 21/6428* (2013.01); *G01N 21/6452* (2013.01); *C12N 2500/00* (2013.01); *C12N 2527/00* (2013.01); *G01N 2021/6439* (2013.01)

(58) Field of Classification Search
CPC ...... C12M 41/36; C12M 23/16; C12M 23/20; C12M 29/00; C12M 35/04; C12M 35/08; C12M 41/46; C12M 47/04; C12M 35/00; C12M 41/00; C12N 5/0693; C12N 2500/00; C12N 2527/00; G01N 21/6428; G01N 21/6452; G01N 2021/6439
See application file for complete search history.

(56) References Cited

U.S. PATENT DOCUMENTS

| | | | | |
|---|---|---|---|---|
| 5,989,835 A | * | 11/1999 | Dunlay | G02B 21/16 |
| | | | | 977/881 |
| 7,968,287 B2 | * | 6/2011 | Griffiths | B01J 19/0046 |
| | | | | 435/375 |
| 8,658,349 B2 | * | 2/2014 | Teich | C12M 23/12 |
| | | | | 435/4 |
| 10,336,997 B2 | * | 7/2019 | Liu | C12N 15/85 |
| 10,578,633 B2 | * | 3/2020 | West | G01N 35/08 |
| 11,946,035 B2 | * | 4/2024 | Ludlam | C12M 41/48 |
| 2006/0199260 A1 | | 9/2006 | Sinskey | |
| 2007/0178023 A1 | | 8/2007 | Russo et al. | |
| 2007/0275455 A1 | | 11/2007 | Hung et al. | |
| 2008/0166795 A1 | * | 7/2008 | Shuler | C12M 35/08 |
| | | | | 435/287.1 |

(Continued)

FOREIGN PATENT DOCUMENTS

| | | |
|---|---|---|
| CN | 1369039 A | 9/2002 |
| CN | 1778900 A | 5/2006 |

(Continued)

OTHER PUBLICATIONS

Jang, et al. 2011 "Deep wells integrated with microfluidic valves for stable docking and storage of cells" Biotechnology Journal 6.2: 156-164 (Year: 2011).*
Stevenson, et al. 2013. "In vitro directed evolution of enzymes expressed by *E. coli* in microtiter plates". Methods in Molecular Biology 978, 237-249; doi: 10.1007/978-1-62703-293-3_18 (Year: 2013).*
National Cancer Institute (NIH-NCI) Dictionary of Cancer "Small-Molecule Drug"; <http//www.cancer.gov/publications/dictionaries/cancer-terms/def/small-molecule-drug> accessed on May 2, 2024, 1 page (Year: 2024).*

(Continued)

*Primary Examiner* — Aaron J Kosar
*Assistant Examiner* — Andrew T Moehlman
(74) *Attorney, Agent, or Firm* — Morrison & Foerster LLP

(57) ABSTRACT

A method for dynamic evolution and/or adaptation and monitoring of characteristics in living cells is provided, wherein the method may be performed at a microfluidic-enabled cell-culture device comprising pneumatic layer for directing flow of fluid to a plurality of individually addressable wells, and one or more sensors configured to detect data regarding environments inside one or more of the plurality of wells. The method may involve culturing a population of cells in a first well of the plurality of wells, perturbing one or more characteristics of an environment in the first well following the culturing of the population of cells, monitoring one or more characteristics of the population of cells in the first well, and removing all or part of the evolved/adapted population of cells from the first well.

38 Claims, 50 Drawing Sheets

(56) References Cited

U.S. PATENT DOCUMENTS

| | | | |
|---|---|---|---|
| 2011/0039303 A1* | 2/2011 | Jovanovich | B01L 3/50273 536/23.1 |
| 2012/0245042 A1 | 9/2012 | Liu et al. | |
| 2014/0356849 A1 | 12/2014 | Wikswo et al. | |
| 2015/0298121 A1* | 10/2015 | Cooper-White | B01L 3/5027 435/309.1 |
| 2016/0025761 A1 | 1/2016 | West | |
| 2016/0263572 A1 | 9/2016 | Gaige et al. | |
| 2017/0081625 A1 | 3/2017 | Wikswo | |
| 2017/0227525 A1* | 8/2017 | Griffith | F04B 43/12 |
| 2020/0199568 A1* | 6/2020 | Bashor | C12N 1/18 |
| 2021/0002602 A1 | 1/2021 | Ludlam et al. | |

FOREIGN PATENT DOCUMENTS

| | | | | |
|---|---|---|---|---|
| CN | 101506643 | A | 8/2009 | |
| CN | 101715483 | A | 5/2010 | |
| CN | 101827931 | A | 9/2010 | |
| CN | 104245917 | A | 12/2014 | |
| CN | 106085846 | A | 11/2016 | |
| CN | 111315485 | B | 5/2023 | |
| EP | 1190229 | B1 * | 10/2011 | B01L 3/502761 |
| EP | 2935559 | B1 | 9/2020 | |
| WO | 0101025 | A2 | 1/2001 | |
| WO | 0101025 | A3 | 7/2001 | |
| WO | 03027223 | A2 | 4/2003 | |
| WO | 2008008149 | A2 | 1/2008 | |
| WO | 2008008149 | A3 | 7/2008 | |
| WO | 2008115626 | A2 | 9/2008 | |
| WO | 2008115626 | A3 | 11/2008 | |
| WO | 2010023497 | A1 | 3/2010 | |
| WO | 2013082612 | A1 | 6/2013 | |
| WO | 2015191916 | A1 | 12/2015 | |
| WO | 2017062609 | A1 | 4/2017 | |
| WO | 2018213357 | A1 | 11/2018 | |

OTHER PUBLICATIONS

El-Ali, J. et al. (Jul. 27, 2006). "Cells on Chips," Nature 442:403-411.

Gómez-Sjöberg, R. et al. (Nov. 15, 2007, e-pub. Oct. 23, 2007). "Versatile, Fully Automated, Microfluidic Cell Culture System," Anal. Chem. 79:8557-8563.

International Preliminary Report on Patentability mailed on May 27, 2021, for PCT Application No. PCT/US2019/061514, filed on Nov. 14, 2019, 9 pages.

International Preliminary Report on Patentability, mailed on Nov. 28, 2019, for PCT Application No. PCT/US2018/032838, filed on May 15, 2018, 7 pages.

International Search Report and Written Opinion mailed on Feb. 18, 2020, for PCT Application No. PCT/US2019/061514, filed on Nov. 14, 2019, 14 pages.

International Search Report and Written Opinion mailed on Sep. 6, 2018, for PCT Application No. PCT/US2018/032838, filed on May 15, 2018, 15 pages.

Nunes, P.S. et al. (Mar. 22, 2010). "Refractive Index Sensor Based on a 1D Photonic Crystal in a Microfluidic Channel," Sensors 10:2348-2358.

Peng, C-C. et al. (2013). "A Microfluidic Cell Culture Array With Various Oxygen Tensions," Lab Chip p. 1-11.

Reichen, M. et al. (2013). "Development of a Multiplexed Microfluidic Platform for the Automated Cultivation of Embryonic Stem Cells," Journal of Laboratory Automation 18(6):519-529.

Wang, H-Y. (Oct. 31, 2008, e-pub. Jun. 12, 2008). "A Microfluidic Cell Array With Individually Addressable Culture Chambers," Biosensors and Bioelectronics 24(4)613-617.

Yu, H. et al. (2007, e-pub. Jan. 2, 2007). "A Plate Reader-Compatible Microchannel Array for Cell Biology Assays," Lab Chip 7:388-391.

Zhang, B. et al. (Dec. 2009, e-pub. Jul. 21, 2009). "A Self-Contained Microfluidic Cell Culture System," Biomed. Microdevices 11(6):1233-1237.

Grover, W. H. et al. (2006, e-pub. Apr. 6, 2006). "Development and Multiplexed Control of Latching Pneumatic Valves Using Microfluidic Logical Structures," Lab Chip 6:623-631.

Liding, W. et al. (2012). Polymer Micro-Nanofabrication Technology, National Defense Industry Press, p. 94, 5 pages. (English Translation).

Machinery Industry Press. (Oct. 31, 1997). "Machine Tool Design Manual," vol. 4, Design of Hydraulic Pneumatic System and Modern Design Method of Machine Tool, Hydraulic and Pneumatic System Design and Unit Modern Bed Design, Machinery Industry Press, p. 492, 5 pages. (English Translation).

Weltin, A. et al. (2014). "Cell Culture Monitoring for Drug Screening and Cancer Research: A Transparent, Microfluidic, Multi-Sensor Microsystem," Lab Chip 14:138-146.

\* cited by examiner

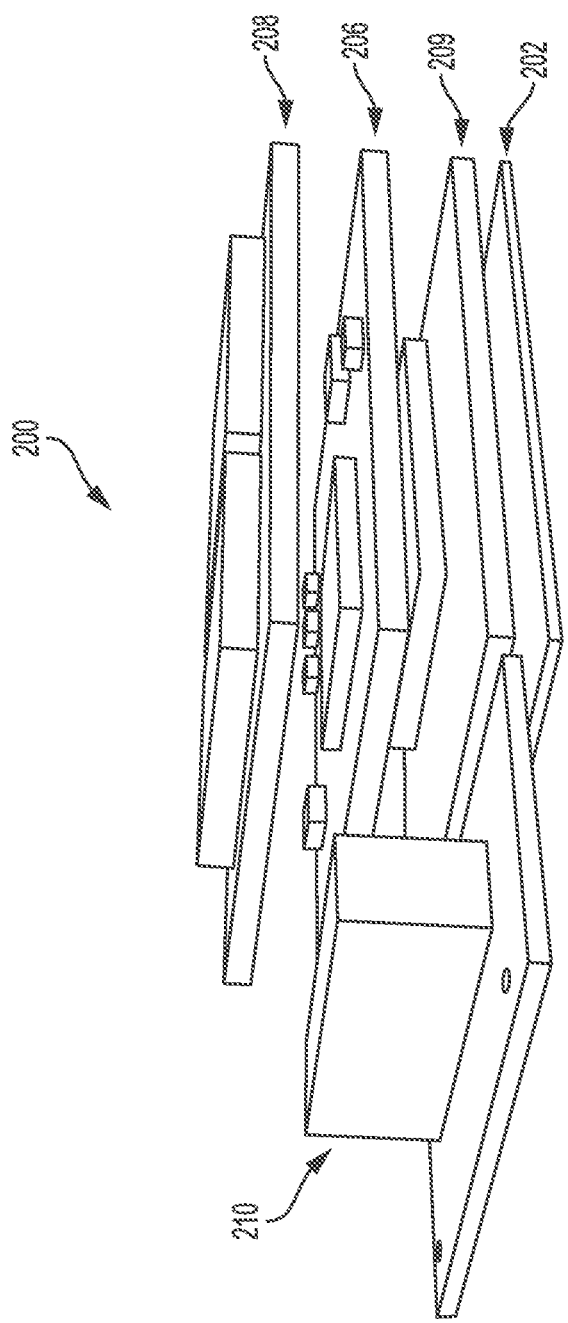

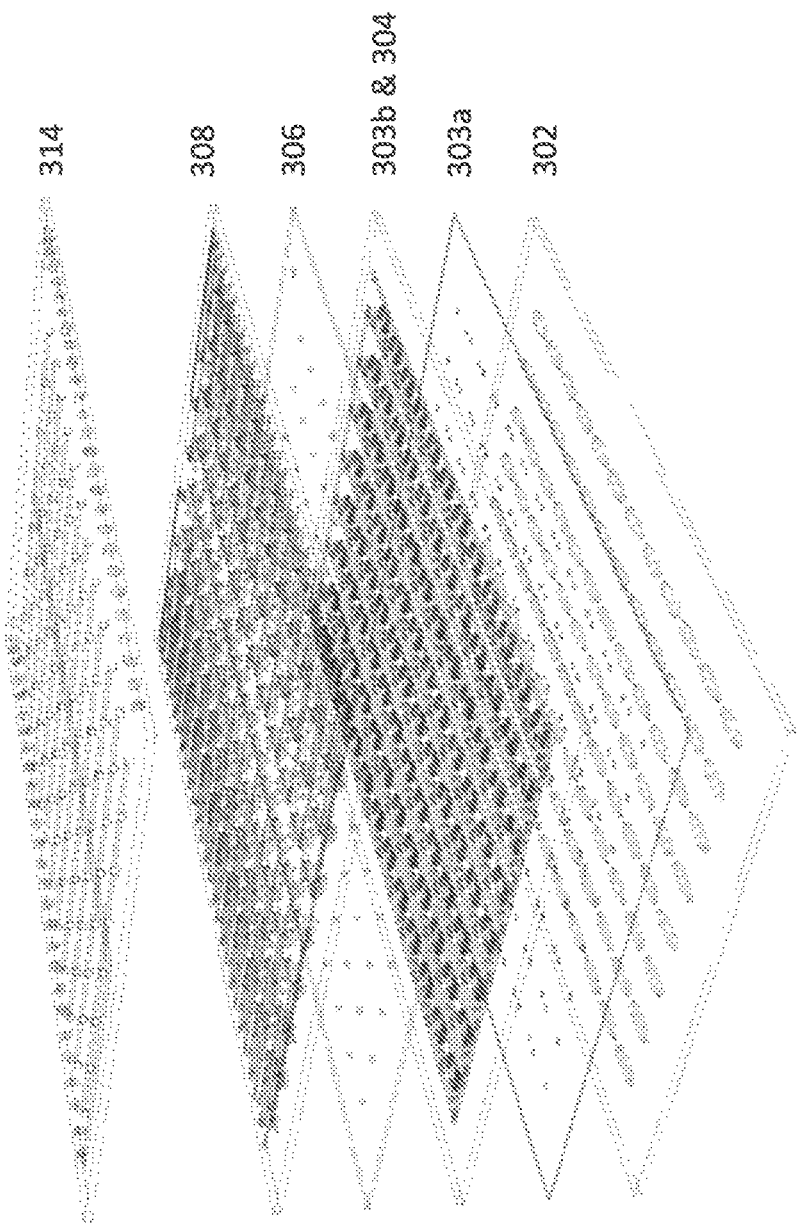

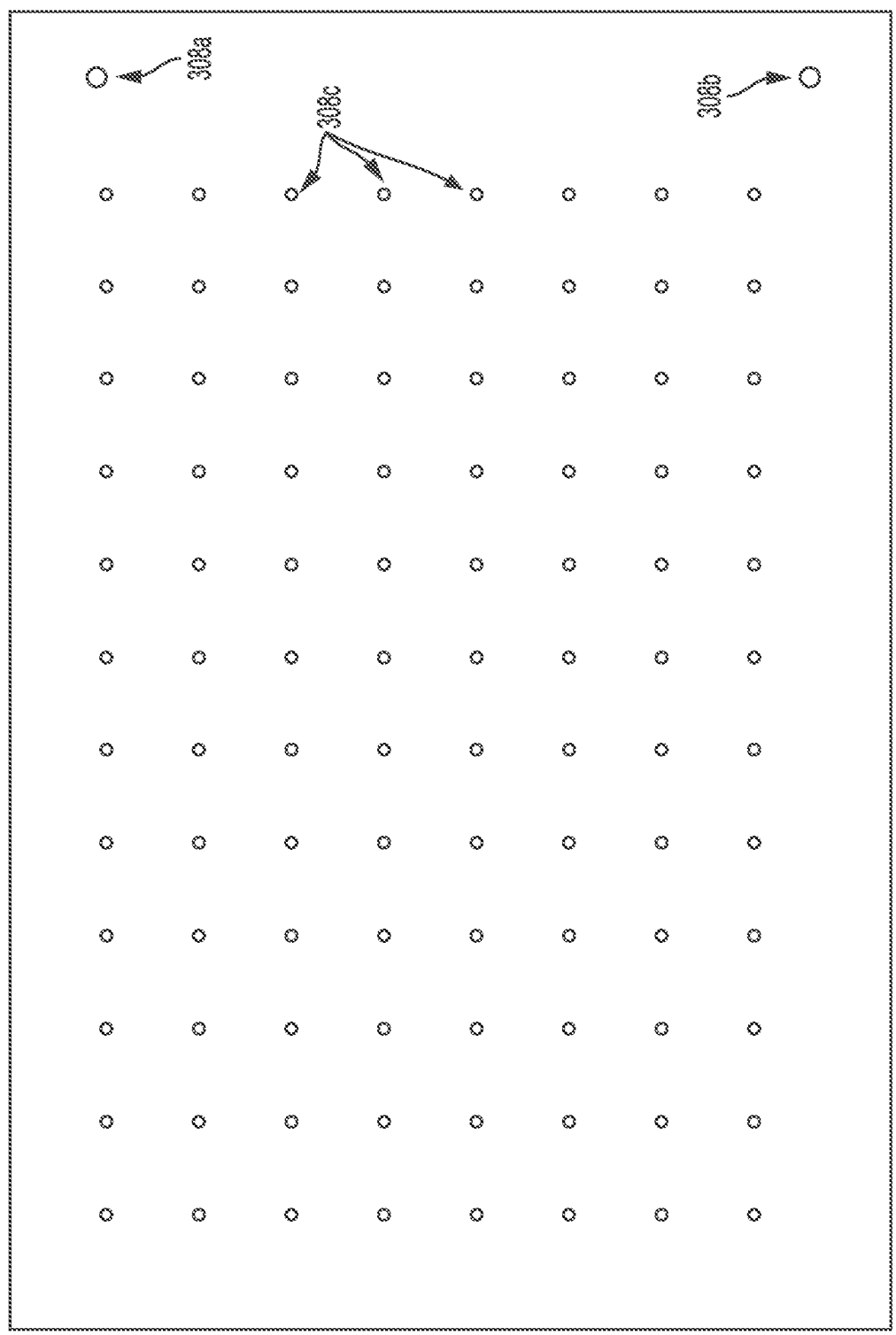
FIG. 3H

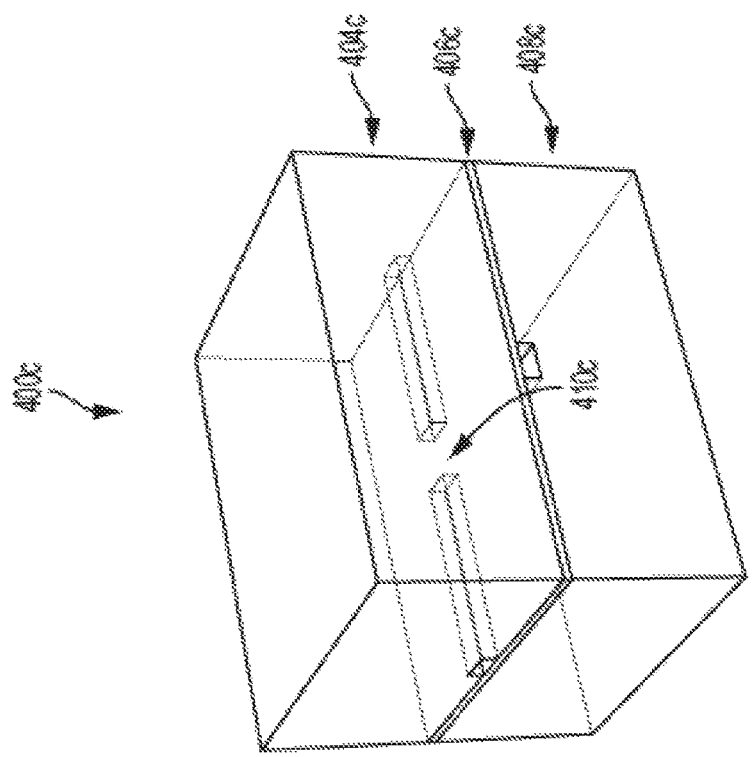
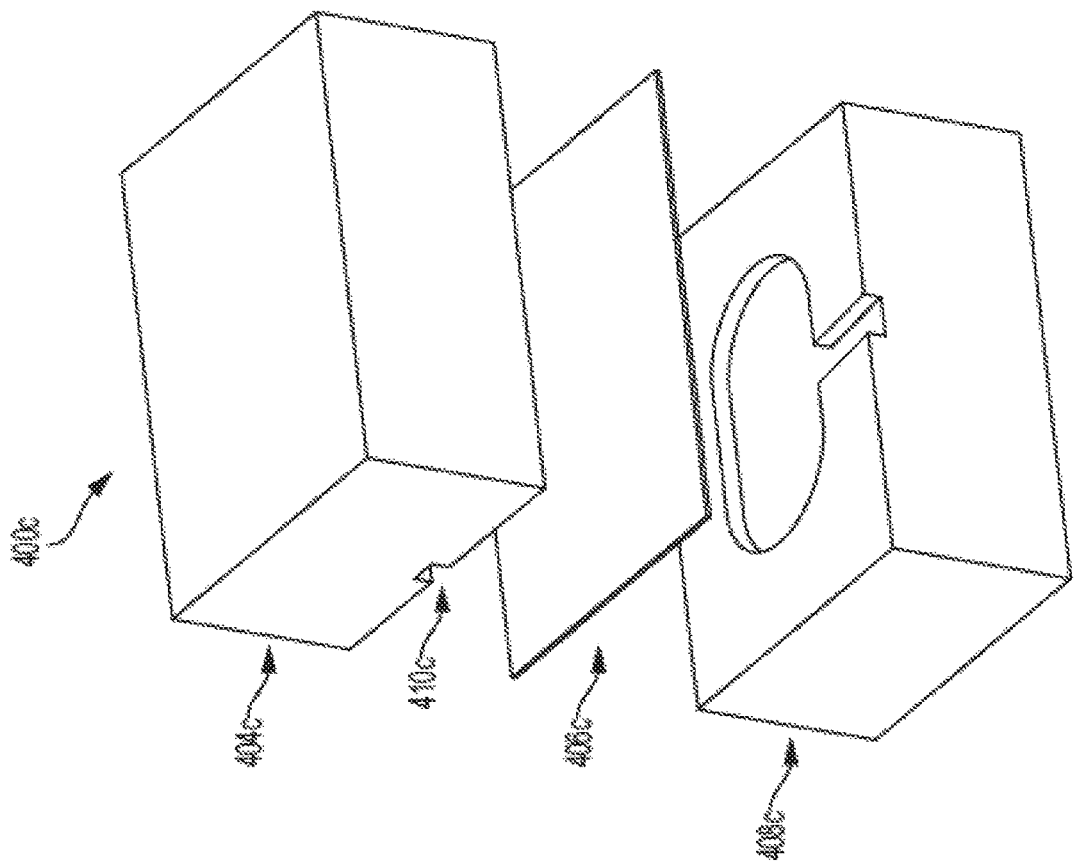
FIG. 5

| NUMBER | AREA (mm^2) | CELL DIAMETER (μm) = | | | | |
|---|---|---|---|---|---|---|
| | | 5 | 10 | 15 | 20 | 25 |
| 1 | 22.79 | 1.16E+06 | 2.90E+05 | 1.29E+05 | 7.25E+04 | 4.64E+04 |
| 2 | 22.33 | 1.14E+06 | 2.84E+05 | 1.26E+05 | 7.11E+04 | 4.55E+04 |
| 3 | 15.50 | 7.89E+05 | 1.97E+05 | 8.77E+04 | 4.93E+04 | 3.16E+04 |
| 4 | 17.02 | 8.67E+05 | 2.17E+05 | 9.63E+04 | 5.42E+04 | 3.47E+04 |
| 5 | 28.84 | 1.47E+06 | 3.67E+05 | 1.63E+05 | 9.18E+04 | 5.88E+04 |
| 6 | 24.38 | 1.24E+06 | 3.10E+05 | 1.38E+05 | 7.76E+04 | 4.97E+04 |
| 7 | 19.55 | 9.96E+05 | 2.49E+05 | 1.11E+05 | 6.22E+04 | 3.98E+04 |
| 8 | 23.71 | 1.21E+06 | 3.02E+05 | 1.34E+05 | 7.55E+04 | 4.83E+04 |

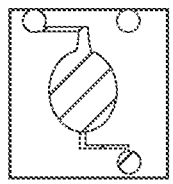
16
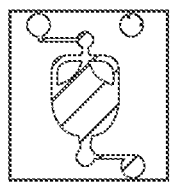
15
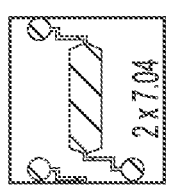
14
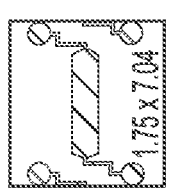
13
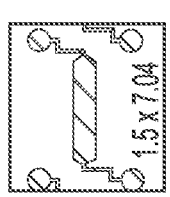
12
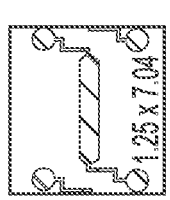
11
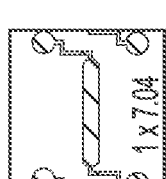
10
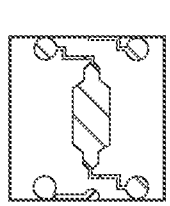
9
| NUMBER | AREA (mm^2) | CELL DIAMETER ($\mu$m) = | | | | |
|---|---|---|---|---|---|---|
| | | 5 | 10 | 15 | 20 | 25 |
| 9 | 17.82 | 9.08E+05 | 2.27E+05 | 1.01E+05 | 5.67E+04 | 3.63E+04 |
| 10 | 11.92 | 6.07E+05 | 1.52E+05 | 6.75E+04 | 3.80E+04 | 2.43E+04 |
| 11 | 13.59 | 6.92E+05 | 1.73E+05 | 7.69E+04 | 4.33E+04 | 2.77E+04 |
| 12 | 15.26 | 7.77E+05 | 1.94E+05 | 8.64E+04 | 4.86E+04 | 3.11E+04 |
| 13 | 16.93 | 8.62E+05 | 2.16E+05 | 9.58E+04 | 5.39E+04 | 3.45E+04 |
| 14 | 18.60 | 9.48E+05 | 2.37E+05 | 1.05E+05 | 5.92E+04 | 3.79E+04 |
| 15 | 23.71 | 1.21E+06 | 3.02E+05 | 1.34E+05 | 7.55E+04 | 4.83E+04 |
| 16 | 25.04 | 1.28E+06 | 3.19E+05 | 1.42E+05 | 7.97E+04 | 5.10E+04 |
FIG. 8B

| NUMBER | AREA (mm^2) | CELL DIAMETER (μm) = | | | | |
|---|---|---|---|---|---|---|
| | | 5 | 10 | 15 | 20 | 25 |
| 17 | 24.33 | 1.24E+06 | 3.10E+05 | 1.38E+05 | 7.75E+04 | 4.96E+04 |
| 18 | 13.11 | 6.68E+05 | 1.67E+05 | 7.42E+04 | 4.17E+04 | 2.67E+04 |
| 19 | 15.63 | 7.96E+05 | 1.99E+05 | 8.85E+04 | 4.98E+04 | 3.18E+04 |
| 20 | 15.26 | 7.77E+05 | 1.94E+05 | 8.63E+04 | 4.86E+04 | 3.11E+04 |
| 21 | 14.79 | 7.53E+05 | 1.88E+05 | 8.37E+04 | 4.71E+04 | 3.01E+04 |

1600

- 1602 – Select and attach well layer to microfluidics device
  - 1604 – Selected well layer comprises cells loaded into first well before attaching the well layer to microfluidics device

- 1606 – Seed first well by causing cell suspension to flow to first well
  - 1608 – Cause, by pneumatic layer, one or more valves to actuate to cause cell suspension to flow to first well
  - 1610 – Cause, by pneumatic layer, one or more valves to actuate to prevent cell suspension from flowing to one or more wells aside from first well
  - 1612 – Cause cells in cell suspension to be retained in first well by geometric confinements

- 1614 – Culture a population of cells in the first well
  - 1616 – Monitor environmental parameters of first well during cell population culturing
  - 1618 – Control environmental parameters of first well without modifying corresponding environmental parameters in or more wells aside from first well (A)

1620 – Perturb one or more characteristics of environment in first well

1622 – Introduce a fluid into first well by causing one or more valves to actuate to cause the fluid to flow to first well 1624 – Prevent first fluid from being introduced into one or more wells aside from first well by causing one or more valves to actuate to prevent the fluid from flowing to the one or more wells aside from first well 1626 – Alter one or more microenvironmental parameters of first well 1628 – Maintain corresponding microenvironmental parameters of one or more wells aside from first well 1630 – Perform first perturbation at first time followed by second perturbation at second time, a predefined period of time after the first time 1632 – After first perturbation and before second perturbation, cause fluid media in first well to be removed from first well

FIG. 16B

METHODS FOR DYNAMIC EVOLUTION AND MONITORING OF CHARACTERISTICS IN LIVING CELLS USING A MICROFLUIDIC-ENABLED MULTI-WELL CELL CULTURE DEVICES AND SYSTEMS

RELATED APPLICATIONS

This application is a national stage application under 35 U.S.C. § 371 of International Application No. PCT/US2019/061514, filed internationally on Nov. 14, 2019, which is related to and claims priority to U.S. Provisional Patent Application No. 62/768,493, titled "METHODS FOR DYNAMIC EVOLUTION AND MONITORING OF CHARACTERISTICS IN LIVING CELLS USING A MICROFLUIDIC-ENABLED MULTI-WELL CELL CULTURE DEVICES AND SYSTEMS" filed Nov. 16, 2018, which are hereby incorporated by reference in its entirety

STATEMENT AS TO FEDERALLY SPONSORED RESEARCH

This invention was made with government support under contract no. HHSN271201600007C and contract no. HHSN271201800012C awarded by the National Institutes of Health. The government has certain rights in the invention.

FIELD

This relates generally to dynamic changes in populations in living cells (including dynamic evolution of cell populations and/or dynamic adaptation of living cells), and particularly to methods for dynamic evolution and/or adaptation of living cells using microfluidic-enabled multiwell cell-culture devices and systems.

BACKGROUND

The culture, monitoring, manipulation and assaying of living cells is a cornerstone of modern biomedical research, and a major component of preclinical drug discovery activities. The maintenance and inspection of cells is typically carried out manually, relying on repeated, visual inspections and manual media exchanges. Alternatively, these manipulations may be carried out using automated robotic instrumentation that reduces error and variability while using smaller reagent volumes.

SUMMARY

Known solutions for maintenance, inspection, and other manipulation of live cells and for execution of drug discovery assays and protocols in modern biomedical research are poorly suited to enabling the accurate, robust, and scalable monitoring of dynamically changing (e.g., adapting and/or evolving) cell properties. Manual techniques for control and inspection of equipment, device, and media, and for performance of cell culture, cell perturbation, and monitoring of changes in cell-population characteristics including evolved phenotypes and/or adapted characteristics, are cumbersome and time consuming, are susceptible to human error, and are poorly standardized. Some known techniques require manual media exchanges that may be poorly standardized, and consume large volumes of reagents and cells. Robotic systems occupy large footprints, are costly to implement, are frequently run as a core facility by specialist staff, and are generally used solely for complex, high-throughput screening applications. Furthermore, robotic systems are also not optimized for long-term cell culture, especially concerning small volumes and large arrays, as they may introduce contaminants and air bubbles into cultured cells from repeated manual manipulation. Additionally, robotic systems are poorly suited for passaging of cells, due to robotic systems being poorly adapted for manipulations required for cell passaging. These factors mean that culturing cells for longer periods of time in robotics systems requires plating cells at limiting dilutions, which is not physiologically relevant and leads to low cell-survival rates. Other known techniques (e.g., digital or droplet microfluidics) do not facilitate the culturing of physiologically-relevant numbers of cells, and/or cannot replicate physiologically-relevant environments (e.g., they require cells in an aqueous solution to be suspended in oil or subjected to electrical fields). New approaches to enable the reliable, efficient monitoring and manipulation of live cells and performance of drug discovery protocols using live cells over a period of several weeks or months in a cost-effective format are therefore needed.

Disclosed herein are systems, methods, and techniques that address these needs through use of microfluidic-enabled multiwell plate systems (e.g., a "SmartPlate") that enable robust, scalable long-term culture, monitoring, and manipulation of live cells in a miniaturized multiwell format that incorporates microenvironment monitoring and closed-loop control capabilities. The use of microfluidic-enabled multiwell plate systems, as described herein, may address the needs noted above by enabling high-throughput, highly precise drug discovery techniques and methods by facilitating microfluidic-enabled cell culture, cell perturbation, micro-environmental control, and monitoring of changes to cell-population characteristics including evolved phenotypes and/or adapted characteristics, and selective removal of cell populations following perturbation in multiwell devices having individually addressable wells that may be controlled on a micro-environmental individual-well basis to simulate physiologically relevant conditions for the evolution and/or adaptation of living cells over multiple weeks or months. As described herein, the microfluidic-enabled cell culture devices and systems may comprise a plurality of individually-addressable wells and may use microfluidic controls to cause the flow of one or more inputs (e.g., cell suspension, media, reagents, detachment agents, dugs agents, etc.) to a well, to cause the flow of one or more outputs (e.g., cells, media, reagents, detachment agents, etc.) from a well, wherein the one or more outputs may be used for additional experimental manipulation or analysis (e.g., in another well, or off-chip) in some applications, and may be disposed of in other applications.

The footprint and well positioning of integrated multiwell devices as described herein may conform to ANSI/SLAS microplate standards, making them compatible with a wide range of standard laboratory instrumentation. The multiwell plate's tiered design may comprise disposable and/or reusable substrate, a microfluidic module, and/or sensing and control modules. The overall system (e.g., including docking stations, control systems, and the like) may be miniaturized for use in tabletop, laboratory, mobile, portable, clinical, field, and/or point-of care settings.

In some embodiments, the substrate may form the lower layer of the multiwell device and may be configured with materials, geometries, and coatings according to various applications. Disposable and/or reusable substrates may include a well layer that may be selected, attached, removed, and/or replaced in order to provide well geometries, coatings, and other properties specifically configured for use in certain drug discovery protocols, including being specifically configured for certain kinds of cell culture, perturbations, and characteristic monitoring and phenotype monitoring techniques.

The microfluidic module may be the central layer of the multiwell device and may enable media exchange and perfusion on an individual-well basis, such that a single well may be addressed with flow of a fluid (and/or evacuated of a fluid therein) without causing flow to or from any other wells in the same multiwell plate, including other wells in a common row and/or common column. This may facilitate scheduled, staggered, and/or iterative addition, removal, and/or replacement of test compounds, as well as sampling of media, and may thereby enable complex drug discovery protocols requiring seeding by multiple cell suspensions, perturbation by multiple reagents at various different timed intervals (and/or continuously), repeated removal and/or replacement of reagents or media, and/or repeated removal of a portion of the population of cells (e.g., evolved cells, adapted cells, perturbed cells, etc.) from the well. This disclosure refers to exemplary embodiments in which all or part of an adapted and/or evolved cell population may be removed from a well of the system; it should be understood that similar methods and techniques as those described herein may additionally or alternatively be sued to remove non-cell media from a well of the system. By facilitating the removal of cell material and/or non-cell material (e.g., supernatant) from wells of the system, the techniques disclosed herein may enable sampling from wells of the system, and may enable the systems disclosed herein to be used as sample-generation systems.

The sensing and control unit may be the top layer of the multiwell device and may be configured to accommodate monitoring and control of multiple parameters including temperature, pH, and confluency, according to experimental needs. The ability to control environmental parameters on a per-well basis, combined with individually-addressable wells, may enable high-throughput for drug discovery experiments and protocols in which each well in a well plate (e.g., 48 different wells or more, 96 different wells or more) may be individually monitored, and in which environmental perturbations (e.g., temperature change, pH change, etc.) may be applied (and monitored) with respect to individual wells to the exclusion of others, including other wells in a common row or column of the well plate.

The systems disclosed herein may thus enable cost-effective and programmable implementation of long-term cell culture and of highly adaptable and scalable drug discovery techniques in a miniaturized multiwell format that is accessible to researchers in laboratory and field environments. The systems may also be well-suited to a wide range of drug discovery applications that involve the culture and perturbation of mammalian cells, insect cells, pathogens, infectious agents, fungus, microorganisms, bacteria cells, biofilms, virus, retrovirus, immortalized cells, reporter cells, dissociated biopsies, patient-derived cell lines, 3D cultures, co-cultures, model organisms, *C. elegans, S cerevisae,* and/or cells with an evolved phenotype and/or adapted characteristic. The system may also be well-suited to a wide range of drug discovery applications that involve perturbation of live cells via the introduction of small molecule reagents, the introduction of one or more reagents enabling genetic perturbations to a cell, the introduction of antibodies, manipulation of one or more environmental parameters, CRISPRi/CRISPRa gene engineering, RNA interference mediated gene knockdown, and/or metabolic perturbations. The system may also be well-suited to a wide range of drug discovery applications that involve ongoing, real-time, and/or intermittent monitoring of cell-population, single cell or subcellular characteristics (e.g., evolving phenotypes/dynamic adaptions) via one or more well-specific assays for analysis of cell-population, single cell or subcellular characteristics including evolved phenotypes and/or adapted characteristics, one or more integrated sensors, integrated microscopy read-outs and visualizations, and interfacing with various standard laboratory equipment for observation and analysis of cell-population characteristics including evolving phenotypes and/or adapted characteristics.

This disclosure refers to exemplary embodiments involving monitoring of cell populations; it should be understood that monitoring of cell populations may include monitoring of a cell populations comprising a plurality of cells, monitoring of cell populations involving a single cell (e.g., single cell monitoring), and/or monitoring of subcellular characteristics of one or more cells.

More generally, the systems may also be well-suited to a wide range of applications that entail long term cell culture ranging from the culture and assaying of immortalized 2D cell cultures to the complex applications such as the generation, culture, and assaying of 3D cell-based models, co-culture models, or reprogramming and differentiation of induced pluripotent stem (IPS) cells. Furthermore, the systems may be compatible with the culture of clinical samples, enabling, for example, testing of patient samples. The multiwell nature of the systems may enable highly parallelized testing of multiple experimental conditions at a scale that conserves significant volumes of reagents and samples compared with both manual and robotic implementation of comparable protocols.

The systems and techniques disclosed herein, along with the next-generation drug discovery techniques, assays, and models that they will enable, may benefit public health by significantly enhancing the throughput and robustness of live cell systems used to evaluate the efficacy of therapeutics, in turn improving the ability to identify beneficial drugs and therapies for unmet medical needs.

BRIEF DESCRIPTION OF THE DRAWINGS

FIGS. 2A-2C depict various views of a multiwell plate device for use in a cell culture system, in accordance with some embodiments.

FIG. 3A depicts an exploded view of a microfluidics layer of a multiwell plate device, in accordance with some embodiments.

FIG. 3H depicts a pneumatic membrane layer of a microfluidics layer of a multiwell plate device, in accordance with some embodiments.

FIG. 3I depicts a degasser control layer of a microfluidics layer of a multiwell plate device, in accordance with some embodiments.

FIG. 5 depicts two cross-sectional views of a respective microfluidics layer including a pneumatic valve, in accordance with some embodiments.

FIGS. 8A-8C different well geometries and tables depicting seeding densities for each of the well geometries, in accordance with some embodiments.

FIGS. 16A-16C depict a flow-chart representation of a method for dynamic evolution/adaptation and monitoring of characteristics in living cells, in accordance with some embodiments

DETAILED DESCRIPTION

The use of advanced cell-based disease models and long-term live cell assays in drug discovery is increasing rapidly. Maintaining these cellular systems in industry standard multiwell plates typically relies on repeated cumbersome and time-consuming visual inspections and manual media exchanges, as explained above. New approaches to enable efficient and high-throughput monitoring, manipulation, and perturbation of cell cultures in multiwell plates over a period of several weeks to several months, while enabling non-disruptive media exchanges at physiologically-relevant scales and in physiologically-relevant environments, are therefore needed.

Disclosed herein are various systems, devices, and techniques that may address this need by leveraging multiwell systems that enables plate-based sensing of microenvironment parameters and automated microfluidic-enabled media exchange and perfusion capabilities in an integrated device with a footprint and well positioning that conforms to the ANSI/SLAS microplate standards. Further disclosed herein are methods and techniques for leveraging the various systems and devices disclosed herein for efficient, precise, parallelized drug discovery methods involving culture, perturbation, and monitoring of live cells in physiologically-relevant environments inside microfluidic-enabled multiwell devices.

Figure 1:
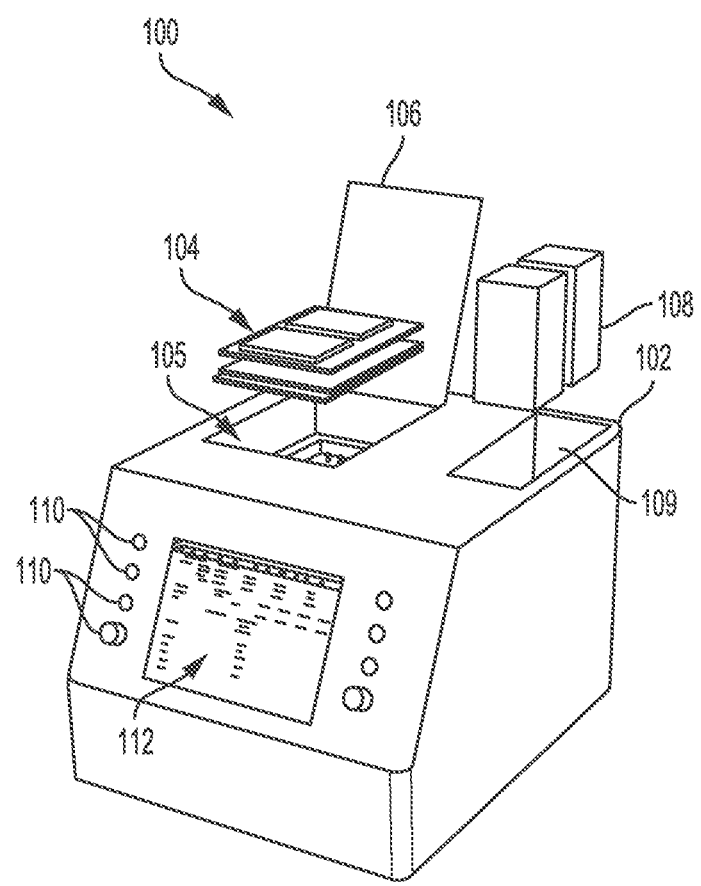
FIG. 1 depicts a cell culture system, in accordance with some embodiments.

FIG. 1 depicts a cell culture system 100, in accordance with some embodiments. As shown in FIG. 1, cell culture system 100 may comprise docking station 102, microfluidic-enabled multiwell plate 104, plate docking portion 105, cover 106, fluid cartridge 108, input devices 110, and display 112. In some embodiments, as described further hereinbelow, system 100 may constitute a tabletop laboratory system configured to manipulate and monitor live cells for various cultures, assays, and/or protocols carried out inside multiwell plate 104. Microfluidic-enabled multiwell plate 104 may comprise a plurality of wells for culture and/or assaying of live cells, one or more sensors for collection of information including data regarding the microenvironment inside plate 104, and one or more valves and/or pumps for automated control of flow of fluid inside plate 104. Components and characteristics of microfluidic-enabled multiwell plates such as multiwell plate 104, in some embodiments, will be discussed below in greater detail.

In some embodiments, docking station 102 may be a tabletop laboratory device having an exterior housing and configured to be placed on a tabletop or bench top and operated by a user. In some embodiments, docking station 102 may be less than or equal to 10 cm, 20 cm, 30 cm, 40 cm, or 50 cm in width. In some embodiments, docking station 102 may be greater than or equal to 10 cm, 20 cm, 30 cm, 40 cm, or 50 cm in width. In some embodiments, docking station 102 may be less than or equal to 10 cm, 20 cm, 30 cm, 40 cm, or 50 cm in height. In some embodiments, docking station 102 may be greater than or equal to 10 cm, 20 cm, 30 cm, 40 cm, or 50 cm in height. In some embodiments, docking station 102 may be less than or equal to 10 cm, 20 cm, 30 cm, 40 cm, or 50 cm in depth. In some embodiments, docking station 102 may be greater than or equal to 10 cm, 20 cm, 30 cm, 40 cm, or 50 cm in depth.

As shown in FIG. 1, docking station 102 may comprise plate docking portion 105 configured to receive multiwell plate device 104. In some embodiments, plate docking portion 105 may be configured to fluidly connect docking station 102 and multiwell plate device 104 such that media and/or cell suspensions may flow between the two.

Furthermore, plate docking portion 105 may be configured to electronically communicatively couple docking station 102 and multiwell plate device 104 such that information may be electronically transmitted between the two. In some embodiments, docking station 102 and multiwell plate device 104 may be configured to communicate with one another via signals sent over one or more physical electronic connections that are connected when multiwell plate 104 is inserted into docking portion 105. In some embodiments, docking station 102 and multiwell plate device 104 may be configured to communicate with one another via signals sent over one or more wireless electronic communications links, which in some embodiments may be activated/deactivated when multiwell plate 104 is inserted into/removed from docking portion 105. In some embodiments, an electrical connection may be formed between docking portion 105 and multiwell plate 104 such that one or more batteries of multiwell plate 104 may be charged by docking station 102 while multiwell plate 104 is inserted into docking portion 105.

As shown in FIG. 1, docking station 102 may comprise cover 106, which may be configured to cover plate device 104 and shield it from external light, air, heat, and/or contaminants while it is connected to docking station 102.

As shown in FIG. 1, docking station 102 may comprise cartridge docking portion 109 configured to receive cartridge 108. In some embodiments, cartridge docking portion 109 may be configured to fluidly connect docking station 102 and cartridge 108 such that media and/or cell suspensions may flow from cartridge 108 to docking station 102 under the force of one or more pumps. In some embodiments, fluid flow may be caused by pneumatic actuation of microvalves, diaphragm valves, and/or electrically driven pumps. In some embodiments, the pumps or vacuums that cause fluid to flow from cartridge 108 to docking station 102 may be located in cartridge 108, in docking station 102, external to docking station 102 (e.g., laboratory vacuum equipment), and/or in a mutliwell device docked with docking station 102. In some embodiments, system 100 may be configured to be able to be used with external and/or internal pneumatic sources, and the pneumatic source used may be chosen by a user depending on available resources (e.g., in a remote field application, internal pneumatic sources may be required to be used).

In some embodiments, cartridge 108 may be configured to house fluid media and/or cell suspensions inside an exterior housing, and may be configured to be able to be physically inserted by a user into docking portion 109, wherein physically inserting cartridge 108 may cause a fluid connection between docking station 102 and cartridge 108 to be connected. In some embodiments, using a cartridge such as cartridge 108 may ensure sterility of cell suspension and other fluids used in system 100 by minimizing the need for users or robots to physically manipulate the fluids in open space.

In some embodiments, in addition to or alternately to a media cartridge docking to cartridge docking portion 109, a media cartridge may be configured to dock directly to a multiwell device. In some embodiments, a media cartridge configured to dock directly to a multiwell device may have a smaller physical form factor than a media cartridge configured to dock to cartridge docking portion 109. In some embodiments, a miniaturized media cartridge configured to dock directly to a multiwell device may allow the multiwell device to be moved to and/or from docking station 102 to other laboratory equipment (e.g., microscopes) or to other locations without interrupting media supply. In some embodiments, system 100 may comprise a first adapter configured to allow a media cartridge configured to dock to cartridge docking portion 109 to alternately dock directly to a multiwell device; in some embodiments, system 100 may comprise a second adapter configured to allow a media cartridge configured to dock directly to a multiwell device to alternately dock to cartridge docking portion 109. In some embodiments, multiwell device 104 may comprise one or more reservoirs configured to be filled with reagent and/or other fluid by docking portion 109 such that multiwell device 104 may be removed from docking station 102 (for example to be transported to another piece of laboratory equipment) without interrupting the continuous availability of media supply.

In some embodiments, in addition to or alternately to a media cartridge docking to cartridge docking portion 109, cell suspension and/or other fluids may be fed into a multiwell device via a one or more pipettes, one or more tubes, one or more syringes, one or more gravitational systems, one or more reservoirs located on the multiwell device, or any other suitable fluid communication mechanism.

In some embodiments, in addition to or alternately to media cartridge 108, system 100 may comprise a separate cell-loading cartridge, vial, or other device configured to dispense cell suspension and optionally be disposed after use. In some embodiments, a small epi-like vial may be loaded into docking station 102 by a user, and the vial or cartridge may maintain the cell suspension in a sterile tissue culture environment.

In some embodiments, docking station 102 may comprise various pneumatic connection ports configured to pneumatically couple docking station 102 to a multiwell device inserted into docking station 102 and/or to pneumatically couple docking station 102 to a source of pressure and/or vacuum. In some embodiments, a pneumatic manifold (discussed in further detail below) may be disposed inside a housing of docking station 102 and may be configured to selectively pneumatically connect a common source of pressure and/or vacuum to one of various pneumatic connections to a multiwell device; by selectively pneumatically connecting one of various pneumatic lines of the multiwell device to the source of pressure and/or vacuum, valves and/or pumps of the multiwell device may be selectively pneumatically actuated in order to control the flow of fluid inside the multiwell device.

In some embodiments, in addition to cartridge 108 and/or one or more other input sources, system 100 may further comprise an output reservoir that may be connected to a multiwell device and/or docking station 102. In some embodiments, an output reservoir may be any well, reservoir, bag, or other fluid container, and may be configured to receive flow of cell suspension and/or other fluid media from other components of system 100 following use of the fluids. In some embodiments, an output reservoir may comprise a plurality of separate compartments or wells for keeping collected fluid separate following collection. In some embodiments, as described below, the ability to individually address flow to and/or from any well of a multiwell device may allow collection of cell suspension from separate wells in a multiwell device (e.g., smart plate device) into separate compartments, wells, or containers of an output reservoir. In some embodiments, an output reservoir may comprise or be associated with one or more sensors configured to detect flow of fluid into and/or inside the output reservoir.

As further shown in FIG. 1, docking station 102 may comprise user input devices 110, which may comprise electronic and/or physical buttons, keys, knobs, switches, levers, joysticks, touch-pads, touch-screens, microphones, cameras, or the like. Input devices 110 may be configured to detect one or more inputs executed by a user, and to accordingly send one or more signals to a processor associated with system 100, wherein the signal sent indicates the detection of the input executed by the user.

As further shown in FIG. 1, docking station 102 may comprise display 112, which may in some embodiments be a touch-screen display that may also serve as an input device. Display 112 may be configured to display information regarding microenvironment data collected from multiwell plate 104, environmental data collected from a physical environment surrounding multiwell plate 104 and/or station 102, instructions for a user, alerts for a user, queries for a user, information regarding a status of system 100, and/or log data stored locally or remotely from system 100.

In some embodiments, system 100, including docking station 102 and multiwell plate 104 (in addition to other multiwell devices described herein) may be configured to enable performing cultures, assays, and other protocols on live cells over extended periods of time, with no human or robotic intervention (or minimized human or robotic intervention), and without the use of an incubator. In some embodiments, system 100 may enable performing cultures, assays, and other protocols over a period of greater than 24 hours, 48 hours, 72 hours, 1 week, or 2 weeks, 1 month, 3 months, or 6 months. In some embodiments, system 100 may enable performing cultures, assays, and other protocols over a period of less than 24 hours, 48 hours, 72 hours, 1 week, or 2 weeks. In some embodiments, minimizing physical intervention by humans or robots may minimize opportunities for a sample to become contaminated or compromised.

In some embodiments, system 100 may enable performing cultures, assays, and other protocols involving sampling of materials from wells (e.g., removal of cell material, non-cell material, and/or supernatant from wells) at user-specified and/or automatically-determined sampling intervals. In some embodiments, sampling may follow a pre-defined schedule. In some embodiments, sampling may be performed at regular and/or irregular intervals. In some embodiments, sampling intervals may be less than 1 minute, less than 5 minutes, less than 30 minutes, less than 1 hour, less than 24 hours, or less than 1 week. In some embodiments, sampling intervals may be greater than 1 minute, greater than 5 minutes, greater than 30 minutes, greater than 1 hour, greater than 24 hours, or greater than 1 week.

In some embodiments, system 100 may comprise one or more computing components such as processors, memory, storage, and communication interfaces for wireless and/or wired communication. In some embodiments, system 100 may be configured to receive stores and/or execute instructions for controlling one or more control, monitoring, input receiving, data outputting, and/or logging functions of system 100 for the execution of cultures, assays, and or other live cell protocols. In some embodiments, system 100 may be configured to be the primary control module for controlling the functioning of a multiwell device inserted in system 100, such as by being inserted in docking station 102. In some embodiments, one or more computing components of system 100 may be located locally to docking station 102 (e.g., they may be comprised in docking station 102), and/or they may be located remotely from docking station 102 (e.g., they may communicate with docking station 102, and/or with other components of system 100) via wired or wireless (e.g., network) electronic communication.

Figure 2A:
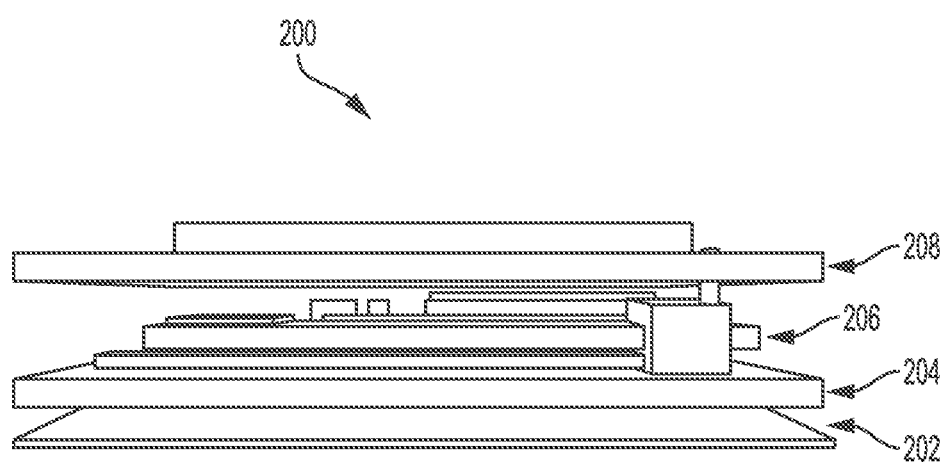
Figure 2B:
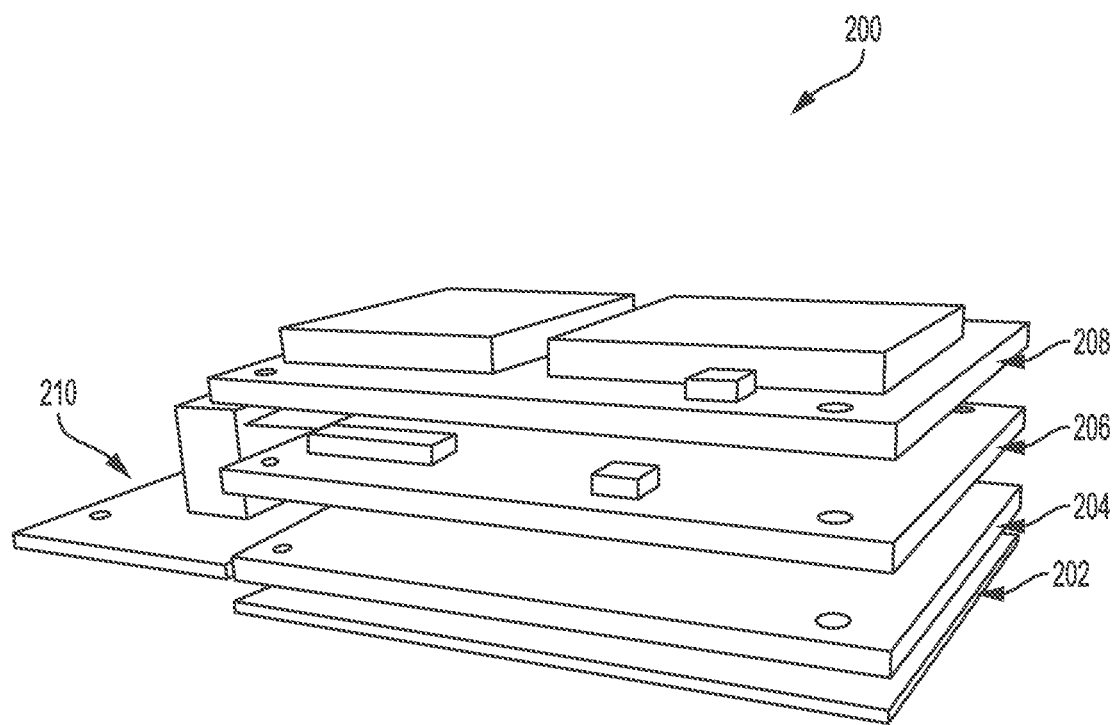

FIGS. 2A-2C depict various views of multiwell plate device 200 for use in a cell culture system such as system 100, in accordance with some embodiments. In some embodiments, multiwell plate device 200 may share some or all characteristics in common with multiwell plate 104 as discussed above with reference to FIG. 1. As shown in FIGS. 2A-2C, multiwell plate device 200 may comprise microfluidics layer 200, sensor layer 204, microcontroller layer 206, and battery layer 208. In some embodiments, any one or more of the four layers 202-208 may be configured to be able to be removed from the other layers and reattached to the other layers. In this way, the layers may act as modules that may be removed, used in one or more downstream analysis procedures or other procedures, disposed of, replaced, and/or recombined by a user. In some embodiments, a user may select a microfluidics layer or a sensor layer having channel arrangements or properties, well arrangements or properties, and/or sensor arrangements or properties suitable for a desired culture, assay, or protocol. In some embodiments, the layers may be attached to one another by a mechanical connection, an adhesive connection, a magnetic connection, and/or by application of external force (e.g., they may be clamped or pressed together). In some embodiments, any one or more of the four layers 202-208 may be referred to as modules.

In some embodiments, multiwell plate device 200 may be configured to enable culture and/or assaying of live cells in a plurality of individually-addressable wells in the microfluidic layer. As explained below in detail with reference to FIG. 3, configuration of various layers in multiwall plate device 200 may allow individual wells to be addressed to the exclusion of other wells in the device, including to the exclusion of other wells in the same row and/or other wells in the same column as the well that is being addressed. In some embodiments, multiwell plate device 200 may be configured to enable automated control and monitoring of microenvironment conditions and external conditions by one or more sensors in device 200; and may be configured to enable automated control of flow of fluid to and from the wells in the microfluidic layer via one or more micro-valves and/or micro-pumps.

In some embodiments, multiwell plate device 200 may have a length and/or width of less than 7 inches, 5 inches, less than 3 inches, less than 2 inches, or less than 1 inch. In some embodiments, multiwell plate device 200 may have a length and/or width of greater than 7 inches, 5 inches, less than 3 inches, less than 2 inches, or less than 1 inch. In some embodiments, multiwell plate device 200 may have a height of less than 5 mm, 10 mm, 25 mm, or 50 mm. In some embodiments, multiwell plate device 200 may have a height of greater than 5 mm, 10 mm, 25 mm, or 50 mm. In some embodiments, multiwell plate device 200 may be configured to have a footprint that enables the device to be inserted into docking station 102 and/or into other laboratory or field equipment such as a microscope.

In some embodiments, microfluidics layer 202 may comprise a plurality of wells configured to house live cells for culture, assaying, and/or other live-cell protocols. Media and or cell suspensions may flow to and/or from one or more of the wells via microfluidic channels in microfluidics layer 202. Flow of fluid in microfluidics layer 202 may be driven by one or more pneumatic micro-pumps and controlled by one or more micro-valves, which may be automatically driven and/or actuated by a local or remote electronic controller.

In some embodiments, a single pump-stroke of a micropump of microfluidics layer 202, may be configured to displace a volume of fluid per cycle (e.g., per pump-stroke) of less than 2000 nL, 1500 nL, 1000 nL, 500 nL, 250 nL, 100 nL, 50 nL, 10 nL, or 5 nL. In some embodiments, a single pump-stroke a micropump of microfluidics layer 202 may be configured to displace a volume of fluid per cycle of greater than 2000 nL, 1500 nL, 1000 nL, 500 nL, 250 nL, 100 nL, 50 nL, 10 nL, or 5 nL. In some embodiments a diaphragm volume of a micropump of microfluidics layer 202 may be less than 2000 nL, 1500 nL, 1000 nL, 500 nL, 250 nL, 100 nL, 50 nL, 10 nL, or 5 nL. In some embodiments a diaphragm volume of a micropump of microfluidics layer 202 may be greater than 2000 nL, 1500 nL, 1000 nL, 500 nL, 250 nL, 100 nL, 50 nL, 10 nL, or 5 nL. In some embodiments, a pump step of a micropump of microfluidics layer 202 may be less than 500 mS, 400 mS, 300 mS, 200 mS, or 100 mS. In some embodiments, a pump step of a micropump of microfluidics layer 202 may be greater than 500 mS, 400 mS, 300 mS, 200 mS, or 100 mS.

In some embodiments, a valve actuation vacuum for a microvalve of microfluidics layer 202 may be −90 kPa±50 kPa, −90 kPa±30 kPa, or −90 kPa±10 kPa. In some embodiments, a valve actuation pressure for a microvalve of microfluidics layer 202 may be +40 kPa±20 kPa, +40 kPa±10 kPa, or +40 kPa±5 kPa.

In some embodiments, sensor layer 204 may be adjacent to microfluidics layer 202. Sensor layer 204 may comprise a printed circuit board and one or more sensors configured to detect one or more characteristics of a microenvironment inside a well and/or channel of microfluidics layer 202. In some embodiments, the detected characteristics of the microenvironment may include one or more of temperature, pressure, pH, humidity, CO2 level, O2 level, confluency, fluid flow, shear stress, alkalinity, acidity, basicity, input fluid temperature, output fluid temperature, ambient light intensity, electrical potential, impedance, or resistance. In some embodiments, the sensors used in detecting the characteristics of the microenvironment may be located in sensor layer 204, in microfluidics layer 202, or both.

In some embodiments, a microfluidic multiwell device and/or associated system may be configured to generate a two-dimensional or three-dimensional gradient heat-map of a microfluidic layer such as microfluidic layer 202, in accordance with temperature data received from one or more temperature sensors such as sensors disposed on sensor layer 204.

In some embodiments, confluency monitoring may be achieved electronically through impedance spectroscopy (e.g., the use of interdigitated electrodes that may be controlled and operated by sensor layer 204) or by microscopic imaging and deep learning image analysis software/AI.

In some embodiments, sensor layer 204 may comprise all or part of one or more components such as pneumatic pumps, microvalves, heating elements, and/or other components configured to control or modify one or more detected characteristics of the microenvironment. Thus, multiwell device 200 may detect the characteristics of the microenvironment and may automatically cause them to be controlled to be modified or maintained, such as by adjusting them to a predefined value or range, or by ensuring that they do not deviate from a predefined value or range.

In some embodiments, humidity may be regulated to be maintained at or near 100%, as cells may be harmed by contact with air.

In some embodiments, CO2 levels may be adjusted by the addition of CO2 to a delivered media, such as chemically and/or physically by adding CO2 gas. In some embodiments, CO2 content may determine pH of media. In some embodiments, pH buffer may be added into media to stabilize it, and through continuous exchange of media pH may not change dramatically.

In some embodiments, oxygen regulation (which may be based on measurement of environmental and/or internal oxygen conditions) may include use of one or more degassers to achieve hypoxic conditions.

In some embodiments, pressure may be monitored environmentally for data logging and regulated internally for pneumatic actuation of micropumps, degassers, and/or general fluid actuation.

In some embodiments, temperature may be regulated internally for cell culture conditions using one or more heating or cooling elements based on external and/or internal temperature measurements.

In some embodiments, confluence may be regulated by measuring cell culture conditions and viability of cells, and performing assays and protocols to decrease numbers of cells in a certain area of a well.

In some embodiments, regulation and/or adjustment of any one or more microenvironmental, internal, environmental, and/or external conditions may be performed at least in part on the basis of monitoring of any one or more microenvironmental, internal, environmental, and/or external conditions.

In some embodiments, microcontroller layer 206 may be adjacent to sensor layer 204, such as by being located on the opposite side of sensor layer 204 as microfluidics layer 202. Microcontroller layer 206 may comprise one or more computing components such as processors, memory, storage, and communication interfaces for wireless and/or wired communication. In some embodiments, microcontroller layer 206 may be configured to receive stores and/or execute instructions for controlling one or more control, monitoring, input receiving, data outputting, and/or logging functions of multiwell device 200 for the execution of cultures, assays, and or other live cell protocols. In some embodiments, microcontroller layer 206 may be configured to be the primary control module for controlling the functioning of multiwell device 200.

In some embodiments, microcontroller layer 206 may comprise, or may be communicatively coupled with, one or more sensors configured to sense environmental data regarding an environment surrounding multiwell device 200 (e.g., as distinct from microenvironmental data regarding the microenvironment inside microfluidics layer 202. In some embodiments, the environmental data regarding an environment surrounding multiwell device 200 may comprise one or more of temperature, pressure, humidity, CO2, O2, and/or ambient light characteristics and intensity. In some embodiments, microcontroller layer 206 may be configured to change or maintain one or more characteristics of multiwell device 200 and/or of the contents of microfluidics layer 202 in accordance with the detected surrounding environmental data.

In some embodiments, the ability to control the temperature of the microenvironment, such as via one or more heating elements integrated into multiwell device 200 or included in an associated device docking station 102, may enable performing long-term cell cultures and assays without the use of an incubator. That is, by monitoring and controlling the temperature of the system via heating elements of the system, cultures, assays, and other protocols may be performed in a tabletop or benchtop (e.g., room-temperature) environment, or even outdoors.

In some embodiments, battery layer 208 may be adjacent to microcontroller layer 206, such as by being located on the opposite side of microcontroller layer 206 as sensor layer 204. Battery layer may in some embodiments comprise one or more batteries or other power sources configured to provide electrical power for one or more components of multiwell device 200. In some embodiments, multiwell device may be configured to draw power from one or more other sources or electrical power aside from battery layer 208, such as from batteries located elsewhere inside or outside device 200, or from one or more electrical power connections, such as a connection to a docking station or other laboratory equipment to which device 200 may be connected.

As shown in FIGS. 2B and 2C, multiwell device 200 may in some embodiments comprise $CO_2$ sensor 210, which may be configured to detect $CO_2$ levels of a microenvironment of device 200 and/or of the environment surrounding device 200, and may be configured to send signals regarding the detected $CO_2$ levels to sensor layer 204 and/or microcontroller layer 206. In some embodiments, $CO_2$ sensor 210 may be included as part of sensor layer 204; in some embodiments, $CO_2$ sensor 210 may have a height that is greater than a height of sensor layer 204, and $CO_2$ sensor 210 may be positioned in device 200 alongside one or more of the layers and may span a height of two or more of the layers of device 200.

In some embodiments, multiwell device 200 may be configured to form a sterile microenvironment that may not be contaminated by physical handling of the outside of multiwell device 200. In this way, multiwell device 200 may be used in a non-sterile environment to perform sterile cultures, assays, and protocols.

In some embodiments, in addition to the layers discussed above, multiwell device 200 may comprise a substrate layer, which may be a bottommost layer of a multiwell device and may be a glass or plastic (e.g., borofloat glass, any suitable polymer, any suitable copolymer, etc.) layer that may be disposed opposite a microfluidics layer from other layers such as a sensor layer or control layer. In some embodiments, a substrate layer may be configured for imaging, such as by being a thin, antireflective layer configured for high-resolution imaging. In some embodiments, the substrate layer may be configured to be strong enough to support the assembly of the microfluidics module and the multiwell device in which it is disposed. In some embodiments, the substrate layer may have a thickness of less than 25 μm, 50 μm, 100 μm, 500 μm, 1 mm, or 1.5 mm, or 2 mm. In some embodiments, the substrate layer may have a thickness of greater than 25 μm, 50 μm, 100 μm, 500 μm, 1 mm, or 1.5 mm, or 2 mm. In some embodiments, the substrate layer (and other layers such as those in the microfluidics layer) may be configured to not be autofluorescent, to be sufficiently transparent, to be sufficiently flat, to be sufficiently thin, and/or to be sufficiently uniform in thickness such that high-resolution microscopic images may be captured through the layer. In some embodiments, a substrate layer may comprise one or more wells, and may thereby serve as a part of the microfluidics layer (e.g., it may replace the well layers discussed below). In some embodiments, a microfluidics layer may be micropatterned or microengraved and may contain one or more structures such as micropillars or nanopillars.

FIG. 3A depicts an exploded view of a microfluidics layer 300 of a multiwell plate device, in accordance with some embodiments. In some embodiments, microfluidics layer 300 may share any one or more characteristics in common with microfluidics layer 202 as discussed above with reference to FIGS. 2A-2C. In some embodiments, microfluidics layer 300 may be configured to be permanently or impermanent attached to other layers and/or modules (e.g., sensor layers, control layers, and/or battery layers) of a plate device, thereby forming a multiwell plate device configured for performing cultures, assays, and other protocols for live cells. In some embodiments, microfluidics layer 300 may comprise a plurality of wells configured to hold cell suspensions, reagents, and/or other media for use in performing cultures, assays, and other protocols. Microfluidics layer 300 may further comprise microfluidic channels connected to one or more fluid inputs and fluid output, such that the microfluidic channels may be used to deliver fluid to and/or from the microfluidic wells. In some embodiments, one or more of the layers in microfluidics layer 300 may be formed from glass, plastic, Teflon, PDMS, gas-permeable membranes, cyclic olefin copolymer (COC), or other suitable materials. In some embodiments, a substrate layer of microfluidics layer 300 may be made from glass while one or more of the other layers may be made from PDMS or other types of polymers.

As shown in FIG. 3A, microfluidic layer 300 may itself comprise a plurality of sub-layers, including well layer 302, degasser membrane layer 303a, degasser layer 303b, fluid routing layer 304, pneumatic membrane layer 306, pneumatic layer 308, degasser control layer 314, and sealing layer 316. In some embodiments, microfluidics layer 300 may further comprise one or more additional layers and/or sub-layers not depicted in FIG. 3A.

In some embodiments, well layer 302 may comprise the plurality of wells themselves, while fluid routing layer 304 may comprise microfluidic channels through which fluid may flow to and/or from the channels. In some embodiments, pneumatic membrane layer 306 and pneumatic layer 308 may work together to use pneumatic force to cause the opening and/or closing of microvalves and/or the actuation of micropumps to control the flow of fluid through the microfluidic channels of layer 304 and into and/or out of the wells of layers 302.

In some embodiments, the layers included in microfluidics layer 300 may be stacked with well layer 302 on one side (e.g., the bottom of microfluidics layer 300), followed by fluid routing layer 304, then pneumatic membrane layer 306, then pneumatic layer 308 on the opposite side (e.g., the top of microfluidics layer 300) as well layer 302.

In some embodiments, one or more of layers 304, 306, and 308 may be permanently bonded to one another, such as by being molded, pressed, and/or heated and melted together, and may thereby create a reusable and/or autoclavable control layer. Well layer 302 may then be impermanently connected to the control layer, such as by adhesives, such that well layer 302 may be removed upon experiment completion. In some embodiments, UV ozone treatments may be used to create a strong bond between layers, and that bond may thereafter be released via the use of acids and/or organic solvents. In some embodiments, the layers may be pressed or forced together via external mechanical force without being permanently and/or adhesively bonded to one another. In some embodiments, one or more alignment devices such as guiding pillars, which may be included in a multiwell device itself or may be included in an external device such as docking station 102, may be used in order to align different layers as they are being permanently or impermanently attached to one another.

In some embodiments, one or more of the layers of microfluidics layer 300 may be customized according to experimental needs, for example, to comprise impedance sensors, micro-engraved structures, well geometry for 3D cultures, organoids, artificial organs, one or more materials, geometries, and/or structures configured for the study of model organisms (e.g., C. elegans, S. cerevisiae), and/or alternative substrate material.

In some embodiments, pneumatic membrane layer 306 may comprise a flexible (e.g., PDMS/teflon) membrane that separates pneumatic layer 308 from fluid routing layer 304, such that pneumatic membrane layer 306 may be caused to deform by pressure exerted on pneumatic membrane layer 306 by pneumatic layer 308. As pneumatic membrane layer 306 deforms, one or more gates or valves may be caused to be actuated such that flow of fluid in fluid routing layer 304 may be controlled by the deformation of pneumatic membrane layer 306. In some embodiments, pneumatic membrane layer 306 may have a thickness of less than 200 μm, 150 μm, 100 μm, or 50 μm. In some embodiments, pneumatic membrane layer 306 may have a thickness of greater than 200 μm, 150 μm, 100 μm, or 50 μm.

In some embodiments, microfluidics layer 300 may have a footprint of 2 inches by 3 inches, or may have a footprint of any other suitable size. In some embodiments, microfluidics layer 300 may have a length and/or width of less than 5 inches, less than 3 inches, less than 2 inches, or less than 1 inch. In some embodiments, microfluidics layer 300 may have a length and/or width of greater than 5 inches, less than 3 inches, less than 2 inches, or less than 1 inch. In some embodiments, microfluidics layer 300 may conform with ANSI/SLAS footprint standards. In some embodiments, microfluidics layer 300 may have a height of less than 1 mm, 2 mm, 3 mm, 4 mm, 5 mm, or 10 mm. In some embodiments, microfluidics layer 300 may have a height of greater than 1 mm, 2 mm, 3 mm, 4 mm, 5 mm, or 10 mm.

In some embodiments, it may be important that one or more components of microfluidics layer 300 remains clean and free from contaminants prior to microfluidic chip fabrication. In some embodiments, one or more cleaning procedures may be performed before and/or during chip fabrication; in some embodiments, cleaning procedures may not be required before and/or during cell loading, cell culture, and/or biological assay procedures. In some embodiments, cleaning of one or more components of microfluidics layer 300 may comprise Piranha cleaning, which may be used to remove organic residues. Two different solutions may be used in Piranha cleaning. In some embodiments, an acid may be used: the acid may comprise a 3:1 mixture of concentrated sulfuric acid (H2SO4) with hydrogen peroxide (H2O2). In some embodiments, a base may be used: the base may comprise a 3:1 mixture of ammonium hydroxide (NH4OH) with hydrogen peroxide (H2O2). Both the acid and the base may be dangerous when hot; in some embodiments, the reaction in the acid is self-starting whereas the base piranha may be required to be heated to 60 degrees Celsius before the reaction initiates. Piranha acids and bases may be prepared in a clean and prepared chemical hood. Once the solution is made, the one or more components of microfluidics layer 300 may be carefully placed inside and be gently agitated for about 10 minutes, then rinsed sufficiently with water and blown dry with an air gun.

In some embodiments, lab cleaning of one or more components of microfluidics layer 300 substrate layer may comprise placing the one or more components in a dish and add a 20 mM Triton-X solution, or other detergent solution; the one or more components may then be placed in ultrasound bath for about five minutes. The one or more components may be rinsed with water and placed in a new dish, where Acetone may be added and the one or more components may be sonicated for about 10 minutes. The one or more components may then be transferred to isopropanol and sonicated for about 10 minutes. The one or more components may then be removed and blown dry and placed in a dish with a lid. In some embodiments, the one or more cleaned components may be placed on a hot plate at about 150 degrees Celsius for about 30 minutes to remove excess humidity.

In some embodiments, sterilization of one or more components of microfluidics layer 300 may after fabrication and prior to execution of a cell culture, assay, and/or protocol may comprise autoclaving and washing. (In some embodiments, the sterilization may comprise one or more aspects of techniques discussed below in Example 1.) In some embodiments, a rinse using 70% ethanol may be performed for about 15 minutes, a rinse using 1M NaOH may then be performed for about 30 minutes, and a rinse PBS/media may then be performed for about one hour.

In some embodiments, one or more components may be packaged and/or shipped in a sterile (e.g., sealed) condition, such that sterilization before use in a culture, assay, and/or protocol by an end user may not be necessary, and such that the one or more components may be ready for use upon being unsealed. In some embodiments in which one or more components may be removed and replaced from a multiwell device, a new sterile component may be used rather than cleaning a previously used component for subsequent use.

Figure 3B:
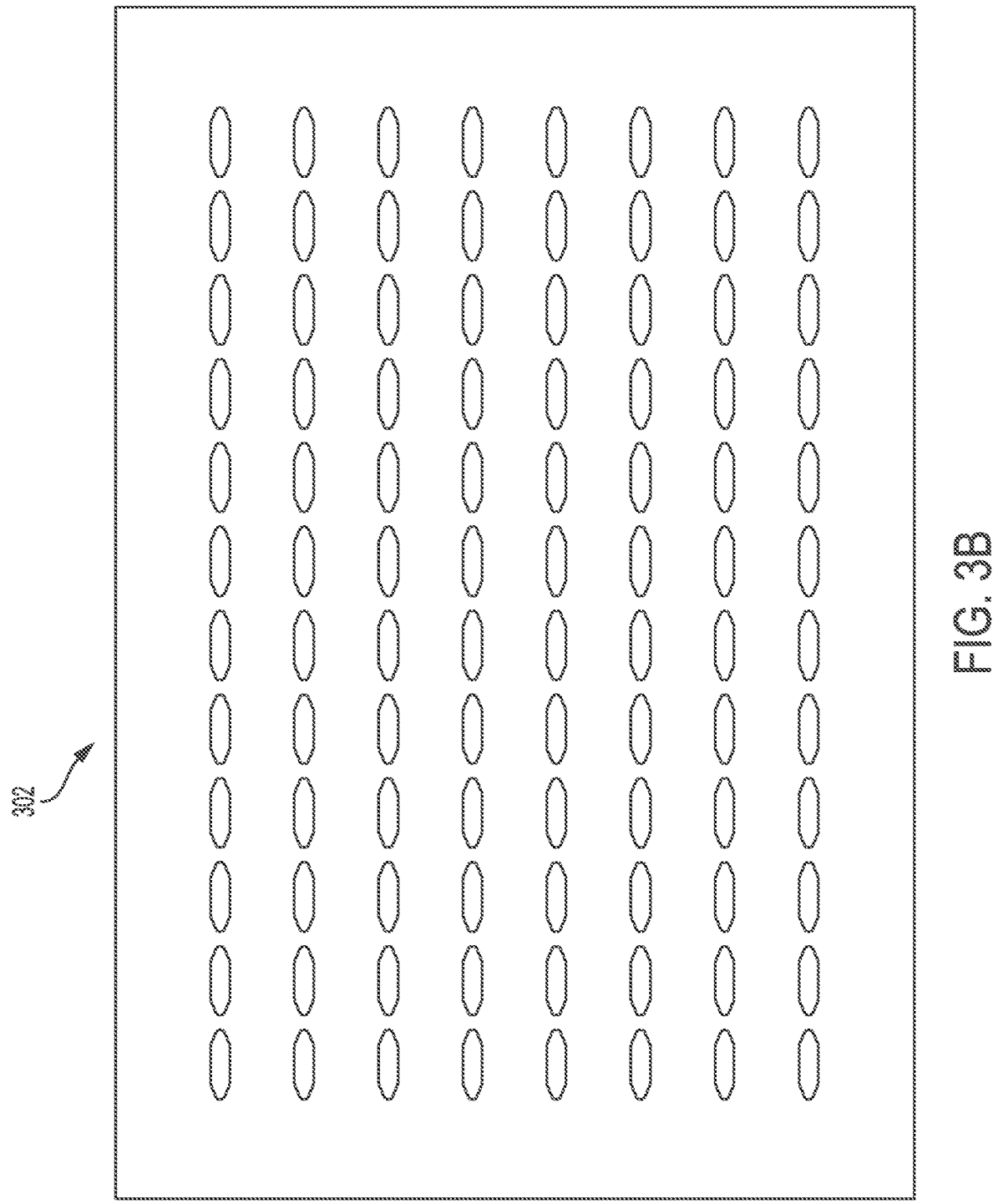
FIG. 3B depicts a well layer of a microfluidics layer of a multiwell plate device, in accordance with some embodiments.

FIG. 3B shows an isolated view of well layer 302, in accordance with some embodiments. As shown, well layer 302 may comprise 96 wells arranged in an 8×12 grid. In some embodiments, well layer 302 may comprise a smaller total number of wells, such as 6, 12, 24, or 48 wells. In some embodiments, well layer 302 may comprise a total number of wells greater than 96. In some embodiments, the effective area of one or more of the wells in well layer 302 may be less than 5 $mm^2$, less than 10 $mm^2$, less than 20 $mm^2$, less than 30 $mm^2$, or less than 50 $mm^2$. In some embodiments, the effective area of one or more of the wells in well layer 302 may be greater than 5 $mm^2$, less than 10 $mm^2$, less than 20 $mm^2$, less than 30 $mm^2$, or less than 50 $mm^2$.

In some embodiments, wells of well layer 302 may each have an input channel (e.g., inlet) and/or an output channel (e.g., outlet), which may open to a layer adjacent to well layer 302. Thus, input channels and/or output channels of well layer 302 may be in fluid communication with microfluidic channels of fluid routing layer 304, such that fluid may be delivered into the inputs from fluid routing layer 304 and out of the outputs to fluid routing layer 304. In some embodiments, the inlets and/or outlets of well layer 302 may have a width of less than 2 mm, less than 1 mm, less than 0.75 mm, less than 0.5 mm, or less than 0.25 mm. In some embodiments, the inlets and/or outlets of well layer 302 may have a width of greater than 2 mm, less than 1 mm, less than 0.75 mm, less than 0.5 mm, or less than 0.25 mm.

In some embodiments, well layer 302 may have a height of less than 0.05 mm, 0.1 mm, 0.25 mm, 0.5 mm, 0.75 mm, 1 mm, or 2 mm. In some embodiments, well layer 302 may have a height of greater than 0.05 mm, 0.1 mm, 0.25 mm, 0.5 mm, 0.75 mm, 1 mm, or 2 mm.

In some embodiments, well layer 302 may be provided as a separate (e.g., detachable and replaceable) module from the rest of the layers of microfluidics layer 300, which may provide flexibility to vary its configuration to include, in some embodiments, additional sensors (e.g. impedance sensing electrodes); alternative well geometries (e.g. micropatterning or specialized well shape for 3D cultures);

alternative materials (e.g. glass, COC, others); and/or alternative coatings (e.g. fibronectin, polylysine etc.). In some embodiments, multiple different well layers having varying characteristics may nonetheless be configured to attach to the same fluid routing layer of a microfluidic device to be in fluid communication with the device; that is, multiple different well layers may be configured such that, by aligning either or any of the well layers with the same fluid routing layer, either or any of the well layers will be in fluid communication with the well layer and thereby be compatible for use with the same microfluidic device. In some embodiments, one or more well layers may be configured such that one or more wells may be used as reservoirs, mixing areas, and/or compartment etc. for application-specific operations and/or assays.

In some embodiments, well layer 302 may be a substrate layer of microfluidics layer 300 and/or of a multiwell device.

In some embodiments, well layer 302 may be micropatterned and/or microengraved, and/or may contain micropillars and/or nanopillars. In some embodiments, one or more of a thickness, material, micropatterning, coating, and geometrical configuration of well layer 302 may be configured for microscopic imaging. In some embodiments, one or more of a material, micropatterning, coating, and geometrical configuration of well layer 302 may be configured for 2D culture of adherent cells. In some embodiments, one or more of a material, micropatterning, coating, and geometrical configuration of well layer 302 may be configured for co-culture of more than one type of cell (e.g., more than one type of adherent cell). In some embodiments, a system may be configured to address one cell suspension having a first type of adherent cell to a well, and to then address a second cell suspension having a second type of adherent cell to the same reservoir. In some embodiments, the first and second cell suspensions may be drawn from separate reservoirs or other separate sources. In some embodiments, one or more of a material, micropatterning, coating, and geometrical configuration of well layer 302 may be configured for co-culture of adherent cells with other cell types. In some embodiments, one or more of a material, micropatterning, coating, and geometrical configuration of well layer 302 may be configured for co-culture of any two types of cells disclosed herein, and/or for co-culture of any type of cell disclosed herein with one or more additional types of cells. In some embodiments, one or more of a material, micropatterning, coating, and geometrical configuration of well layer 302 may be configured for culture of suspension cells. In some embodiments, one or more of a material, micropatterning, coating, and geometrical configuration of well layer 302 may be configured for culture of 3D culture models. In some embodiments, the 3D models comprise one or more of tumor spheroids, organoids, vascular networks, bioprinted 3D tissue models, and iPSC-derived 3D tissue models. In some embodiments, one or more of a material, micropatterning, coating, and geometrical configuration of well layer 302 may be configured for culture of one or more of immortalized cells, iPSC, iPSC-derived, or primary cells. In some embodiments, any one or more of the characteristics of well layer 302 set out in this paragraph, and/or any one or more characteristics of a well layer set out elsewhere in this application, may apply equally to a substrate layer that is separate from a well layer.

In some embodiments, well layer 302 may be provided to a user after cells have been seeded into one or more layers and frozen there, such that the user could then attach the well layer to a system and thaw the cells and start an experiment after the cells have thawed. In some embodiments, this process could reduce user input regarding cells and allow specific cell lines engineered for certain biological application to be provided to users.

Figure 3C:
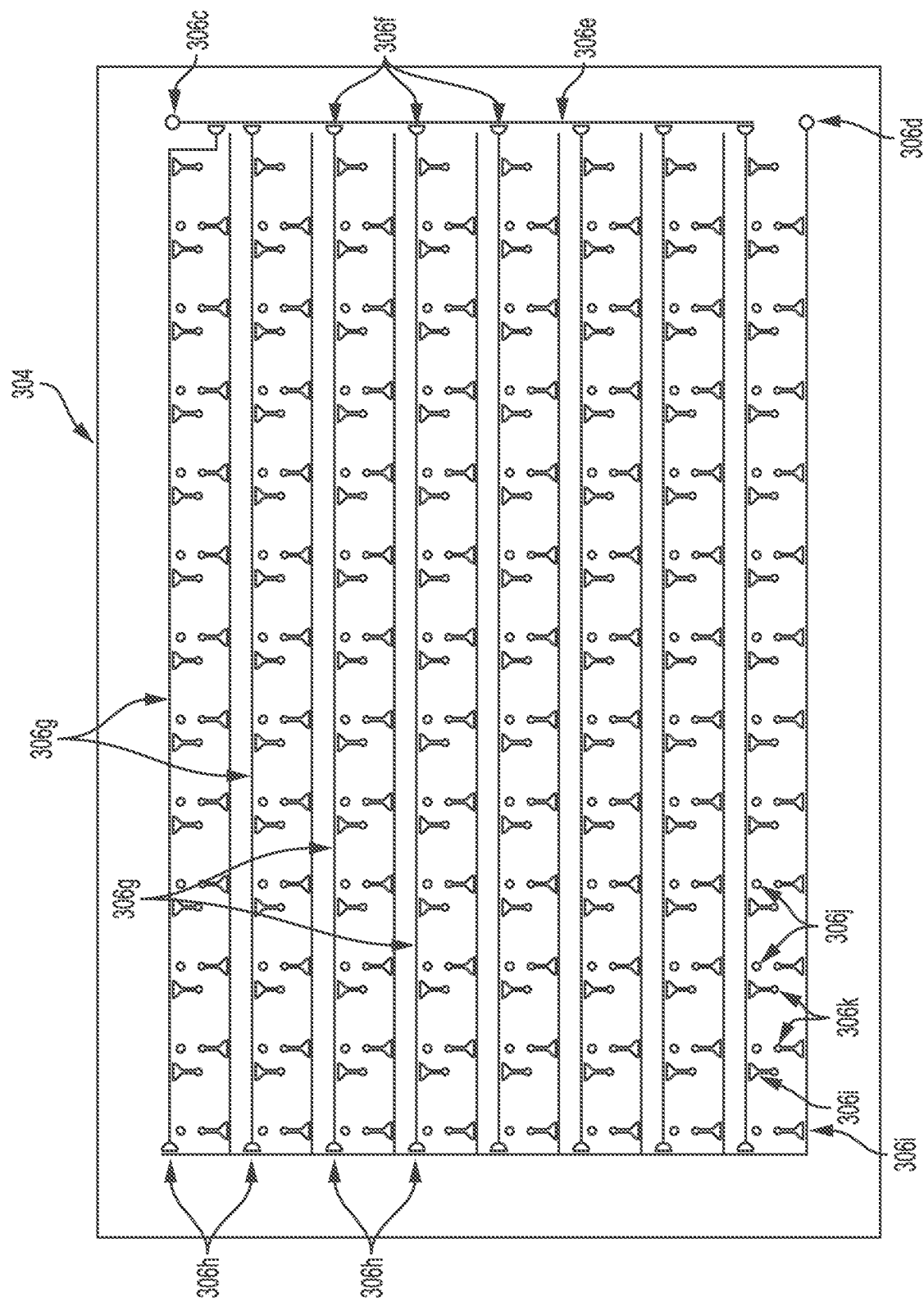
FIG. 3C depicts a fluid routing layer of a microfluidics layer of a multiwell plate device, in accordance with some embodiments.

FIG. 3C shows an isolated view of fluid routing layer 304, in accordance with some embodiments. In some embodiments, fluid routing layer 304 may be formed as a sub-layer of a layer that includes both a fluidic routing sub-layer (and/or a fluid routing side) and a micro-degasser layer (and/or a micro-degasser side). In some embodiments, fluid routing layer 304 may be formed as a sub-layer of a layer that also includes a degasser layer such as degasser layer 303b, discussed below with reference to FIG. 3G. In combined configurations, fluid routing features may face toward a pneumatic membrane layer, while degassing features may face in the opposite direction toward a degassing membrane. In some embodiments, fluid routing layer 304 may be fabricated by being milled, injection molded, and/or etched.

In some embodiments, fluid routing layer 304 may comprise a plurality of microfluidic channels configured to permit the flow of cell suspensions, reagents, and/or other fluids to and/or from the wells of well layer 302. In some embodiments, the microfluidic channels of fluid routing layer 304 may be in fluid communication with one or more of the wells of well layer 302, and may be configured to allow the flow of fluid to be individually addressed to any one of the wells in well layer 302 (as will be discussed in further detail below).

Fluid routing layer 304 may comprise fluid inlet 306c, which may connect to and receive fluid from a docking station, such as docking station 102, manifold connector 1200, and/or individual fluid connectors such as, but not limited to, pipette tips, tubing, reservoirs, and/or other outside sources of fluid.

Fluid routing layer 304 may comprise fluid outlet 306d, which may be fluidly connected to an output reservoir or other downstream fluid destination. In some embodiments, fluid outlet 306d may be connected to docking station 102, manifold connector 1200, and/or other fluid connectors.

Fluid routing layer 304 may comprise fluid inlet channel 306e, which may fluidly connect inlet 306c to a plurality of row channels (e.g., channels 306g) to allow flow of fluid (e.g., reagents, cell suspension, drugs) from inlet 306c to one or more of the row channels.

Fluid routing layer 304 may comprise row selection valves 306f, which may be configured to selectively open and close to allow and disallow flow of fluid from inlet channel 306e to a corresponding row channel (e.g., channels 306g). In some embodiments, row selection valves 306f may be configured as one of two or more bus valves that is configured to be opened and/or closed simultaneously with one or more other bus valves by a single pneumatic control action; for example, row channel inlet bus valves and row channel outlet bus valves may be opened and closed together with one another. In some embodiments, row-selection valves 306f may be configured to be pneumatically actuated by a movement of a pneumatic membrane of microfluidics layer 300, as discussed elsewhere herein.

Fluid routing layer 304 may comprise row channels 306g, which may be fluid channels corresponding to a respective row of wells and configured to select the first order of specificity towards addressing individual valves. Individual row valves (e.g., row-selection valves 306f) may select the row to which and/or from which fluid may be delivered.

Fluid routing layer 304 may comprise flush valves 306h, which may be configured to selectively open and close to allow and disallow flow of fluid from a corresponding row channel (e.g., channels 306g) into an outlet channel.

Fluid routing layer 304 may comprise well-selection valves 306i, which may be configured to selectively open and close to allow and disallow flow of fluid from row channels (e.g., channels 306g) into an individual corresponding well and/or to allow flow of fluid out of an individual well into a row outlet channel and toward an outlet (e.g., outlet 306d). In some embodiments, well-selection valves 306i may be configured as pairs or sets of two or more bus valves that are configured to be opened and/or closed simultaneously by a single pneumatic control action; for example, well inlet bus valves and well outlet bus valves may be opened and closed together with one another. In some embodiments, well-selection valves 306i may be configured to be pneumatically actuated by a movement of a pneumatic membrane of microfluidics layer 300, as discussed elsewhere herein.

Fluid routing layer 304 may comprise via-holes 306j, which may be configured to pneumatically connect a degasser structure (e.g., in degasser layer 303b) on one side of fluid routing layer 304 to a degasser control layer (e.g., layer 314) on an opposite side of fluid routing layer 304.

Fluid routing layer 304 may comprise well inlets/outlets 306k, which may comprise via-holes fluidly connecting the channels of fluid routing layer 304 to wells of well layer 302.

In some embodiments, features 306c-i may be micro-engraved, injection molded, and/or etched into a surface of fluid routing layer 304, facing pneumatic membrane 306.

In some embodiments, fluid routing layer 304 may have a thickness of less than 1 mm, less than 0.75 mm, less than 0.5 mm, or less than 0.25 mm. In some embodiments, fluid routing layer 304 may have a thickness of greater than 1 mm, greater than 0.75 mm, greater than 0.5 mm, or greater than 0.25 mm. In some embodiments, fluid routing layer 304 may have a depth (e.g., an etch depth) of less than 50 μm, less than 40 μm, or less than 30 μm. In some embodiments, fluid routing layer 304 may have a depth (e.g., an etch depth) of greater than 50 μm, greater than 40 μm, or greater than 30 μm.

In some embodiments, microfluidic channels of fluid routing layer 304 may have a width or diameter of less than 1 mm, less than 0.5 mm, less than 0.4 mm, less than 0.3 mm, less than 0.2 mm, or less than 0.1 mm. In some embodiments, microfluidic channels of fluid routing layer 304 may have a width or diameter of greater than 1 mm, greater than 0.5 mm, less than 0.4 mm, less than 0.3 mm, less than 0.2 mm, or less than 0.1 mm.

Figure 3D:
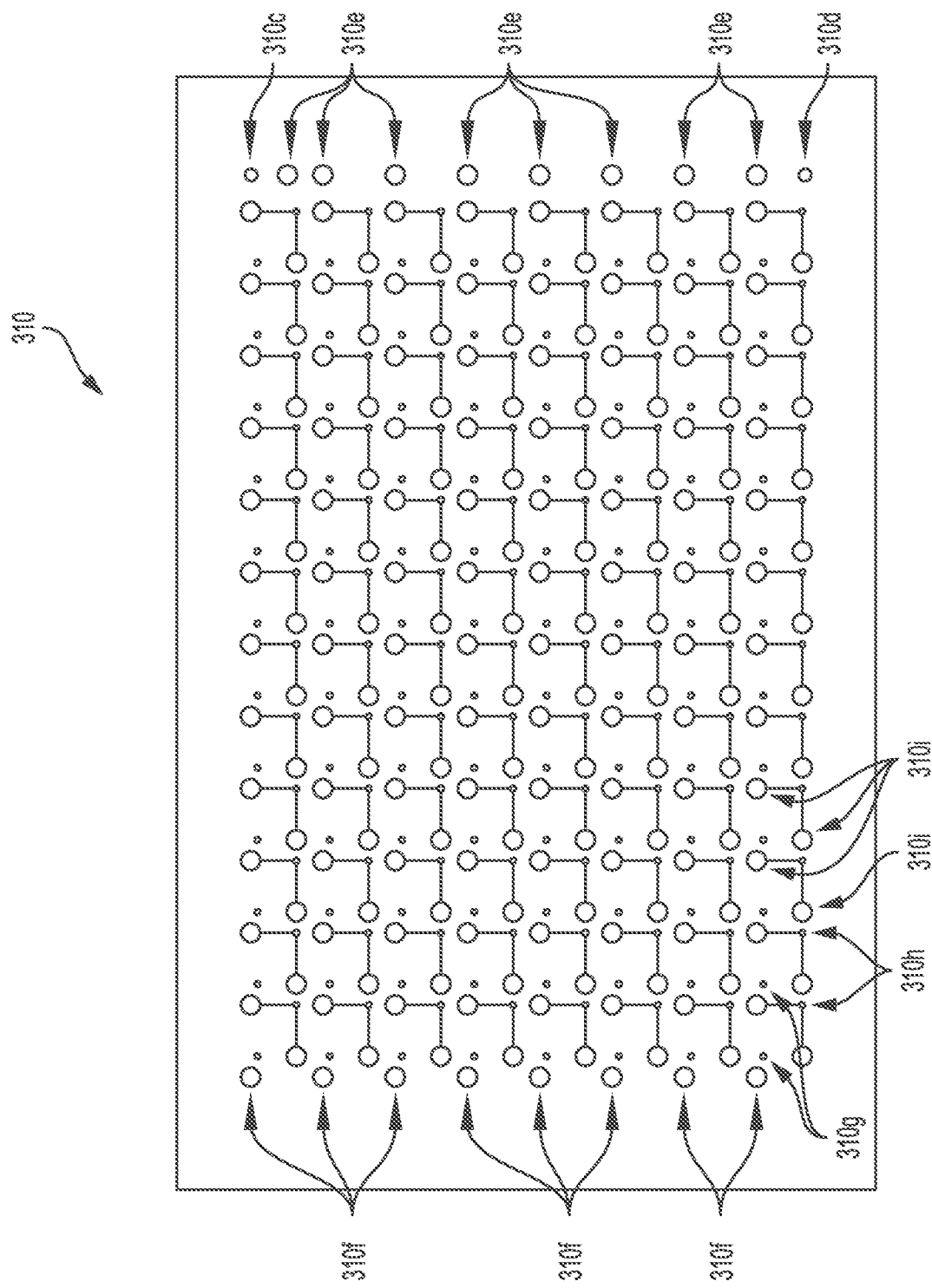
FIG. 3D depicts a pneumatic well-selection layer of a microfluidics layer of a multiwell plate device, in accordance with some embodiments.
Figure 3E:
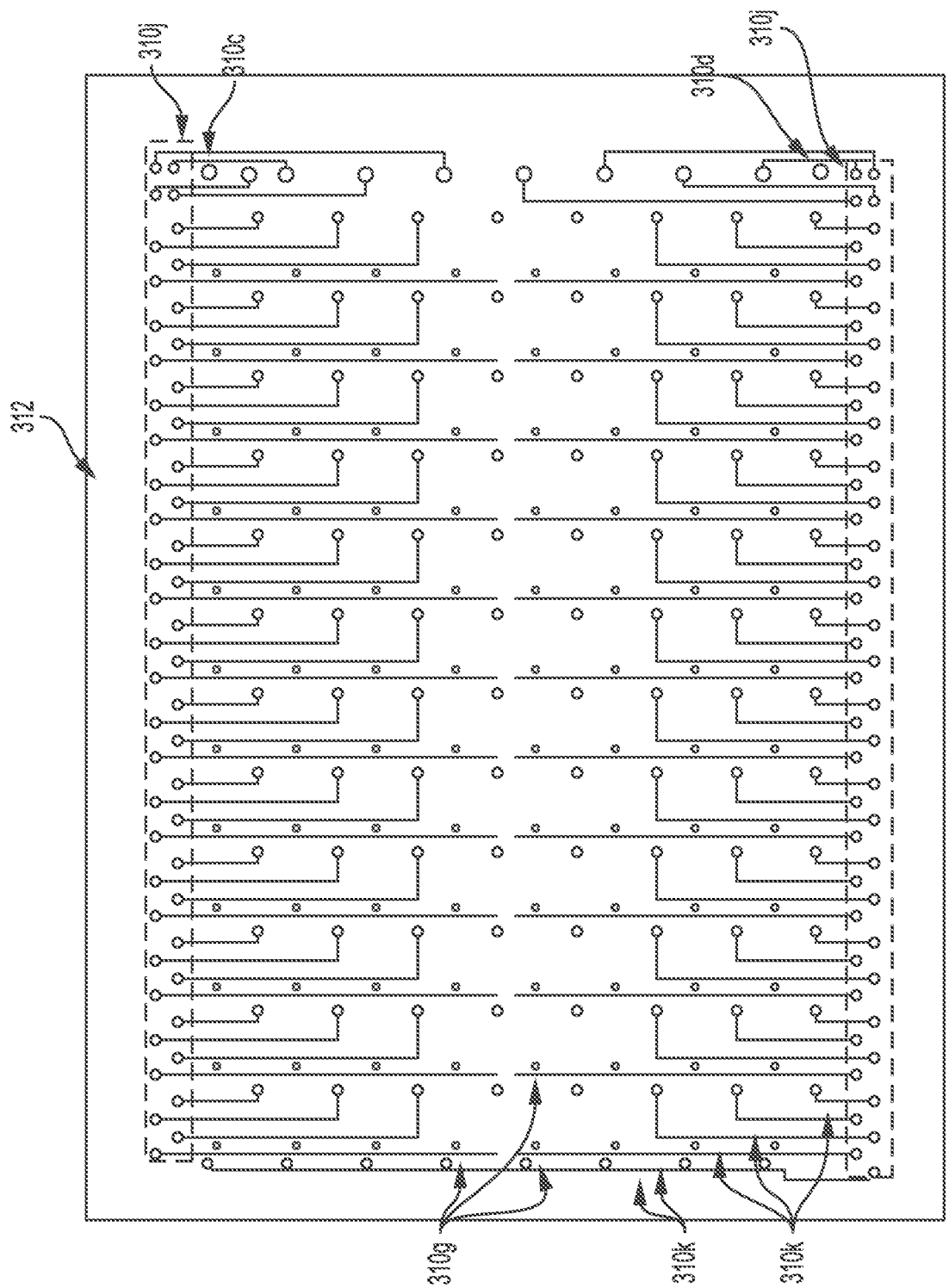
FIG. 3E depicts a pneumatic channel layer of a microfluidics layer of a multiwell plate device, in accordance with some embodiments.

FIGS. 3D and 3E each show a portion of pneumatic layer 308. In some embodiments, pneumatic layer 308 comprises two sublayers: pneumatic well-selection layer 310 and pneumatic control layer 312. In some embodiments, pneumatic well-selection layer 310 may be referred to as forming one "side" (e.g., a bottom side) of pneumatic layer 308, while pneumatic control layer 312 may be referred to as forming another "side" (e.g., a top side) or pneumatic layer 308. Thus, FIG. 3D shows pneumatic well-selection layer 310, in accordance with some embodiments; and FIG. 3E shows pneumatic control layer 312, in accordance with some embodiments. In some embodiments, pneumatic well-selection layer 310 and pneumatic control layer 312 may be bonded, embossed, milled, and/or injection molded to one another and may be connected via one or more via-holes. In some embodiments, pneumatic well-selection layer 310 may be adjacent to pneumatic membrane layer 306, while pneumatic control layer 312 may be on the other side of pneumatic well-selection layer 310 from pneumatic membrane layer 306.

As shown in FIG. 3D, pneumatic well-selection layer 310 may be used to actuate pneumatic membrane 306; changes of pneumatic pressure may deflect pneumatic membrane 306 within pneumatic bus valve area (deflection chamber) 310i for a respective well-specific fluidic valve in fluid routing layer 304, thus allowing fluid to be transported into and/or out of the well in well layer 302.

Pneumatic well-selection layer 310 may comprise inlet 310c, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Pneumatic well-selection layer 310 may comprise fluid outlet 310d, which may be fluidly connected to an output reservoir or other downstream fluid destination. In some embodiments, fluid outlet 310d may be connected to docking station 102, manifold connector 1200, and/or other fluid connectors.

In some embodiments, one or both of inlet 310c and fluid outlet 310d may be via holes that connect respectively to corresponding inlets and/or outlets in other layers discussed herein.

Pneumatic well-selection layer 310 may comprise pneumatic deflection chambers 310e, which may be chambers configured to apply pressure and/or vacuum to a pneumatic membrane (e.g., pneumatic membrane layer 306) in order to cause the membrane to deflect and to open or close a fluid valve (e.g., lifting gate valve, doormat valve, etc.). Pneumatic deflection chambers 310e may correspond to respective row selection valves 306f (discussed with respect to fluid routing layer 304) and may be configured to control actuation of those valves 306f.

Pneumatic well-selection layer 310 may comprise pneumatic deflection chambers 310f, which may be pneumatic deflection chambers corresponding to respective flush valves 306h (discussed with respect to fluid routing layer 304) and may be configured to control actuation of those valves 306h.

Pneumatic well-selection layer 310 may comprise via-holes 310g, which may be configured to pneumatically connect a degasser structure (e.g., in degasser layer 303b) on one side of fluid routing layer 304 to a degasser control layer (e.g., layer 314) on an opposite side of fluid routing layer 304. In some embodiments, the pneumatic connections may be formed through respective via-holes 306j (discussed with respect to fluid routing layer 304).

Pneumatic well-selection layer 310 may comprise pneumatic via hole connector 310h, which may be configured to be pneumatically connected to pneumatic deflection chambers 310i, discussed below.

Pneumatic well-selection layer 310 may comprise deflection chambers 310i, which may be deflection chambers corresponding to respective well-selection valves 306i (discussed with respect to fluid routing layer 304) and may be configured to control actuation of those valves 306i.

In some embodiments, pneumatic well-selection layer 310 may be fabricated such features on one or both sides may be milled, injection molded, and/or etched into the layer.

In some embodiments, one or both sub-layers of pneumatic layer 308 maybe formed by a soft photolithography process, injection molding, and/or hard embossing.

In some embodiments, in order to allow for each well to be addressed individually, each well may be gated by two bus valves that may be controlled by a single input line from pneumatic control layer 312.

In some embodiments, pneumatic control layer 312 is connected to pneumatic connection ports/manifold in system 100 through pneumatic port connectors 314a. A system unit controller may operate internal solenoid valves and/or a pneumatic manifold unit 1100 in either vacuum or pressure state, thus filling pneumatic lines in pneumatic control layer 312 with either vacuum or pressure. The pressure state may then translate to the membrane on pneumatic well-selection layer 310 through individual pneumatic channels and via holes to the well selection layer 310. Applied vacuum may deflect pneumatic membrane layer 306 and open bus-valves in the fluid routing layer 304. This may allow fluid to be routed into the individual wells connected to those valves and allow fluid to be delivered into through the actuation of a micropump, diaphragm pump, or piezo-electrical pump which may in some embodiments be disposed in microfluidic layer 300 and may in some embodiments be disposed outside microfluidic layer 300.

As shown in FIG. 3E, pneumatic control layer 312 may comprise inlet 310c and outlet 310d, as discussed above with respect to pneumatic well-selection layer 310. Pneumatic control layer 312 may also comprise via-holes 310g, as discussed above with respect to pneumatic well-selection layer 310.

Pneumatic control layer 312 may comprise pneumatic connection ports 310j, which may be configured to be respectively pneumatically connected to primary pneumatic connection ports, such as primary pneumatic connection ports 314a, discussed below with respect to sealing layer 316. Thus, pneumatic connection ports 310j may provide a pneumatic connection from pneumatic control layer 312 to a source of pressure and/or vacuum outside microfluidic layer 300.

Pneumatic control layer 312 may comprise pneumatic routing channels 310k, which may be individual pneumatic routing channels configured to connect pneumatic connection ports 310j to pneumatic deflection chambers 310e, 310f and/or 310i, as shown.

Figure 3F:
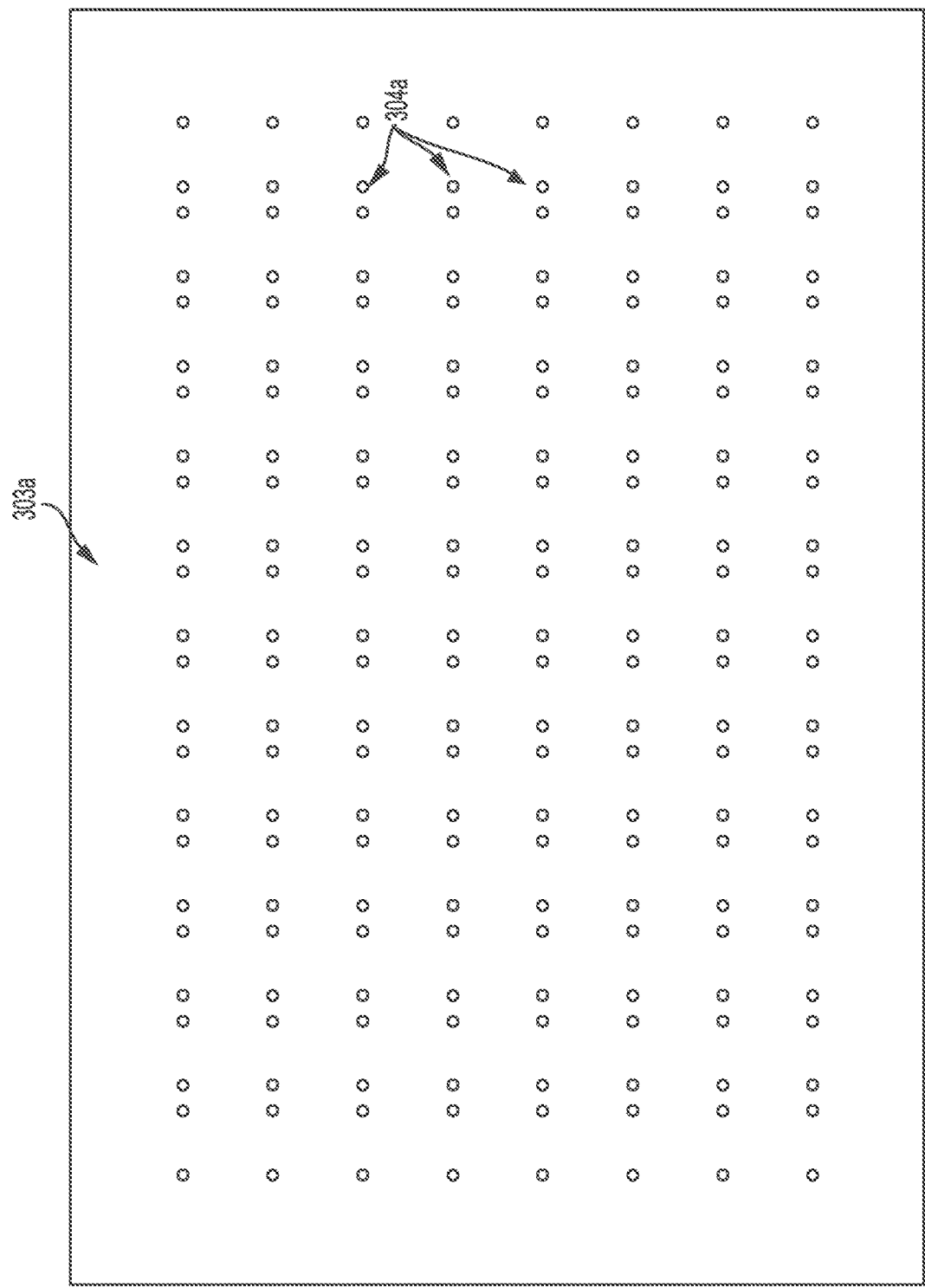
FIG. 3F depicts a degasser membrane layer of a microfluidics layer of a multiwell plate device, in accordance with some embodiments.

FIG. 3F depicts a degasser membrane layer 303a of a microfluidics layer of a multiwell plate device, in accordance with some embodiments. In some embodiments, degasser membrane layer 303a may be disposed between well-selection layer 302 and degasser layer 303b (discussed below). In some embodiments, degasser membrane layer 303a may comprise a gas-permeable membrane such as PDMS, and may be configured to allow air bubbles (and/or other gas bubbles) to escape (e.g., be actively removed) from wells in well layer 302 under vacuum force applied by degasser layer 303b on the other side of degasser membrane layer 303a.

In some embodiments, degasser membrane layer 303a may have a thickness of less than 10 µm, 25 µm, 50 µm, 100 µm, 250 µm, or 500 µm. In some embodiments, degasser membrane layer 303a may have a thickness of greater than 10 µm, 25 µm, 50 µm, 100 µm, 250 µm, or 500 µm.

Degasser membrane layer 303a may comprise via-holes 304a, which may be via-holes configured to fluidly connect channels in fluid routing layer 304 to respective wells in well layer 302.

Figure 3G:
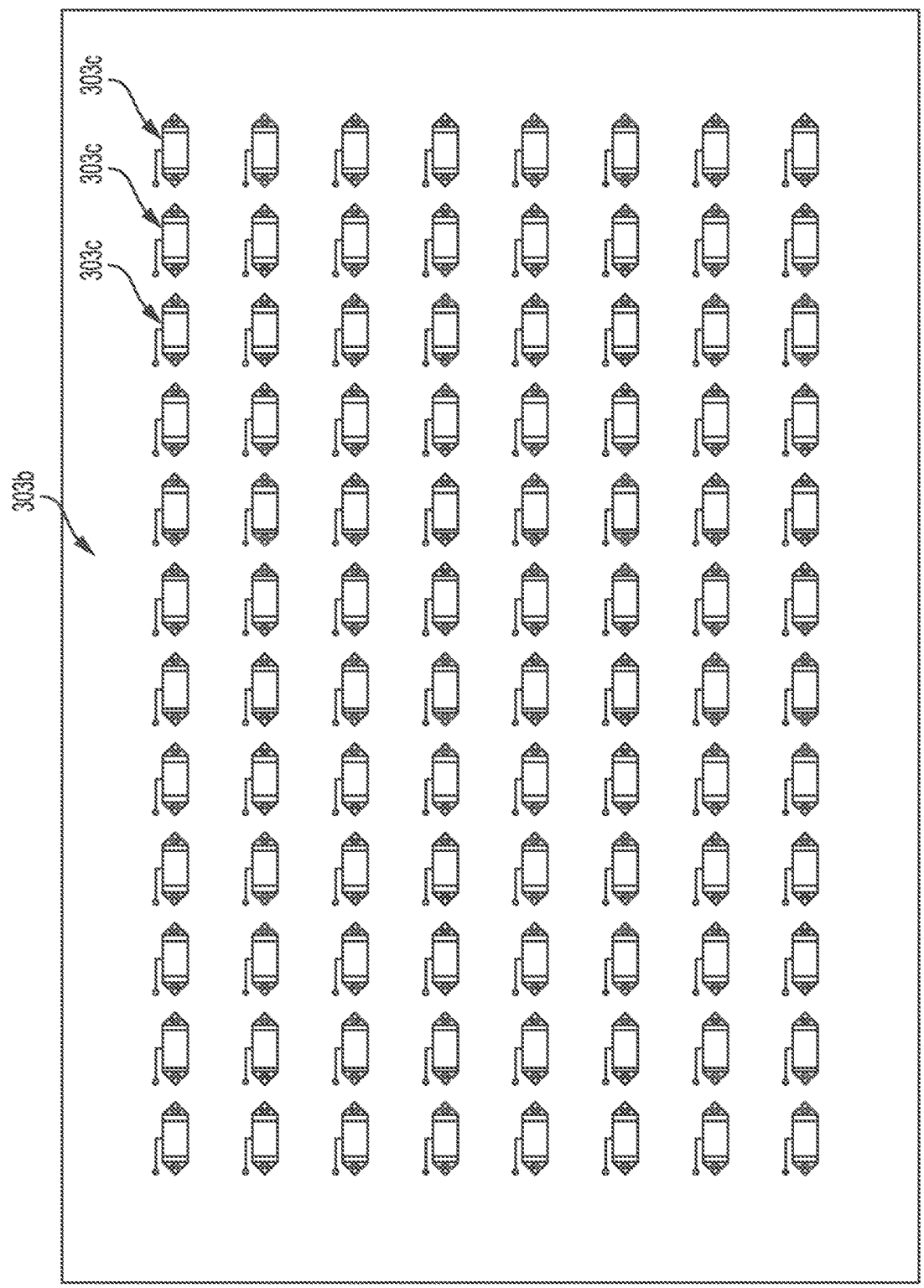
FIG. 3G depicts a degasser layer of a microfluidics layer of a multiwell plate device, in accordance with some embodiments.
Figure 31:
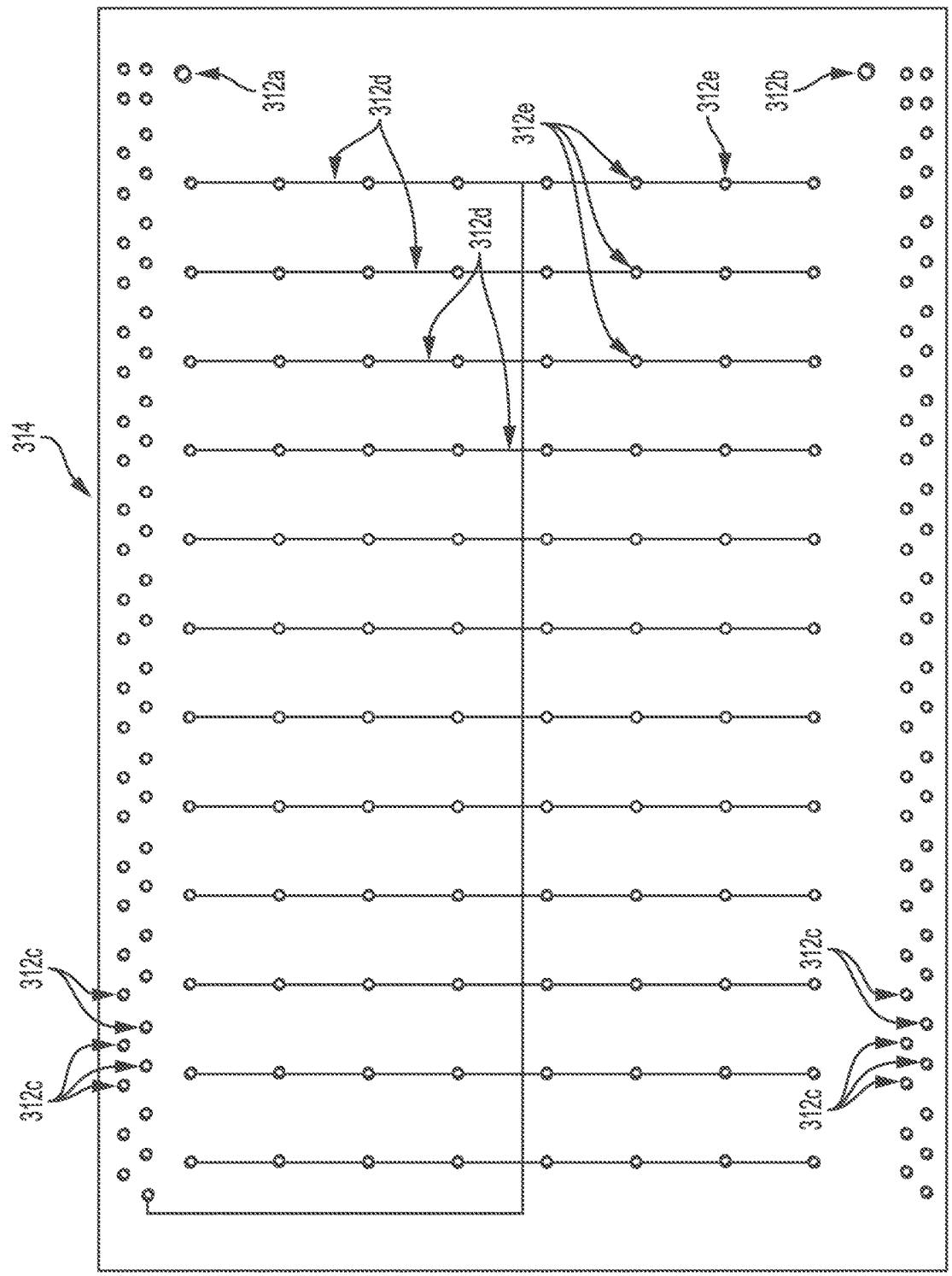

FIG. 3G depicts a degasser layer 303b of a microfluidics layer of a multiwell plate device, in accordance with some embodiments. In some embodiments, degasser layer 303b may be disposed between degasser membrane layer 303a and fluid routing layer 304.

In some embodiments, degasser layer 303b may be formed as a sub-layer of a layer that includes both a fluidic routing sub-layer (and/or a fluid routing side) and a micro-degasser layer (and/or a micro-degasser side). In some embodiments, degasser layer 303b may be formed as a sub-layer of a layer that also includes a fluid routing layer such as fluid routing layer 304. In combined configurations, fluid routing features may face toward a pneumatic membrane layer, while degassing features may face in the opposite direction toward a degassing membrane. In some embodiments, degasser layer 303b may be fabricated by being milled, injection molded, and/or etched.

In some embodiments, degasser layer 303b may comprise a plurality of localized degassers 303c, which in some embodiments may be secondary degassers provided in addition to a primary, global degasser. While a primary degasser may degas a common input channel, each one of the plurality of localized, secondary degassers 303c in degasser layer 303b may be located above (and across degasser membrane layer 303a) a respective well in well layer 302, and may be configured to degas a specific well.

In some embodiments, each of the secondary degassers 303c may comprise one or more via-holes configured to pneumatically connect to a degasser control layer 314, such that vacuum may be applied from degasser control layer 314 to degasser layer 303b. The via hole(s) may be connected by one or more channels or other pneumatic routing structures to a series of pillars or other support elements configured to support the vacuum applied to degasser membrane 303a such that it does not deflect into the microdegasser.

Degasser layer 303b may additionally comprise a plurality of well inlets/outlets, which may take the form of via holes formed in degasser layer 303b configured to fluidly connect well inlets/outlets as discussed above with reference to fluid routing layer 304 to well layer 302.

FIG. 3H depicts pneumatic membrane layer 306 of a microfluidics layer of a multiwell plate device, in accordance with some embodiments.

Pneumatic membrane layer 306 may comprise inlet 308a, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Pneumatic membrane layer 306 may comprise fluid outlet 308b, which may be fluidly connected to an output reservoir or other downstream fluid destination. In some embodiments, fluid outlet 308b may be connected to docking station 102, manifold connector 1200, and/or other fluid connectors.

In some embodiments, one or both of inlet 308a and fluid outlet 308b may be via holes that connect respectively to corresponding inlets and/or outlets in other layers discussed herein.

Pneumatic membrane layer 306 may comprise pneumatic via-holes 308c, which may be configured to pneumatically connect a degasser structure (e.g., in degasser layer 303b) on one side of pneumatic membrane layer 306 to a degasser control layer (e.g., layer 314) on an opposite side of pneumatic membrane layer 306.

FIG. 3I depicts a degasser control layer 314 of a microfluidics layer of a multiwell plate device, in accordance with some embodiments. In some embodiments, degasser control layer 314 may be disposed between pneumatic control layer 312 and a sealing layer 316 (discussed below in FIG. 3J). In some embodiments, degasser control layer 314 may comprise one or more pneumatic routing channels configured to route vacuum to one or more via-holes to be conveyed to well-specific micro-degassers of a degasser layer such as degasser layer 303b. In some embodiments, a single vacuum inlet may be sufficient to apply constant negative vacuum pressure to be conveyed to the micro-degasser structures in degasser layer 303b.

In some embodiments, one or more features of degasser control layer 314 may be formed on a side of degasser control layer 314 facing toward a degasser layer such as degasser layer 303b.

Degasser control layer 314 may comprise inlet 312a, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Degasser control layer 314 may comprise fluid outlet 312b, which may be fluidly connected to an output reservoir or other downstream fluid destination. In some embodiments, fluid outlet 312b may be connected to docking station 102, manifold connector 1200, and/or other fluid connectors.

In some embodiments, one or both of inlet 312a and fluid outlet 312b may be via holes that connect respectively to corresponding inlets and/or outlets in other layers discussed herein.

Degasser control layer 314 may comprise pneumatic via-hole connection ports 312c, which may be configured to be respectively pneumatically connected to primary pneumatic connection ports, such as primary pneumatic connection ports 314a, discussed below with respect to sealing layer 316. Thus, pneumatic connection ports 312c may provide a pneumatic connection from degasser control layer 314 to a source of pressure and/or vacuum outside microfluidic layer 300.

Degasser control layer 314 may comprise pneumatic routing channels 312d, which may be configured to pneumatically connect connection ports 312c to pneumatic via-holes 312d, discussed below.

Degasser control layer 314 may comprise pneumatic via-holes 312e, which may be pneumatically connected to connection ports 312c via routing channels 312d and may be configured to transmit vacuum force to one or more micro-degasser structures of degasser layer 303b. In some embodiments, pneumatic via-holes 312e may transmit vacuum force to one or more micro-degasser structures of degasser layer 303b via one or more of holes 310g and 306j, as discussed above.

Figure 3J:
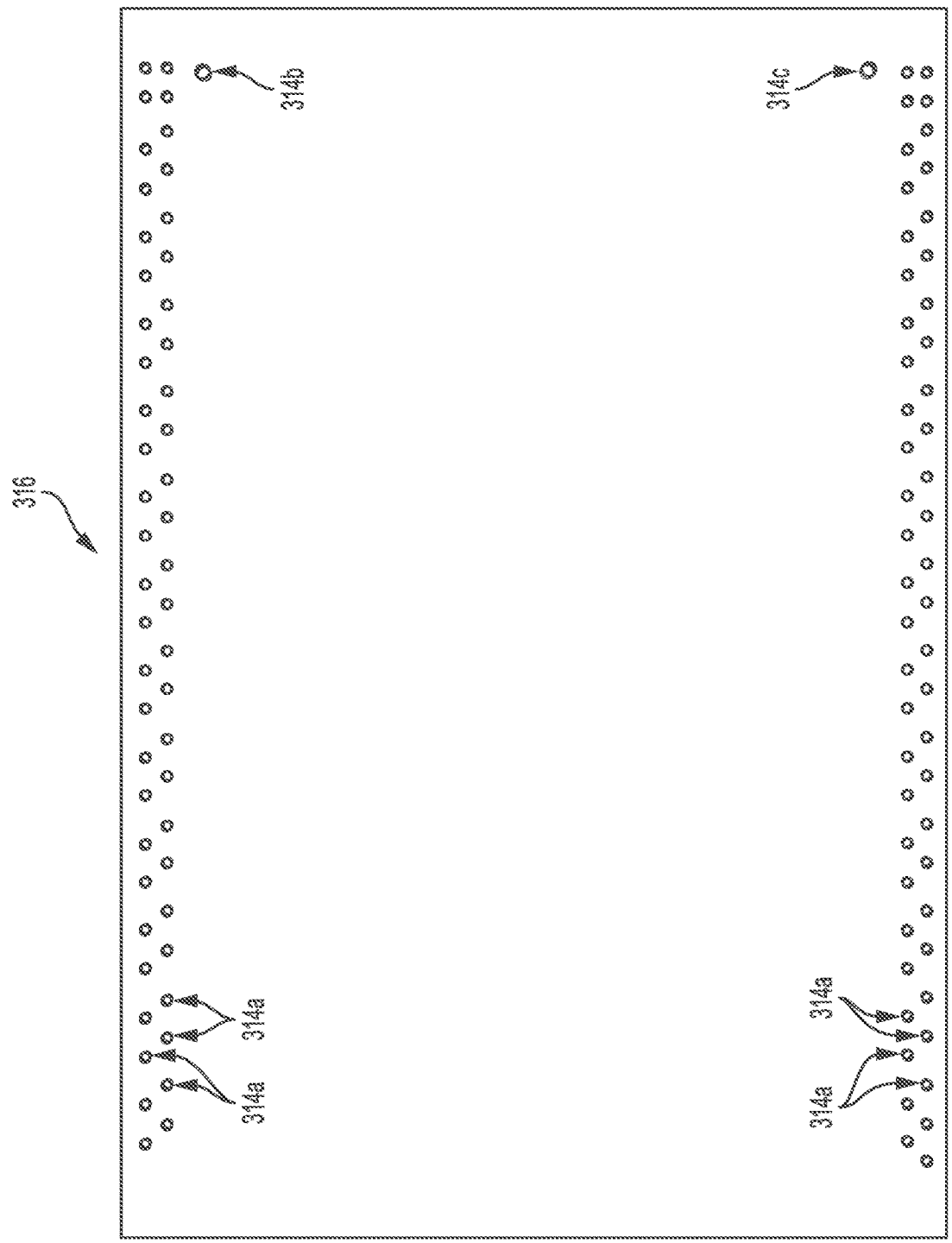
FIG. 3J depicts a sealing layer of a microfluidics layer of a multiwell plate device, in accordance with some embodiments.

FIG. 3J depicts a sealing layer 316 of a microfluidics layer of a multiwell plate device, in accordance with some embodiments. In some embodiments, sealing layer 316 may be disposed on an opposite side of degasser control layer 314 as pneumatic control layer 312. In some embodiments, sealing layer 316 may be referred to as a lid layer. Sealing layer 316 may be configured to seal and close pneumatic features of degasser control layer 314 to ensure proper functioning of microfluidics layer 300.

In some embodiments, sealing layer 316 may comprise primary pneumatic connection ports 314a, which may be configured to provide pneumatic connections between external equipment and pneumatic channels and chambers and other structures inside microfluidics layer 300. Connection ports 314a may be configured to pneumatically couple to one or more sources of vacuum (and/or positive pressure), such as a manifold connector, one or more tubes, or the like. In some embodiments, connection ports 314a may couple to a portion or component of a docking station such as docking station 102.

Sealing layer 316 may comprise inlet 314b, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid. In some embodiments, inlet 314b may connect directly to any one of the sources mentioned above, and may convey the flow of fluid to other corresponding inlet holes in other layers of microfluidics layer 300 discussed above.

Sealing layer 316 may comprise fluid outlet 314c, which may be fluidly connected to an output reservoir or other downstream fluid destination. In some embodiments, fluid outlet 314c may be connected to docking station 102, manifold connector 1200, and/or other fluid connectors. In some embodiments, fluid outlet 314b may connect directly to any one of the downstream fluid destinations mentioned above, and may receive the flow of fluid from other corresponding outlet holes in other layers of microfluidics layer 300 discussed above.

In some embodiments, one or both of inlet 314b and fluid outlet 314c may be via holes that connect respectively to corresponding inlets and/or outlets in other layers discussed herein.

Figure 3K:
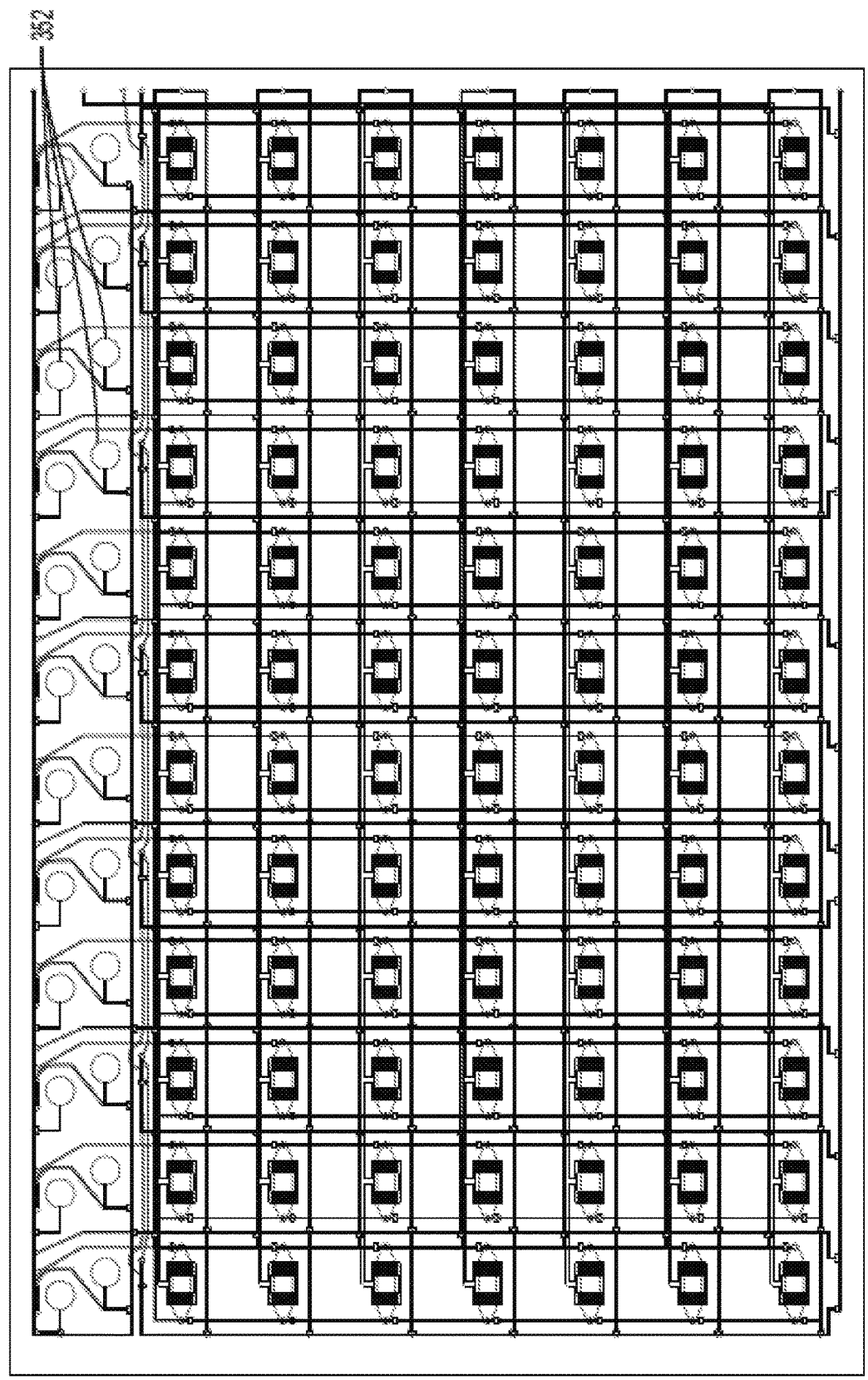
FIG. 3K depicts a schematic view of a microfluidics layer of a multiwell plate device, in accordance with some embodiments.

FIG. 3K depicts a schematic view of a microfluidics layer 350 of a multiwell plate device, in accordance with some embodiments. In some embodiments, microfluidics layer 350 may share any one or more characteristics in common with microfluidics layer 202 as discussed above with reference to FIGS. 2A-2C and/or with microfluidics layer 300 as discussed above with reference to FIGS. 3A-3J. In some embodiments, microfluidics layer 350 may differ from microfluidics layer 300 in that it may comprise an array of 84 wells rather than an array of 96 wells. In some embodiments, microfluidics layer 350 may differ from microfluidics layer 300 in that it may comprise one or more on-chip reservoirs 352 configured to store compounds and/or to serve as mixing areas.

In some embodiments, any one or more of the features of microfluidics layer 300 and microfluidics layer 350 may be interchanged with one another in whole or in part. For example, in some embodiments, microfluidics layer 300 may comprise a plurality of on-chip reservoirs; in another example, in some embodiments, microfluidics layer 352 may not comprise any on-chip reservoirs. In some embodiments, any one or more of the techniques, systems, devices, and/or methods disclosed herein using either microfluidics layer 300 or microfluidics layer 352 may be implemented using the other one of the microfluidics layers, and/or may be implemented using one or more microfluidics layers having any one or more characteristics of one or both of microfluidics layer 300 and microfluidics layer 352.

In some embodiments, setup of the well array of microfluidics layer 352 may be performed in a same or similar manner as described above with respect to one or more components described in FIGS. 3B-J. On-chip reservoirs 352 may extend, in some embodiments, from a fluidic layer of microfluidics layer 352 throughout various layers of microfluidics layer 300, through one or more via-holes in corresponding layers, and may be closed through a lid layer (or may be left open in a lid layer and may instead be closed via a membrane, sealing film, or similar component for manual access and filling of the reservoirs). In this way, volume of on-chip reservoirs 352 may depend on height of the combined layers of microfluidics layer 300.

On-chip reservoirs 352 may extend from a fluidic layer throughout the chip and may be closed through a lid layer (e.g., a cover layer) (or may be left open in a lid layer and instead be closed with a membrane or sealing film for manual access and filling of the reservoirs). In some embodiments, individual on-chip reservoirs may be addressed through pneumatic actuation of a membrane in a pneumatic membrane layer that is deflected in deflection chambers in another layer of a multiwall plate device, resulting in opening/closing of one or more valves, for example in accordance with one or more of the pneumatic actuation and/or individual well-addressing techniques described elsewhere herein. Selection and opening/closing of fluidic connections of the reservoirs may be controlled through software and/or other control elements, for example in accordance with the automated well-addressing techniques described elsewhere herein. In some embodiments, on-chip reservoirs 352 may allow the storage of reagents, compounds, and/or consumables directly on a multiwall plate device and/or directly on microfluidics layer 350, for example for use in automated protocols and assays. On-chip reservoirs 350 may, in some embodiments, reduce dead volume and need for multiple off-chip storage containers and fluidic connections.

As shown in FIG. 3K, on-chip reservoirs 352 may in some embodiments be disposed along one edge of microfluidics layer 350, and may in some embodiments be disposed laterally to one side of an array of wells of microfluidics layer 350. In some embodiments, on-chip reservoirs 352 may be arranged in a single row; in some embodiments, on-chip reservoirs 352 may be arranged in multiple rows; in some embodiments, on-chip reservoirs 352 may be arranged in an array. In some embodiments, on-chip reservoirs 352 may be arranged in a single spatial grouping with respect to wells of a microfluidics layer; in some embodiments, on-chip reservoirs 352 may be arranged in multiple spatial groupings with respect to wells of a microfluidics layer (e.g., located along two opposite edges of the layer).

In some embodiments, one or more of the on-chip reservoirs 352 may have a volume of greater than 5 µL, greater than 10 µL, greater than 15 µL, greater than 20 µL, greater than 25 µL, greater than 50 µL, or greater than 100 µL. In some embodiments, one or more of the on-chip reservoirs 352 may have a volume of less than 5 µL, less than 10 µL, less than 15 µL, less than 20 µL, less than 25 µL, less than 50 µL, or less than 100 µL. In some embodiments, volume of one or more of the on-chip reservoirs 352 may be set or adjusted in accordance with a height of the layer in which the reservoir is disposed.

Figure 4A:
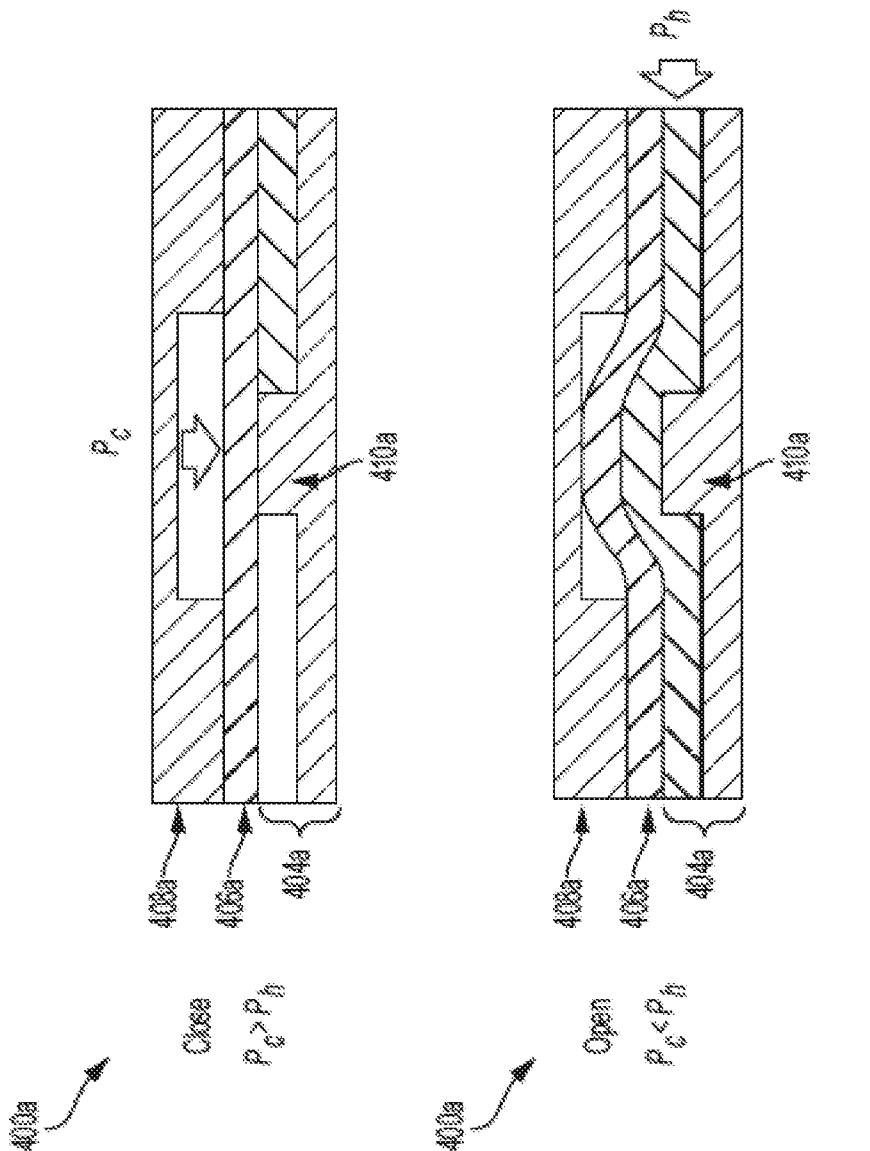
FIGS. 4A & 4B each depict two cross-sectional views of respective microfluidics layers including a pneumatic valve, in accordance with some embodiments.
Figure 4B:
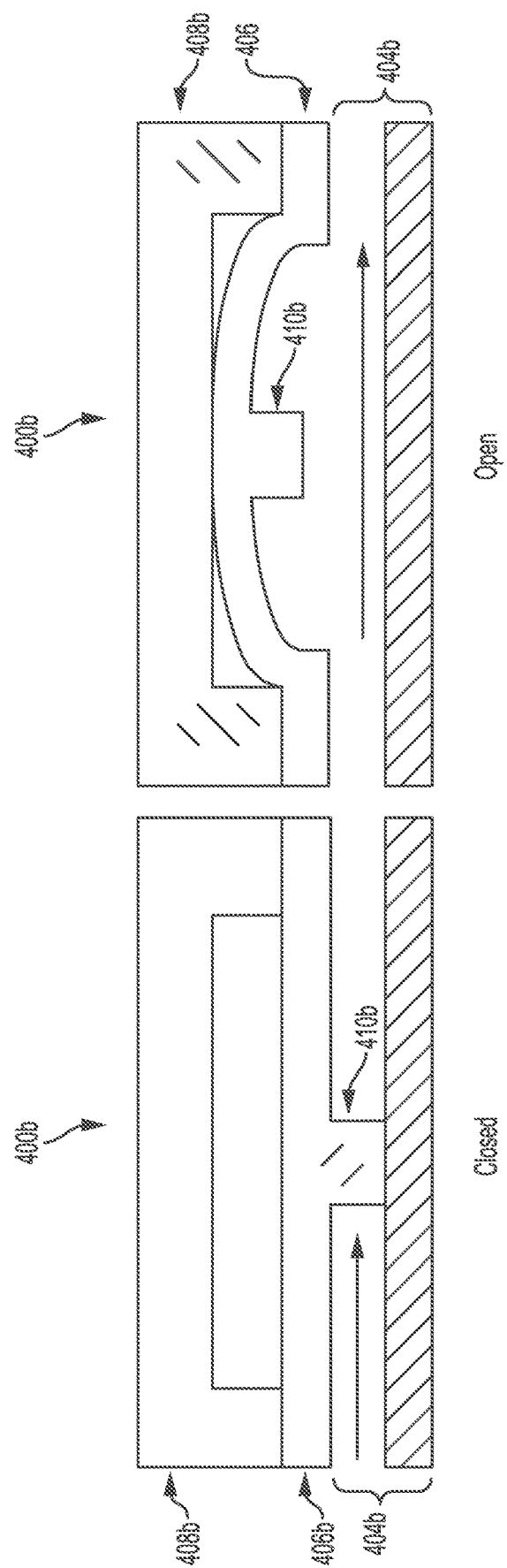

FIGS. 4A, 4B, and 5 each depict two cross-sectional views of respective microfluidics layers including a pneumatic valve, in accordance with some embodiments. FIG. 4A shows two views (top: closed; bottom: open) of an embodiment wherein a pneumatic valve is formed by a gate protruding from a surface of a channel formed in a fluid routing layer. FIG. 4B shows two views (left: closed; right: open) of an embodiment wherein a pneumatic valve is formed by a gate protruding from a surface of a membrane that defines at least one wall of a fluid channel. FIG. 5 shows two views (left: exploded; right: non-exploded) of an embodiment wherein a pneumatic valve is formed by a gate protruding from a surface of a channel formed in a fluid routing layer (similar to the embodiment in FIG. 4A).

As shown in FIG. 4A, microfluidics layer 400a may comprise fluid routing layer 404a, pneumatic membrane layer 406a, pneumatic layer 408a, and gate 410a. In some embodiments, microfluidics layer 400a, fluid routing layer 404a, pneumatic membrane layer 406a, and pneumatic layer 408a may share one or more characteristics in common with the corresponding elements discussed above in with reference to FIG. 3A (e.g., microfluidics layer 300, fluid routing layer 304, pneumatic membrane layer 306, and pneumatic layer 308, respectively).

As shown in FIGS. 4A, fluid routing layer 404a may define one or more microfluidic channels through which fluid may flow, and the microfluidic channels may be sealed on one side (e.g., on the top side) by pneumatic membrane layer 406a. Pneumatic membrane layer 406a may be flexible such that it may be caused to selectively deform into a displacement chamber (e.g., a hollow cavity) formed in pneumatic layer 408a, which may be on an opposite side of pneumatic membrane layer 406a from fluid routing layer 404a.

In the upper diagram of FIG. 4A, the (pneumatic) force exerted on pneumatic membrane layer 406a by the pressure (e.g., air pressure) inside the displacement chamber of pneumatic layer 408a is greater than the (pneumatic) force exerted on pneumatic membrane layer 406a by the pressure (e.g., fluid pressure) from the fluid in the channel of fluid routing layer 404a; accordingly, the force exerted on pneumatic membrane layer 406a by the pressure (e.g., air pressure) inside the displacement chamber of pneumatic layer 408a is sufficient to force pneumatic membrane layer 406a toward and against gate 410a, thereby closing the valve by creating a seal and preventing flow of fluid (from right to left, in the embodiment shown) through the channel in fluid routing layer 404a.

In the lower diagram of FIG. 4A, the force exerted on pneumatic membrane layer 406a by the pressure (e.g., air pressure) inside the displacement chamber of pneumatic layer 408a is less than the force exerted on pneumatic membrane layer 406a by the pressure (e.g., fluid pressure) from the fluid in the channel of fluid routing layer 404a; accordingly, the force exerted on pneumatic membrane layer 406a by the pressure (e.g., air pressure) inside the displacement chamber of pneumatic layer 408a is insufficient to force pneumatic membrane layer 406a toward and against gate 410a; instead, the force exerted on pneumatic membrane layer 406a by the pressure (e.g., fluid pressure) from the fluid in the channel of fluid routing layer 404a is sufficient to force pneumatic membrane layer 406a away from gate 410a, thereby opening the valve by allowing flow of fluid (from right to left, in the embodiment shown) through the channel in fluid routing layer 404a.

It should be noted that, in some embodiments, applied vacuum to the displacement chamber lifts and holds pneumatic membrane layer 406a away from the gate and thus opens the fluid channel. In some embodiments, through micropump actuation of the fluid, the fluid pressure within the channel may be increased. However, it may not be possible to create a fluid flow without applying a vacuum since otherwise the fluid pressure may be equal to atmospheric pressure and the gate may remain closed. Thus, in some embodiments, applying vacuum may be necessary to allow the gate to be opened.

Thus, by causing the pressure (e.g., air pressure) inside the displacement chamber in pneumatic layer 408a to increase or decrease, the valve in FIG. 4A may be selectively opened and closed to selectively allow and disallow flow of fluid through the channel in fluid routing layer 404a.

FIG. 4B shows microfluidics layer 400b, which may comprise fluid routing layer 404b, pneumatic membrane layer 406b, pneumatic layer 408b, and gate 410b. In some embodiments, microfluidics layer 400b and its components may share one or more characteristics in common with microfluidics layer 400a discussed above with reference to FIG. 4A. In some embodiments, microfluidics layer 400b may differ from microfluidics layer 400a in that gate 410b may be formed as a part of or may be attached to pneumatic membrane layer 406b, rather than being formed as a part of or attached to fluid routing layer 404b. Thus, pressure changes in the displacement chamber in pneumatic layer 408b may pneumatic membrane layer 406b to selectively move up and down in order to open the valve by causing gate 410b to form a seal by being pressed against a wall of the channel in fluid channel layer 404 (as shown in the diagram at left in FIG. 4B), or alternately to open the valve by causing gate 410b to move away from a wall of the channel in fluid channel layer 404 (as shown in the diagram at right in FIG. 4B). This type of valve, which may be called a lifting gate valve, can be used in a configuration/embodiment of fluid routing layer 304 in which the microfluidic wells are incorporated within the same to allow the use of a very thin substrate layer 302 in order to facilitate high resolution imaging capabilities.

Thus, by causing the pressure (e.g., air pressure) inside the displacement chamber in pneumatic layer 408b to increase or decrease, the valve in FIG. 4B may be selectively opened and closed to selectively allow and disallow flow of fluid through the channel in fluid routing layer 404b.

FIG. 5 depicts two cross-sectional views of a respective microfluidics layer including a pneumatic valve, in accordance with some embodiments. FIG. 5 shows microfluidics layer 500, which may comprise fluid routing layer 504, pneumatic membrane layer 506, pneumatic layer 508, and gate 510. In some embodiments, microfluidics layer 500 and its components may share one or more characteristics in common with microfluidics layer 400a discussed above with reference to FIG. 4A. The diagram at left in FIG. 5 shows an exploded view of microfluidics layer 500, while the diagram at right in FIG. 5 shows a non-exploded, partially transparent view of microfluidics layer 500. By causing the pressure (e.g., air pressure) inside the displacement chamber in pneumatic layer 508 to increase or decrease, the valve in FIG. 5 may be selectively opened and closed to selectively allow and disallow flow of fluid through the channel in fluid routing layer 504; this principle may similarly apply to the valves shown in FIGS. 4A and 4B.

In the valves of FIGS. 4A, 4B, and/or 5, if no pressure is applied to a deflection chamber, then the valve may default to a closed position. This may allow for detachment of a device including one of the valves from pneumatic connections (e.g., for transfer to another location or another piece of equipment), without opening valves and allowing fluid to freely flow in the device.

In some embodiments, microfluidics layers, including microfluidics layers 202, 300, 400a, 400b, and/or 500, of multiwell plate devices may be made in accordance with all or part of one or more known fabrication processes for PDMS chips, including for example known replica molding processes.

Figure 6A:
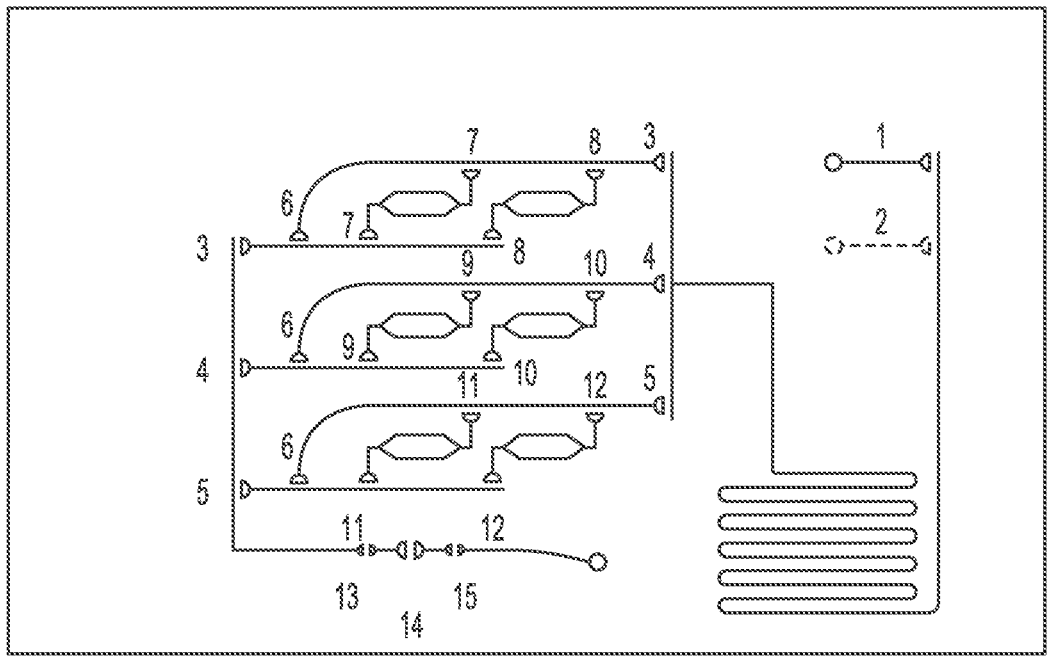
FIGS. 6A-6V depict a schematic view of a fluid flowing through a microfluidics layer of a multiwell plate device having individually-addressable wells, in accordance with some embodiments.
Figure 6B:
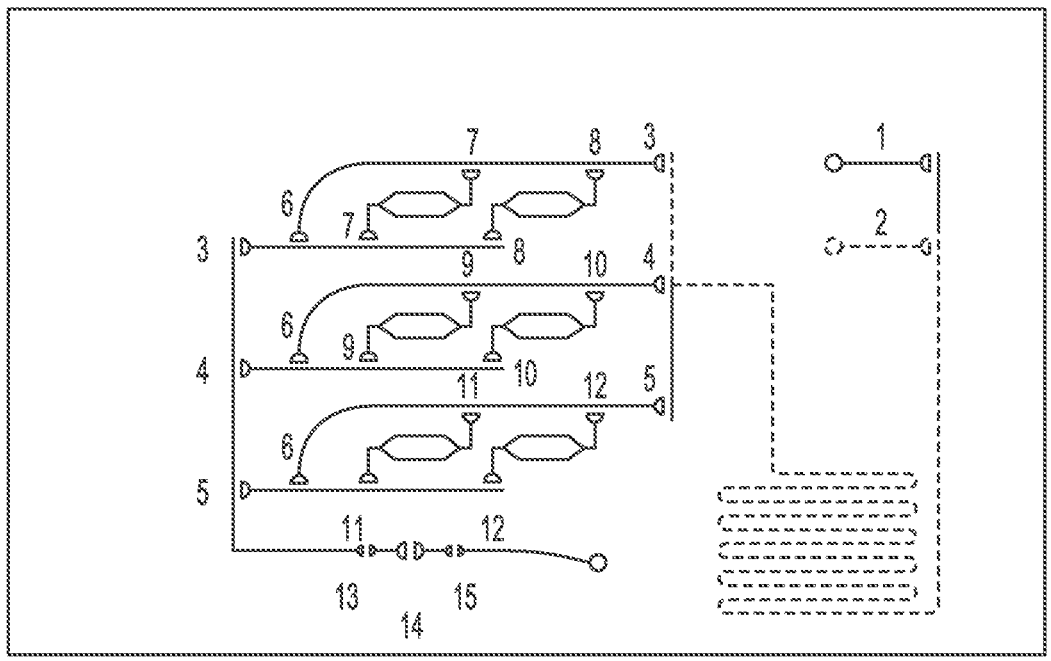
FIG. 6W depicts a graphical representation of the operation of various components or features of a multiwell system over time, in accordance with some embodiments.
Figure 6C:
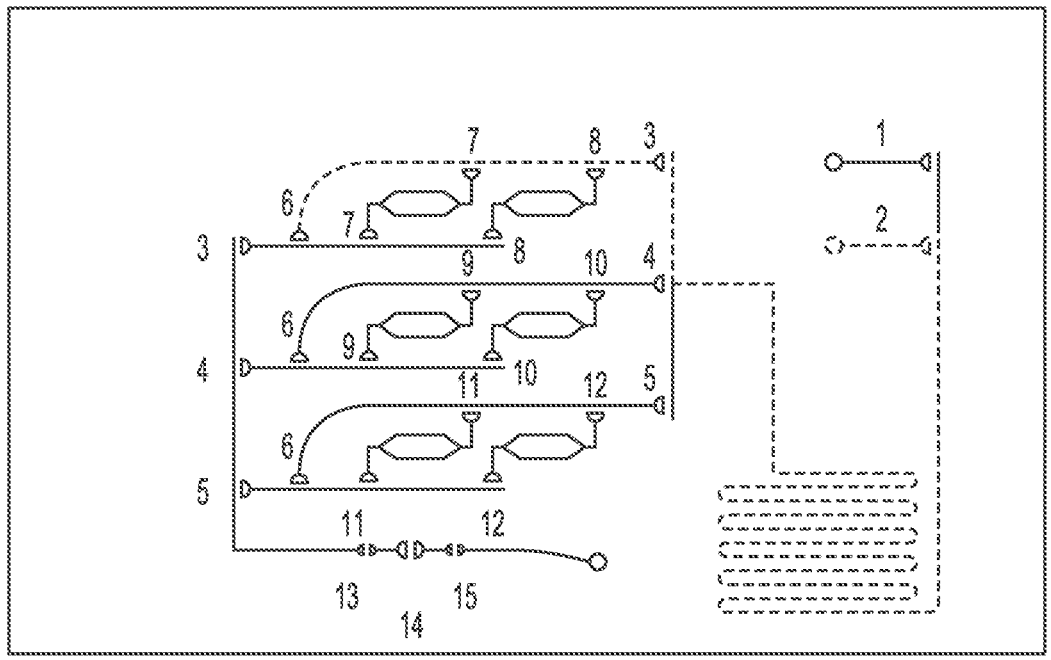
Figure 6D:
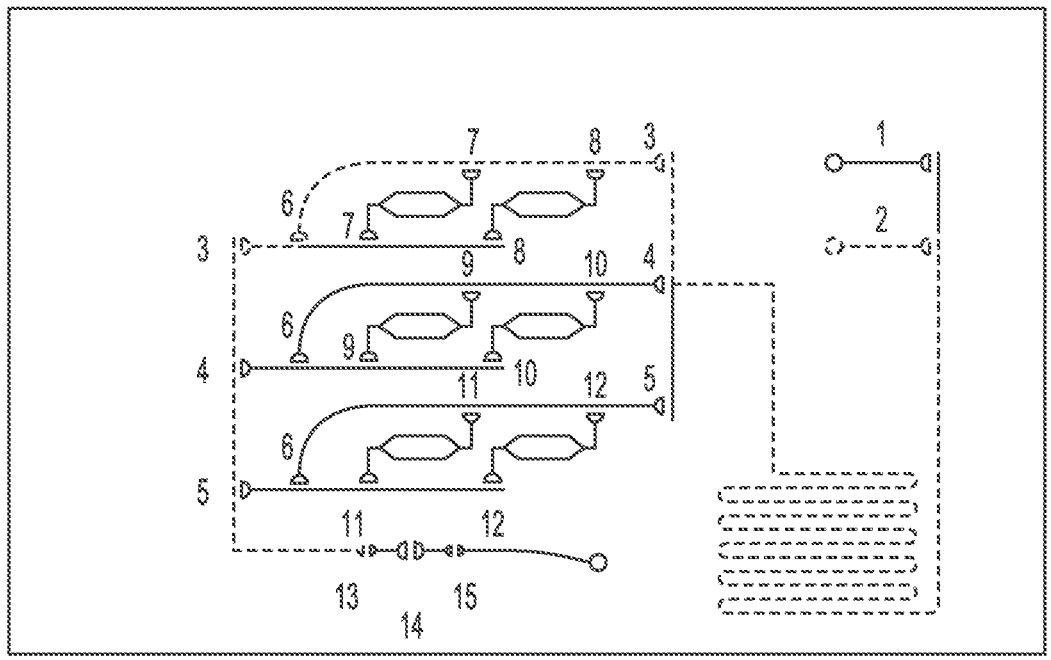
Figure 6E:
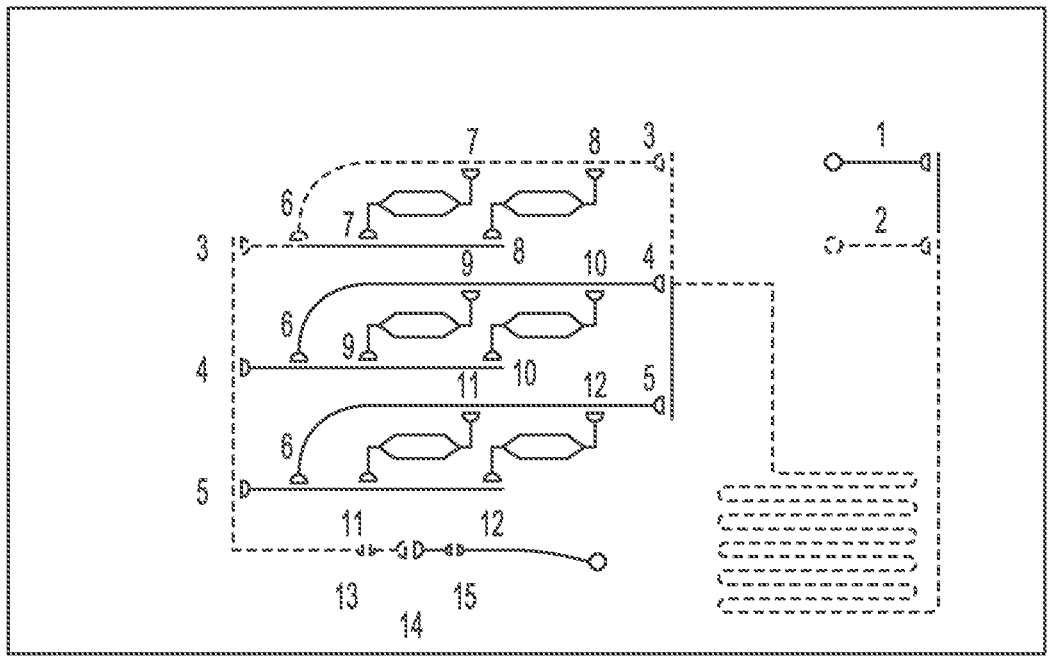
Figure 6F:
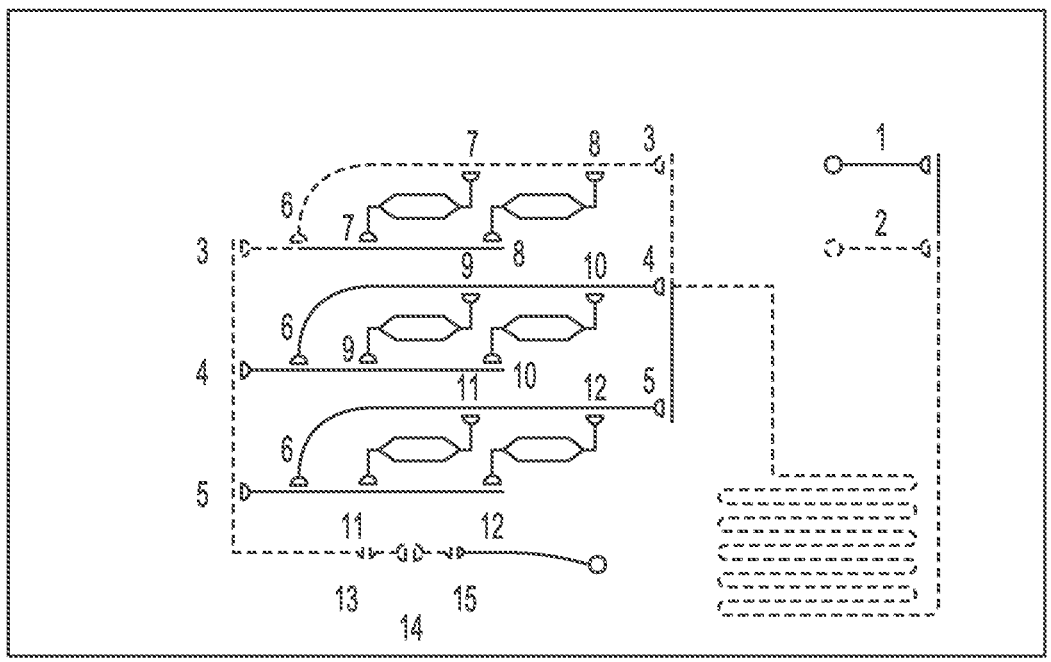
Figure 6G:
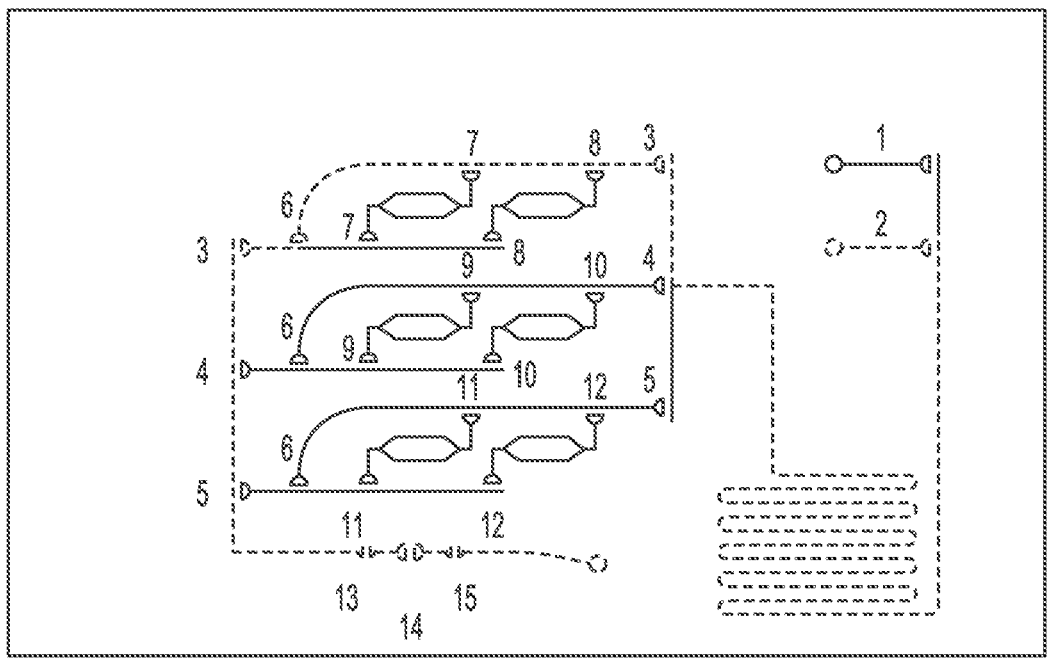
Figure 6H:
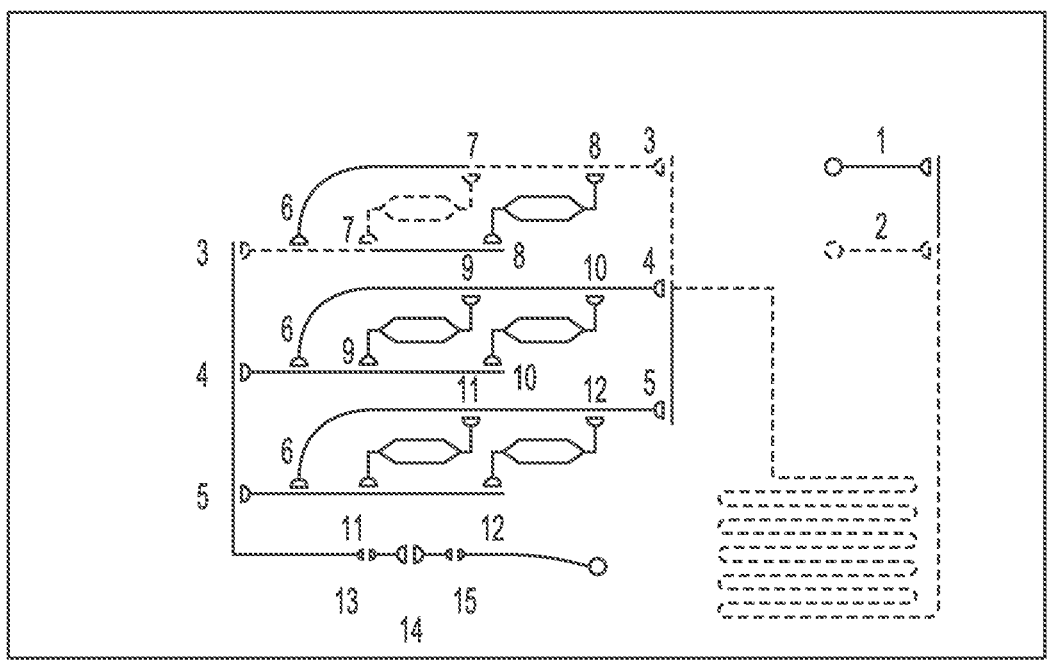
Figure 6I:
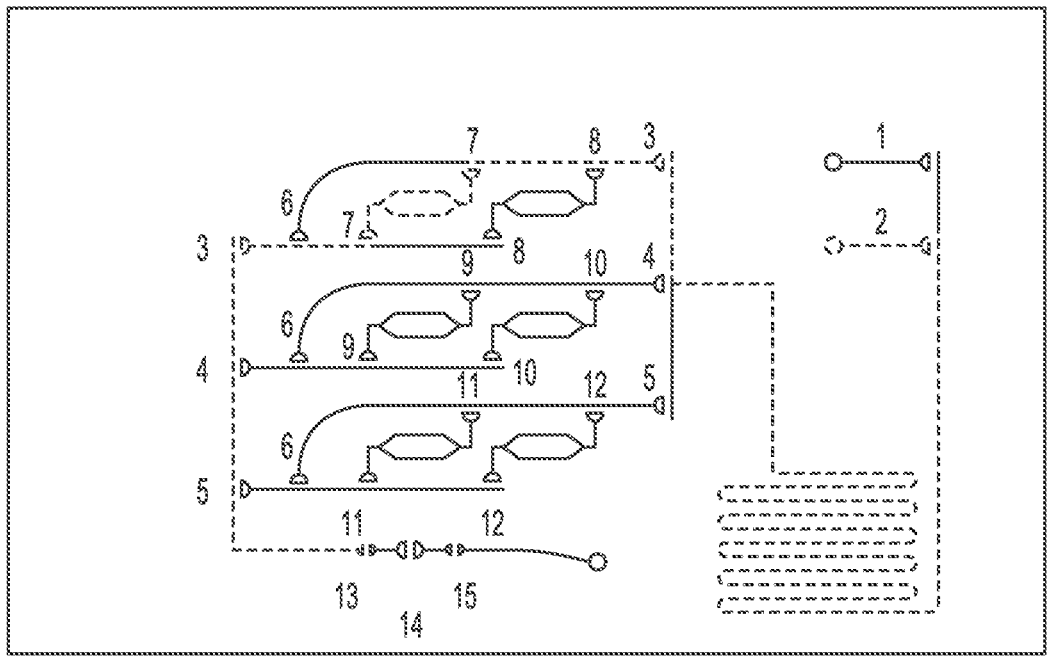
Figure 6J:
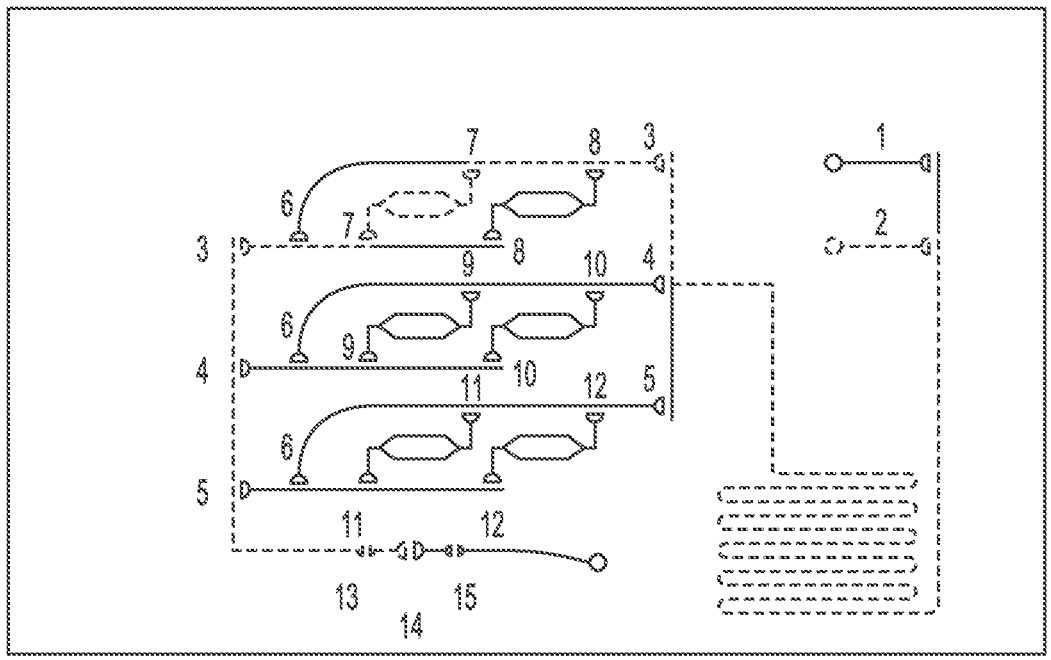
Figure 6K:
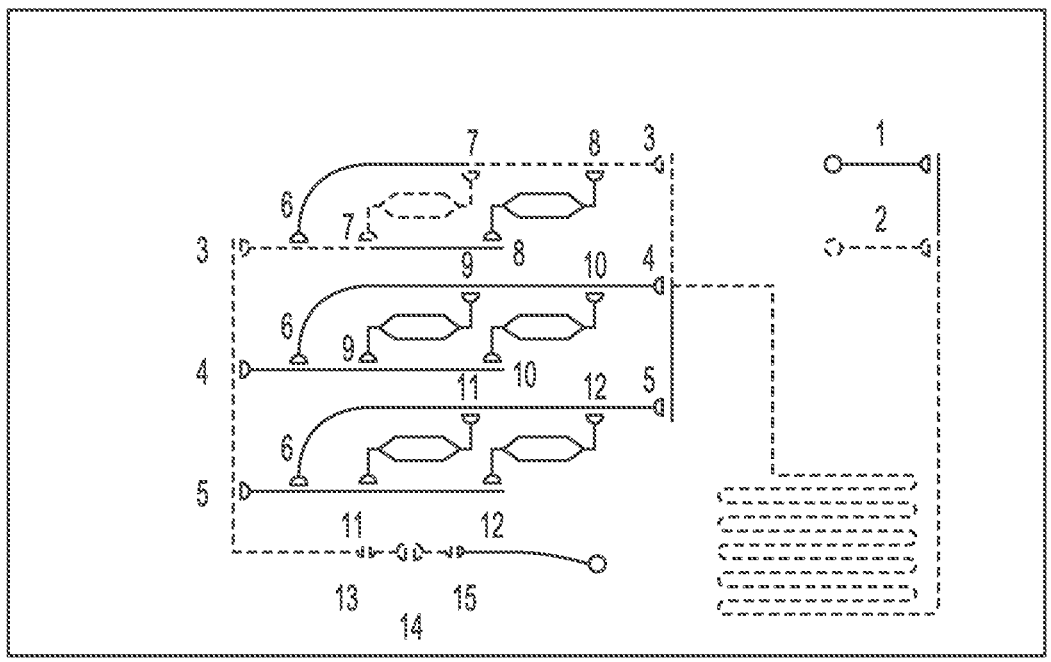
Figure 6L:
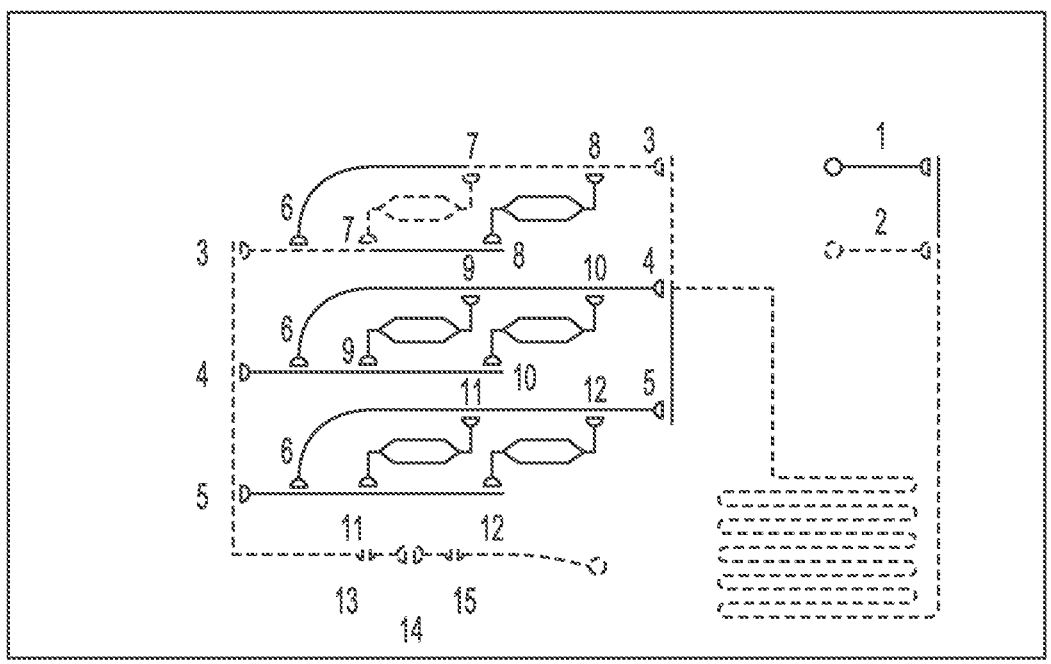
Figure 6M:
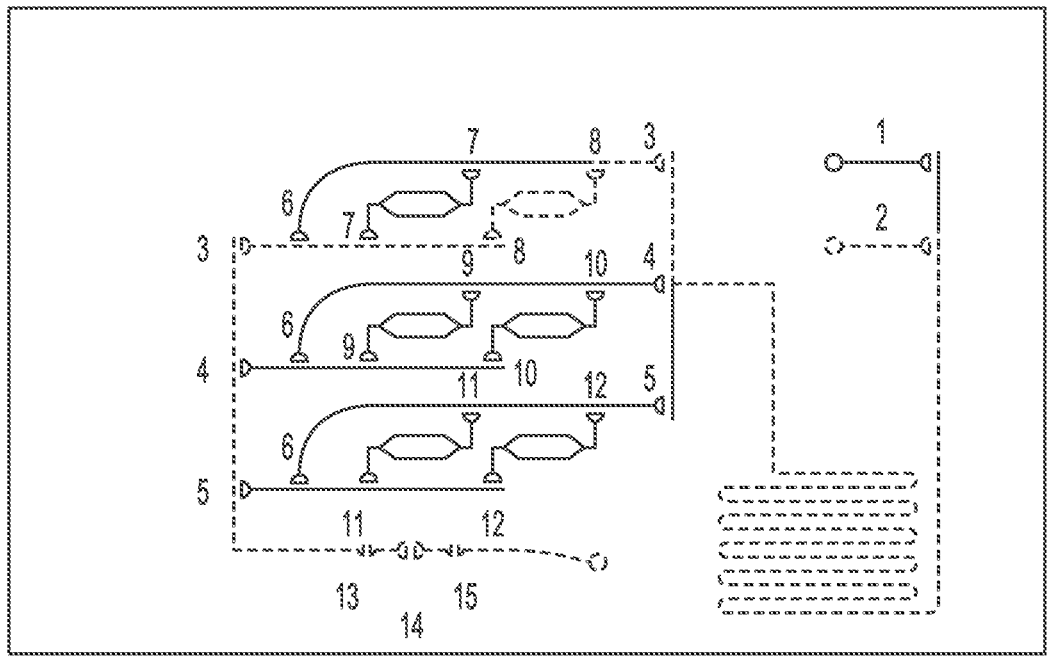
Figure 6N:
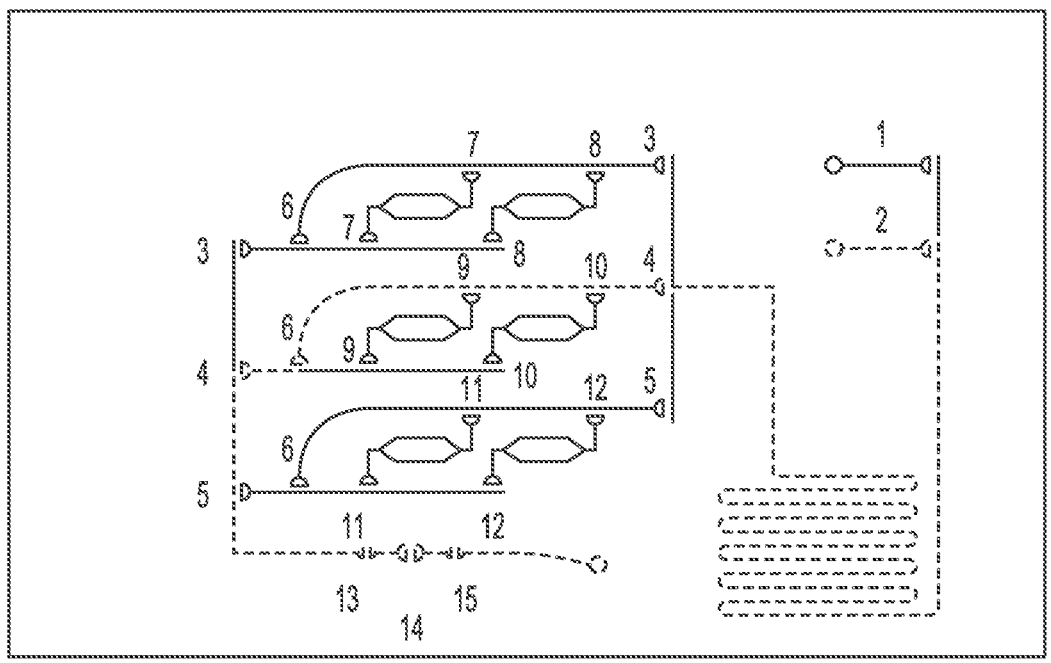
Figure 6O:
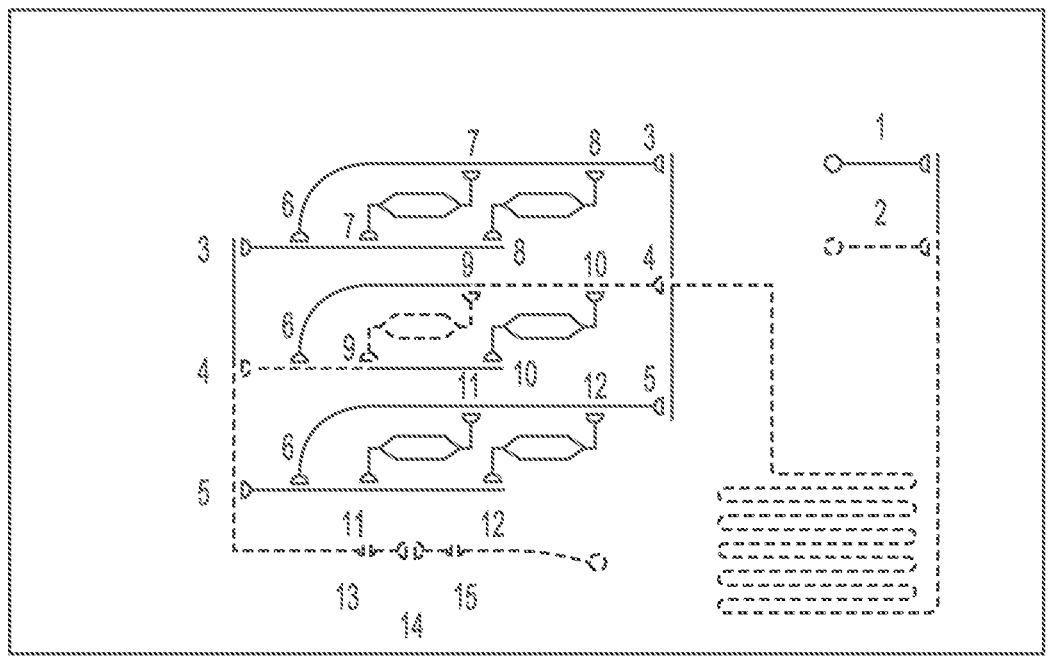
Figure 6P:
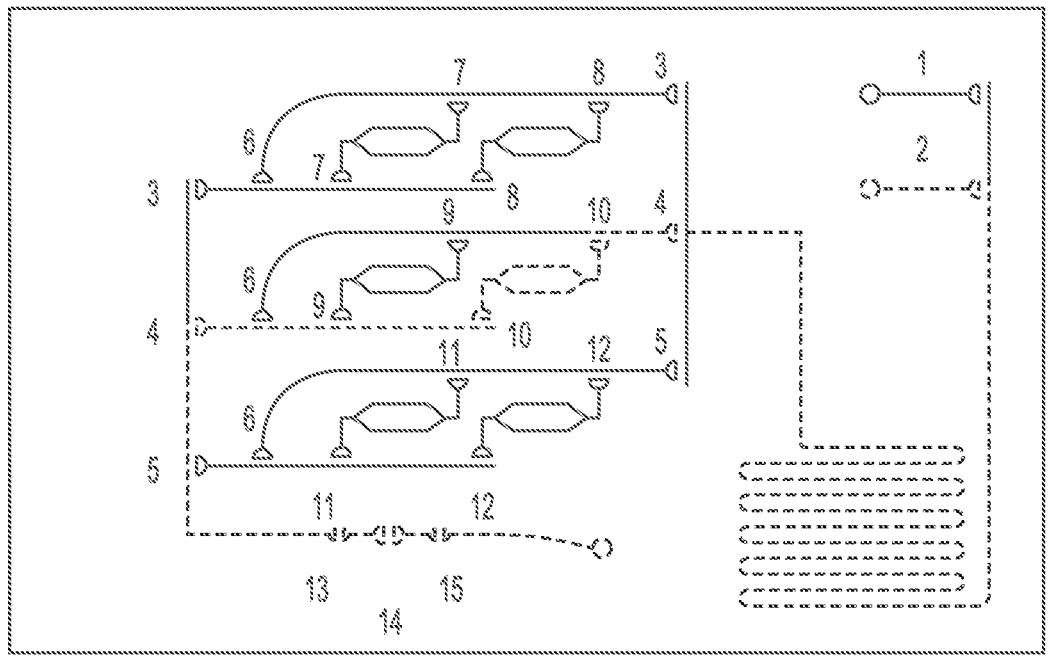
Figure 6Q:
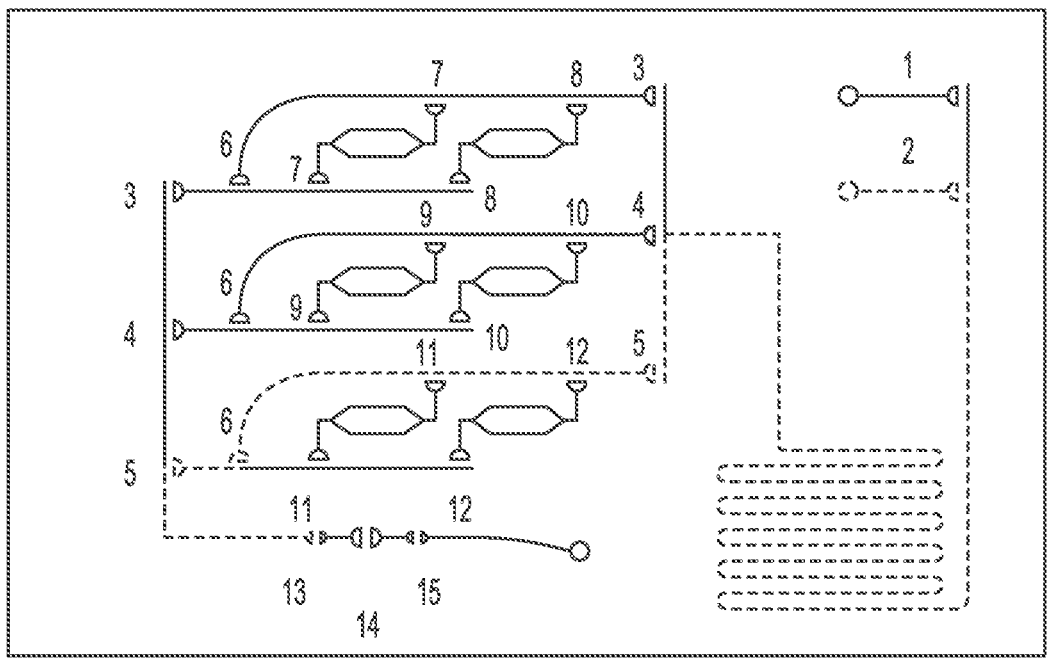
Figure 6R:
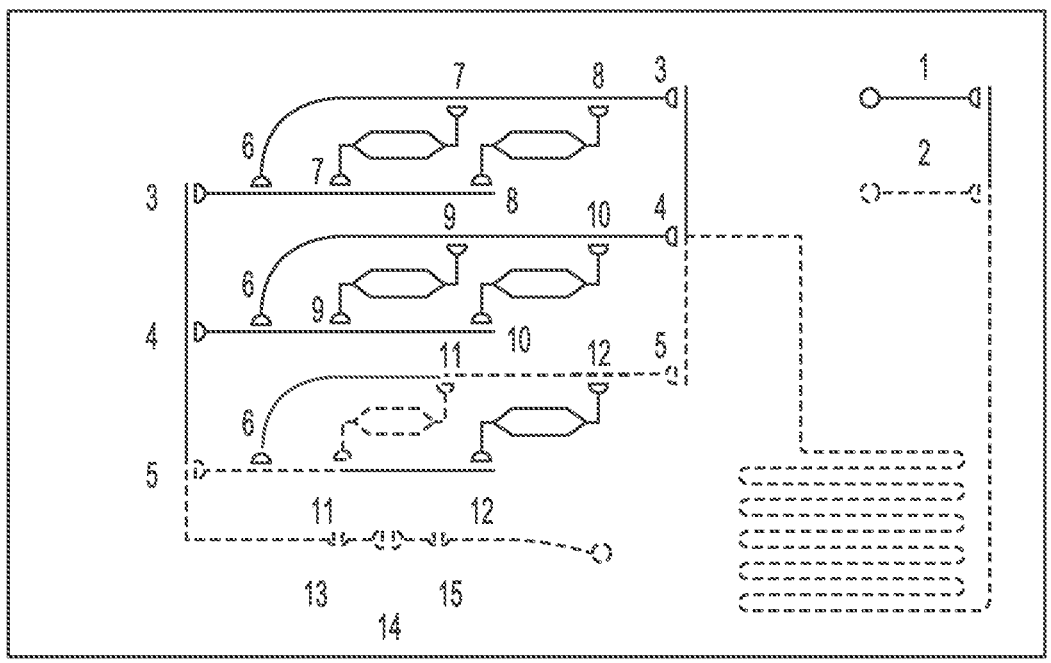
Figure 6S:
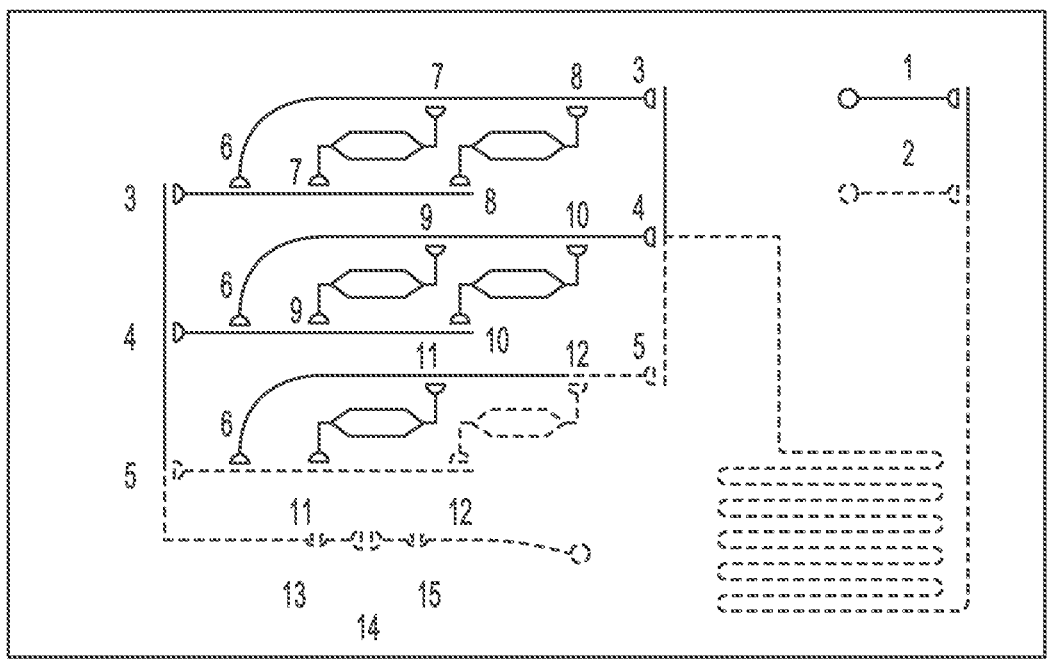
Figure 6T:
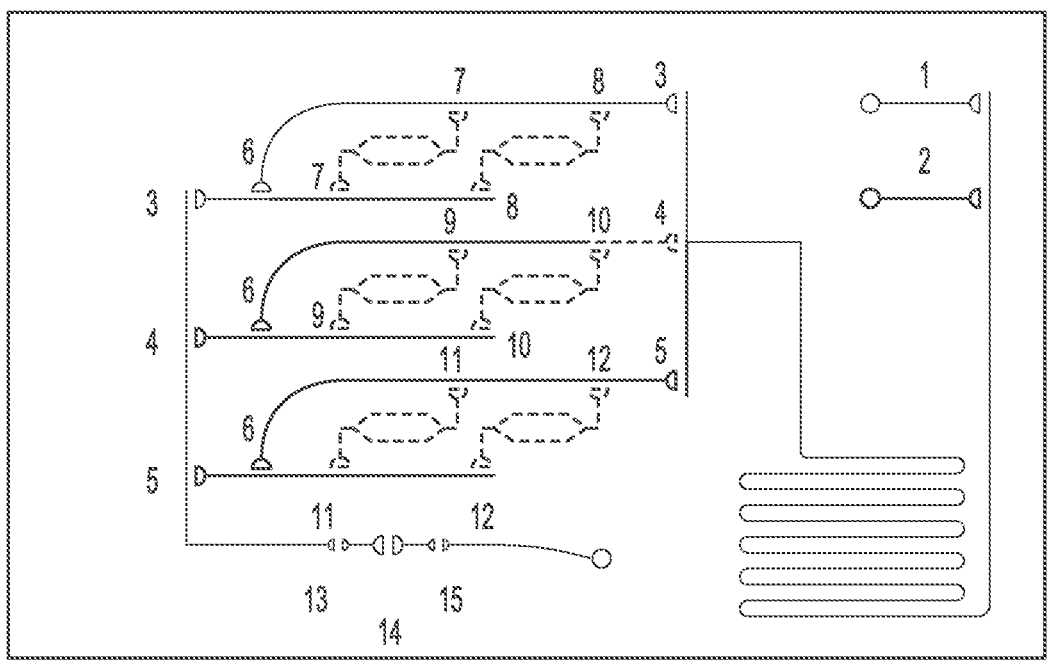
Figure 6U:
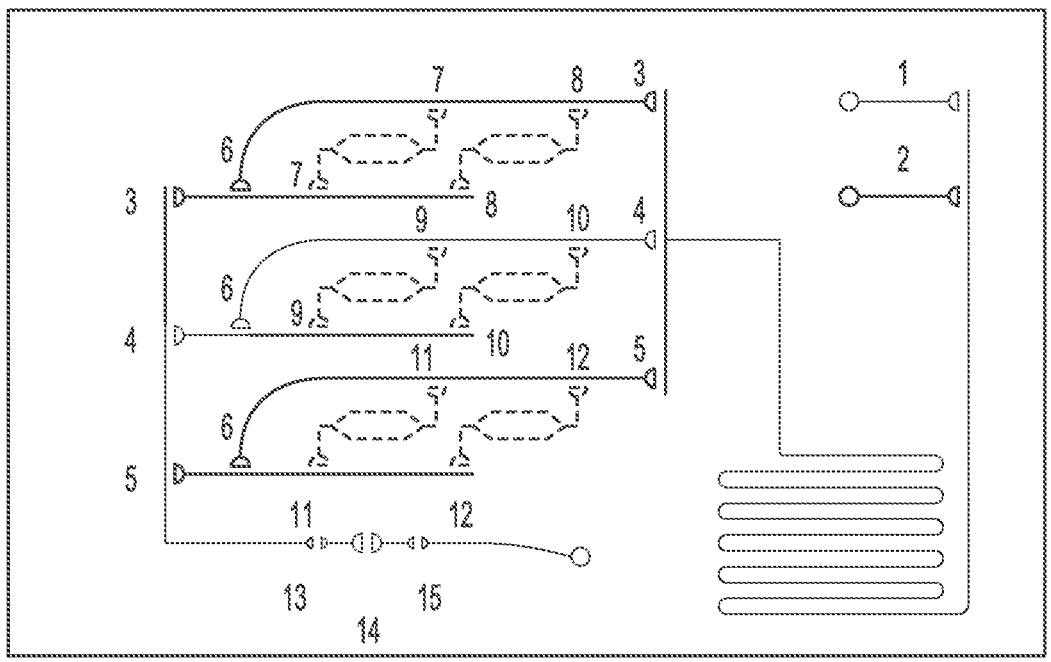
Figure 6V:
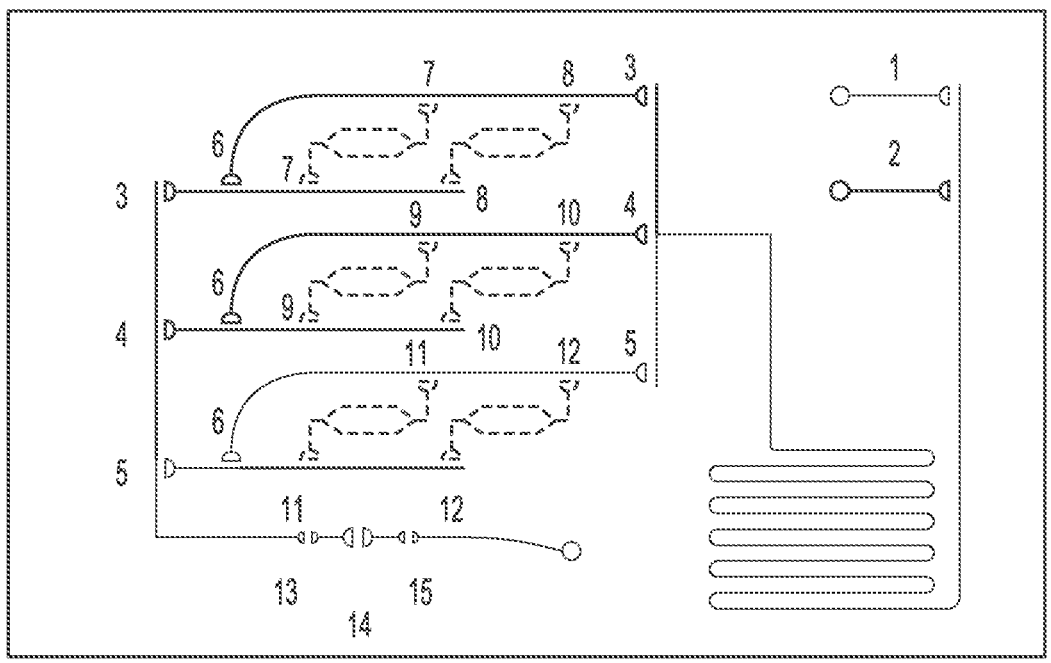

FIGS. 6A-6V depict schematic views of a fluid (e.g., cell suspension) flowing through a microfluidics layer of a multiwell plate device having individually-addressable wells, in accordance with some embodiments. In some embodiments, FIGS. 6A-6V may depict an automated cell loading protocol and rinsing of a chip. Each of FIGS. 6A-6V shows the state of the flow of fluid through the multiwell plate device at a different chronological point in time. In FIGS. 6A-6V, the schematic views show that the multiwell plate depicted comprises six hexagonal wells connected by microfluidic channels; each of the wells has an inlet channel and an outlet channel. Flow through the microfluidic channels is controlled by a plurality of numbered valves, represented by triangles in the schematics of FIGS. 6A-6V, and the channels lead from two fluid inputs near valves 1 and 2 to a single output near valve 15. The chronological process shown in FIGS. 6A-6V depicts how each of the wells in a multiwell device may be individually addressed to control the flow of fluid to any specific desired one of the wells. Taken together, FIGS. 6A-6V may depict a process for automated cell seeding and subsequent media perfusion to clear the channels of excess cell suspension, in accordance with some embodiments.

In each of FIGS. 6A-6V, valves 13, 14, and 15 may constitute a micropump that creates a vacuum force to pull fluid from the inlets near valves 1 and 2 through one or more of the intermediate microchannels toward the outlet near valve 15.

In FIG. 6A, valve 2 may be opened to allow the flow of fluid from the inlet to the right of valve 2, as shown by the dashed line representing the channel. In some embodiments, the inlet next to valve 2 may be configured to provide cell suspension, while the inlet next to valve 1 may be configured to media exchange fluid. In some embodiments, the two inlets may be configured to provide flow of any two different fluids. In some embodiments, more than two inlets may exist, and each may be configured to provide different fluids. In some embodiments, the same fluid may be provided by two or more fluids.

In FIG. 6B, valve 3 may be opened to select the upper row of two wells and to fill the channel between the inlet nearest valve 2 and the upper row with cell suspension. (As used with reference to FIGS. 6A-6V the "upper" row refers to the row shown at nearest the top of the illustration, as oriented by the direction of the text of the reference numerals. Similarly, the "lower" row will refer to the row nearest the bottom of the illustration.) In some embodiments, valve 3 may remain open until all fluid operations in the first row have been done, and then it may be closed and valve 4 may open the next row.

In FIG. 6C, valve 6 may be opened to perfuse the any one or more of the rows by allowing the flow of cell suspension, media, and/or reagents along the channel above the wells in any one or more of the rows. In some embodiments, valve 6 may open each valve with the same number. However, since only the first row is opened by valve 3, fluid may only be transported through the upper row. In some embodiments, selecting valve 4 in combination may allow fluid only to be transported through row 2, and so forth.

In FIG. 6D, the cell suspension may flow from row 1 through the leftmost bus valve of valve 3, down toward valve 13. In some embodiments, valve 3 comprises two bus-valves that may both open (and/or close) simultaneously. Note that certain valves in FIGS. 6A-6V are numbered so as to indicate that two different bus-valves correspond to the same valve number. In these cases, both bus valves may be configured to be opened and/or closed simultaneously with one another, such as by being actuated by a single pneumatic action. In some embodiments, configuring more than one bus valve to be actuated by a single pneumatic action as part of a single overall valve may save space on pneumatic connections, and for example may allow a row to be selected (e.g., by having its upstream and downstream bus valves simultaneously opened or simultaneously closed) via a single pneumatic input.

In FIG. 6E-6G, valves 13, 14, and 15 are opened in sequence, such that the cell suspension flows through them toward the outlet near valve 15. As mentioned above, valves 13, 14, and 15 may constitute a micropump that creates a vacuum force within the fluidic channel to pull fluid from the inlets near valves 1 and 2 through one or more of the intermediate microchannels toward outlet 15. The operation of valves 13-15 as a micropump will be discussed below in greater detail with respect to FIG. 7. In some embodiments, several pump-strokes of the micropump, or any other means of fluid actuation through methods described elsewhere herein, may be required in order to fill channels and ensure equal cell distribution.

In FIG. 6H, after the channel above the upper row has been perfused, valve 7 may be opened to cause cell suspension to flow from the channel above the uppermost row into the well corresponding to valve 7, and out of the well and into the microchannel below the uppermost row of wells and toward the leftmost bus valve of valve 3, which may have remained open since the step shown in FIG. 6B. Note that, in FIG. 6H, the area between the upper side of well 7 and valve 6 is no longer shown in dashed lines. This is not intended to indicate that the area is no longer filled with fluid; rather, it is intended merely to highlight the areas newly shown in dashed lines, where fluid flow is new. In some embodiments, the areas previously shown in dashed lines may still be fully filled with fluid. The same convention is applied throughout several of the following figures included in FIGS. 6H-6V.

In FIG. 6I, the cell suspension may flow from the well corresponding to valve 7 through the leftmost bus valve of valve 3, down toward valve 13.

In FIG. 6J-6L, valves 13, 14, and 15 are opened in sequence, such that the cell suspension, media, and/or reagents flows through them toward the outlet near valve 15.

In FIG. 6M, after the well corresponding to valve 7 has been filled with cell suspension, media, and/or reagents, then valve 8 may be opened to begin filling the well associated with valve 8, to cause cell suspension, media, and/or reagents to flow from the channel above the uppermost row into the well corresponding to valve 8, and out of the well and into the microchannel below the uppermost row of wells and toward the leftmost bus valve of valve 3, which may have remained open since the step shown in FIG. 6B. In some embodiments, valve 7 may be closed. In some embodiments, a multiwell device may be configured such that all previous wells are closed before a new well is opened to be filled with fluid and/or cell suspension, media, and/or reagents.

In FIG. 6N, after all of the wells in the uppermost row have been filled, wells in the middle row may be filled. As shown in FIG. 6N, valve 4 may be opened to select the middle row of wells and to perfuse the middle row by allowing the flow of cell suspension along the channel above the wells in the middle row.

In FIG. 6O, after the channel above the middle row has been perfused, valve 9 may be opened to cause cell suspension to flow from the channel above the middle row into the well corresponding to valve 9, and out of the well and into the microchannel below the middle row of wells and toward the leftmost bus valve of valve 4, which may have remained open since the step shown in FIG. 6N.

In FIG. 6P, after the well corresponding to valve 9 has been filled with cell suspension, media, and/or reagents, then valve 10 may be opened to begin filling the well associated with valve 10, to cause cell suspension, media, and/or reagents to flow from the channel above the middle row into the well corresponding to valve 10, and out of the well and into the microchannel below the middle row of wells and toward the leftmost bus valve of valve 4, which may have remained open since the step shown in FIG. 6N. In some embodiments, valve 9 may be closed.

In FIG. 6Q, after all of the wells in the middle row have been filled, wells in the lower row may be filled. As shown in FIG. 6Q, valve 5 may be opened to select the lower row of wells and to perfuse the lower row by allowing the flow of cell suspension, media, and/or reagents along the channel above the wells in the lower row.

In FIG. 6R, after the channel above the lower row has been perfused, valve 11 may be opened to cause cell suspension, media, and/or reagents to flow from the channel above the lower row into the well corresponding to valve 11, and out of the well and into the microchannel below the lower row of wells and toward the leftmost bus valve of valve 5, which may have remained open since the step shown in FIG. 6Q.

In FIG. 6S, after the well corresponding to valve 11 has been filled with cell suspension, then valve 12 may be opened to begin filling the well associated with valve 12, to cause cell suspension, media, and/or reagents to flow from the channel above the lower row into the well corresponding to valve 12, and out of the well and into the microchannel below the lower row of wells and toward the leftmost bus valve of valve 5, which may have remained open since the step shown in FIG. 6Q. In some embodiments, valve 11 may be closed.

In FIG. 6T, after each of the wells (or all of the desired wells) in the plate have been addressed to be filled with cell suspension, media, and/or reagents, valve 2 may be closed and valve 1 may be opened. Accordingly, the inlet corresponding to valve 2 may be blocked such that cell suspension, media, and/or reagents may no longer flow into the microchannels, while the inlet next to valve 1 may be fluidly connected to the microchannels by the opening of valve 1 such that fluid media may flow from inlet 1 through the microchannels. In some embodiments, media determined in accordance with the cell suspension used may be selected, and the media may be used to rinse the microchannels.

As shown in FIGS. 6T-6V, the rinsing media may first flow through the channels of the uppermost row, then through the channels of the middle row, then through the channels of the lowermost row. In order to enable this flow process, valve 3 may first be opened; then valve 3 may be closed and valve 4 may be opened; then valve 4 may be closed and valve 5 may be opened. In FIGS. 6T-6V, flow of rinsing media through the various channels is shown by the use of thinner lines.

After each of the above steps in which one or more valve is opened or closed, the system may be configure to pause for a predefined period of time and/or to execute a predefined number of pump-strokes via a micropump. In some embodiments, different rows, channels, and/or wells may be known to take a longer amount of time or a greater number of strokes to fill/perfuse/evacuate/rinse, so the system may pause for different amounts of time and/or execute different predefined numbers of pump strokes at different steps of the above process. In some embodiments, one or more sensors of the system may be used to determine whether the desired perfusion, well-filling, evacuation, and/or rinsing has occurred, and the sensors may be used to trigger the system to advance to the next step, for example by opening or closing a next valve.

In some embodiments, after the rows are rinsed, the system may pause for a predefined period of time (see FIG. 6W below) defined by a user input and/or a characterized cell line adhesion profile. After expiration of the predefined adhesion time, the system may change the protocol to automated cell culture and may perfuse the wells in predefined intervals.

In some embodiments of the layout shown in FIGS. 6A-6V, channel width to the right (e.g., upstream) of the channels above the rows of wells may be 500 μm, while channel width to the left (e.g., downstream) of the beginning of the channels above the rows of wells may be 250 µm. In some embodiments, different channel widths may have different flow speed at the same micropump actuation cycle.

In some embodiments, the layout and change in channel width shown in FIGS. 6A-6V may allow incoming media to be reduced in flow speed so that it can stabilize in temperature and so that any unintentionally introduced air-bubbles can be captured in a degasser in a layer above the fluid routing layer at a location above the serpentine portion of the microfluidic channel. In some embodiments, a micro-degasser may be incorporated in a fluid control layer. In some embodiments, the degasser may comprise a grid disposed in a pneumatic layer over a fluid routing layer included in the layout depicted in FIGS. 6A-6V. By applying a vacuum to the grid (e.g., a constant vacuum), gas bubbles may be extracted from the serpentine channel beneath the grid. Heated and air-bubble free media may then be dispersed into the individual row channels, where the media may then introduced into the individual wells. In some embodiments, one or more additional degassers (e.g., secondary degassers) may further be included such that gas bubbles may be extracted at the location of one or more individual wells, or at the location of one or more inlets to one or more individual wells.

Figure 6W:
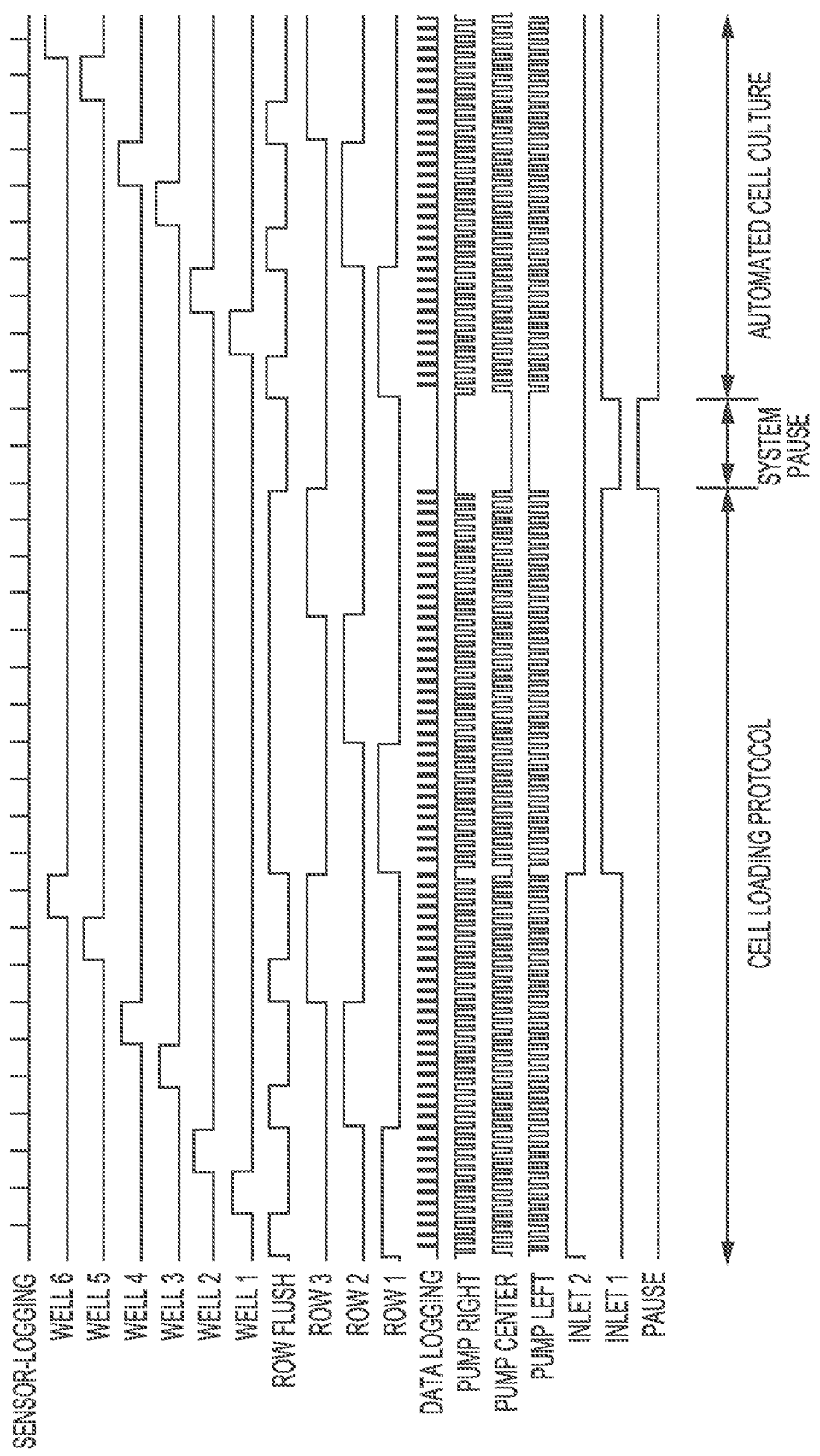

FIG. 6W depicts a graphical representation of the operation of various components or features of a multiwell system over time. In some embodiments, the multiwell system operated in accordance with FIG. 6W may be the multiwell system schematically depicted in FIGS. 6A-6V. FIG. 6W shows a chronological representation of 18 components or features of a multiwell device over time. The 18 horizontal lines in FIG. 6W each represent the state of a respective component over time during operation of the device, where the step-function changes in each line represents an event or occurrence or change in state of the respective component or feature. The operation of each of the 18 components or features is shown in chronological synchronization.

The first (top-most) line in FIG. 6W represents operation of a sensor logging function of the multiwell device and/or docking station 100 and or portable manifold connector 1200. At each of the spikes in the line, the system may log, record, store, and/or transmit information regarding one or more sensors associated with the device at those times.

The second line in FIG. 6W represents operation of a valve associated with well 6; in some embodiments, this may represent valve 12 as discussed above with respect to FIGS. 6A-6V. Where the line is shown in a raised position, the valve may be in an open position during those times.

The third line in FIG. 6W represents operation of a valve associated with well 5; in some embodiments, this may represent valve 11 as discussed above with respect to FIGS. 6A-6V. Where the line is shown in a raised position, the valve may be in an open position during those times.

The fourth line in FIG. 6W represents operation of a valve associated with well 4; in some embodiments, this may represent valve 10 as discussed above with respect to FIGS. 6A-6V. Where the line is shown in a raised position, the valve may be in an open position during those times.

The fifth line in FIG. 6W represents operation of a valve associated with well 3; in some embodiments, this may represent valve 9 as discussed above with respect to FIGS. 6A-6V. Where the line is shown in a raised position, the valve may be in an open position during those times.

The sixth line in FIG. 6W represents operation of a valve associated with well 2; in some embodiments, this may represent valve 8 as discussed above with respect to FIGS. 6A-6V. Where the line is shown in a raised position, the valve may be in an open position during those times.

The seventh line in FIG. 6W represents operation of a valve associated with well 1; in some embodiments, this may represent valve 7 as discussed above with respect to FIGS. 6A-6V. Where the line is shown in a raised position, the valve may be in an open position during those times.

The eighth line in FIG. 6W represents operation of a row flush function. Where the line is shown in a raised position, the system may be performing a row flush function during those times. In some embodiments, row flushing may comprise causing a corresponding row valve to remain is opened while the well valves in that row remain closed. Opening the flush valve may thus allow the channel to be rinsed and cleaned of cell suspension, media, and/or reagent that was previously introduced into the channel before. In some embodiments, channels may be rinsed prior to addressing individual wells, in order to deliver fresh and untainted media to the wells.

The ninth line in FIG. 6W represents operation of valves associated with row 3; in some embodiments, this may represent valve 5 as discussed above with respect to FIGS. 6A-6V. Where the line is shown in a raised position, the valve may be in an open position during those times.

The tenth line in FIG. 6W represents operation of valves associated with row 2; in some embodiments, this may represent valve 4 as discussed above with respect to FIGS. 6A-6V. Where the line is shown in a raised position, the valve may be in an open position during those times.

The 11th line in FIG. 6W represents operation of valves associated with row 1; in some embodiments, this may represent valve 3 as discussed above with respect to FIGS. 6A-6V. Where the line is shown in a raised position, the valve may be in an open position during those times.

The 12th line in FIG. 6W represents operation of a data logging function of the multiwell device. At each of the spikes in the line, the system may log, record, store, and/or transmit information regarding associated with the device at those times.

The 13th, 14th, and 15th lines in FIG. 6W represents operation of a right, center, and left valve, respectively, where the three valves together form a micro-pump, as discussed in further detail below with respect to FIG. 7. Where each of the lines is shown in a raised position, the respective valve may be in an open position during those times.

The 16th line in FIG. 6W represents operation of a valve associated with inlet 2; in some embodiments, this may represent valve 2 as discussed above with respect to FIGS. 6A-6V. Where the line is shown in a raised position, the valve may be in an open position during those times.

The 17th line in FIG. 6W represents operation of a valve associated with inlet 1; in some embodiments, this may represent valve 1 as discussed above with respect to FIGS. 6A-6V. Where the line is shown in a raised position, the valve may be in an open position during those times.

The 18th bottom-most line in FIG. 6W represents a pause function of a multiwell device. Where the line is shown in a raised position, the valve device may be in a pause state during those times. In some embodiments, the system pause may be a pause of varying length with respect to the cycles of the other functions shown in the system. For example, the system pause shown by the 18th bottom-most line in FIG. 6W (and the corresponding pause in regular cycles of other lines in FIG. 6W) may in some embodiments be longer or shorter than shown in the example of FIG. 6W.

As shown by the annotation at the bottom of the figure, FIG. 6W represents a cell loading protocol stage, followed by a system pause stage, followed by an automated cell culture stage for media exchange within the individual wells that have been seeded with cells in the first stage.

In some embodiments, microfluidic-enabled devices and/or systems disclosed herein may be configured to perform automated addition of one or more compounds to cells. In some embodiments, operation of drug or reagent delivery may be similar to the protocol explained above in FIGS. 6A-6W for cell loading and/or media exchange. In some embodiments, for drug or reagent delivery, an appropriate input port besides a media and/or cell loading port may be selected. In some embodiments, dilution and gradient generation may be achieved by targeted well addressing and/or dilution through active microfluidic mixing in channels with media.

In some embodiments, microfluidic-enabled devices and/or systems disclosed herein may be configured to perform automated exchange of cell culture media.

In some embodiments, microfluidic-enabled devices and/or systems disclosed herein may be configured to perform automated addition of reagent(s) (e.g., trypsin) to dissociate attachment-dependent cell lines of cultured cells. In some embodiments, for example, the addition of trypsin may cause cells in a multiwell device to detach and then flow out from the device upon media exchange.

Figure 7:
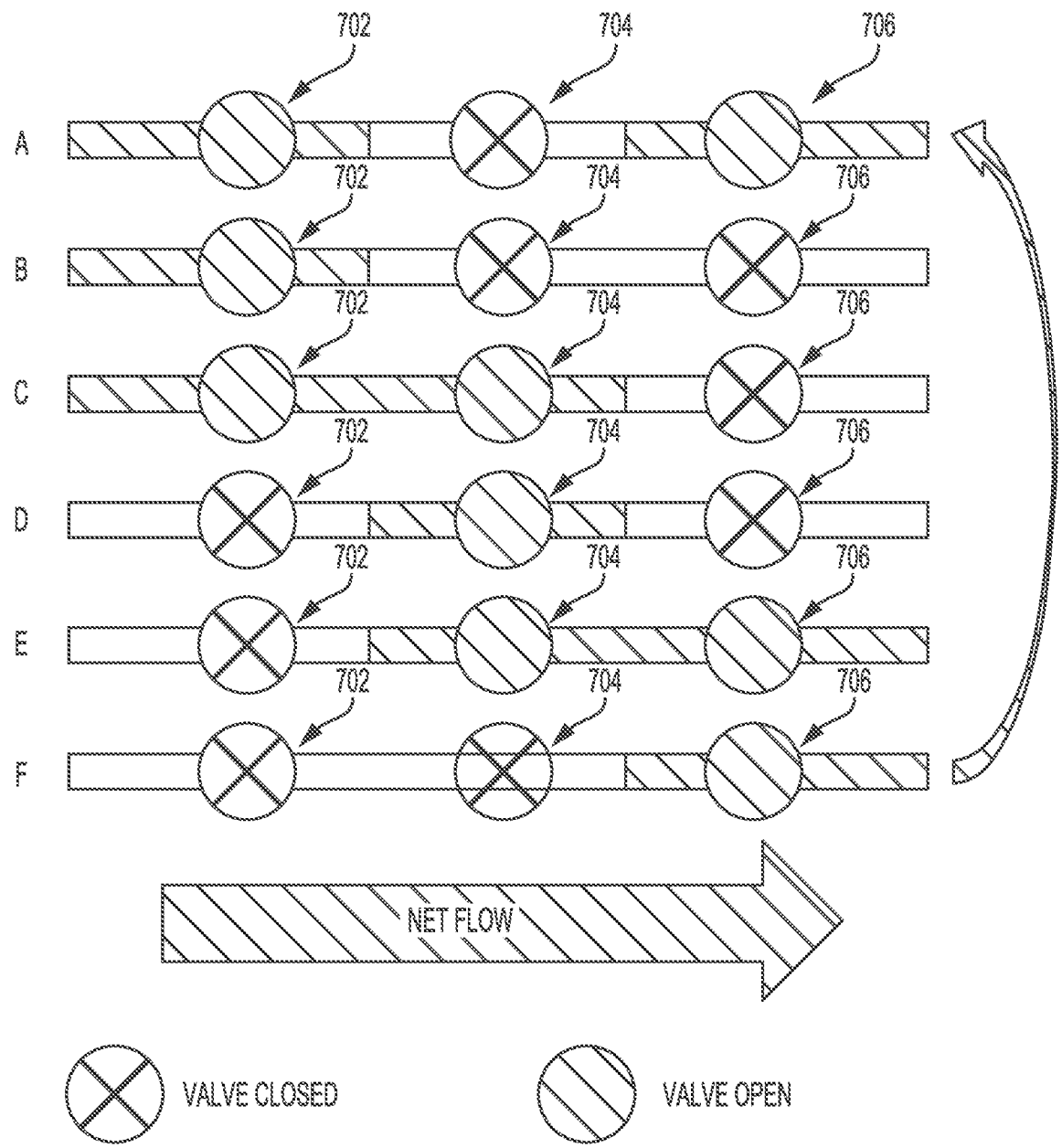
FIG. 7 schematically depicts six different stages of micropump operation using a three-valve structure, in accordance with some embodiments.

FIG. 7 schematically depicts six different stages of micro-pump operation using a three-valve structure, in accordance with some embodiments. In some embodiments, the micropump comprises valves 702, 704, and 706, with the flow of fluid from left to right in the figure, flowing from valve 702 to valve 706. In some embodiments, valves 702, 704, and 706 may correspond respectively to valves 13, 14, and 15 as discussed above with respect to FIGS. 6A-6V. In some embodiments, valves 702, 704, and 706 may share some or all characteristics in common with any one or more other valves discussed herein.

In FIG. 7, six stages labeled A-F are shown from top to bottom in the figure, with the stages progressing chronologically from A to F.

In stage A, valve 702 is open, valve 404 is closed, and valve 706 is open.

In stage B, valve 702 is open, valve 404 is closed, and valve 706 is closed.

In stage C, valve 702 is open, valve 404 is open, and valve 706 is closed.

In stage D, valve 702 is closed, valve 404 is open, and valve 706 is closed.

In stage E, valve 702 is closed, valve 404 is open, and valve 706 is open.

In stage F, valve 702 is closed, valve 404 is closed, and valve 706 is open.

In some embodiments, the six chronological stages shown in FIG. 7 may together constitute a single pump-stroke of the micro-valve formed by valves 702, 704, and 706. Multiwell microfluidic systems discussed herein may, in some embodiments, comprise one or more micro-pumps configured to automatically execute one or more pump-strokes of multivalve micro-pumps such as the one shown in FIG. 7.

In some embodiments, fluid actuation in microfluidics may be achieved by placing three bus valves in sequence and facilitating a cyclic actuation, as shown in one example by the six chronological stages shown in FIG. 7.

In some embodiments, three parameters may influence fluid flow using micro pumps: (1) geometry of the bus-valves; (2) applied pressure/vacuum to the pneumatics; and (3) step-time/actuation interval.

Regarding geometry of the bus-valves (e.g., size and diameter of the individual valves), smaller valve diameters may have a short actuation time (the time the applied vacuum requires in order to deflect the membrane over/with the gate), and larger valves may require longer actuation time for the membrane to deflect.

Regarding applied pressure/vacuum to the pneumatics, vacuum and pressure settings may be modulated to increase or decrease flow rates as the pneumatic strength directly controls the deflection of the membrane.

Regarding step-time/actuation interval, higher step-times may allow more time for the membrane to deflect, thus creating a larger volume displacement, while lower step-times may allow less time for the membrane to deflect, thus creating a smaller volume displacement. Furthermore, the actuation time may also change the flow-speed pattern in the channels. Since a change in actuation time may result in different flow speeds of the fluid, this effect may be used to control the shear stress directed upon the biological sample by precisely adjusting flow rates. Higher flow rates may create higher shear stress conditions, while lower flow rates may reduce the shear stress. Control over shear stress may be an important factor, for example, for the differentiation of stem cells and or endothelial cells.

Figure 8A:
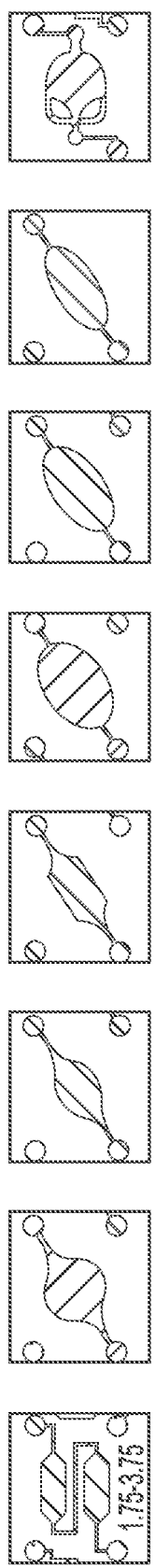
Figure 8C:
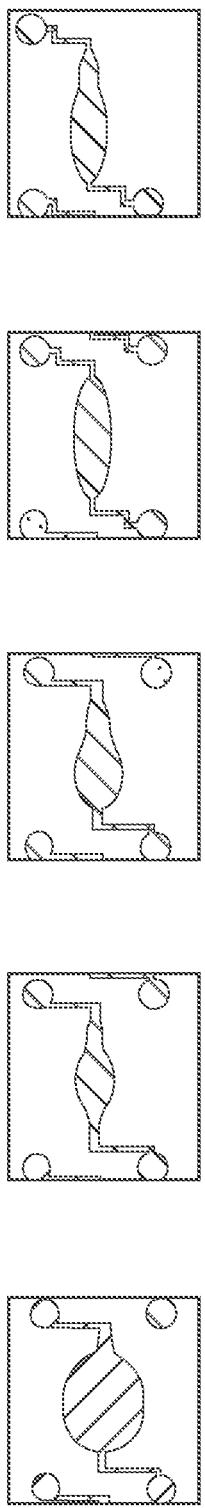

FIGS. 8A-8C depict different well geometries and tables depicting seeding densities for each of the well geometries, in accordance with some embodiments.

In the tables in FIGS. 8A-8C, the first column denotes a number corresponding to a well geometry, the shapes of which are shown across the tops of the figures. The second column denotes the area, in square millimeters, of the corresponding well geometry. The fourth column denotes a seeding density, in cells per well, cells having a diameter of 5 µm, for the corresponding well geometry. The fifth column denotes a seeding density, in cells per well, cells having a diameter of 10 µm, for the corresponding well geometry. The sixth column denotes a seeding density, in cells per well, cells having a diameter of 15 µm, for the corresponding well geometry. The seventh column denotes a seeding density, in cells per well, cells having a diameter of 20 µm, for the corresponding well geometry. The eighth column denotes a seeding density, in cells per well, cells having a diameter of 25 µm, for the corresponding well geometry.

As shown by the different hashing of the well geometries shown across the top of FIGS. 8A-8C, experimental data indicated that, in some embodiments, well geometries 1, 3, 4, 6, 7, 9, 10, 11, 12, 13, 14, 15, 18, 19, 20, and 21 were less likely to experience a buildup of air bubbles; while, in some embodiments, well geometries 2, 5, 8, 15, 16, and 17 were more likely to experience a buildup of air bubbles (or bubbles of other gas or gases). In some embodiments, other well geometries (not shown) were found to be even more likely to experience a buildup of air bubbles or undesirable fluid routing within wells; in some embodiments, air bubbles may be more likely to build up in well geometries featuring internal pillars or micro-patterns inside the wells themselves.

In some embodiments, well geometries in which air bubbles are less likely to build up may be preferred. However, use of degassers, especially well-specific microdegassers as discussed herein, may sufficiently alleviate formation of air bubbles such that well geometries susceptible to build-up of air bubbles may be able to be depleted of air bubbles and may therefore be acceptable for various applications.

In some embodiments, in addition to or alternately to selecting and/or optimizing well geometries for minimization of air bubbles, well geometries may be selected and/or optimized for the minimization of "dead spaces" where fluid flow is slow or nonexistent. In some embodiments, elongated well geometries, such as geometry 20 in FIG. 8C, may more effectively minimize dead spaces than more circular geometries such as geometry 17 in FIG. 8C. In some embodiments, well geometries having multiple laterally-distributed inlets, such as geometry 15 in FIG. 8B, may more effectively minimize dead spaces that well geometries with fewer inlets, or with only one inlet.

Figure 9:
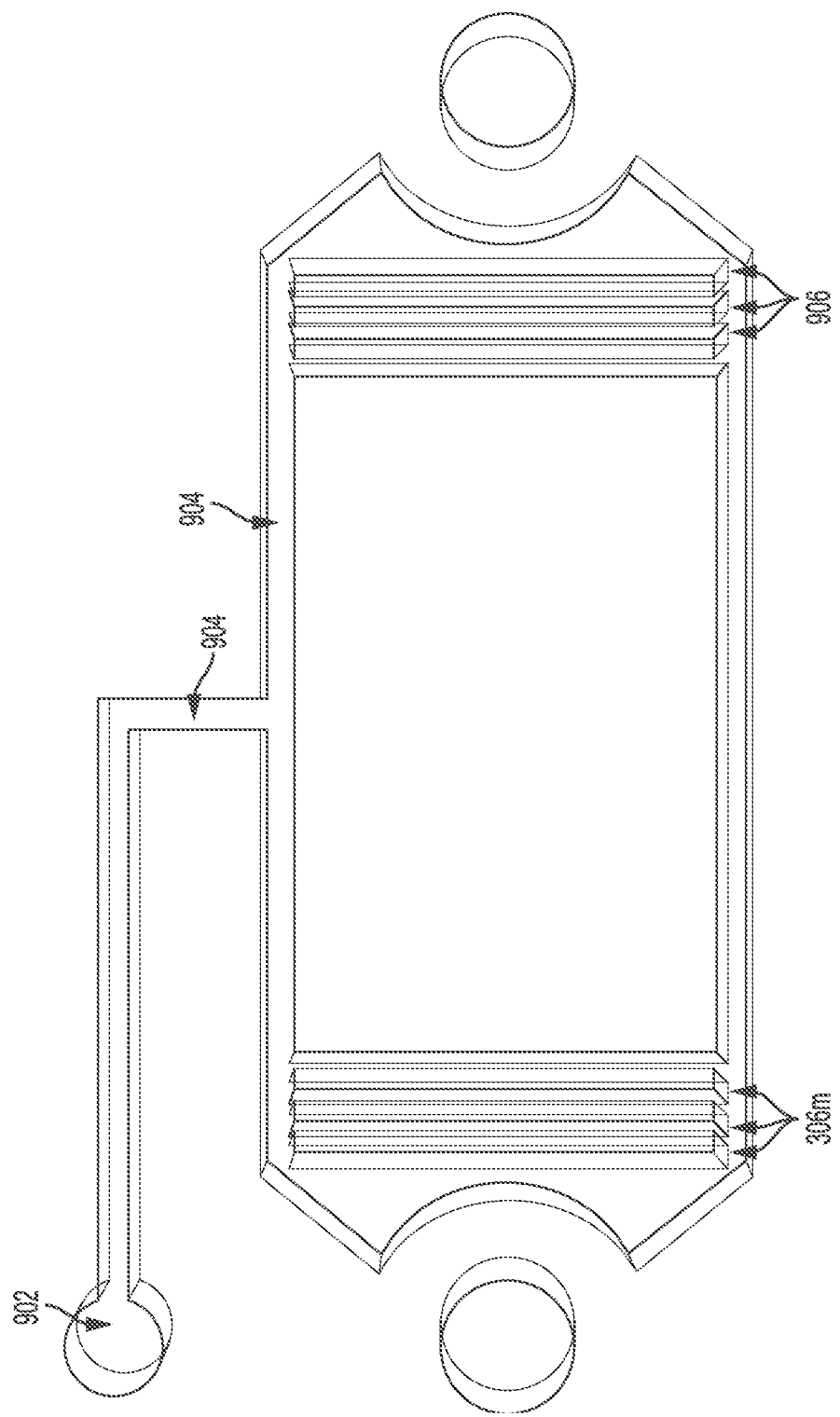
FIG. 9 shows a schematic view of a micro-degasser, in accordance with some embodiments.

FIG. 9 shows a schematic view of a micro-degasser 900, in accordance with some embodiments. In some embodiments, micro-degasser 900 may be included in a microfluidics layer of any of the multiwell devices described herein, and may be configured to remove gas bubbles from one or more microchannels and/or from one or more wells of the device. Micro-degasser 900 may operate in principle same or similar manner as described above regarding the degasser discussed with respect to FIGS. 6A-6V. However, while the degasser discussed above with respect to FIGS. 6A-6V may be a "global" degasser configured to degas a global fluid input line of a multiwell device, micro-degasser 900 may be configured with an adapted geometry for use with an individual well geometry. That is, micro-degasser 900 may be configured to degas a single well of a multiwell device, rather than a global input line corresponding to multiple wells of a multiwell device. The structural components of micro-degasser 900 may comprise a lattice/grid structure that may be the same or similar as a lattice/grid structure used in a primary (e.g., global) media degasser such as the one discussed above. In some embodiments, micro-degasser 900 may be connected in series with the vacuum inlet to the primary degasser. Additional pneumatic channels on top of pneumatic control layer 312 may be routed towards individual via holes that connect corresponding individual micro-degassers above respective wells. In some embodiments, micro-degassers may be located in the same layer as the primary degasser structure; in some embodiments, micro-degassers may be located in a separate layer and/or a separate module of a device from the primary degasser structure. Well-specific micro-degassers such as micro-degasser 900 may rely on the same gas-permeable membrane located between a well layer and fluid routing layer. Since primary degassers and micro degassers may be connected in series, once vacuum is applied to the pneumatic lines it may evacuate any air bubbles delivered to the individual well chambers.

As shown in FIG. 9, degasser 900 may comprise vacuum input hole 902, which may be configured to pneumatically connect to a source of vacuum (such as a pneumatic control layer, or any outside vacuum source). Degasser 900 may further comprise pneumatic channels 904, which may be pneumatic routing structures configured to pneumatically connect input hole 902 to the one or more pillars 906, which may be pillars or other support elements configured to prevent a gas-permeable membrane (through which air may escape (e.g., be actively removed) from a well into the degasser under the applied vacuum force) from deflecting into the degasser itself.

Figure 10A:
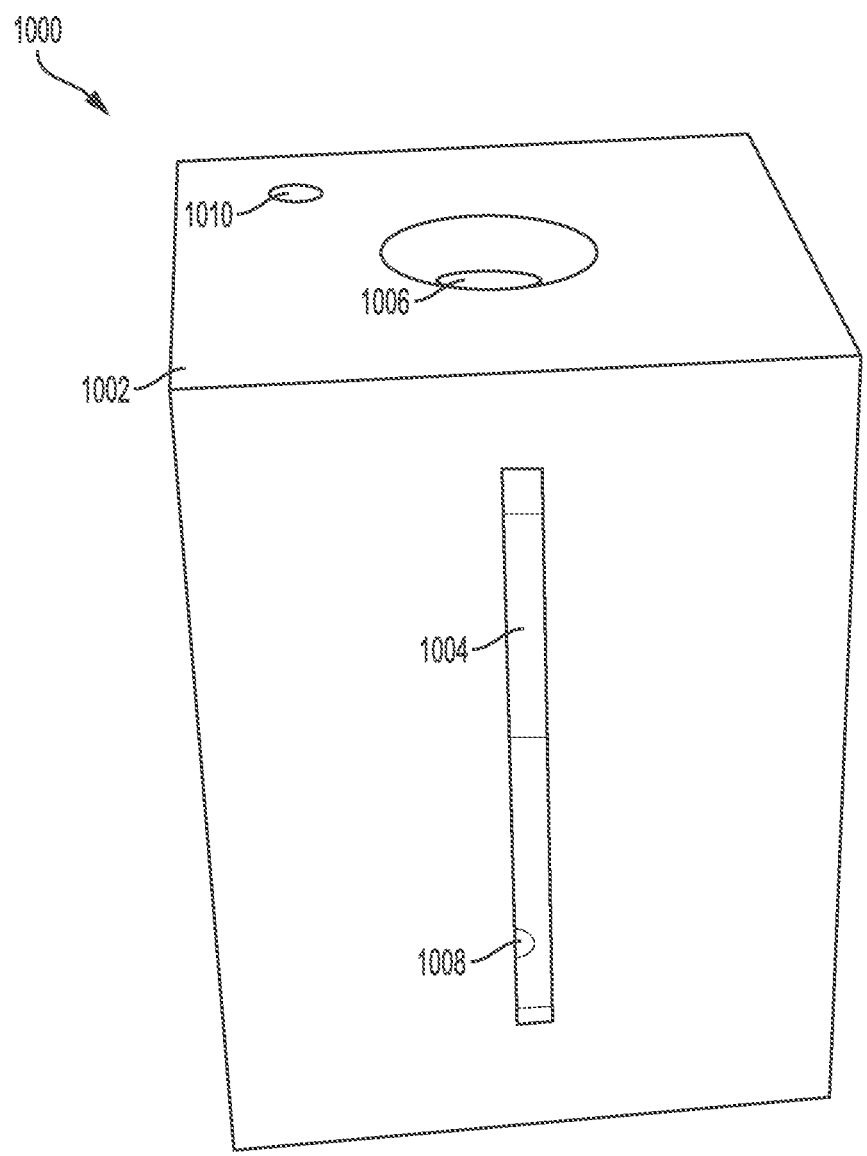
FIGS. 10A & 10B depict two views of a media cartridge for use in a cell culture system, in accordance with some embodiments.
Figure 10B:
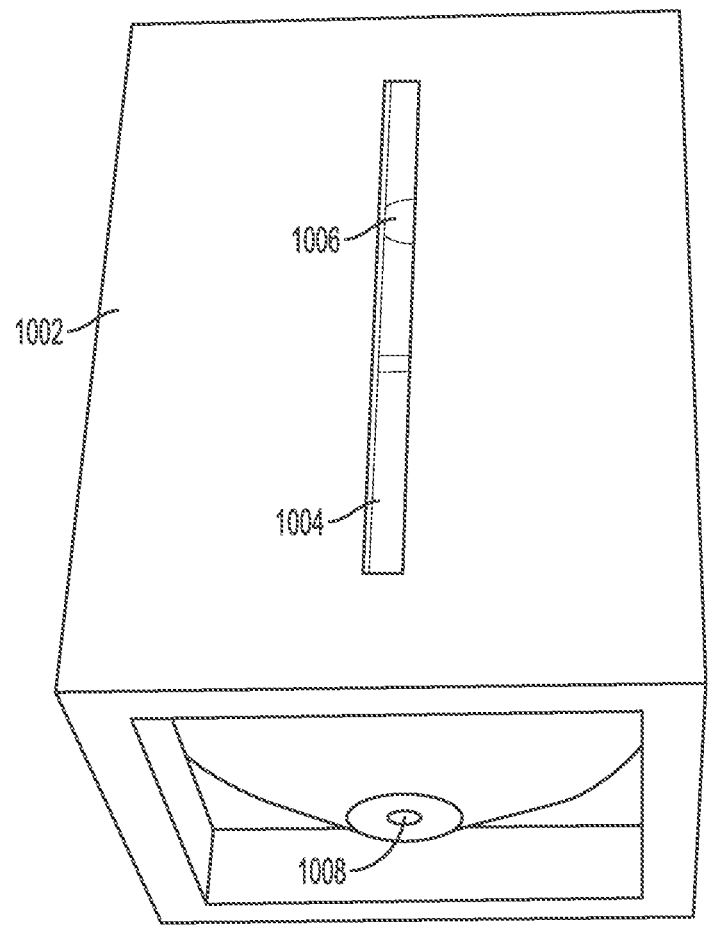

FIGS. 10A & 10B depict two views of a media cartridge 1000 for use in a cell culture system, in accordance with some embodiments. In some embodiments, media cartridge 1000 may share some or all characteristics in common with media cartridge 108 discussed above with respect to FIG. 1.

As shown in FIGS. 10A & 10B, media cartridge 1000 may comprise enclosure 1002, which may be any body structure such as a rigid outer housing configured to be handled by a user and to be inserted into a docking station or other receiving device.

Media cartridge 1000 may further comprise indicator 1004, which may be an indicator configured to indicate a level of fluid inside the cartridge. In some embodiments, indicator 1004 may be a transparent window configured to provide a view of the level of fluid inside cartridge 1000 for visual inspection by a user.

Media cartridge 1000 may further comprise input syringe rubber diaphragm seal 1006, which may be configured to provide a seal protecting an inlet to cartridge 1000. In some embodiments, seal 1006 may securely close cartridge 1000 from contaminants and environmental effects. Furthermore seal 1006 may allow the user to reuse the cartridge and sterilize/autoclave it. Refilling of the media may be done in sterile, tissue-culture conditions to avoid contamination. Using a syringe, a user may poke through seal 1006 and refill media. In some embodiments, a HEPA filter comprised in cartridge 1000 may allow for pressure equilibration since pulling media from the cartridge may create negative partial pressure and at some point may stop the operation of a micropump or decrease the efficiency of fluid transport.

Media cartridge 1000 may further comprise output connector rubber diaphragm seal 1008, which may be configured to provide a seal protecting an outlet from cartridge 1000. In some embodiments, seal 1008 may function in a same or similar manner as seal 1006. In some embodiments, a needle or similar component of a docking station may poke through seal 1008 to allows fluid to be transported out of cartridge 1000 and into the docking station or another component of the system.

Figure 11:
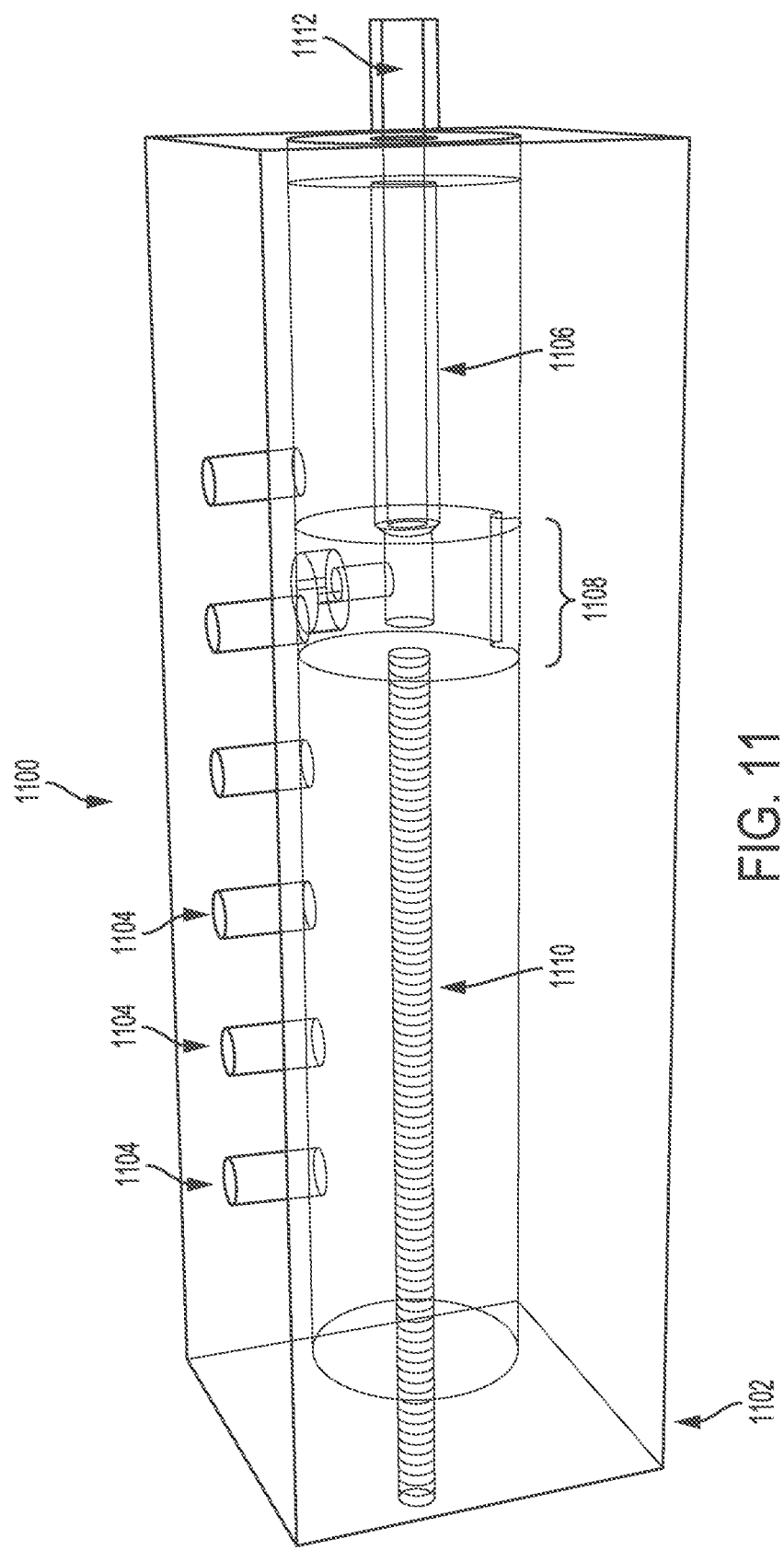
FIG. 11 depicts a pneumatic manifold for use in a cell culture system, in accordance with some embodiments.

FIG. 11 depicts a pneumatic manifold 1100 for use in a cell culture system, in accordance with some embodiments. In some embodiments, pneumatic manifold 1100 may share one or more characteristics in common with the pneumatic manifold discussed above with reference to FIG. 1, including that it may be configured for use with and/or incorporation in a docking station such as docking station 102. As discussed above, a pneumatic manifold may in some embodiments be used to selectively pneumatically couple a single source of vacuum/pressure with one or many pneumatic input lines of a multiwell device, in order to selectively actuate pneumatically-controlled elements of the device such as valves and/or pumps.

In some embodiments, such as those having fewer wells on a single plate (e.g., 6-well plates), one solenoid valve may be used per well. However, in some embodiments, a design with one solenoid valve per plate may not be cost-effective, spatially feasible, or convenient to manufacture for a plate having a higher number of wells (e.g., 48 wells or more, 96 wells or more). Thus, in some embodiments, the pneumatic layers discussed herein may be used in order to enable each of a large number of wells (e.g., 48 wells, 96 wells, or more) to be individually addressable by allowing for selective connection and disconnection of dozens or scores of pneumatic input lines from a single source of vacuum and/or pressure. In some embodiments, a pneumatic manifold may be driven by a stepper motor. The manifold may reduce the number of solenoid valves for individual well addressing of a 96-well plate from 96 (using a one-solenoid-valve-to-one-well ratio) to just one solenoid valve, thereby greatly reducing cost and manufacturing efficiency.

As shown in FIG. 11, pneumatic manifold 1100 may comprise enclosure 1102, output ports 1104, piston rail 1106, port selector 1108, piston screw 1110, and input port 1112.

As shown, enclosure 1102 may form a housing for one or more of the other components of pneumatic manifold 1100, and enclosure 1102 may comprise a plurality of output ports 1104. In some embodiments, each one of output ports 1104 may be configured to be pneumatically coupled to a pneumatic input port of a multiwell device, such that vacuum and/or pressure may be conveyed from manifold 1100 to a selected one of the input ports of the connected multiwell device.

Inside enclosure 1102, piston rail 1106 and piston screw 1110 may be configured to enable lateral movement of port selector 1108 along the length of manifold 1100. By moving laterally along the length of manifold 1100 via piston rail 1106 and piston screw 1110, port selector 1108 may selectively pneumatically couple and decouple with any one of output ports 1104. In some embodiments, the position of port selector 1108 may be driven by a stepper motor. Thus, by selectively pneumatically coupling with one of output ports 1104, port selector 1108 may couple the selected output port to input port 1112, such that pneumatic force may be conveyed from a pneumatic source connected to input port 1112 through manifold 1100 and to a connected multiwell device.

In some embodiments, operation of pneumatic manifold 1100 may be controlled by a stepper motor, and may be electronically controlled by one or more computerized control systems of an associated device or system, such as a control system of docking station 102 and/or system 100.

Figure 12:
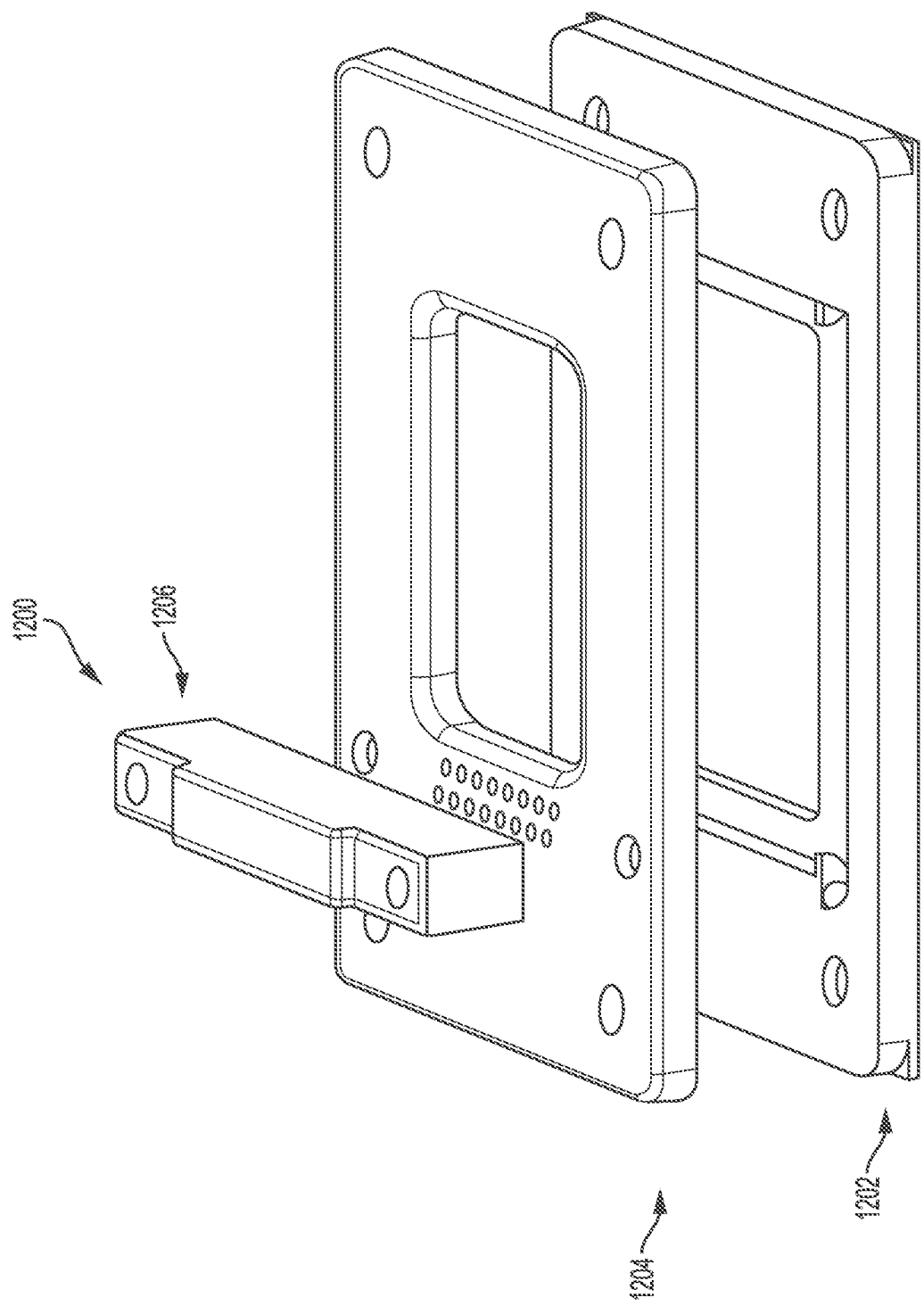
FIG. 12 depicts a manifold adapter for use in a cell culture system, in accordance with some embodiments.

FIG. 12 depicts a manifold adapter 1200 for use in a cell culture system, in accordance with some embodiment. In some embodiments, manifold adapter 1200 may be a portable device, and/or may allow for fast, reliable, and convenient connection of a microfluidic chip without the need for UV/$O_3$ bonding with a glass substrate. In some embodiments, manifold adapter 1200 may allow for pneumatic connection of a multiwell device to a pneumatic source of pressure and/or vacuum, in a similar manner as discussed above with respect to pneumatic manifold 1100. Where pneumatic manifold 1100 may facilitate selective pneumatic connection between input 1112 and one of outputs 1104 (for connection to a multiwell device), manifold adapter 1200 may facilitate pneumatic connection between a plurality of pneumatic inputs and a plurality of pneumatic outputs (for connection to a multiwell device).

As shown in FIG. 12, manifold adapter 1200 may comprise base portion 1202, which may be configured to receive a multiwell device and which may in some embodiments comprise one or more heating elements (e.g., an Indium Tin Oxide (ITO) heating element, or other suitable heating element) configured to regulate a temperature of the multiwell device when the multiwell device is inserted in the base portion.

Base portion 1202 may further comprise one or more electronic connection ports configured to send and/or receive electronic signals regarding monitoring and control of a multiwell device, and its functionalities, connected to adapter 1200. For example, the electronic connection ports of base portion 1202 may be configured to send and receive signals regarding monitoring and/or adjusting one or more characteristics of an environment inside a multiwell device, and/or may be configured to send and receive signals regarding electronic control of one or more valves controlling flow of fluid inside a multiwell device.

Manifold adapter 1200 may further comprise lid portion 1204, which may be configured to hold the multiwell device in place in base portion 1202, such as by fitting over top of the multiwell device and being secured in place by one or more clamps and/or screws.

Manifold adapter 1200 may further comprise pneumatic line connector 1206, which may be configured to pneumatically connect a source of vacuum and/or pressure to one or more pneumatic lines of a multiwell device. In some embodiments, pneumatic line connector 1206 may be configured such that a user may connect one or more pneumatic source lines to connector 1206 such that each of the lines may be connected to a corresponding pneumatic line of a multiwell device via a respective via-hole formed in the body of connector 1206. In some embodiments, connector 1206 may be secured to lid portion 1204 by one or more screws. In some embodiments, pneumatic line connector 1206 may be configured such that a user may disconnect connector 1206 from lid portion 1204, and the multiwell device inserted in adapter 1200 may then be in a sealed or closed condition and may, for example, be able to be physically moved or otherwise handled without being internally contaminated or otherwise compromised.

In some embodiments, manifold adapter 1200 may share some or all of the characteristics and capabilities of docking station 102 discussed above with reference to FIG. 1, including the capability to electronically, pneumatically, and/or fluidly connect to an inserted multiwell device such that one or more cell cultures, assays, and/or protocols may be carried out in the multiwell device while the multiwell device is connected. In some embodiments, manifold adapter 1200 may have a smaller physical form factor than docking station 102; in some embodiments docking station 102 may be configured for use in a benchtop or laboratory setting, while manifold adapter 1200 may be configured for use for microscopy and/or imaging application. (In some embodiments, one or more assays performed by a system disclosed herein may comprise microscopy measurements, such as live/dead staining of U2OS following a culture (see Example 1 below).)

In some embodiments, manifold adapter 1200 may comprise one or more computing elements configured to electronically communicate with a multiwell device inserted into manifold adapter 1200. In some embodiments, manifold adapter 1200 may connect to a multiwell device via wired electronic connections in a same or similar manner as docking station 102. In some embodiments, manifold adapter 1200 may be configured to communicate with one or more sensors and/or a sensor layer of a multiwell device inserted into manifold adapter 1200

In some embodiments, manifold adapter 1200 may comprise a sensor array configured to be attached to a multiwell device or to otherwise sense one or more characteristics of a microenvironment of a multiwell device and/or of an environment surrounding a multiwell device or surrounding manifold adapter 1200.

Described below are three Examples consistent with the systems, methods, techniques, and devices set out herein.

Example 1—Seeding and Culturing U2OS Cells for at Least 24 Hours

Materials and Reagents:
Cleaning/sterilization solutions: 70% ethanol (EtOH), 1M sodium-hydroxide (NaOH), 1× phosphate-buffered saline (PBS);

Cell culture reagents: Media—DMEM/F-12, Gluta-MAX™ supplement (Giboco)+20 mM HEPES (4-(2-hydroxyethyl)-1-piperazineethanesulfonic acid)+1× Penicillin Streptomycin (Pen-Strep)+10% fetal bovine serum (FBS), TrypLE™ Express Enzyme (1×), phenol red Cell Preparation:

Cell line derived from U2OS cells were seeded in a standard 6 well (35 mm) multi well plate and cultured for 3-5 days prior transfer into the microfluidic chip. Cells were prepared in standard tissue culture environment and after seeding (2.5E5 cells/mL) in a standard 6 well plate, 2 ml of cell culture media was added into each well containing U2OS cells. The 6 well plate was then transferred into a tissue culture incubator (5% CO2). Media was exchanged every 48 hours to ensure proper cell culture conditions and nutrient supply. Visual inspection was used to determine a cell confluency. U2OS cells were then selected for microfluidic cell culture once confluency of the wells reached approximately 75-80% per well. The 6 well plate was then transferred to a biological safety hood, surface sterilization of the closed well plate and any equipment and components used was ensured by spraying a 70% EtOH solution over the surface for a contact time of at least 1 min before further handling.

In the meantime the media and other used reagents were warmed up to 37 C using a water-bath.

Dissociation of Cultured Cells:

To dissociate the cultured cells in the standard 6 well plate the media from the wells was aspirated using a sterile pipet and a liquid waste trap under the vacuum. After aspiration of the media the cell layer was rinsed with 3 mL of sterile 1×PBS solution, aspirated and 0.5 mL of TrypLE was added to the wells for 2 minutes 30 seconds.

Determination of the exact/best contact time of the disassociation reagent with the cells was determined in several iterations of post seeding and adhesion experiments in the assembled microfluidic chip. The disassociation/contact time has direct effect on the adhesion ability of the cells within the microfluidic chip; the adhesion to the glass substrate layer. Higher disassociation times result in longer adhesion times to the substrate layer of the microfluidic chip, since more surface proteins for adhesion are denatured and need to be resynthesized or replaced.

After the 2 min 30 sec contact time with TripLE 3 mL of media was added to each well with the disassociation reagent to quench the effect of the reagent. The 6 well plate was manually agitated by vigorously rocking the well plate against the palm of the hand to dissociate the cells within the well.

The disassociated cell-media-reagent suspension was then transferred to a 15 mL falcon tube, transferred to a bench top centrifuge and centrifuged at 1200 rpm for 3 min. The supernatant TripLE/media solution was eluted from the 15 mL falcon tube within the biosafety cabinet, again any transfer in/out was associated with a surface sterilization of the equipment using a 70% EtOH solution.

The cell pellet was then resuspended with 0.5 mL of fresh media by careful agitation of the solution within the tube using a standard pipet. Thereafter the cell suspension is then transferred to a 1.5 mL Eppendorf tube.

The cell suspension is now prepared for seeding to the microfluidic chip. Prior to seeding 10 μL of the cell suspension were used for cell counting. Target cell concentration for seeding into the microfluidic chip is about 1.0-4.0E6 cells/mL.

Microfluidic Chip Preparation/Cleaning:

Prior cell loading to the microfluidic chip the assembled chip was cleaned with several solvents to ensure full sterility of the microenvironment. At the same time as the cleaning protocol will rinse and clean the chip, the integrated indium-tin oxide (ITO) heating element will be connected to the systems' heating port connection and the element will heat the microfluidic chip to 37 C throughout the cleaning protocol.

To clean the chip four 15 mL falcon tubes are filled with 1) 70% ethanol, 2) 1M sodium-hydroxide (NaOH), 3) 1×PBS and 4) media for later automated cell culture.

Each falcon tube lid will be punctured with a 1.5 mm biopsy punch to insert the tubing as well as a secondary 1.5 mm hole in which a sterile, HEPA filtered, 200 μL pipet tip will be inserted. This filtered pipet tip will ensure sterility and pressure equilibration due to extracted media through the tubing through the micro pump operation.

To connect the reagents from the falcon tubes to the microfluidic chip Tygon tubing (0.64 mm I.D./1.59 mm O.D.) was connected to both inlets and to the outlet of the microfluidic chip. The outlet tubing was then connected to a 50 mL empty falcon tube to collect the waste and reagents from the cleaning cycle. Tubing at inlet 1 as well as tubing connected to inlet 2 are connected to the 70% ethanol solution. (Note that the numbering conventions used in this example protocol the same as shown in FIG. 6W.) The individual falcon tubes with the cleaning solutions and the waste tube were placed in close proximity of the microfluidic chip in standard falcon tube holder.

Using the graphical user interface (GUI) the cleaning cycle was initiated using a similar protocol of the automated perfusion program that later will be configured for the automated media exchange during the long term cell culture experiments.

Prior to using the automated protocol, the connected tubing was filled with the ethanol solution using a direct system control setting by opening main inlet 1, row valve 2 and perfusion valve at 175 ms step-time and 500 pump-strokes. This facilitates that the tubing will be filled with the ethanol solution and the main perfusion channels of the chip are filled as well. After this step the same settings (with the only difference being inlet 2 instead of inlet 1) are used to rinse inlet 2 and corresponding tubing with the ethanol solution. Once this process has finished the tubing from inlet 2 is transferred to the 1M NaOH solution and the process is repeated. Thereafter the tubing from inlet 2 is transferred to the PBS solution and the process is repeated.

The main parameter to be configured in the interface for cleaning the chip with an automated cleaning protocol are 1) step-time of the micro-pump actuation, 2) number of repetitions/pump-strokes per a) rinsing the fluidic perfusion channels and b) perfusing/cleaning the individual addressable wells and 3) system pause between one cycle of operation (rinsing of each perfusion row and each individual well). The parameters used for the microfluidic chip cleaning protocol are 1) 175 ms step-time, 2) a) 15 pump-strokes per perfusion channel and b) 10×8 pump-strokes per individual addressable well and 3) 2 minute pause in-between each cycle of operation.

The system then starts automatically to cycle between the perfusion channels and the individual addressable wells and rinses these chip compartments with the ethanol solution connected to inlet 1. The rinsed waste is collected in the 50 ml falcon tube connected to the outlet port.

After 15 minutes of cleaning with the ethanol solution, the tubing from inlet 1 is then transferred from the ethanol falcon tube to the 1M NaOH solution during a system pause step. Now the system will continue the cleaning protocol but instead of pulling ethanol the 1M NaOH solution will be perfused into the chip and the individual chip compartments. This cleaning cycle will be left to operate for another 60 minutes with the same system configurations for perfusion. After 60 minutes of rinsing the system with 1M NaOH the tubing is then transferred from the 1M NaOH solution to the 1×PBS solution in the same fashion as the first change from 70% ethanol to 1M NaOH during a system pause between cleaning cycles.

After another 60 minutes of perfusion of the microfluidic chip with 1×PBS the inlet is then transferred to the falcon tube containing the media for the later automated cell culture experiment in the same fashion as the prior transfers from one falcon tube to the next.

A final cleaning cycle of 30 minutes using the media from inlet port 1 ensures that the micro-environment in the microfluidic chip is already adjusted to the later cell culture conditions.

At the same time the user can prepare the cell suspension used for the experiment as described above. Once the last cleaning step, rinsing the microfluidic chip with media, is completed the automated cleaning protocol is stopped. The connected media in inlet 1 will be left connected to the chip. Prior to detachment of tubing in inlet 2, the tubing from that inlet is also transferred to the media solution and a final perfusion of media through inlet 2 at 175 ms step-time and a perfusion of 150-250 pump-strokes is performed. Thereafter tubing from inlet 2 is detached and a sterile 200 μL pipet tip with HEPA filter is placed in the inlet port 2 to avoid contamination. The waste tube connected to the outlet will be removed and replaced with a new empty/sterile 50 mL falcon tube.

By now the ITO heating element will also have adjusted the temperature of the chip to 37 C (the temperature for individual cell lines and biological applications might vary and can be adjusted by the user in the system settings).

Cell Loading and Adhesion Time Setting:

While the system performs the microfluidic chip cleaning protocol the user can prepare the cell suspension used for seeding as discussed earlier.

The systems' GUI can now be reprogrammed for the automated cell culture experiment including automated seeding of cells to the individual addressable wells.

Main parameter required (parameters might differ from cell line to cell line and biological application and assay) for this protocol are 1) step-time for the micro-pump actuation, 2) number of repetitions/pump-strokes per a) rinsing the fluidic perfusion channels and b) perfusing the individual addressable wells, 3) number of pump-strokes for seeding cells into the individual addressable wells, 4) adhesion time for the cells in the wells after seeding and 5) system pause in-between perfusion interval of the individual wells determining the perfusion duty cycle. Once these parameters are set the user can proceed to add the cell suspension and start the automated cell culture protocol.

The used settings for culturing a cell line derived from U2OS cells are 1) 175 ms, 2a) 15 pump-strokes per perfusion channel, 2b) 3×8 pump strokes per individual addressable well, 3) 5 pump-strokes for seeding the cell suspension into the individual addressable wells, 4) 60 minutes adhesion time after cells have been loaded into the individual addressable wells and 5) 15 minutes pause in-between the individual perfusion cycles.

The user now uses a standard laboratory pipet and a 200 μL pipet tip with HEPA filter to extract 100 μL of the prepared cell suspension. The pipet tip is then inserted into inlet 2 where it replaces the empty pipet tip placed earlier to avoid contaminations on the microfluidic chip and detached from the pipet. The HEPA filter within the pipet tip ensures that the cell suspension is not exposed to environmental contaminations.

Now the automated cell culture and cell loading profile can be started by the user. An interactive interface checks the inserted parameters with the user and after confirmation the protocol is initiated. A short delay of 60 seconds allows the cell suspension to sediment slightly within the attached pipet tip.

The system now opens inlet valve 2, row valve 1 and the flush valve and pumps 50+15 pump-strokes of the cell suspension into the microfluidic chip to ensure that the cell suspension is inserted into the microfluidic chip. Once the perfusion channel 1 is filled the flush valve closes and well 1 valves open and a total of 5 pump-strokes (earlier defined by the user as described above in point 3) of the protocol settings) are delivered to well 1. Thereafter well 1 valves close and well 2 valves open and 5 pump-strokes are delivered to well 2. After the wells in row 1 are filled the row 1 valve closes and row valve 2 and the flush valve open. The perfusion channel in row 2 is now perfused with 15 pump-strokes after which the flush valve closes and well 3 valves open and 5 pump-strokes are delivered to well 3.

Thereafter well 3 valves close and well 4 valves open and 5 pump-strokes are delivered to well 4. After the wells in row 2 are filled the row 2 valve closes and row valve 3 and the flush valve open. The perfusion channel in row 3 is now perfused with 15 pump-strokes after which the flush valve closes and well 5 valves open and 5 pump-strokes are delivered to well 5.

Thereafter well 5 valves close and well 6 valves open and 5 pump-strokes are delivered to well 6.

Now each well in the chip has been filled with 5 pump-strokes of the cell suspension from inlet 2. Immediately after inlet 2 is closed.

The system now opens inlet valve 1, row valve 1 and the flush valve and pumps 75 pump-strokes of the connected media from inlet 1 into the microfluidic chip to rinse any remaining cell suspension still within the perfusion channel in row 1 out of the microfluidic system and into the waste.

After the perfusion channel in row 1 is rinsed the row 1 valve closes and row valve 2 opens (flush valve still open). The perfusion channel in row 2 is now perfused with 75 pump-strokes.

After the perfusion channel in row 2 is rinsed the row 2 valve closes and row valve 3 opens (flush valve still open). The perfusion channel in row 3 is now perfused with 75 pump-strokes.

During the cleaning of the perfusion channels all well valves remain closed. After this cleaning cycle of the perfusion channels in the rows, the system repeats the same perfusion channel cleaning process once more.

Once the cleaning of the second cycle of cleaning the perfusion channels is complete the system is initiating the cell adhesion pause for 60 minutes (specified by the user earlier in point 4) of the protocol settings) and closes inlet valve 1, row valve 3 and flush valve. In this time the cells will start to sediment within the wells and adhere to the substrate and start attaching.

Now the user can replace the remaining cell suspension within the pipet tip in inlet 2 with a sterile pipet tip with HEPA filter and dispose or reseed the remaining cell suspension in a standard well plate in the tissue culture and run it as a control experiment in the standard incubator conditions.

After the predetermined cell adhesion time the system reopens inlet valve 1, row valve 1 and flush valve and will exchange the media in the perfusion channel in row 1. Therefore, the system uses the by the user specified pump-strokes per perfusion channel in 2a) and exchanges the media in the perfusion channel by 15 pump-strokes.

Once the perfusion channel 1 is filled the flush valve closes and well 1 valves open and a total of 3×8 pump-strokes (earlier defined by the user as described above in point 2b) of the protocol settings) are delivered to well 1. Thereafter well 1 valves close and well 2 valves open and 3×8 pump-strokes are delivered to well 2. After the wells in row 1 are filled the row 1 valve closes and row valve 2 and the flush valve open. The perfusion channel in row 2 is now perfused with 15 pump-strokes after which the flush valve closes and well 3 valves open and 3×8 pump-strokes are delivered to well 3.

Thereafter well 3 valves close and well 4 valves open and 3×8 pump-strokes are delivered to well 4. After the wells in row 2 are filled the row 2 valve closes and row valve 3 and the flush valve open. The perfusion channel in row 3 is now perfused with 15 pump-strokes after which the flush valve closes and well 5 valves open and 3×8 pump-strokes are delivered to well 5. Thereafter well 5 valves close and well 6 valves open and 3×8 pump-strokes are delivered to well 6. Once the well 6 has been exchanged with fresh media the next system pause is initiated for 15 minutes (previously defined by the user in point 5). This completes the general operational procedure of media perfusion to the individual wells for an automated cell culture protocol.

Using the portable manifold connector, the user can position the microfluidic chip within and place the assembled setup on either a standard inverted microscope or automated plate reader system. This configuration allows for visual inspection during cell loading and the later automated cell culture of the wells. Furthermore, it allows for time-lapse recording of the microfluidic automated cell culture within the individual addressable wells. Using such a system configuration we were able to record images of cell adhesion and proliferation within the wells over the period of at least 72 hours.

Example 2—Long-Term Cell Culture of U2OS in a Multiwell Device

Figure 13A:
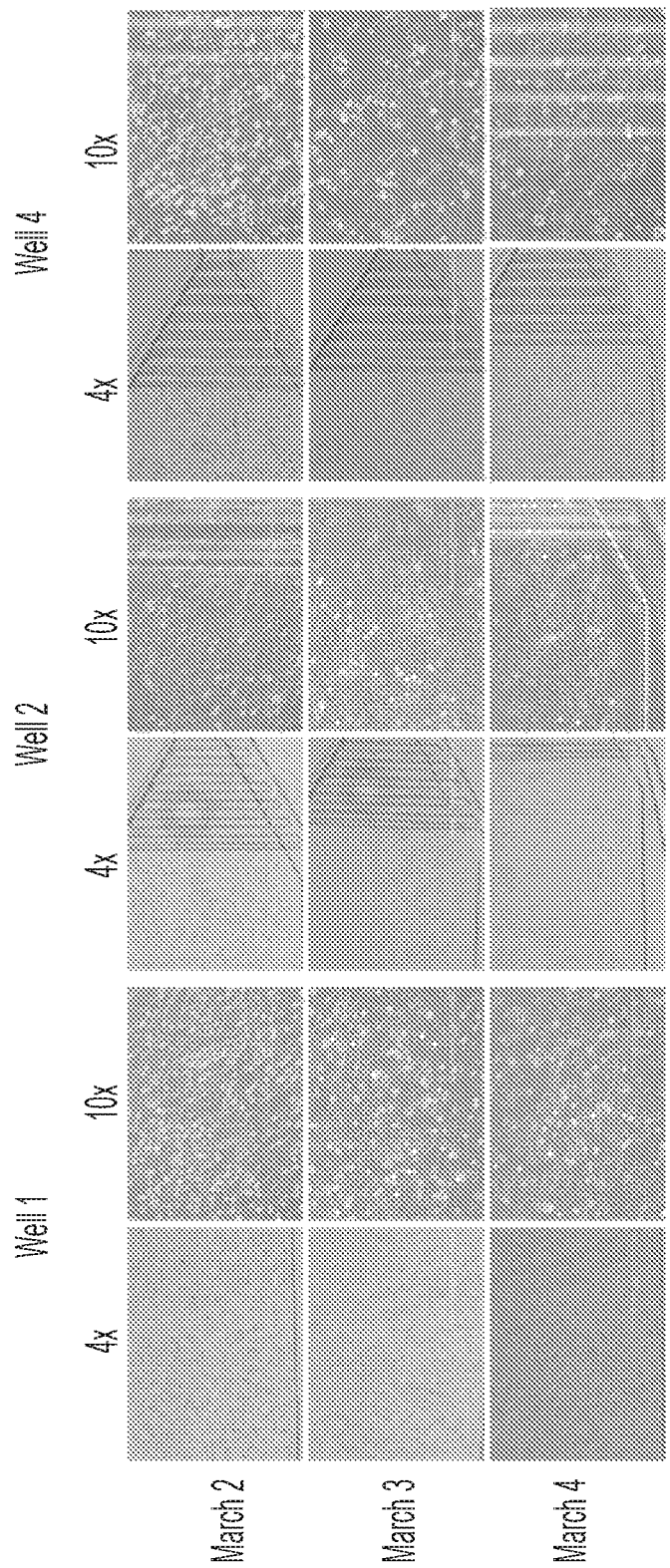
FIG. 13A depicts long term cell culture in a multiwell device, in accordance with some embodiments.

FIG. 13A depicts long term cell culture in a multiwell device, in accordance with some embodiments. Cells were seeded in a microfluidic chip and reached confluency the day after seeding in wells 1 and 2. Wells 1 and 2 were passaged using TrypLE after imaging on the day after seeding. Cultures were maintained with media exchanges every 15 minutes for 3×8 pump-strokes per well.

In some embodiments, the cell culture depicted in FIG. 13A may be consistent with all or part of the protocol set out above in Example 1.

Example 3—Long-Term Cell Culture of U2OS in a Multiwell Device

Figure 13B:
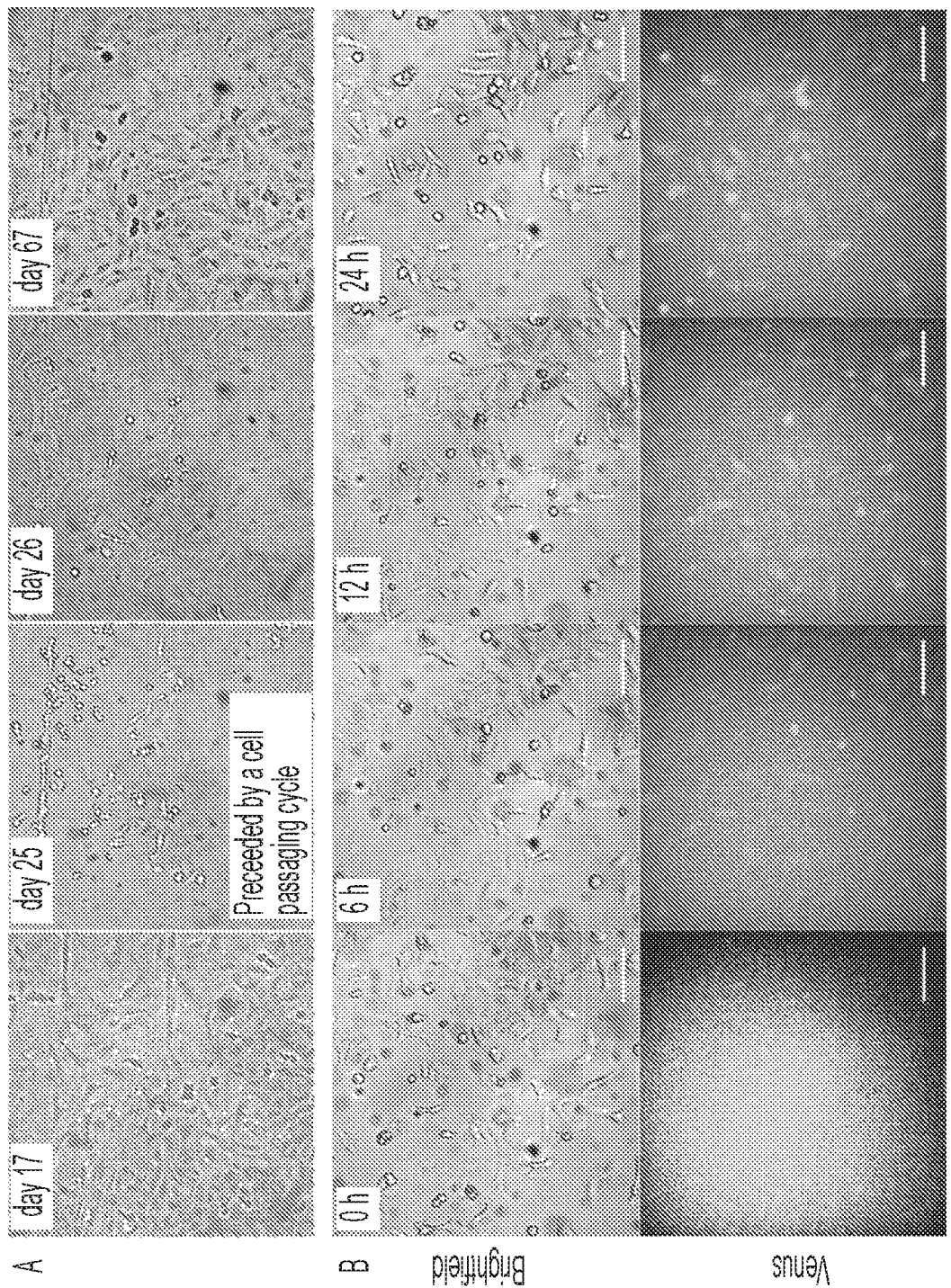
FIG. 13B depicts long term cell culture in a multiwell device, in accordance with some embodiments.

FIG. 13B depicts long term cell culture in a multiwell device, in accordance with some embodiments.

Part A depicts long-term culture in a multiwell device. U2OS cells were seeded in one well in a microfluidic chip and growth was monitored (days 17, 25, 26, and 67 are shown). Cultures were maintained with media exchanges every 15 minutes for 3×8 pump-strokes over a period of 72 days during which they were automatically passaged every two days. An example of a cell passaging event is shown on day 25: cells were passaged before acquisition of the image and reattachment and growth of the passaged cells is evident on day 26.

Part B depicts induction of Venus fluorescent reporter expression in a U2OS reporter cell line. Brightfield and fluorescence image pairs are shown. Six hours after changing to media with 100 ng/mL doxycycline, expression of an inducible Venus reporter is observed and fluorescence levels continue increasing until 24 h when the experiment was terminated. (Scalebar=100 µm.)

Example 4—Perturbation by Nutrient Starvation

Figure 13C:
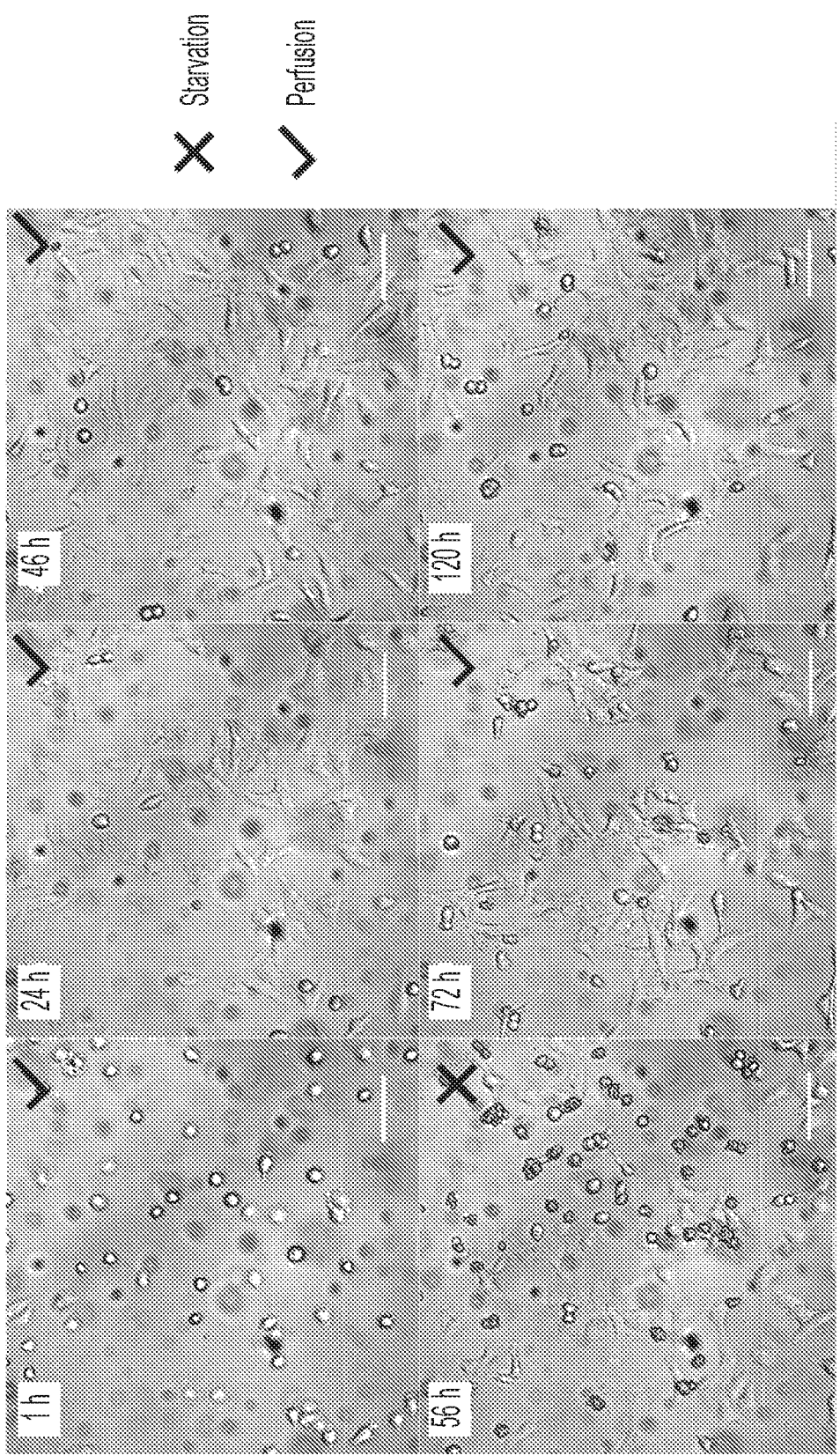
FIG. 13C depicts perturbation of a cell culture in a multiwell device by nutrient starvation, in accordance with some embodiments.

FIG. 13C depicts perturbation of a cell culture in a multiwall device by nutrient starvation, in accordance with some embodiments.

Images show U2OS cells at different time points after automated seeding of the cell culture and adhesion to a glass substrate (at 1, 24, 46, 52 and 72 hours). Cultures were maintained by perfusion with fresh media every 15 minutes (indicated by a check mark), and nutrient starvation conditions were generated by pausing perfusion (indicated by a cross). Cells were starved for 16 hours immediately following the 46-hour time point. Cells show significant changes in morphology and decreased substrate attachment during starvation (see 56-hour time point). To stop starvation, regular media exchanges by perfusion were resumed, and cells were observed to recover and continue proliferating (see 72-hour and 120-hour time points). (Scalebar=100 µm.)

Example 5—Perturbation by Nutrient Starvation

Figure 13D:
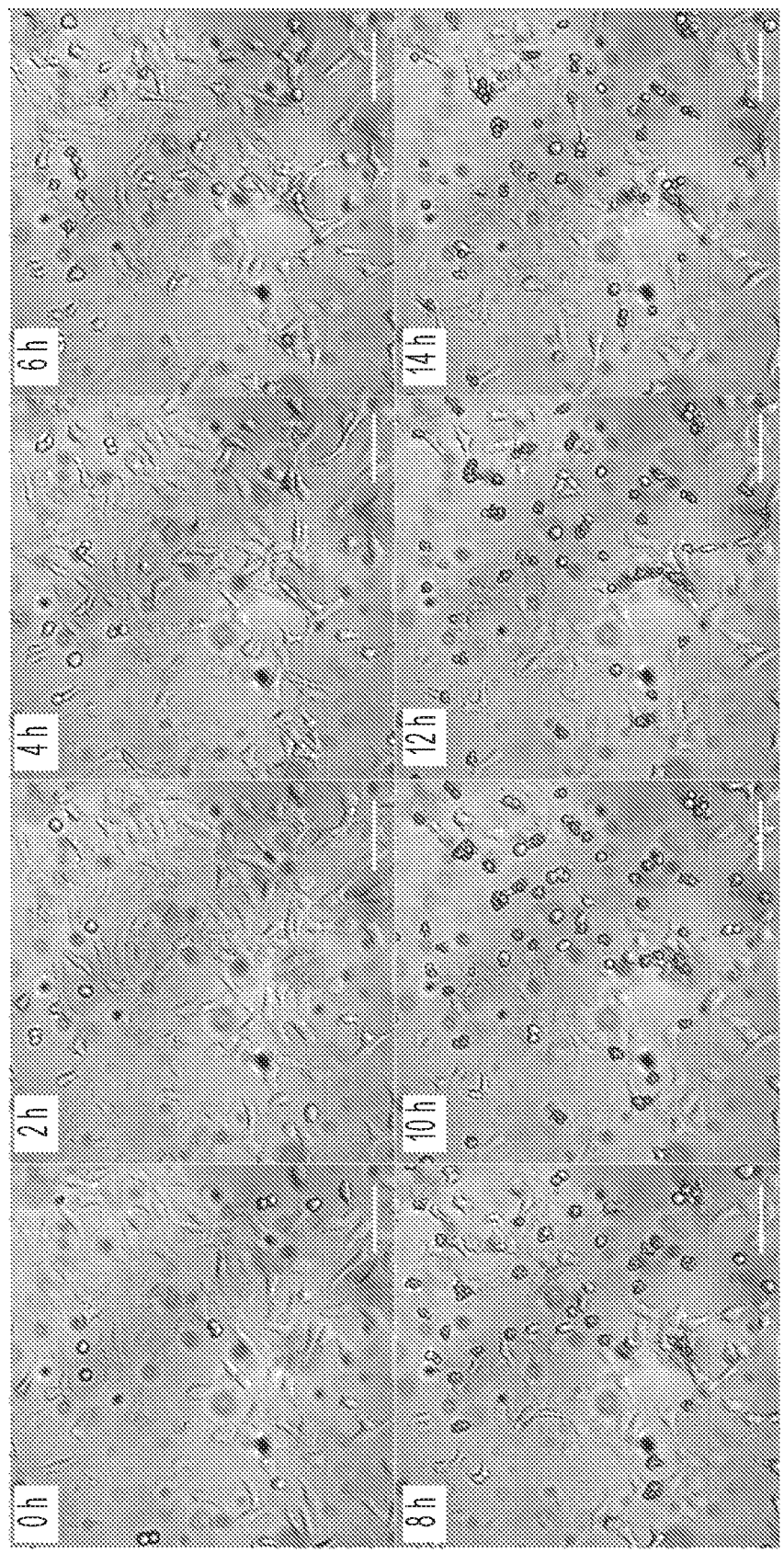
FIG. 13D depicts perturbation of a cell culture in a multiwell device by nutrient starvation, in accordance with some embodiments.

FIG. 13D depicts perturbation of a cell culture in a multiwall device by nutrient starvation, in accordance with some embodiments.

FIG. 13D shows the response of a U2OS cell culture in a microfluidics chip during nutrient starvation as a perturbation, as described above with respect to FIG. 13C. Time-lapse images acquired every two hours are shown. Starvation conditions resulting from paused media perfusion were started at time 0, which corresponds to the 46-hour timepoint in FIG. 13C. During starvation, rapid changes in cellular morphology were observed after six to eight hours, with cells rounding up and detaching from the substrate, indicative of cellular stress and apoptotic pathways. These changes became progressively more apparent with a corresponding increase in cell detachment in subsequent hours of nutrient starvation. (Scalebar=100 µm.)

Example 6—Sampling and Recovery of U2OS Cells

Figure 13E:
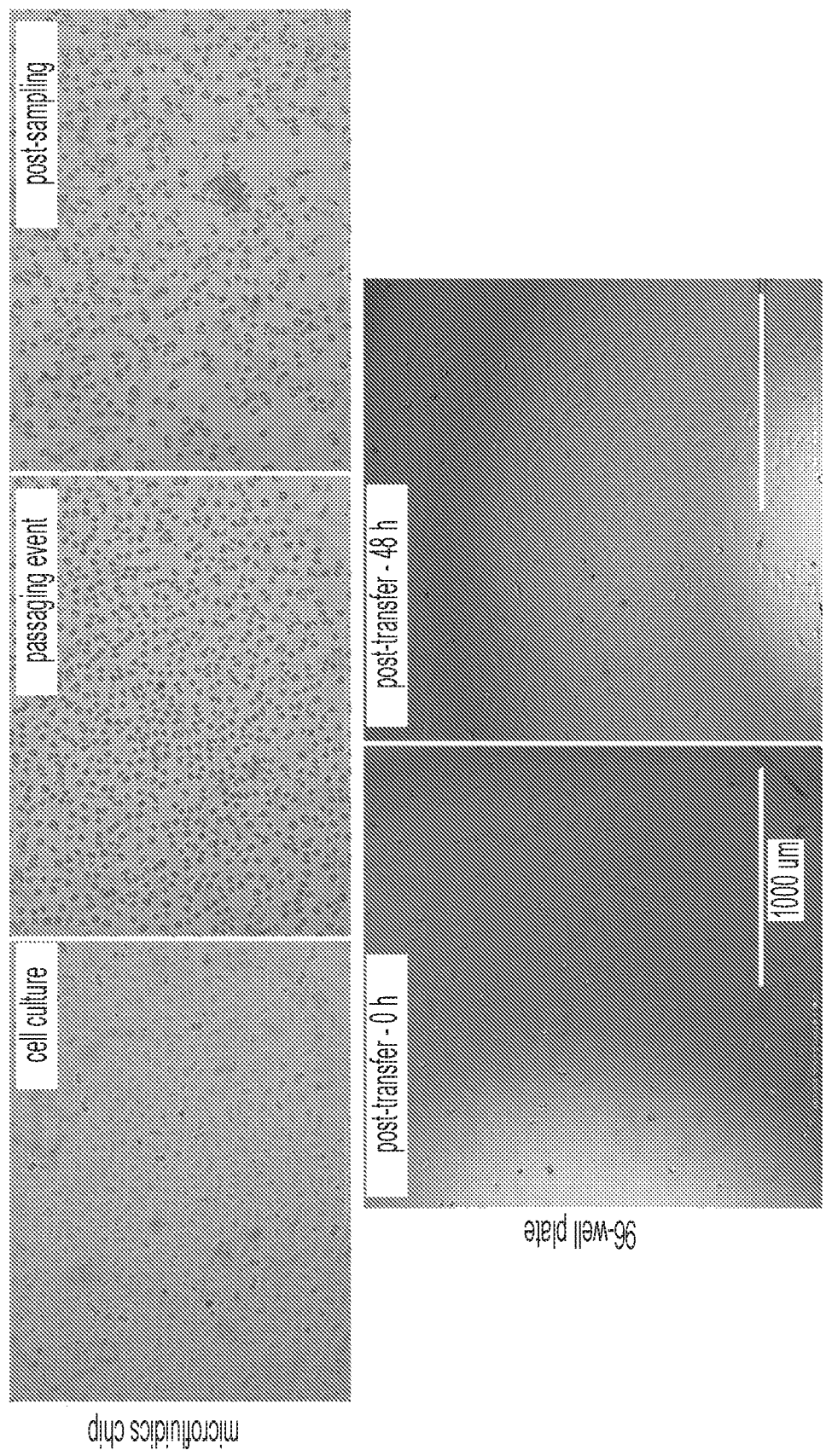
FIG. 13E depicts sampling and recovery of U2OS cells, in accordance with some embodiments.

FIG. 13E depicts sampling and recovery of U2OS cells, in accordance with some embodiments. U2OS cells maintained in culture in the microfluidics chip for two days (top left panel) were detached using TrypLE by triggering a passaging event (top middle panel). A sample of the cells was collected in an Eppendorf tube to transfer to standard tissue culture growth conditions (96-well plate; bottom panels). A large fraction of the cells, which remained in the chip after the sampling event (top right panel) continued to grow and proliferate. Prior to transfer to the 96-well plate (bottom left panel), cells were spun down and media was exchanged. Cells grew and proliferated normally post-transfer as evidenced after 48 hours (bottom right panel). (Scalebar=1 mm.)

Example 7—Cell Adhesion of U2OS in a Microfluidic Chip

Figure 14:
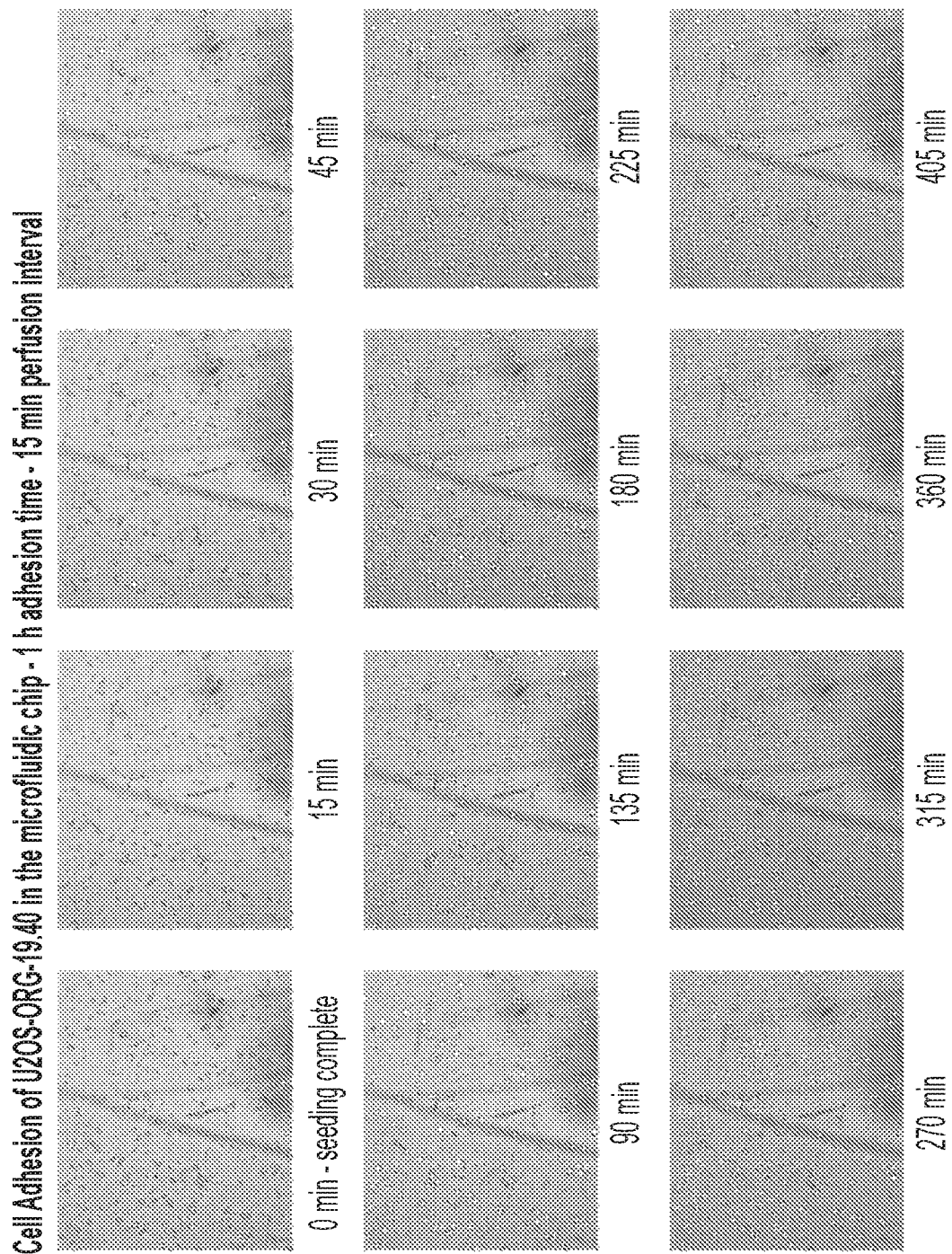
FIG. 14 depicts cell adhesion in a microfluidic chip, in accordance with some embodiments.

FIG. 14 depicts cell adhesion in a microfluidic chip, in accordance with some embodiments. FIG. 14 depicts cell adhesion of a cell line derived from U2OS cells in a microfluidic chip, with one hour adhesion time and 15 minute perfusion interval. The 0-minute image shows the added cells in a well after seeding was completed.

Described below are methods and techniques for dynamic evolution/adaptation and monitoring of characteristics in living cells using a microfluidic-enabled multi-well cell culture device, such as the microfluidic-enabled multi-well cell culture devices and/or any one or more associated systems described above.

Figure 15:
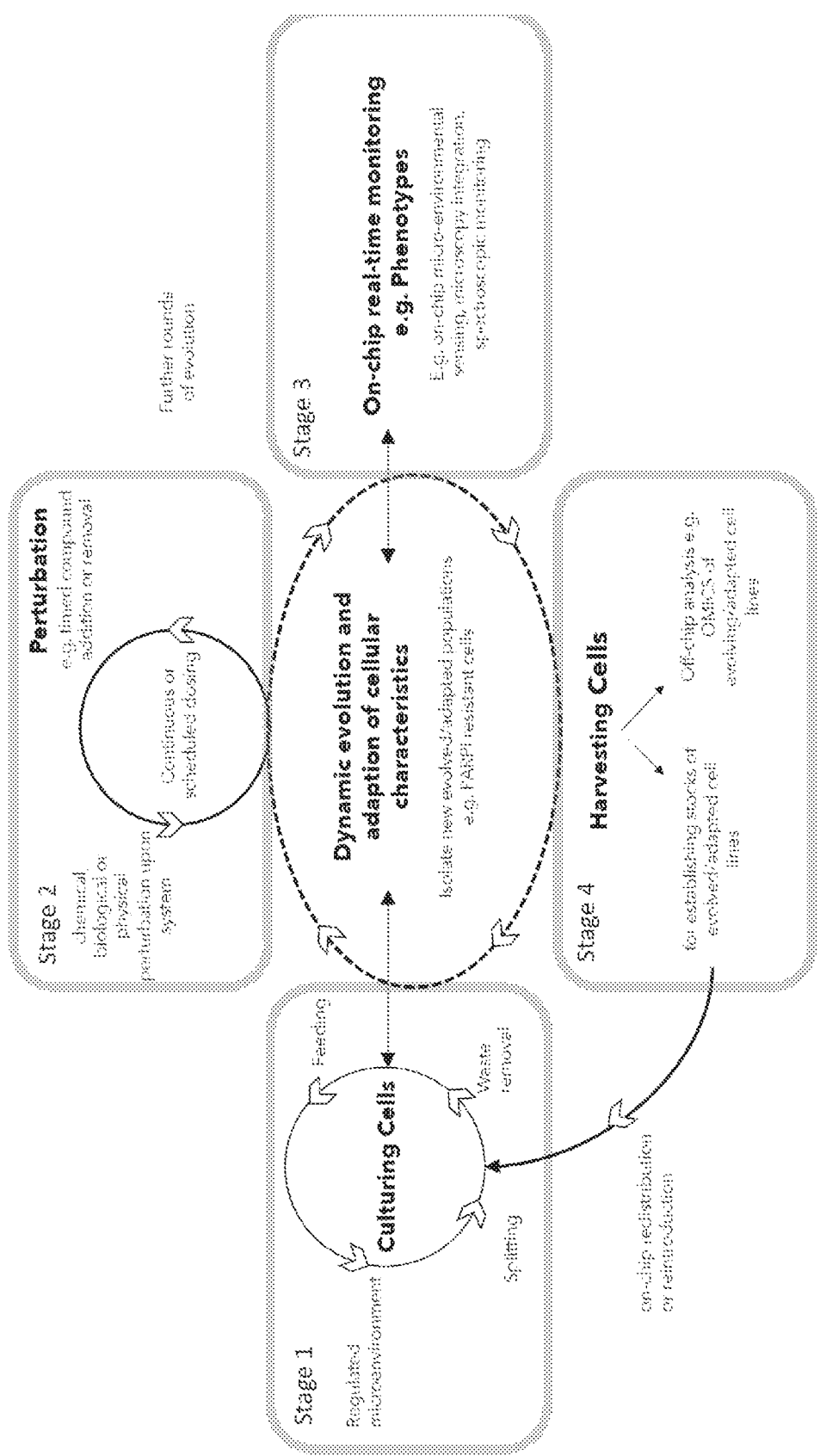
FIG. 15 depicts a graphical representation of a method for dynamic evolution/adaptation and monitoring of characteristics in living cells, in accordance with some embodiments.

FIG. 15 shows a graphical representation of a method 1500 for dynamic evolution/adaptation and monitoring of characteristics in living cells, in accordance with some embodiments. Method 1500 may be executed, in some embodiments, in whole or in part by an automated microfluidic-enabled cell-culture system and/or device as described herein, such as (but not limited to) system 100 and/or device 200.

As shown in FIG. 15, method 1500 may comprise four stages.

At block 1502, stage 1 comprises cell growth (e.g., cell culturing). At stage 1, cells may be seeded into one or more wells or the microfluidic device and may be allowed to culture into a larger cell population. In some embodiments, cell culturing at stage 1 may comprise feeding the cell population, splitting the cell population, and regulating a microenvironment of the one or more wells in which the cell population is growing such that the cell population is maintained in a live and healthy state so that the cell population may multiply and grow.

In some embodiments, seeding a well in advance of culturing a cell population at stage 1 may comprise causing a cell suspension to flow into the well. In some embodiments, the well may be an individually-addressable well as described elsewhere herein, and a microfluidic-enabled cell-culture system and/or device may cause the cell suspension to flow to the well without flowing to one or more other wells of the same device, including without flowing to one or more other wells of a same row and/or a same column of the same device. By enabling seeding a single individually addressable well to the exclusion of all other wells in a system, including other wells in the same row and the same column, overall experimental throughput may be drastically increased by allowing many experiments (e.g., many cycles as shown in FIG. 15) to be run in parallel with one another.

It should be noted that, in some embodiments, rather than seeding an individual well to the exclusion of all other wells in the plate, one or more wells may be seeded to the exclusion of one or more (but not necessarily all) other wells in the plate. That is, by operation of microfluidic valves and pumps in accordance with the techniques explained above, fluid may be caused to flow to two or more wells simultaneously to the exclusion of one or more other wells in the same well layer. For example, an entire row may be seeded simultaneously or an entire column may be seeded simultaneously. This may increase fluid throughput (and thereby increase efficiency) in experiments in which the same fluid is to be used for seeding of multiple wells. The same principle of optionally being able to address fluid to (or cause fluid to flow from) either (a) a single well to the exclusion of all other wells in the well layer, or (b) a plurality of wells to the exclusion of one or more other wells in the well layer, may apply equally to other method steps herein, including perturbing a well or wells by fluid flow, performing an assay on one or more wells involving directing the flow of fluid, and/or causing fluid to flow from one or more wells during a multi-stage perturbation step or a cell harvesting step.

In some embodiments, regulation of the microenvironment may be accomplished by one or more of the integrated components of a microfluidic-enabled cell-culture system or device, such as by using one or more integrated temperature sensors to monitor a temperature of a well and/or by using one or more integrated heating elements to control a temperature of the well. The systems described herein may enable monitoring and/or control of the microenvironment of an individual well, including the exclusion of other wells in the same row and/or the same column on a common plate, which may enable increased parallelization and efficiency as discussed above.

At block 1504, stage 2 comprises perturbation of the cell population that has grown in the well. Perturbing the cell population in the well may affect one or more observable characteristics of the cell population inside the first well, including the manner in which one or more phenotypes evolves and or in which one or more characteristic adapts in the cell population. In some embodiments, perturbation may include the introduction of any physical and/or environmental influence to the cell population in the well (e.g., introduction of a variable), including introduction of physical media/reagents and/or the modification of one or more environmental (e.g., microenvironmental) parameters.

In some embodiments, perturbing the cell population in the well may comprise introducing one or more fluids into the well and/or expelling one or more fluids from the well. In accordance with the systems described herein allowing individually addressing fluid flow to and from single wells, perturbation by flow of one or more fluids may be performed on an individual-well basis, therefore enabling increased experimental throughput by allowing parallelized experimentation as mentioned above with respect to block 1502. In some embodiments, a microenvironmental parameter modified by the flow of one or more fluids to or from the well may include one or more of temperature, pressure, pH, humidity, $CO_2$ level, $O_2$ level, confluency, fluid flow, shear stress, alkalinity, acidity, basicity, input fluid temperature, output fluid temperature, ambient light intensity, electrical potential, impedance, or resistance.

In some embodiments, perturbing the cell population in the well may comprise control of a microenvironmental parameter of a well, such as by using one or more control devices external to the microfluidic device (e.g., an external heating element, an external light source, etc.) and/or by using one or more integrated control devices (e.g., a heating element built into the microfluidic device, a light source built into the microfluidic device, a micromanipulator built into the microfluidic device, a mechanical actuator built into the microfluidic device, a pneumatic actuator built into the microfluidic device, a sonicator built into the microfluidic device, etc.) to modify the environmental parameter. For example, as discussed above with reference to regulating a microenvironmental temperature during culturing at stage 1, an integrated heating-element may also be used to alter a temperature of a microenvironment inside a well as part of a perturbation of the cell population in the well at stage 2. In some embodiments, a microenvironmental parameter modified by use of an external control device and/or an integrated control device may include one or more of temperature, pressure, humidity, $CO_2$ level, $O_2$ level, confluency, ambient light intensity, electrical potential, impedance, or resistance of the environment in the well.

In some embodiments, one or more perturbations may be performed in accordance with a predefined schedule. For example, reagents may be introduced into a well in a continuous manner, or they may be introduced into a well at predefined intervals (e.g., to simulate a drug dosing regimen, for example by introducing an amount of the reagent at four-hour intervals or six-hour intervals). Perturbations may be performed in accordance with user inputs, system settings, and/or dynamic/automatic determinations. Perturbations may thus be performed cyclically, in accordance with one or more cycles (e.g., pulsed, duty cycles, etc.), and/or in accordance with any predetermined schedules and/or timing regimens.

In some embodiments, all or part of the cell population (and/or non-cell material inside a well) may be removed from the well (e.g., caused to flow out of the well) following culturing and/or perturbation for a certain amount of time, and a portion of cells remaining in the well may then be subject to additional perturbations, or allowed to continue to grow and multiply. In some embodiments, removing a portion of cells (and/or non-cell material inside a well) from the well at this stage may be performed in accordance with techniques for removing cells (e.g., at a harvesting stage) as discussed below. In some embodiments, removing a portion of cells (and/or non-cell material inside a well) from the well at this stage may be performed in accordance user input, system settings, and/or automatic/dynamic determinations. In some embodiments, a portion of cell population (and/or non-cell material inside a well) may be removed from the well after the cells have become confluent and/or space in the well has become limited due to growth of the cell population. In some embodiments, removal of a portion of cell population (and/or non-cell material inside a well) may comprise allowing another portion of cell population (and/or another portion of non-cell material inside a well) to remain in the well, thereby allowing the remaining portion to continue to grow/culture/evolve/adapt and thereby enabling splitting/passaging of cells.

At block 1506, stage 3 comprises monitoring of the cell population following perturbation, including monitoring the cell population as it evolves/adapts. FIG. 15 shows the monitoring stage as occurring following the perturbation stage, though in some embodiments they may be performed at least partially simultaneously. Monitoring of the cell population before, following, and/or during perturbation may allow for the detection and observation of one or more characteristics (such as one or more phenotypes) of the perturbed cell population (including during and following evolution/adaptation of the cell population). In some embodiments, monitoring may be performed via one or more sensors integrated into the microfluidic-enabled cell-culture system and/or device, while in some embodiments the monitoring may be performed via one or more external or associated monitoring devices, such as an external microscope that may be used to observe the perturbed cell population while inside the well.

As with the culturing and perturbation stages discussed above, monitoring may also be performed, in some embodiments, on an individual-well basis, such that integrated sensors may detect one or more characteristics of a cell population (e.g., an evolved and/or adapted cell population) in a single well, external sensors may detect one or more characteristics of a cell population (e.g., an evolved and/or adapted cell population) in a single well, and performing one or more assays on the cell population in a single well (including by causing fluid to flow to the single well to the exclusion of other wells). In this way, monitoring parallelization may be improved.

Finally, at block 1508, stage 4 comprises harvesting of the cell population following perturbation and optionally following evolution and/or adaptation of the population of cells. As used herein, harvesting cells may refer to the removal of viable cells from a well. However, in some embodiments, techniques discussed herein with respect to removal of viable cells from a well for use in downstream culturing, perturbation, monitoring, or analysis, may also be applied to the removal of waste cells and/or waste fluids from a well in a microfluidic-enabled cell-culture device. Harvesting of cells may comprise the output of viable cells, including viable evolved and/or adapted cells, which may in some embodiments be facilitated by automated microfluidic automated addition of reagent(s) (e.g., trypsin) to dissociate attachment-dependent cell lines, and/or automated microfluidic removal of cells in the well. In some embodiments, the microfluidic control techniques discussed herein may be leveraged to allow harvesting of cells from a single well without harvesting cells from other wells in the same device, thereby increasing parallelization and efficiency as discussed above.

In some embodiments, a cell population may be harvested for off-chip analysis of the cell lines (e.g., evolved and/or adapted cell lines), for establishing stocks of cell lines (e.g., stocks of evolved and/or adapted cell lines), or for both. As shown in FIG. 15, the four stages shown at blocks 1502-1508 may proceed one after the other, and cells harvested at block 1508 may be used to establish stocks of cell lines and/or to seed cell culture for one or more additional cycles of stages 1-4.

Figure 16C:
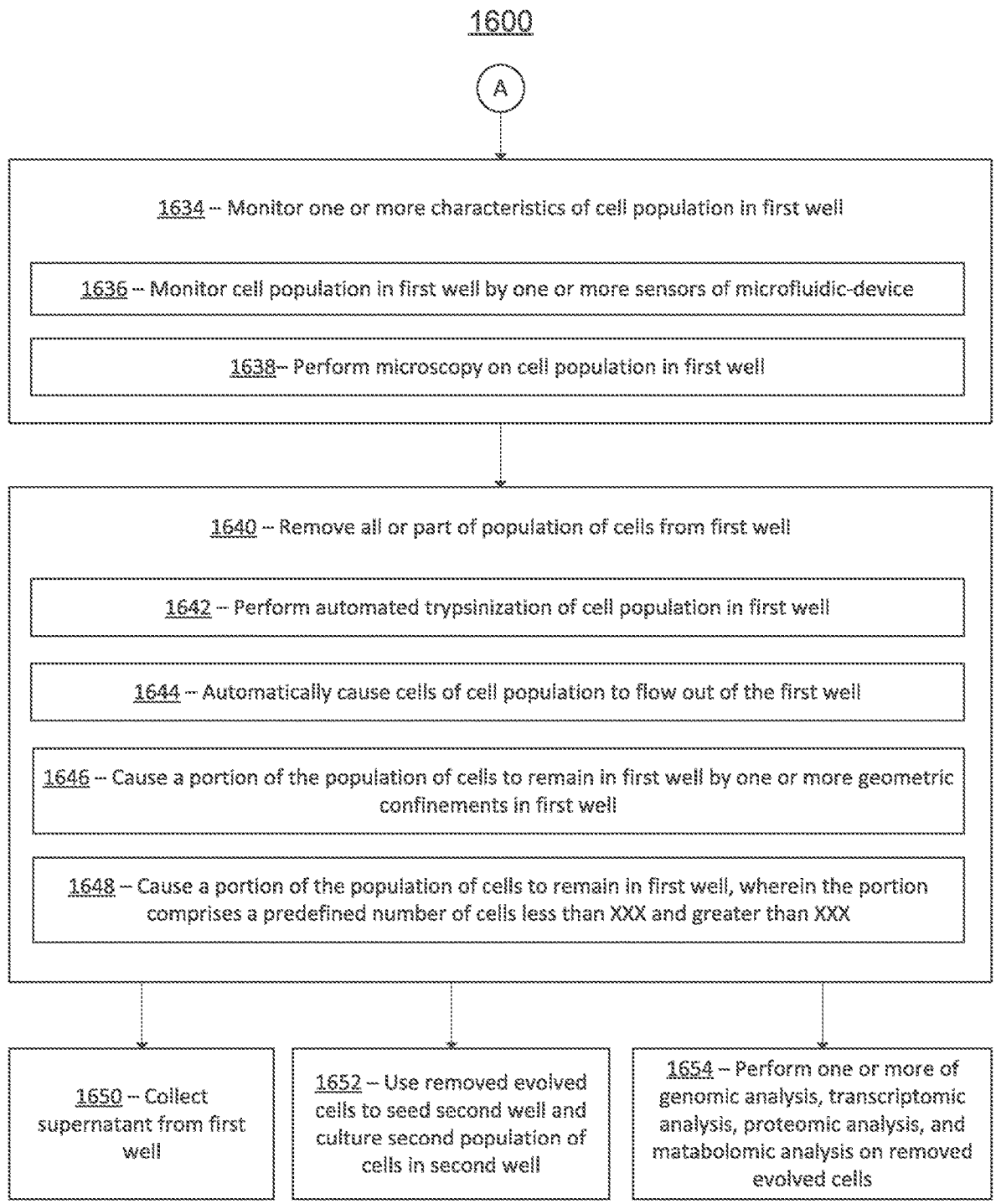

FIGS. 16A-16C shows a flow-chart representation of a method 1600 for dynamic evolution/adaptation and monitoring of characteristics in living cells, in accordance with some embodiments. In some embodiments, method 1600 may share some or all characteristics in common with method 1500 described above with respect to FIG. 15, including that it may comprise a culturing stage, a perturbation stage, a monitoring stage, and a harvesting stage. Method 1600 is be executed, in some embodiments, in whole or in part by an automated microfluidic-enabled cell-culture system and/or device as described herein, such as (but not limited to) system 100 and/or device 200.

At block 1602, in some embodiments, a well layer for a microfluidics device may be selected and attached to the microfluidics device. In some embodiments, a modular well layer such as well layer 302 described above with reference to FIG. 3 may be selected and attached to a microfluidic-enabled cell-culture device such as device 200. In some embodiments, this selection and attachment may be performed manually by a human user, or it may in some embodiments be performed automatically by one or more robotic systems.

As described above, modular systems with removable well layers may allow for a microfluidic-enabled cell-culture device to be reused many times over many different experiments, as the well layer may simply be replaced between different experiments without the need to replace one or more other layers or components of the system.

In some embodiments, utilizing a modular system in which a well layer (such as well layer 302) may be selected and attached to the system may allow the system to be adaptable to different experimental needs, such as different well geometries (e.g., specialized well geometries for 3D cultures), different well properties, different well layer materials, different micropatterning, different coating(s), different geometric confinements in one or more wells, and/or different optical properties of the well layer for monitoring/observation. Accordingly, a well layer may be selected in consideration of experimental needs of the culture/assays/protocols to be performed (e.g., experimental needs for seeding, culturing, perturbing, monitoring, removing, and/or harvesting the cells), including being automatically selected by a system (e.g., system 100) in accordance with inputs from a user regarding experimental needs.

At block 1604, in some embodiments, the selected well layer comprises cells loaded into a first well of the plurality of wells before attaching the well layer to the microfluidics device. That is, in some embodiments, rather than all cells being seeded into the well layer via microfluidic means, some or all cells for the cell culture method may be pre-loaded into (and in some embodiments cryopreserved in) a well layer before it is attached to the microfluidic cell-culture device. (Note that, herein with reference to FIG. 16, operations and techniques with respect to a "first well" of the plurality of wells are discussed. The first well as discussed herein may be any well of the plurality of wells. In some embodiments, these operations and techniques may be equally applicable any other well of the plurality of wells in addition to and/or in place of the first well.) Utilizing a modular microfluidic device in which a well layer may be selected and attached to the device may allow for efficient and simple use of pre-seeded wells by selecting and attaching a pre-seeded well layer based on the one or more kinds of cells that are pre-loaded into the well layer. In some embodiments, cells may be cryopreserved and the well layers may be shipped with cryopreserved cells already inside the wells, such that the cells may be thawed before being used with the cell culture system as described herein. Using wells that are pre-loaded with cells may, in some embodiments, allow for precise cell seeding, such as for co-culture seeding. Furthermore, using wells that are pre-loaded with cells may, in some embodiments, allow for seeding of multiple wells on the same plate and/or across multiple different plates with cells that are of the same passage; the cells could then be cryopreserved and thawed at the same time or at different times from one another for experimental applications in which multiple different wells and/or plates containing cells of the same passage are required.

At block 1606, in some embodiments, the first well of the plurality of wells may be seeded by causing a cell suspension to flow to the first well. In some embodiments, a system such as system 100 may automatically cause a fluid cell suspension to flow to the first well. This action may be performed by the system at a predefined time (e.g., in accordance with a predefined regimen or schedule) and may be performed automatically in accordance with a protocol or assay indicated by a user. In some embodiments, a system such as system 100 may cause the cell suspension to flow to the first well, which may be an individually addressable well, in accordance with all or part of the well-addressing technique explained above with reference to FIGS. 6A-6W.

At block 1608, in some embodiments, causing the cell suspension to flow to the first well may comprise causing, by a pneumatic layer of the microfluidic-enabled multi-well device, one or more valves to actuate to cause the cell suspension to flow to the first well. At block 1610, in some embodiments, causing the cell suspension to flow to the first well may comprise causing, by a pneumatic layer of the microfluidic-enabled multi-well device, one or more valves to actuate to prevent the cell suspension form flowing to one or more of the other wells, aside from first well, of the well plate.

In some embodiments, a pneumatic layer such as pneumatic layer 308 described above with reference to FIG. 3 may work together with a pneumatic membrane layer to use pneumatic force to selectively open and/or close microvalves and/or to actuate micropumps to control the flow of fluid through microfluidic channels of a microfluidic device. As described above, the selective opening and closing of valves and selective actuation of micropumps may allow for precise routing of fluid flow, such that wells in a multi-well device may be individually addressed with the flow of a cell suspension for seeding the well prior to cell culture.

In some embodiments, using one or more micropumps and/or microvalves of a microfluidic-enabled cell-culture device as described herein may enable delivering small and precise volumes of fluid to an individual well. In some embodiments, a volume of fluid (e.g., of cell suspension, and/or of fluid discussed below with respect to perturbation, monitoring assays or protocols, automated addition of reagent(s) (e.g., trypsin) to dissociate attachment-dependent cell lines, media/reagent exchange, and/or microfluidic removal/replacement of cell suspension from a well) that is less than 2000 nL, 1500 nL, 1000 nL, 500 nL, 250 nL, 100 nL, 50 nL, 10 nL, 5 nL, 1 nL, 100 µL, 10 µL, 1 µL, 100 fL, or 10 fL may be delivered to the first well. In some embodiments, a volume of fluid that is greater than 2000 nL, 1500 nL, 1000 nL, 500 nL, 250 nL, 100 nL, 50 nL, 10 nL, 5 nL, 1 nL, 100 µL, 10 µL, 1 µL, 100 fL, or 10 fL may be delivered to the first well. In some embodiments, the volumes of fluid recited in this paragraph may be pumped per pump stroke of a pump of a microfluidic-enabled cell-culture device as described herein.

In some embodiments, the types of actuation methods, devices, and/or pumps used to generate fluid flow (e.g., as described above) as well as the specific configuration of the pump-settings (e.g., as described above) may be adapted and/or parallelized in a plurality of combinations such that, for example, several sets of micro-pumps with various geometries may allow for fluid actuation of smaller volumes (e.g., volumes including the fL and µL volumes recited above), while diaphragm and/or electrical pumps may allow for fluid actuation larger volumes (e.g., volumes including and ranging upward from the µl volumes recited above). The various combinations of microfluidic fluid actuation may be included within the microfluidic layer 304 or may be part of the system 100 and or 200. In some embodiments, the positions of individual pumps and/or sets of microfluific actuators may be distributed throughout microfluidic layer 304 and/or elsewhere in a system and/or device such as those discussed herein.

In some embodiments, controlling flow of cell suspension (and other fluids) by a pneumatic layer when performing cell cultures, assays, and other protocols may enable precise control over fluid volume, in addition to allowing precise control over the wells to which flow is and is not directed, including by allowing fluid to be addressed to an individual well to the exclusion of other wells in a common row and/or common column of a single well plate. The precision and adaptability that may be achieved through pneumatic control of microfluidic volumes of flow of fluid to individually addressable wells may enable more accurate and precise experiments; more efficient use and conservation of cells, reagents, and media; and increased experimental throughput via parallelization by running different experiments simultaneously in different wells of the same well plate (including in the same row or column).

In some embodiments, seeding the first well may comprise causing multiple different cell suspension (e.g., two different cell suspensions from two different sources) to flow to the first well. The second suspension may be caused to flow to the first well in a same or similar manner as the first suspension, including by actuating one or more valves using a pneumatic layer of a microfluidic-enabled cell-culture device in order to address the second cell suspension exclusively to the first well. In some embodiments, causing two different cell suspensions to flow to a single well may be used to co-culture seed the first well. (In some embodiments of co-culturing, a co-culture environment may comprise two different cell types in a co-culture environment separated by a membrane, hydrogels, or the like.) In some embodiments, two different cell suspensions may be caused to mix together in one or more channels of the microfluidic device, and then the mixed suspension formed from both original suspensions may be caused to flow into the first well. (In some embodiments, a co-culture executed using the systems and/or methods disclosed herein may comprise any one or more of the cell types disclosed herein.)

In some alternate embodiments, co-culture seeding may be achieved by geometrical confinements, pre-seeding and cryopreserving, surface chemistry, use of multiple well inlets that allow individually adding different cell suspensions to wells, or use of micro-environments that may be separated by a micro-structured barrier. The latter embodiments utilizing multiple inlets and/or micro-structured barriers may be implemented, in some embodiments, via a 48-co-culture-well layer rather than a 96-well layer, if the co-culture is implemented via spatially separated environments and/or individual perfusion connections.

In some embodiments, seeding the first well may comprise seeding the well using techniques relying on a statistical average number of cells predicted to be present in a given volume of suspension at a given concentration. By pumping a known precise volume of cell suspension into a well or out of a well, a reasonable estimate within a given confidence range may be made as to the number of cells that are included in the fluid volume that is actuated. Thus, for example, a known precise volume of cell suspension may be pumped into a well, and an estimate as to the number of cells pumped into the well via the suspension may thereby be made. Alternately or additionally, a known precise volume of cell suspension may be pumped out of a well following addition of reagent(s) (e.g., trypsin) to dissociate attachment-dependent cell lines, and an estimate as to the number of cells pumped out of the well may thereby be made. In some embodiments, using geometric confinements as discussed below may allow for more precise control over the numbers of cells retained in a well than using statistical-average-based methods.

At block 1612, in some embodiments, causing the cell suspension to flow to the first well may comprise causing cells in the cell suspension to be retained in the first well by one or more geometric confinements in the first well. In some embodiments, one or more geometric confinements in the first well may be configured such that the confinements trap and retain cells in the cell suspension in the first well, even when fluid is removed from the cell (or replaced by another fluid in the cell) after delivery of the cell suspension to the well. The size and shape of the one or more confinements may be configured so as to retain a predefined volume of cells and/or a predefined number of cells. The number of cells retained by a geometric confinement may depend in part on the type or types of cells being retained, including by depending on cell size and cell culturing density. In some embodiments, a user or system may select a well plate for attachment to the cell culture device in accordance with a desired number of cells to be retained in the first well during cell seeding.

In some embodiments, the techniques discussed here with regard to seeding a well with a controlled number of cells using statistical-average-based techniques and/or using geometric confinements may also be applied at other steps of method 1600, including the steps discussed below regarding removing all or part of the cell population from the well following perturbation (and potentially following evolution and/or adaptation) of the cell population.

At block 1614, in some embodiments, a population of cells may be cultured in the first well. In some embodiments, the population of cells may be cultured in whole or in part from cells seeded into the first well at block 1606, and/or from cells pre-loaded into the first well as described at block 1604. In some embodiments, the system (e.g., system 100) may be configured such that the cell population is allowed to culture for a predefined period of time. In some embodiments, the cultured population of cells comprises one or more of mammalian cells, human cells, primate cells, rodent cells, insect cells, fish cells, marsupial cells, biofilms, microorganisms, pathogens, infectious agents, fungus, bacteria cells, reporter cells, immortalized cells, hiPSC lines, hiPSC derived tissue specific lineages (e.g. cardiac, neural), co-cultured cells comprising one or more cell types disclosed herein, co-cultured iPSC derived tissue specific lineages expressing fluorescent reporters including a fluorescent lineage identifier (e.g. co-cultured iPSC derived neural or cardiac lineages expressing fluorescent reporters including a fluorescent lineage identifier), iPSCs and/or iPSC-derived cells co-cultured with supporting cells, co-cultured immortalized cells expressing fluorescent reporters including a fluorescent reporter cell line identifier that enables identification of a given reporter cell line in a mixed population, dissociated biopsies, patient-derived cell lines, and cells with an evolved phenotype and/or adapted characteristic. In some embodiments of co-culturing, different lineages of a tissue type (e.g., ventricular and nodal cardiac cells) may be co-cultured, different cancer cell lines may be co-cultured, cancer cells and immune cells may be co-cultured, epithelial cancer cells and mesenchymal cancer cells may be co-cultured, mammalian cells and a pathogen may be co-cultured, mammalian cells and bacterial cells may be co cultured, and/or mammalian cells and a microbiome may be co-cultured. In some embodiments, in addition to or alternately to culturing a population of cells, a population of viruses or retroviruses, pathogens, infectious agents, fungus, and/or bacteria may be cultured, for example for the study of evolved resistances.

In some embodiments, the number of cells cultured in the first well may be greater than 500; 1,000; 5,000; 10,000; 100,000; 500,000; 1 million; or 5 million. In some embodiments, the number of cells cultured in the first well may be less than 500; 1,000; 5,000; 10,000; 100,000; 500,000; 1 million; or 5 million. In one example, about 5,500 cells having diameters of about 50 µm may be cultured in a well having an area of about 11 mm$^2$. In another example, about 500,000 cells having diameters of about 5 µm may be cultured in a well having an area of about 11 mm$^2$.

At block 1616, in some embodiments, culturing the population of cells comprises monitoring one or more environmental parameters of the first well during cell population culturing. In some embodiments, the system (e.g., system 100) and/or device (e.g., device 200) may automatically monitor one or more parameters of the first well during cell culturing, including by using one or more sensors integrated into the system or into a sensor layer of the device.

In some embodiments, the parameters monitored may be environmental parameters specific to the first well (e.g., microenvironmental parameters) and not shared by one or more other wells of the device, such as well-specific temperature, pressure, pH, humidity, CO2 level, O2 level, confluency, fluid flow, shear stress, alkalinity, acidity, basicity, input fluid temperature, output fluid temperature, ambient light intensity, electrical potential, impedance, or resistance. In some embodiments, any one or more of the same parameters may be monitored with respect to an environment of multiple wells (e.g., an ambient light measurement of the ambient light intensity adjacent to the device itself).

In some embodiments, one or more parameters may be monitored continuously, intermittently, at one or more predefined time periods, and/or in accordance with a predefined schedule or regimen for a cell culture protocol.

At block 1618, in some embodiments, culturing the population of cells comprises controlling one or more environmental parameters of the first well during cell population culturing. In some embodiments, the system (e.g., system 100) and/or device (e.g., device 200) may automatically control one or more parameters of the first well during cell culturing, including by using one or more components integrated into the system or into the device to affect a parameter of the first well.

In some embodiments, the parameters controlled may be environmental parameters specific to the first well (e.g., microenvironmental parameters) and not shared by one or more other wells of the device, such as well-specific temperature, pressure, pH, humidity, CO2 level, O2 level, confluency, fluid flow, shear stress, alkalinity, acidity, basicity, input fluid temperature, output fluid temperature, ambient light intensity, electrical potential, impedance, or resistance. For example, a well-specific pH may be controlled by controlling flow of one or more fluids to or from a specific well without changing a pH of any other well. In some embodiments, any one or more of the same parameters may be altered with respect to an environment of multiple wells (e.g., a temperature of multiple wells may be adjusted by using a heating element to heat an environment surrounding the device itself).

In some embodiments, one or more of the controlled parameters may be a parameter that is being or has been measured at block 1616; in some embodiments, one or more of the controlled parameters may be a parameter that is not monitored by the system. In some embodiments, one or more parameters may be controlled continuously, intermittently, at one or more predefined time periods, and/or in accordance with a predefined schedule or regimen for a cell culture protocol. In some embodiments, the system may control one or more parameters in accordance with a determination made by the system, such as a determination that, in accordance with monitoring of the parameter, controlling the parameter is necessary to maintain the parameter within a predefined acceptable range.

In some embodiments, culturing the population of cells may comprise selecting appropriate media and reagents, selecting an appropriate adhesion time, selecting an appropriate passaging interval, selecting an appropriate perfusion interval, selecting appropriate micro-environmental parameters to monitor and/or control, and/or selecting appropriate geometrical confinements, all in consideration of the specific cell line to be cultured (and/or specific perturbations to be executed, as discussed below).

In accordance with the techniques discussed above with respect to blocks 1614-1618, closed-loop, automated, adaptive cell culture may be enabled using the microfluidic cell-culture devices described herein. In some embodiments, cell cultures may thus be carried out without human intervention, in accordance with predefined automated actions taken in response to predefined conditions being met (e.g., cells split at pre-defined confluency), and using adaptive controls to monitor, control, and maintain one or more environmental characteristics of the cell population environment during culturing.

At block 1620, in some embodiments, one or more characteristics of the environment in the first well may be perturbed. The perturbation may, in some embodiments, be caused automatically by one or more components of the system (e.g., system 100) and/or device (e.g., device 200). In some embodiments, the perturbation may be performed following culturing of the population of cells, as shown in FIGS. 16A and 16B; however, it should be understood that the population of cells may be allowed to continue to grow and evolve/adapt following the perturbation, such that one or more phenotypes may evolve and/or one or more characteristics may adapt and be observed in response to the one or more perturbations.

In some embodiments, perturbing one or more characteristics of the environment of the first well may comprise the introduction of any physical and/or environmental influence to the cell population in the well (e.g., introduction of a variable), including introduction of physical media/reagents and/or the modification of one or more environmental (e.g., microenvironmental) parameters.

At block 1622, in some embodiments, perturbing one or more characteristics of the environment in the first well comprises introducing a fluid into the first well by causing one or more valves of the device to actuate to cause the fluid to flow to the first well. At block 1624, in some embodiments, perturbing one or more characteristics of the environment in the first well comprises preventing the first fluid from being introduced into one or more wells aside from first well by causing one or more valves to actuate to prevent the fluid from flowing to the one or more wells aside from first well.

In some embodiments, a fluid introduced into the first well during a perturbation step may comprise small molecules, antibodies, drugs, chemical compounds, peptides, components of a chemical library, one or more cells (e.g., a cell type different from the cell type being cultured), a fluid with a different pH than fluid already in the well, a fluid with a different growth factor than fluid already in the well, one or more cytokines, one or more hormones, one or more growth factors, RNAi, CRISPRi/CRISPRa, one or more reprogramming factors (e.g., for hiPSC cultures), one or more differentiation factors (e.g., for hiPSC cultures), one or more factors to transfect cells (e.g., virus, retrovirus, lentivirus, liposome, etc.), one or more pathogens, one or more infectious agents, one or more fungi, one or more microorganisms, dyes, stains, microbeads, quantum dots, or any other substance that will interact with the cell population inside the first well and affect one or more characteristics of the cell population, including the evolution of one or more phenotypes of the cell population.

In some embodiments, actuation of the one or more valves may be controlled by a pneumatic layer of the system, such as pneumatic layer 308 described above with reference to FIG. 3. In some embodiments, a pneumatic layer may work together with a pneumatic membrane layer to use pneumatic force to selectively open and/or close microvalves and/or to actuate micropumps to control the flow of the fluid through microfluidic channels of a microfluidic device. As described above, the selective opening and closing of valves and selective actuation of micropumps may allow for precise routing of fluid flow, such that wells in a multi-well device may be individually addressed with the flow of a fluid reagent or other fluid used for perturbation of the environment inside the well.

In some embodiments, controlling flow of a fluid used to perturb an environment of a well by a pneumatic layer may enable precise control over fluid volume used for perturbation, in addition to allowing precise control over the wells to which flow is and is not directed, including by allowing fluid to be addressed to an individual well to the exclusion of other wells in a common row and/or common column of a single well plate. The precision and adaptability that may be achieved through pneumatic control of microfluidic volumes of flow of fluid to individually addressable wells may enable more accurate and precise experiments; more efficient use and conservation of cells, reagents, and media; and increased experimental throughput via parallelization by running different experiments (e.g., perturbing different wells with different amounts, concentrations, and/or types of fluid) simultaneously in different wells of the same well plate (including in the same row or column).

At block 1626, in some embodiments, perturbing one or more characteristics of the environment in the first well comprises altering one or more microenvironmental parameters of the first well. In some embodiments, the system (e.g., system 100) and/or device (e.g., device 200) may automatically alter one or more parameters of the first well during perturbation, including by using one or more components integrated into the system or into the device to affect a parameter of the first well. In some embodiments, altering one or more microenvironmental parameters of the first well may share one or more characteristics in common with controlling environmental parameters, as discussed above with reference to block 1618.

In some embodiments, the parameters altered may be environmental parameters specific to the first well (e.g., microenvironmental parameters) and not shared by one or more other wells of the device, such as well-specific temperature, pressure, pH, humidity, CO2 level, O2 level, confluency, fluid flow, shear stress, alkalinity, acidity, basicity, input fluid temperature, output fluid temperature, ambient light intensity, electrical potential, impedance, or resistance. For example, a well-specific pH may be altered by controlling flow of one or more fluids to or from a specific well without changing a pH of any other well. In some embodiments, any one or more of the same parameters may be altered with respect to an environment of multiple wells (e.g., a temperature of multiple wells may be adjusted by using a heating element to heat an environment surrounding the device itself).

In some embodiments, one or more of the altered parameters may be a parameter that is being or has been measured and/or monitored (e.g., at block 1616 during cell culturing, or previously during perturbation); in some embodiments, one or more of the altered parameters may be a parameter that is not monitored by the system. In some embodiments, one or more parameters may be altered continuously, intermittently, at one or more predefined time periods, and/or in accordance with a predefined schedule or regimen for a perturbation protocol. For example, in some embodiments, parameters may be perturbed in such a way so as to simulate a dosing schedule for a human patient (e.g., simulating environmental conditions for human cells and introducing reagents in accordance with a real or hypothetical drug dosing schedule, etc.), and/or parameters may be perturbed in accordance with pharmacokinetic-pharmacodynamic (PK-PD) modeling.

At block 1628, in some embodiments, perturbing one or more characteristics of the environment in the first well comprises altering one or more microenvironmental parameters of the first well while maintaining a corresponding microenvironmental parameter of one or more wells aside from the first well. In some embodiments, the system (e.g., system 100) and/or device (e.g., device 200) may automatically maintain one or more corresponding parameters of a well during perturbation, including by using one or more components integrated into the system or into the device to affect a parameter of the well. A corresponding parameter may be a parameter of the same type as the first parameter (e.g., a temperature of a second well when the first parameter is a temperature of the first well; an ambient light intensity of a second well when the first parameter is an ambient light intensity of the fist well, etc.). In some embodiments, maintaining a corresponding microenvironmental parameter of one or more wells aside from the first well comprises monitoring the corresponding microenvironmental parameter of the one or more other wells (for example in accordance with one or more of the monitoring techniques discussed above with respect to block 1616) and automatically controlling the corresponding microenvironmental parameter of the one or more other wells so as to maintain the corresponding parameter within a predefined range. In some embodiments, the system may control a corresponding parameter of a second well in such a way so as to compensate for an effect on the second well caused by controlling the parameter of the first well. In this way, the system may prevent the corresponding parameter from being altered while altering the parameter of the first well.

At block 1630, in some embodiments, perturbing one or more characteristics of the environment in the first well comprises performing a first perturbation at a first time followed by a second perturbation at a second time, wherein the second time is a predefined period of time after the first time. In some alternate embodiments, a second perturbation may be performed at a second time after a first time, wherein the second time is dynamically determined in accordance with one or more conditions (e.g., environmental parameters) detected by the system and/or in accordance with user input. In some embodiments, a system (e.g., system 100) may be configured to perform multiple perturbations in accordance with a predefined schedule, regimen, cycle, or the like. The predefined sequence of multiple perturbations may be configured, in some embodiments, so as to simulate a dosing schedule for a patient, such as by introducing reagents in accordance with a real or hypothetical drug dosing schedule, etc.

At block 1632, in some embodiments, after performing the first perturbation and before performing the second perturbation, fluid media in the first well may be exchanged, (e.g., a first fluid media in the well may be removed from the well and replaced by a second fluid media). In some embodiments, the system (e.g., system 100) may cause fluid to automatically be expelled from the first well following a first phase of a perturbation schedule, for example as the fluid is replaced by a different fluid for a second phase of the perturbation schedule. Because the systems described herein may enable well-specific control of the flow of fluid to and from individual wells, complex perturbation regimens may be performed in which a variety of fluid reagents are caused to flow to a well, be removed from the well, and subsequently be replaced by a different fluid reagent. In some embodiments, this may be accomplished in the manner discussed above (e.g., controlling microfluidic flow of fluid via one or more valves and/or pumps controlled by a pneumatic layer of the system), including by causing fluid to be expelled from a single well during perturbation without causing fluid to be expelled from any other wells in a common well plate.

By enabling perturbation regimens that include exchange of media during perturbation in accordance with the systems and methods disclosed herein, the complexity, efficiency, and parallelization of cell culture and phenotype evolution and/or cell adaptation may be improved, and the study of complex pharmacodynamic and pharmacokinetic interactions may be enabled. Additionally, using the microfluidic fluid control techniques discussed herein may enable removal of reagents from live-cell culture environments without the use of robotics or human intervention, which may contaminate the environment, introduce bubbles, and/or be destructive to live cells. Furthermore, enabling microfluidic addition and removal of precise volumes of media and reagents may provide for cell culture and perturbation regimens that more closely simulate biologically-relevant and physiologically-relevant conditions and environments, as compared to traditional cell culture systems that merely allow the addition of reagents to a well without the option to exchange the reagent at a later time. Thus, use of the systems, devices, and techniques discussed herein for perturbation, including perturbation protocols including exchange of one or more reagents, may provide a uniquely stable, sterile, biologically-relevant, and physiologically-relevant environment for cell culture and monitoring of cell population characteristics, including evolved phenotypes of the cell population, following perturbation.

In some embodiments, the system may utilize multiple reagent inlets to a single microfluidic device in order to efficiently deliver different reagents simultaneously and/or within a short time of one another. In some embodiments, two different reagents may be delivered by different respective inlets to the same microfluidic-enable cell-culture device for delivery to two different wells, or for sequential or simultaneous delivery to the same well (e.g., for perturbation regimens requiring two different fluid reagents).

At block 1634, in some embodiments, one or more characteristics of the cell population may be monitored in the first well. In some embodiments, monitoring one or more characteristics of the cell population may include monitoring one or more characteristics of the cell population, including one or more evolved phenotypes of the cell population, as the cell population evolves and/or adapts following the perturbation (e.g., as the cell population adapts to continuous and/or intermittent exposure to one or multiple agents and continues to grow). In some embodiments, monitoring may be performed automatically by one or more components of the system (e.g., system 100). For example, monitoring may be performed continuously and/or intermittently in accordance with a predefined schedule or regimen for taking and/or recording one or more measurements. In some embodiments, monitoring may be performed in response to a user input indicating that one or more measurements should be taken and/or recorded. In some embodiments, monitoring may be performed in an automated fashion, for example in response to detection of a trigger condition (e.g., image acquisition or other monitoring operations may be executed in response to detection by a sensor of a trigger condition being met).

In FIGS. 16B and 16C, block 1634 is shown as occurring following perturbation of the cell population at block 1620; however, in some embodiments, monitoring of cell population characteristics and phenotypes, including monitoring characteristics as the cell population adapts and/or monitoring phenotypes as the cell population evolves, may be performed during ongoing perturbation of the cell population (e.g., at least partially simultaneously). Monitoring of the cell population following and/or during perturbation may allow for the detection and observation of one or more characteristics of the cell population, including one or more characteristics as the cell population adapts and/or one or more phenotypes of the cell population as it evolves.

As with the culturing and perturbation steps discussed elsewhere herein, monitoring of characteristics and/or phenotypes at block 1634 may also be performed, in some embodiments, on an individual-well basis. For example, one or more integrated sensors of the device (e.g., device 200) may detect one or more characteristics of a cell population in a single well, external sensors may detect one or more characteristics of a cell population in a single well, and/or one or more assays may be performed on a cell population in a single well (including by causing fluid to flow to the single well to the exclusion of other wells). In this way, monitoring parallelization overall experimental throughput may be improved.

At block 1636, in some embodiments, monitoring one or more characteristics comprises monitoring the cell population in the first well by one or more sensors integrated into the microfluidic-enabled cell-culture system and/or device. For example, one or more sensors of a microfluidics device comprising the first well, such as device 200, may automatically monitor one or more characteristics of an environment inside or associated with the first well. In some embodiments, integrated sensors may include any of the sensors discussed herein, such as sensors located in sensor layer 204, in microfluidics layer 202, or both. The one or more sensors may be configured, in some embodiments, to detect characteristics of the microenvironment inside and/or associated with the first well including one or more of temperature, pressure, pH, humidity, $CO_2$ level, $O_2$ level, confluency, fluid flow, shear stress, alkalinity, acidity, basicity, input fluid temperature, output fluid temperature, ambient light intensity, electrical potential, impedance, or resistance.

In some embodiments, monitoring may be performed via one or more external or associated monitoring devices, such as an external microscope that may be used to observe the cell population while inside the well, including during and/or following perturbation of the cell population, and including during and/or following evolution/adaptation of the cell population.

At block 1638, in some embodiments, monitoring one or more characteristics comprises performing microscopy on the cell population in the first well. As discussed elsewhere herein, the microfluidic-enabled cell-culture system and/or device may be configured such that microscopy may be performed on the cell population in the first well without the need to remove the cell population from the first well. For example, a well layer having a transparent, antireflective, and/or sufficiently thin substrate configured for high-resolution microscopy may be selected and attached to the microfluidic-enabled cell-culture device.

In some embodiments, the microfluidic-enabled cell-culture device and/or system may comprise one or more integrated microscopy elements (e.g., lenses, etc.), such that the system itself may make microscopic observations of the cell population inside the well without the use of other laboratory equipment. For example, in some embodiments, a portable manifold such as those discussed herein may enable integration of microscopy setups for long-term monitoring, such as real-time imaging of characteristics, adapting characteristics, and/or phenotype evolution under perturbation. In some embodiments, the microfluidic-enabled cell-culture device may be configured to be compatible with (e.g., insertable into) standard laboratory equipment, including, for example, an inverted microscope and/or an automated plate reader system (e.g., for rapid low-resolution bright-field, phase contrast, or differential interference contrast imaging of an entire well plate).

In some embodiments, microscopy used in monitoring one or more characteristics may comprise one or more of fluorescent microscopy, bright-field microscopy, phase contrast microscopy, and differential interference contrast microscopy, which may in some embodiments be automatically performed by one or more integrated components of the microfluidic-enabled cell-culture system and/or device. In some embodiments, microscopy used in monitoring one or more characteristics may comprise one or more of attenuated total reflectance spectroscopy, Fourier-transform infrared spectroscopy, and Raman spectroscopy, which may in some embodiments be automatically performed by one or more integrated components of the microfluidic-enabled cell-culture system and/or device. In some embodiments, microscopy performed by a microfluidic-enabled cell-culture system and/or device may comprise automatically generating read-outs and/or visualizations based on the microscopy and/or spectroscopy readings.

In some embodiments, monitoring of one or more characteristics of the population of cells may comprise performing one or more of absorbance-based measurements and luminescence-based measurements on the cell population in first well, which may in some embodiments be automatically performed by one or more integrated components of the microfluidic-enabled cell-culture system and/or device. In some embodiments, in addition to or alternately to performing these measurements by one or more integrated components of the device, the device may be configured to be geometrically, optically, and electronically compatible with industry-standard equipment (e.g., microscopes) for performing the measurements.

In some embodiments, monitoring of one or more characteristics of the population of cells may comprise monitoring activity of signaling networks of the cell population in first well using fluorescently tagged reporters, which may in some embodiments be automatically performed by one or more integrated components of the microfluidic-enabled cell-culture system and/or device. In some embodiments, in addition to or alternately to performing this monitoring by one or more integrated components of the device, the device may be configured to be geometrically, optically, and electronically compatible with industry-standard equipment (e.g., microscopes) for performing the monitoring.

In some embodiments, monitoring of one or more characteristics of the population of cells may comprise monitoring subcellular localization and structure of the cell population in first well using fluorescently tagged reporters, which may in some embodiments be automatically performed by one or more integrated components of the microfluidic-enabled cell-culture system and/or device. In some embodiments, in addition to or alternately to performing this monitoring by one or more integrated components of the device, the device may be configured to be geometrically, optically, and electronically compatible with industry-standard equipment (e.g., microscopes) for performing the monitoring.

In some embodiments, monitoring of one or more characteristics of the population of cells may comprise using one or more of dye and genetically-encoded fluorescent proteins to perform a viability assay on the cell population in first well, which may in some embodiments be automatically performed by one or more integrated components of the microfluidic-enabled cell-culture system and/or device. In some embodiments, in addition to or alternately to performing these assays using one or more integrated components of the device, the device may be configured to be geometrically, optically, and electronically compatible with industry-standard equipment for performing the assays.

In some embodiments, monitoring of one or more characteristics of the population of cells may comprise performing one or more of a functional assay and a structural assay on the cell population in first well, which may in some embodiments be automatically performed by one or more integrated components of the microfluidic-enabled cell-culture system and/or device. In some embodiments, in addition to or alternately to performing these assays using one or more integrated components of the device, the device may be configured to be geometrically, optically, and electronically compatible with industry-standard equipment for performing the assays.

In some embodiments, monitoring of one or more characteristics of the population of cells may comprise independently monitoring the evolution/adaptation of different types of cells in a co-culture. For example, in the case of co-culture of tumor cells with a microbiome cocktail and administration of a tumor therapeutic, the microbiome may be expected to potentially adapt, and tumor cells may similarly be expected to adapt to the presence of other cells (e.g., immune cells that are introduced to a tumor cell culture to "treat" the tumor cells). In this example, one or more characteristics of the tumor cells and microbiome may be monitored independently of one another.

At block 1640, in some embodiments, all or part of the population of cells may be removed from the first well. In some embodiments, this removal may occur following evolution and/or adaptation of the population of cells. In some embodiments, removal of cells may be performed automatically by one or more components of the system (e.g., system 100), such as by automatically causing flow of fluid containing the cells from the first well.

In some embodiments, all or part of an evolved/adapted cell population may be removed from the first well for off-chip analysis of the evolved/adapted cell lines, for establishing stocks of evolved/adapted cell lines, or for both.

In some embodiments, a portion of the population of cells may be removed from the first well in order to create additional space inside the well for the addition of additional reagents and/or for further growth, adaptation, evolution, and multiplication by the remaining portion of the cell population; thus, after removing a portion of the cell population, the method 1600 may in some embodiments revert to the perturbation steps at block 1620, where additional perturbations may be applied to the remaining portion of cells.

In some embodiments, the microfluidic control techniques discussed herein may be leveraged to allow removal of cells from a single well without removing cells from other wells in the same device, including without removing cells from other wells in the same row and/or same column, thereby increasing parallelization and efficiency as discussed above.

In some embodiments, removal of cells from the first well may be performed automatically at a predefined time may (e.g., in accordance with a predefined schedule or timeline), may be performed in response to a user input, and/or may be performed in response to the system detecting that one or more conditions (e.g., conditions regarding information, detected by sensors, regarding a characteristic of the first well and/or the population of cells) has been satisfied. In some embodiments, removal of all or part of the cell population may occur more than 1 minute, 5 minutes, 1 hour, 12 hours, 1 day, 1 week, 1 month, 3 months, or 6 months or longer after culturing the cell population in the first well began, and monitoring of characteristics may continue up until that removal. In some embodiments, removal of all or part of the cell population may occur less than 1 minute, 5 minutes, 1 hour, 12 hours, 1 day, 1 week, 1 month, 3 months, or 6 months after culturing the cell population in the well began.

In some embodiments, alternately to removing all or part of the population of cells from the first well using the microfluidics techniques described herein, the cells may be removed via manual pipetting and/or robotics following removal of the well layer from the microfluidic-enabled device. As discussed above with respect to pre-loaded well layers at the cell seeding stage, the well layer may be removed from a modular device, which may provide direct physical accessibility to the wells. Because a geometric design of the well-layer may be adapted to ANSI/SLAS standards, the positions of the wells may be readily approachable through robotic automation used in removing cells from standard microtiter plates.

At block 1642, in some embodiments, removing all or part of the population of cells from the first well comprises performing automated addition of reagent(s) (e.g., trypsin) to dissociate attachment-dependent cell lines of the cell population in the first well. In some embodiments, a fluid including trypsin may be caused to flow to the first well in order to dissociate adherent cells from the first well. In some embodiments, a fluid including other suitable enzymes or other suitable detachment reagent to break down proteins and/or dissociate adherent cells from the first well may be used. In some embodiments, the microfluidic control techniques discussed herein may be leveraged to allow detachment reagents such as trypsin to be directed to a single well without causing it to flow to other wells in the same device, including without causing it to flow to other wells in the same row and/or same column, thereby increasing parallelization and efficiency as discussed above.

In some embodiments, following addition of a detachment reagent to the well, an interfering agent (such as, e.g., serum) may be added to the well to counteract/interfere with the detachment reagent and thus enable cells remaining in the well to begin reattaching to the surface of the well. Using a specific fluid actuation scheme (e.g., two pump-strokes into the well and one pump-stroke in the reverse direction) may furthermore serve to re-distribute suspended cells again in the well with the lesser total cell number after a portion of the cells have been removed from the well. In some embodiments, the microfluidic control techniques discussed herein may be leveraged to allow the interfering agent to be directed to a single well without causing it to flow to other wells in the same device, including without causing it to flow to other wells in the same row and/or same column, thereby increasing parallelization and efficiency as discussed above.

At block 1644, in some embodiments, removing all or part of the population of cells from the first well comprises automatically causing all or part of the population of cells to flow out of the first well. For example, fluid in the first well may be caused to flow out of the first well (and may be replaced by a second fluid entering the well), thereby carrying the cells of the cell population out of the well. In some embodiments, this operation may occur following addition of reagent(s) (e.g., trypsin) to dissociate attachment-dependent cell lines of the first well. In some embodiments, the microfluidic control techniques discussed herein may be leveraged to allow microfluidic removal of cells from a single well without microfluidic removal of cells from other wells in the same device, including without microfluidic removal of cells from other wells in the same row and/or same column, thereby increasing parallelization and efficiency as discussed above.

At block 1646, in some embodiments, removing all or part of the population of cells from the first well comprises causing, by one or more geometric confinements in the first well, a portion of the cell population to remain in the first well. For example, one or more geometric confinements in the first well, such as those discussed above with respect to cell seeding, may be configured to trap and retain a portion of the cell population even as some or most of the cell population is removed from (e.g., caused to flow out of) the first well. In this way, a portion of the cell population may be removed from the first well (e.g., for analysis and/or for establishing stocks of an evolved/adapted cell line), while another portion of the cell population may remain in the well, for example for additional monitoring, adaptation, evolution, and/or perturbation.

At block 1648, in some embodiments, removing all or part of the population of cells from the first well comprises causing a portion of cells to remain in the first well, wherein the portion of cells comprises a predefined number or range. In some embodiments, a portion of the population of cells may be caused to remain in the well by (a) one or more geometric confinements in the well, or (b) by statistical-average-based techniques, as discussed above with respect to cell seeding procedures.

In some embodiments, a well layer may be selected having geometric confinements configured to retain a predefined volume and/or predefined number of cells. In some embodiments, the size and shape of the one or more confinements may be configured so as to retain a predefined volume of cells and/or a predefined number of cells. The number of cells retained by a geometric confinement may depend in part on the type or types of cells being retained, including by depending on cell size and cell culturing density.

At block 1650, in some embodiments, supernatant may be collected from the first well. In some embodiments, supernatant may be collected from the first well automatically by one or more components of the system (e.g., system 100), such as by automatically causing flow of supernatant from the first well. In some embodiments, the removed supernatant may comprise secreted proteome and metabolites. In some embodiments, the microfluidic control techniques discussed herein may be leveraged to allow removal of supernatant from a single well without removing supernatant from other wells in the same device, including without removing supernatant from other wells in the same row and/or same column, thereby increasing parallelization and efficiency as discussed above. Furthermore, in some embodiments, collected supernatant from an individual may be spatially separated from supernatant collected from other wells, and may be maintained in one or more containers to be used for downstream analysis. In some embodiments, supernatant removed from one well may be directed to another well without being removed from the device; in some embodiments, supernatant removed from one well may be directed to another well after being removed from the device. In some embodiments, supernatant removed from a well may be used for one or more co-cultures.

At block 1652, in some embodiments, the removed cells may be used to seed a second well, distinct from the first well, and to culture a second population of cells in the second well. As mentioned above, removed cells may be used to establish stocks of cell lines (e.g., stocks of evolved/adapted cell lines), and those cell lines may in turn be used to seed other wells for additional cell culturing, perturbation, and monitoring. In some embodiments, the second well may be a well in a different well layer than the first well.

In some embodiments, the second well may be a well in the same well layer as the first well; in some such embodiments, the removed cells may be caused by the system to flow to the second well without being removed from the device. Thus, a second well may be seeded using cells (e.g., evolved/adapted cells) that were previously cultured and perturbed in a different well of the same device, and the cells moved into the second well may then be used to perform further perturbations and observations without the need to remove the cells from the device at all. Because wells of the devices described herein may be individually addressable, perturbed cell populations (e.g., evolved/adapted cell populations) may be caused to flow to new wells in the same well layer in succession, thereby enabling iterative perturbation, monitoring, and/or evolution/adaptation of continuously evolving and/or adapting cells in the same well layer attached to the same device and maintained in the same system.

At block 1654, in some embodiments, one or more of a genomic analysis, transcriptomic analysis, proteomic analysis, epigenetic analysis, metabolomics analysis, and/or any omics analysis may be performed on the removed cells (e.g., evolved/adapted cells). In some embodiments, one or more of these analyses may be performed either on the population of removed cells, a subset of the population of removed cells, or on a single cell of the removed cells. In some embodiments, one or more of these analyses may be performed automatically by laboratory equipment associated with and/or physically connected to the microfluidic-enabled cell-culture system and/or device.

Figure 17:
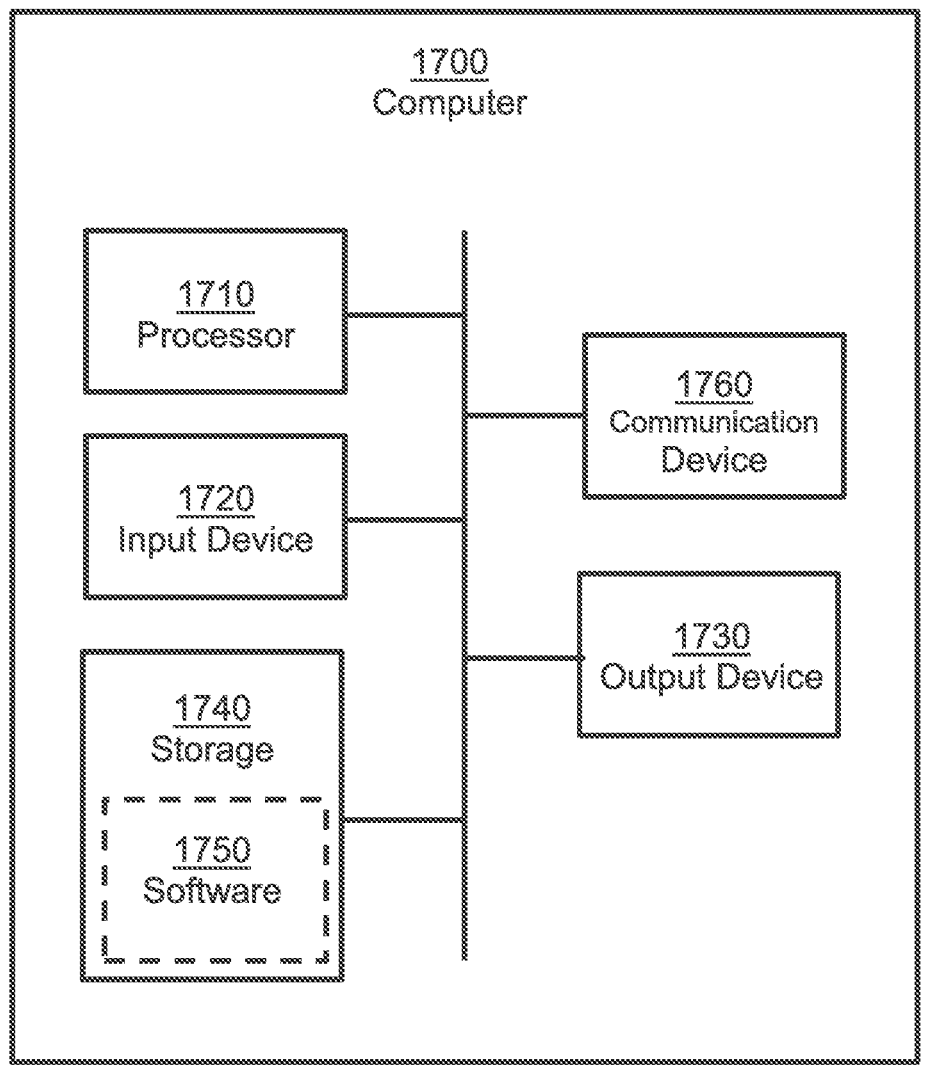
FIG. 17 depicts a computer, in accordance with some embodiments.

FIG. 17 depicts a computer, in accordance with some embodiments. Computer 1700 can be a component of a microfluidic-enabled system for performing live cell cultures, assays, and/or protocols, such as system 100 and/or any of its subcomponents described above with respect to FIG. 1. In some embodiments, computer 1700 is configured to execute a method for performing a live cell culture, assay, and/or protocol, such as any of the methods described herein; and/or execute a method for dynamic evolution/adaptation and monitoring of characteristics in living cells using a microfluidic-enabled multi-well cell culture device and/or system, such as any of the methods and/or techniques described herein with reference to FIGS. 15 and/or 16A-16C. In some embodiments, computer 1700 may be configured to control, monitor, or otherwise send and/or receive electronic signals to and/or from any one or more of the microfluidic-enabled and/or multiwell systems and/or devices described herein. In some embodiments, computer 1700 may be a microprocessing device configured to be disposed on a substrate, layer, or chip included in or provided in association with any one or more of the systems, devices, modules, layers, and/or components described herein.

Computer 1700 can be a host computer connected to a network. Computer 1700 can be a client computer or a server. As shown in FIG. 17, computer 1700 can be any suitable type of microprocessor-based device, such as a personal computer; workstation; server; or handheld computing device, such as a phone or tablet. The computer can include, for example, one or more of processor 1710, input device 1720, output device 1730, storage 1740, and communication device 1760.

Input device 1720 can be any suitable device that provides input, such as a touch screen or monitor, keyboard, mouse, or voice-recognition device. Output device 1730 can be any suitable device that provides output, such as a touch screen, monitor, printer, disk drive, or speaker.

Storage 1740 can be any suitable device that provides storage, such as an electrical, magnetic, or optical memory, including a RAM, cache, hard drive, CD-ROM drive, tape drive, or removable storage disk. Communication device 1760 can include any suitable device capable of transmitting and receiving signals over a network, such as a network interface chip or card. The components of the computer can be connected in any suitable manner, such as via a physical bus or wirelessly. Storage 1740 can be a non-transitory computer-readable storage medium comprising one or more programs, which, when executed by one or more processors, such as processor 1710, cause the one or more processors to execute methods and/or techniques described herein, such as, but not limited to: all or part of any methods for controlling systems and/or equipment including multiwell devices for the automated performance of live cell cultures, assays, and other protocols; and/or all or part of any methods for dynamic evolution/adaptation and monitoring of characteristics in living cells using a microfluidic-enabled multi-well cell culture device and/or system, such as any of the methods and/or techniques described herein with reference to FIGS. 15 and/or 16A-16C, including all or part of any methods for automatically controlling systems and/or equipment including multiwell devices for the automated performance of all or part of said methods.

Software 1750, which can be stored in storage 1740 and executed by processor 1710, can include, for example, the programming that embodies the functionality of the present disclosure (e.g., as embodied in the systems, computers, servers, and/or devices as described above). In some embodiments, software 1750 can be implemented and executed on a combination of servers such as application servers and database servers.

Software 1750 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1740, that can contain or store programming for use by or in connection with an instruction execution system, apparatus, or device.

Software 1750 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1700 can implement any operating system suitable for operating on the network. Software 1750 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Below is an enumerated listing of certain embodiments. In some embodiments, any one or more of the features of any one or more of the embodiments below may be combined with any one or more of the other embodiments, even if the dependencies of the embodiments do not explicitly indicate that the embodiments may be combined.

1. A microfluidic-enabled multiwell device for microfluidic control of fluids for cell cultures comprising:
    a microfluidics module comprising a well layer, a fluid channels layer, and a pneumatic layer,
    a sensor module comprising one or more sensors configured to detect data regarding an environment inside the microfluidic module; and
    one or more processors; and
    memory storing instructions configured to be executed by the one or more processors to cause the multiwell device to execute a cell culture process, comprising:
        receiving data collected from the one or more sensors regarding the environment inside the microfluidic module; and
        based at least in part on the data received, causing fluid to flow to an individually addressable well in the multiwell device.

2. The microfluidic-enabled multiwell device of embodiment 1, wherein the microfluidic-enabled multiwell device further comprises a substrate layer.

3. The microfluidic-enabled multiwell device of any one of embodiments 1-2, wherein the pneumatic layer comprises a pneumatic well-selection layer and pneumatic control layer.

4. The system of any one of embodiments 1-3, wherein the microfluidics module comprises a degasser layer comprising a plurality of well-specific degassers each configured to remove gas bubbles from a specific well in the well layer.

5. The system of embodiment 4, wherein the microfluidics module comprises a gas-permeable degasser membrane between the well layer and the degasser layer.

6. The system of any one of embodiments 4-5, wherein the microfluidics module comprises a degasser control layer comprising a plurality of pneumatic channels pneumatically coupled to one or more of the well-specific degassers.

7. The system of any one of embodiments 4-6, wherein the microfluidics module comprises a global degasser configured to remove gas bubbles from a fluid channel configured to deliver fluid to two or more of the wells of the well layer.

8. The microfluidic-enabled multiwell device of any one of embodiments 1-7, further comprising a control module.

9. The microfluidic-enabled multiwell device of embodiment 8, wherein at least one of the one or more processors are comprised in the control module.

10. The microfluidic-enabled multiwell device of any one of embodiments 1-9, wherein:
    the microfluidics module comprises a plurality of pumps; and
    causing fluid to flow to an individual well in the multiwell device comprises causing one or more of the plurality of pumps to be actuated.

11. The microfluidic-enabled multiwell device of embodiment 10, wherein the plurality of pumps comprise one or more of a syringe driven pump, a micro-diaphragm pump, a pneumatic micropump with doormat valve geometry, or a pneumatic micropump with lifting gate valve geometry.

12. The microfluidic-enabled multiwell device of any one of embodiments 1-11, wherein the multiwell device comprises one or more microfluidics module sensors integrated into the microfluidic module of the multiwell device, wherein the one or more microfluidics module sensors are configured to detect a characteristic of a parameter of the environment inside the microfluidic module.

13. The microfluidic-enabled multiwell device of any one of embodiments 1-12, wherein the sensor layer comprises one or more sensors configured to detect an external characteristic of an environment surrounding the multiwell device.

14. The microfluidic-enabled multiwell device of any one of embodiments 1-13, wherein the instructions are configured to be executed by the one or more processors to cause the device to store, in the memory, the data collected from the one or more sensors regarding the environment inside the microfluidic module.

15. The microfluidic-enabled multiwell device of any one of embodiments 1-14, wherein the instructions are configured to be executed by the one or more processors to cause the device to transmit, to a remote computing device for storage, the data collected from the one or more sensors regarding the environment inside the microfluidic module.

16. The microfluidic-enabled multiwell device of any one of embodiments 1-15, wherein the instructions are configured to be executed by the one or more processors to cause the device to:
    transmit instructions for displaying a graphical user interface;
    detect an input executed by a user of the device via the graphical user interface; and
    in response to detecting the input, cause fluid to flow to a user-indicated individual well of the multiwell device.

17. The microfluidic-enabled multiwell device of any one of embodiments 1-16, wherein a footprint of the multiwell device conforms to one or more SBS/ANSI multiwell plate standards.

18. The microfluidic-enabled multiwell device of any one of embodiments 1-17, wherein the multiwell device is compatible with one of industry-standard laboratory plate-reading and industry-standard automation equipment.

19. The microfluidic-enabled multiwell device of any one of embodiments 1-18, wherein one or more of the microfluidic module and the sensor module are configured to be reusable for multiple cell culture procedures.

20. The microfluidic-enabled multiwell device of any one of embodiments 1-19, wherein one or more of the microfluidic module and the sensor module are configured to be removable from the multiwell device.

21. The microfluidic-enabled multiwell device of any one of embodiments 1-20, wherein one or more of the microfluidic module and the sensor module are configured to be removable from the multiwell device following a first cell culture procedure for replacement by another component prior to a second cell culture procedure.

22. The microfluidic-enabled multiwell device of any one of embodiments 1-21, wherein the well layer is configured to be removable from the microfluidics module.

23. The microfluidic-enabled multiwell device of any one of embodiments 1-22, wherein the well layer is configured to be removable from the microfluidics module following a first cell culture procedure for replacement by another component prior to a second cell culture procedure.

24. The microfluidic-enabled multiwell device of any one of embodiments 1-23, wherein the well layer comprises one or more of glass, cyclo-olefin copolymer, plastics, or PDMS.

25. The microfluidic-enabled multiwell device of any one of embodiments 1-24, wherein a coating of the well layer comprises one or more of poly-lysine, fibronectin, or matrigel.

26. The microfluidic-enabled multiwell device of any one of embodiments 1-25, wherein the well layer is micropatterned.

27. The microfluidic-enabled multiwell device of any one of embodiments 1-26, wherein one or more of a thickness, material, micropatterning, coating, and geometrical configuration of the well layer are configured for microscopic imaging.

28. The microfluidic-enabled multiwell device of any one of embodiments 1-27, wherein one or more of a material, micropatterning, coating, and geometrical configuration of the well layer are configured for 2D culture of adherent cells.

29. The microfluidic-enabled multiwell device of any one of embodiments 1-28, wherein one or more of a material, micropatterning, coating, and geometrical configuration of the well layer are configured for co-culture of more than one type of adherent cell.

30. The microfluidic-enabled multiwell device of any one of embodiments 1-29, wherein one or more of a material, micropatterning, coating, and geometrical configuration of the well layer are configured for co-culture of adherent cells with other cell types.

31. The microfluidic-enabled multiwell device of any one of embodiments 1-30, wherein one or more of a material, micropatterning, coating, and geometrical configuration of the well layer are configured for culture of suspension cells.

32. The microfluidic-enabled multiwell device of any one of embodiments 1-31, wherein one or more of a material, micropatterning, coating, and geometrical configuration of the well layer are configured for culture of 3D culture models.

33. The microfluidic-enabled multiwell device of embodiment 32, wherein the 3D models comprise one or more of tumor spheroids, organoids, vascular networks, bioprinted 3D tissue models, and iPSC-derived 3D tissue models.

34. The microfluidic-enabled multiwell device of any one of embodiments 1-33, wherein one or more of a material, micropatterning, coating, and geometrical configuration of the well layer are configured for culture of one or more of immortalized cells, iPSC, iPSC-derived, or primary cells.

35. The microfluidic-enabled multiwell device of any one of embodiments 1-34, wherein the instructions are configured to be executed by the one or more processors to cause multiwell device to control fluid for the cell culture process for at least 24 hours.

36. The microfluidic-enabled multiwell device of any one of embodiments 1-35, wherein causing fluid to flow to an individually addressable well comprises causing a valve to be actuated in association with displacement of a portion of the pneumatic layer.

37. The microfluidic-enabled multiwell device of any one of embodiments 1-36, wherein the instructions are configured to be executed by the one or more processors to cause the multiwell device to cause perfusion of one or more of nutrients, reagents, and media to a plurality of individually-addressable wells in the multiwell device in accordance with a predefined procedure for one or more of 2D culture of adherent cells, co-culture of more than one type of adherent cell, co-culture of adherent cells with other cell types, culture of suspension cells, culture of 3D culture models, culture of immortalized cells, culture of iPSC, culture of iPSC-derived, or culture of primary cells.

38. The microfluidic-enabled multiwell device of any one of embodiments 1-37, wherein the microfluidic module comprises one or more channels having a diameter of less than 1000 μm.

39. The microfluidic-enabled multiwell device of any one of embodiments 1-38, wherein one or more micro-pumps of the microfluidic module are configured to pump a volume of less than 500 nL per pump stroke.

40. The microfluidic-enabled multiwell device of any one of embodiments 1-39, comprising an array of 48 or more individually-addressable wells.

41. The microfluidic-enabled multiwell device of any one of embodiments 1-40, wherein the instructions are configured to be executed by the one or more processors to cause the microfluidic module to cause automated exchange of cell culture media.

42. The microfluidic-enabled multiwell device of any one of embodiments 1-41, wherein the instructions are configured to be executed by the one or more processors to cause the microfluidic module to cause automated addition of one or more reagents to dissociate attachment-dependent cell lines of cultured cells.

43. The microfluidic-enabled multiwell device of any one of embodiments 1-42, wherein the instructions are configured to be executed by the one or more processors to cause the microfluidic module to cause automated passaging of cells.

44. The microfluidic-enabled multiwell device of any one of embodiments 1-43, wherein the instructions are configured to be executed by the one or more processors to cause the device to execute an automated cell-based assay and protocol in the multiwell device.

45. The microfluidic-enabled multiwell device of embodiment 44, wherein the instructions are configured to be executed by the one or more processors to cause the device to monitor the assay for a period of at least 24 hours during execution of the assay.

46. The microfluidic-enabled multiwell device of any one of embodiments 44-45, wherein the executing the assay comprises causing the automated addition of one or more compounds to cells.

47. The microfluidic-enabled multiwell device of any one of embodiments 44-46, wherein the assay is a clonogenic assay.

48. The microfluidic-enabled multiwell device of any one of embodiments 44-47, wherein the protocol is a transfection protocol.

49. The microfluidic-enabled multiwell device of any one of embodiments 44-48, wherein the protocol comprises reprogramming cells to induce pluripotency.

50. The microfluidic-enabled multiwell device of any one of embodiments 44-49, wherein the protocol is a protocol to differentiate pluripotent cells.

51. The microfluidic-enabled multiwell device of any one of embodiments 44-50, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance evolution.

52. The microfluidic-enabled multiwell device of any one of embodiments 44-51, wherein the assay comprises microscopy measurements.

53. The microfluidic-enabled multiwell device of any one of embodiments 44-52, wherein cells of the assay comprise one or more of immortalized cells, primary cells, pluripotent cells, pluripotent-derived cells, adherent cells, or suspension cells.

54. The microfluidic-enabled multiwell device of any one of embodiments 44-53, wherein cells of the assay are derived from a clinical sample.

55. The microfluidic-enabled multiwell device of any one of embodiments 44-54, wherein cells subject to the assay comprise one or more of a 3D culture model, an organoid model, and a coculture model.

56. The microfluidic-enabled multiwell device of any one of embodiments 44-55, wherein cells subject to the assay comprise reporter cells.

57. The microfluidic-enabled multiwell device of any one of embodiments 44-56, wherein cells subject to the assay comprise a library of cells arrayed in the device.

58. The microfluidic-enabled multiwell device of any one of embodiments 44-57, wherein the assay and protocol is conducted without tissue culture incubators.

59. The microfluidic-enabled multiwell device of any one of embodiments 44-58, wherein the assay and protocol is conducted in a laboratory environment.

60. The microfluidic-enabled multiwell device of any one of embodiments 44-59, wherein assay and protocol is conducted in one of a field location, a point-of-care location, and a pharmacy.

61. The microfluidic-enabled multiwell device of any one of embodiments 1-60, wherein the cell culture is conducted without tissue culture incubators.

62. The microfluidic-enabled multiwell device of any one of embodiments 1-61, wherein at the cell culture is conducted in a laboratory environment.

63. The microfluidic-enabled multiwell device of any one of embodiments 1-62, wherein at the cell culture is conducted in one or more of a field location, a point-of-care, and a pharmacy.

64. The microfluidic-enabled multiwell device of any one of embodiments 1-63, wherein at the well layer contains cryopreserved cells that are thawed during the cell culture.

65. The microfluidic-enabled multiwell device of any one of embodiments 1-64, wherein the instructions are configured to be executed by the one or more processors to cause the device to:
in accordance with receiving the data collected from the one or more sensors regarding the environment inside the microfluidic module, control one or more parameters of an environment inside the microfluidics module,
wherein the one or more parameters includes one or more of temperature, pressure, pH, humidity, $CO_2$, $O_2$, confluency, fluid flow, alkalinity, input fluid temperature, output fluid temperature, ambient light intensity, electrical potential, impedance, or resistance.

66. The microfluidic-enabled multiwell device of any one of embodiments 1-65, wherein the instructions are configured to be executed by the one or more processors to cause the device to:
monitor, by the sensor module, one or more parameters of an environment surrounding the multiwell device;
store data regarding the monitoring of the parameters of the environment surrounding the multiwell device on a computer storage of the device; and
wirelessly transmit the stored data regarding the monitoring of the parameters of the environment surrounding the multiwell device to a user.

67. The microfluidic-enabled multiwell device of any one of embodiments 1-66, wherein the instructions are configured to be executed by the one or more processors to cause the device to:
monitor, by the sensor module, one or more parameters of an environment surrounding the multiwell device;
in accordance with monitoring one or more environmental parameters, adjust one or more parameters of the environment inside the microfluidics module.

68. The microfluidic-enabled multiwell device of any one of embodiments 1-67, wherein:
the well layer comprises a first plurality of wells arranged into a plurality of rows;
the fluid channels layer comprises a first input channel and a first output channel both corresponding to a first row of the plurality of rows;
the fluidic channels layer comprises a second input channel and a second output channel both corresponding to a second row of the plurality of rows;
two wells in the first row are individually fluidly connectible to the first input channel by a first plurality of respective input valves;
the two in the first row are individually fluidly connectible to the first output channel by a first plurality of respective output valves;
two wells in the second row are individually fluidly connectible to the second input channel by a second plurality of respective input valves;
the two wells in the second row are individually fluidly connectible to the second output channel by a second plurality of respective output valves.

69. The microfluidic-enabled multiwell device of embodiment 68, wherein:
the first input channel is fluidly connectible to a common input channel via a first channel input valve;
the first output channel is fluidly connectible to a common output channel via a first channel output valve;
the second input channel is fluidly connectible to the common input channel via a second channel input valve;
the second output channel is fluidly connectible to the common output channel via a second channel output valve.

70. The microfluidic-enabled multiwell device of embodiment 69, wherein causing fluid to flow to an individually addressable well in the multiwell device comprises:
opening the first channel input valve and the first channel output to allow flow into and out of the first output channel;

opening one of the first plurality of input valves and a corresponding one of the first plurality of output valves to allow flow into and out of the individually addressable well.

71. The microfluidic-enabled multiwell device of any one of embodiments 68-70, wherein a micropump is configured to provide vacuum force to selectively cause flow through any individual well of the two wells in the first row and the two wells in the second row.

72. The microfluidic-enabled multiwell device of embodiment 71, wherein the micropump is downstream from the common output channel.

73. The microfluidic-enabled multiwell device of any one of embodiments 1-72, wherein the device is configured to be received by a docking component.

74. The microfluidic-enabled multiwell device of embodiment 73, wherein the device is configured to be fluidly coupled to the docking component.

75. The microfluidic-enabled multiwell device of any one of embodiments 73-74, wherein the device is configured to be pneumatically coupled to the docking component.

76. The microfluidic-enabled multiwell device of any one of embodiments 73-75, wherein the device is configured to be electronically communicatively coupled to the docking component.

77. A system for microfluidic control of fluids for cell cultures, wherein the system comprises:
the microfluidic-enabled multiwell device of any one of embodiments 1-76; and
a docking component configured to receive the multiwell device and to be fluidly coupled to the multiwell device.

78. The system of embodiment 77, wherein the docking component is configured to be pneumatically coupled to the device.

79. The system of any one of embodiments 77-78, wherein the docking component is configured to be electronically communicatively coupled to the device.

80. The system of any one of embodiments 77-79, wherein the docking component comprises a tabletop docking station.

81. The system of any one of embodiments 77-80, wherein the docking component comprises a portable docking module configured to enable operation of the multiwell device when the portable docking module is inserted in one or more of a plate reader or a microscope stage.

82. The system of any one of embodiments 77-81, wherein the docking component comprises a display configured to display a graphical user interface.

83. The system of any one of embodiments 77-82, wherein the docking component comprises a user input device configured to receive a user input comprising an instruction.

84. The system of any one of embodiments 77-83, comprising an inkjet input reservoir system configured to be fluidly coupled to the multiwell device and to supply one or more of media, cell suspension, and reagents to the multiwell device.

85. The system of any one of embodiments 77-84, comprising an output reservoir configured to be fluidly coupled to the multiwell device and to receive flow of one or more of media, cell suspension, and reagents from the multiwell device.

86. The system of any one of embodiments 77-85, comprising a manifold configured to attach to one or more of a reservoir or a vacuum line.

87. A method for microfluidic control of fluids for cell cultures, comprising:
at a microfluidic-enabled multiwell device comprising a microfluidics module comprising a well layer, a fluid channels layer, and a pneumatic layer; and a sensor module comprising one or more sensors configured to detect data regarding an environment inside the microfluidic module:
receiving data collected from the one or more sensors regarding the environment inside the microfluidic module; and
based at least in part on the data received, causing fluid to flow to an individually addressable well in the multiwell device.

88. The method of embodiment 87, comprising, at the microfluidic-enabled multiwell device, storing the data collected from the one or more sensors regarding the environment inside the microfluidic module.

89. The method of any one of embodiments 87-88, comprising, at the microfluidic-enabled multiwell device, transmitting, to a remote computing device for storage, the data collected from the one or more sensors regarding the environment inside the microfluidic module.

90. The method of any one of embodiments 87-89, comprising, at the microfluidic-enabled multiwell device:
transmitting instructions for displaying a graphical user interface;
detecting an input executed by a user of the device via the graphical user interface; and
in response to detecting the input, causing fluid to flow to a user-indicated individual well of the multiwell device.

91. The method of any one of embodiments 87-90, comprising, at the microfluidic-enabled multiwell device, controlling fluid for the cell culture process for at least 24 hours.

92. The method of any one of embodiments 87-91, wherein causing fluid to flow to an individually addressable well comprises causing a valve to be actuated in association with displacement of a portion of the pneumatic layer.

93. The method of any one of embodiments 87-92, comprising, at the microfluidic-enabled multiwell device:
in accordance with receiving the data collected from the one or more sensors regarding the environment inside the microfluidic module, controlling one or more parameters of an environment inside the microfluidics module,
wherein the one or more parameters includes one or more of temperature, pressure, pH, humidity, $CO_2$, $O_2$, confluency, fluid flow, alkalinity, input fluid temperature, output fluid temperature, ambient light intensity, electrical potential, impedance, or resistance.

94. The method of any one of embodiments 87-93, comprising, at the microfluidic-enabled multiwell device:
monitoring, by the sensor module, one or more parameters of an environment surrounding the multiwell device;
storing data regarding the monitoring of the parameters of the environment surrounding the multiwell device on a computer storage of the device; and
wirelessly transmitting the stored data regarding the monitoring of the parameters of the environment surrounding the multiwell device to a user.

95. The method of any one of embodiments 87-94, comprising, at the microfluidic-enabled multiwell device:

monitoring, by the sensor module, one or more parameters of an environment surrounding the multiwell device;
in accordance with monitoring one or more environmental parameters, adjusting one or more parameters of a the environment inside the microfluidics module.

96. The method of any one of embodiments 87-95, wherein:
the well layer comprises a first plurality of wells arranged into a plurality of rows;
the fluid channels layer comprises a first input channel and a first output channel both corresponding to a first row of the plurality of rows;
the fluidic channels layer comprises a second input channel and a second output channel both corresponding to a second row of the plurality of rows;
two wells in the first row are individually fluidly connectible to the first input channel by a first plurality of respective input valves;
the two in the first row are individually fluidly connectible to the first output channel by a first plurality of respective output valves;
two wells in the second row are individually fluidly connectible to the second input channel by a second plurality of respective input valves;
the two wells in the second row are individually fluidly connectible to the second output channel by a second plurality of respective output valves;
the first input channel is fluidly connectible to a to a common input channel via a first channel input valve;
the first output channel is fluidly connectible to a to a common output channel via a first channel output valve;
the second input channel is fluidly connectible to a to the common input channel via a second channel input valve;
the second output channel is fluidly connectible to a to the common output channel via a second channel output valve;
causing fluid to flow to an individually addressable well in the multiwell device comprises:
opening the first channel input valve and the first channel output to allow flow into and out of the first output channel; and
opening one of the first plurality of input valves and a corresponding one of the first plurality of output valves to allow flow into and out of the individually addressable well.

97. A microfluidic enabled multiwell device with closed-loop microenvironment monitoring and control, the device comprising:
a substrate module layer;
a microfluidic module layer; and
a sensor module layer;

98. The device of embodiment 97, wherein the substrate module layer is disposable.

99. The device of any one of embodiments 97-98, wherein the microfluidic module layer is reusable or disposable.

100. The device of any one of embodiments 97-99, wherein the sensor module layer is reusable.

101. The device of any one of embodiments 97-100, wherein one or more of the substrate module layer, the microfluidic module layer, and the sensor module layer are configured to be removable from the device for replacement by a different layer.

102. The device of any one of embodiments 97-101 where the substrate module comprises one or more of glass and cyclo-olefin copolymer.

103. The device of any one of embodiments 97-102, wherein one or more of a thickness, material, micropatterning, coating, and geometrical configuration of the substrate module are configured for microscopic imaging.

104. The device of any one of embodiments 97-103, wherein one or more of a material, micropatterning, coating, and geometrical configuration of the substrate module are configured for 2D culture of adherent cells.

105. The device of any one of embodiments 97-104, wherein one or more of a material, micropatterning, coating, and geometrical configuration of the substrate module are configured for co-culture of more than one type of adherent cell.

106. The device of any one of embodiments 97-105, wherein one or more of a material, micropatterning, coating, and geometrical configuration of the substrate module are configured for co-culture of adherent cells with other cell types.

107. The device of any one of embodiments 97-106, wherein one or more of a material, micropatterning, coating, and geometrical configuration of the substrate module are configured for culture of suspension cells.

108. The device of any one of embodiments 97-107, wherein one or more of a material, micropatterning, coating, and geometrical configuration of the substrate module are configured for culture of 3D culture models.

109. The device of embodiment 108, wherein the 3D models comprise one or more of tumor spheroids, organoids, vascular networks, bioprinted 3D tissue models, and iPSC-derived 3D tissue models.

110. The device of any one of embodiments 97-109, wherein one or more of a material, micropatterning, coating, and geometrical configuration of the substrate module are configured for one or more of culture of immortalized cells, iPSC, iPSC-derived, and primary cells.

111. The device of any one of embodiments 97-110, wherein the microfluidic module comprises one or more channels having a diameter ranging from 10-1000 µm.

112. The device of any one of embodiments 97-111, wherein the microfluidic module comprises one or more micro-pumps configured to pump volumes ranging from 10-500 nl per pump stroke.

113. The device of any one of embodiments 97-112, wherein the microfluidic module comprises pump geometries that include one or more of syringe driven pumps, micro-diaphragm pumps, and pneumatic micropumps with doormat or lifting gate valve geometries.

114. The device of any one of embodiments 97-113, wherein the sensor module applies calibration information and controls microenvironment parameters including one or more of temperature, pH, humidity, $CO_2$, $O_2$, confluency, fluid flow, input fluid temperature, output fluid temperature, a visualized 2D/3D gradient heat-map of the microfluidic/substrate layer, ambient light intensity, electrical potential, impedance, or resistance.

115. The device of any one of embodiments 97-114, wherein the sensor module collects microenvironment data for local storage.

116. The device of any one of embodiments 97-115, wherein the sensor module transmits measurements wirelessly for remote or local user interaction.

117. The device of any one of embodiments 97-116, wherein the substrate module is micropatterned.

118. The device of any one of embodiments 97-117, wherein a coating of the substrate module comprises one or more of poly-lysine, fibronectin, or matrigel.

119. The device of any one of embodiments 97-118, wherein the device comprises up to 48 wells.

120. The device of any one of embodiments 97-119, wherein the device comprises more than 48 wells.

121. The device of any one of embodiments 97-120, wherein a footprint of the device conforms to one or more SBS/ANSI multiwell plate standards and is compatible with a plurality of industry standard laboratory plate-reading and automation devices and equipment.

122. A method of executing and monitoring automated cell culture, comprising: monitoring one or more cells in a multiwell microfluidic-enabled device for a period of at least 24 hours, wherein the one or more cells comprise one or more of an immortalized cell, a primary cell, a pluripotent cell, a pluripotent-derived cell, a 3D model, an organoid, and a co culture.

123. The method of embodiment 122 when the automated cell culture process includes thawing of cells that have been cryopreserved in the device of any one of embodiments 97-121.

124. The method of any one of embodiments 122-123, wherein the multiwell microfluidic-enabled device is configured for closed-loop microenvironment monitoring and control and comprises a substrate module layer, a microfluidic module layer, and a sensor module layer.

125. The method of embodiment 124, comprising: monitoring, by the sensor module, one or more environmental parameters; storing data regarding the monitoring on a computer storage of the device; and wirelessly transmitting the data to a user.

126. The method of embodiment 125, comprising, in accordance with monitoring one or more environmental parameters, adjusting one or more parameters of a cellular microenvironment.

127. The method of any one of embodiments 125-126, wherein the one or more parameters comprises a temperature.

128. The method of any one of embodiments 125-127, wherein the one or more parameters comprises an acidity and/or basicity.

129. The method of any one of embodiments 125-128, wherein the one or more parameters comprises cell confluency.

130. The method of any one of embodiments 124-129, comprising executing, by the microfluidic module, automated exchange of cell culture media.

131. The method of any one of embodiments 124-130, comprising executing, by the microfluidic module, automated addition of one or more reagents to dissociate attachment-dependent cell lines of cultured cells.

132. The method of any one of embodiments 124-131, comprising executing, by the microfluidic module, automated passaging of cells.

133. A method comprising:
  executing an automated cell-based assay and protocol in a multiwell microfluidic-enabled device for a period of at least 24 hours; and
  monitoring the automated cell-based assay and protocol in the multiwell microfluidic-enabled device for a period of at least 24 hours.

134. The method of embodiment 133, wherein the assay entails the automated addition of one or more compounds to cells.

135. The methods of any of any one of embodiments 133-134, wherein the assay is a clonogenic assay.

136. The methods of any of any one of embodiments 133-135, wherein the protocol is a transfection protocol.

137. The methods of any of any one of embodiments 133-136, wherein the protocol comprises reprogramming cells to induce pluripotency.

138. The methods of any of any one of embodiments 133-137, wherein the protocol is a protocol to differentiate pluripotent cells.

139. The methods of any of any one of embodiments 133-138, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance evolution.

140. The method of any of any one of embodiments 133-139, wherein the assay comprises microscopy measurements.

141. The method of any of any one of embodiments 133-140, wherein the cells comprise one or more of immortalized cells, primary cells, pluripotent cells, pluripotent-derived cells, adherent cells, suspension cells.

142. The method of any of any one of embodiments 133-141, wherein the cells are derived from a clinical sample.

143. The method of any of any one of embodiments 133-142, wherein the assayed cells comprise one or more of a 3D culture model, an organoid model, and a coculture model.

144. The method of any of any one of embodiments 133-143, wherein the assayed cells are reporter cells.

145. The method of any of any one of embodiments 133-144, wherein the assayed cells are a library of cells arrayed in the device.

146. The method of any of any one of embodiments 122-145, wherein at least one of the cell culture, assays, and protocols is conducted without tissue culture incubators.

147. The method of any of any one of embodiments 122-146, wherein at least one of the cell culture, assays, or protocols is conducted in a standard laboratory environment.

148. The method of any of any one of embodiments 122-147, wherein at least one of the cell culture, assays, or protocols is conducted in one or more of a field location, a point-of-care, and a pharmacy.

149. A docking station configured to house the device of any one of embodiments 97-121.

150. An ink-jet style input reservoir configured to supply one or more of media and reagents to the device of any one of embodiments 97-121.

151. An output reservoir configured to collect analytes from the device of any one of embodiments 97-121.

152. A manifold configured to connect the device of any one of embodiments 97-121 to one or more of reservoirs, vacuum lines, and other instrumentation.

153. A portable manifold connector/docking module to allow the placement, operation and monitoring of the device of any one of embodiments 97-121 when inserted in standard laboratory equipment such as plate-readers, microscope stages etc.

154. A method for dynamic evolution and monitoring of characteristics in living cells, comprising:
  at a microfluidic-enabled cell-culture device comprising a pneumatic layer for directing flow of fluid to a plurality of individually addressable wells, and one or more sensors configured to detect data regarding environments inside one or more of the plurality of wells:

culturing a population of cells in a first well of the plurality of wells;

perturbing one or more characteristics of an environment in the first well following the culturing of the population of cells;

monitoring one or more characteristics of the population of cells in the first well;

removing all or part of the evolved population of cells from the first well.

155. The method of embodiment 154, comprising, before culturing the population of cells in the first well, seeding the first well by causing a cell suspension to flow to the first well.

156. The method of embodiment 155, wherein causing the cell suspension to flow to the first well comprises causing one or more valves to be actuated in association with displacement of a portion of a pneumatic layer of the cell-culture device.

157. The method of any one of embodiments 155-156, wherein causing the cell suspension to flow to the first well comprises causing one or more valves be actuated in association with displacement of a portion of a pneumatic layer of the cell-culture device such that the cell suspension does not flow to any of the other wells of the plurality of wells.

158. The method of any one of embodiments 155-157, comprising, after seeding the first well and before culturing the population of cells in the first well, co-culture seeding the first well by causing a second cell suspension to flow to the first well.

159. The method of any one of embodiments 155-158, comprising causing a plurality of cells in the cell suspension to be retained in the first well by one or more geometrical confinements in the first well.

160. The method of any one of embodiments 154-159, wherein culturing the population of cells in the first well comprises automatically monitoring and controlling one or more environmental parameters of the first well.

161. The method of embodiment 160, wherein controlling one or more environmental parameters of the first well is performed without modifying a corresponding parameter for any of the other wells of the plurality of wells.

162. The method of any one of embodiments 154-161, comprising, before culturing the population of cells in the first well, selecting and attaching a well layer of a microfluidics module to the microfluidic-enabled cell-culture device, the well layer comprising the plurality of individually addressable wells.

163. The method of any one of embodiments 154-162, wherein:

the well layer comprises cells loaded into the first well before attaching the well layer to the cell-culture device; and culturing the population of cells comprises culturing the population of cells from the cells loaded into the first well.

164. The method of embodiment 163, wherein selecting the well layer comprises selecting a well layer having one or more of a material, micropatterning, coating, and geometrical configuration configured for the culturing of the population of cells.

165. The method of any one of embodiments 163-164, wherein selecting the well layer comprises selecting a well layer having one or more of a material, micropatterning, coating, and geometrical configuration configured for the perturbation of the population of cells.

166. The method of any one of embodiments 154-165, wherein perturbing one or more characteristics of the environment in the first well comprises introducing small molecules into the first well by causing a small molecule mixture to flow to the first well.

167. The method of any one of embodiments 154-166, wherein perturbing one or more characteristics of the environment in the first well comprises introducing antibodies into the first well by causing an antibody mixture to flow to the first well.

168. The method of any one of embodiments 154-167, wherein perturbing one or more characteristics of the environment in the first well comprises altering one or more microenvironmental parameters including one or more of temperature, pressure, pH, humidity, CO2 level, O2 level, confluency, fluid flow, alkalinity, acidity, basicity, input fluid temperature, output fluid temperature, ambient light intensity, electrical potential, impedance, or resistance of the environment in the first well.

169. The method of any one of embodiments 154-168, wherein perturbing one or more characteristics of the environment in the first well is performed without perturbing a corresponding characteristics of any of the other wells of the plurality of wells.

170. The method of any one of embodiments 154-169, wherein perturbing one or more characteristics of the environment in the first well comprises introducing fluid into the first well by pumping less than 1000 nL per pump stroke of a pump controlled by the pneumatic layer.

171. The method of any one of embodiments 154-170, wherein perturbing one or more characteristics of the environment in the first well comprises automatically performing a first perturbation at a first time, waiting for a predefined period, and then performing a second perturbation at a second time.

172. The method of embodiment 171, wherein perturbing one or more characteristics of the environment in the first well comprises, after performing the first perturbation and before performing the second perturbation, causing a fluid media in the first well to be exchanged from the first well.

173. The method of any one of embodiments 154-172, wherein monitoring one or more characteristics of the population of cells comprises monitoring one or more phenotypes of the population of cells as it evolves in the first well.

174. The method of any one of embodiments 154-173, wherein monitoring one or more characteristics of the population of cells comprises monitoring the cell population in the first well by one or more of the sensors of the cell-culture device.

175. The method of embodiment 174, wherein monitoring one or more characteristics of the population of cells comprises performing one or more of fluorescent microscopy, bright-field microscopy, phase contrast microscopy, and differential interference contrast microscopy on the cell population in first well.

176. The method of any one of embodiments 154-175, wherein monitoring one or more characteristics of the population of cells comprises performing one or more of absorbance-based measurements and luminescence-based measurements on the cell population in first well.

177. The method of any one of embodiments 154-176, wherein monitoring one or more characteristics of the population of cells comprises monitoring activity of signaling networks of the cell population in first well using fluorescently tagged reporters.

178. The method of any one of embodiments 154-177, wherein monitoring one or more characteristics of the population of cells comprises monitoring subcellular localization and structure of the cell population in first well using fluorescently tagged reporters.

179. The method of any one of embodiments 154-178, wherein monitoring one or more characteristics of the population of cells comprises using one or more of dye and genetically-encoded fluorescent proteins to perform a viability assay on the cell population in first well.

180. The method of any one of embodiments 154-179, wherein monitoring one or more characteristics of the population of cells comprises performing one or more of a functional assay and a structural assay on the cell population in first well.

181. The method of any one of embodiments 154-180, wherein the monitoring is performed during perturbation of the population of cells.

182. The method of any one of embodiments 154-181, wherein the monitoring is performed following cessation of perturbation of the population of cells.

183. The method of any one of embodiments 154-182, wherein removing all or part of the evolved population of cells from the first well comprises causing a portion of the population of cells to remain in the first well by controlling an amount of fluid caused to flow from the well.

184. The method of any one of embodiments 154-183, wherein removing all or part of the evolved population of cells from the first well comprises causing a portion of the population of cells to remain in the first well by one or more geometrical confinement in the well.

185. The method of any one of embodiments 154-184, wherein removing all or part of the evolved population of cells from the first well comprises automated addition of one or more reagents to dissociate attachment-dependent cell lines of the cell population in first well.

186. The method of any one of embodiments 154-185, wherein removing all or part of the evolved population of cells from the first well comprises automatically causing cells of the cell population to flow out of the first well.

187. The method of any one of embodiments 154-186, comprising:
  after removing all or part of the evolved population of cells from the first well, using the all or part of the evolved population of cells to seed a second well, separate from the first well;
  culturing a second population of cells in a second well;
  perturbing one or more characteristics of an environment in the second well following the culturing of the second population of cells; and
  monitoring one or more characteristics of the second population of cells as it evolves in the second well.

188. The method of any one of embodiments 154-187, comprising collecting supernatant from the first well.

189. The method of embodiment 188, wherein collecting the supernatant from the first well is performed without collecting or removing supernatant from any of the other wells of the plurality of wells.

190. The method of any one of embodiments 188-189, wherein the supernatant comprises secreted proteome and metabolites.

191. The method of any one of embodiments 154-190, comprising, after removing all or part of the evolved population of cells from the first well, performing analysis on the removed evolved population of cells comprising one or more of genomic analysis, transcriptomic analysis, proteomic analysis, epigenetic analysis, and metabolomic analysis.

192. The method of any one of embodiments 154-191, wherein the population of cells comprises one or more of mammalian cells, human cells, primate cells, rodent cells, insect cells, marsupial cells, fish cells, biofilms, microorganisms, bacteria cells, reporter cells, immortalized cells, hiPSC lines, hiPSC derived tissue specific lineages (e.g. cardiac, neural), co-cultured iPSC derived tissue specific lineages expressing fluorescent reporters including a fluorescent lineage identifier (e.g. co-cultured iPSC derived neural or cardiac lineages expressing fluorescent reporters including a fluorescent lineage identifier), co-cultured immortalized cells expressing fluorescent reporters including a fluorescent reporter cell line identifier that enables identification of a given reporter cell line in a mixed population, dissociated biopsies, patient-derived cell lines, and cells with an evolved phenotype.

193. A microfluidic-enabled cell-culture device for dynamic evolution and monitoring of characteristics in living cells, comprising:
  a pneumatic layer for directing flow of fluid to a plurality of individually addressable wells;
  one or more sensors configured to detect data regarding environments inside one or more of the plurality of wells;
  wherein the device is configured to:
  culture a population of cells in a first well of the plurality of wells;
  perturb one or more characteristics of an environment in the first well following the culturing of the population of cells;
  monitor one or more characteristics of the population of cells in the first well;
  remove all or part of the evolved population of cells from the first well.

194. A non-transitory computer-readable storage medium for dynamic evolution and monitoring of characteristics in living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:
  culture a population of cells in a first well of the plurality of wells;
  perturb one or more characteristics of an environment in the first well following the culturing of the population of cells;
  monitor one or more characteristics of the population of cells in the first well;
  remove all or part of the evolved population of cells from the first well.

195. A method for dynamic evolution of living cells, comprising:
  at a microfluidic-enabled cell-culture device comprising pneumatic layer for directing flow of fluid to a plurality of individually addressable wells:
    seeding a first well of the plurality of wells by causing, by the pneumatic layer, a cell suspension to flow to the first well; and
    culturing a population of cells in a first well.

196. The method of embodiment 195, wherein causing the cell suspension to flow to the first well comprises causing one or more valves to be actuated in association with displacement of a portion of a pneumatic layer of the cell-culture device.

197. The method of any one of embodiments 195-196, wherein causing the cell suspension to flow to the first well is performed without causing the cell suspension to flow to any of the other wells of the plurality of wells.

198. The method of any one of embodiments 195-197, comprising causing a plurality of cells in the cell suspension to be retained in the first well by one or more geometrical confinements in the first well.

199. The method of any one of embodiments 195-198, wherein culturing the population of cells in the first well comprises automatically monitoring and controlling one or more environmental parameters of the first well.

200. The method of embodiment 199, wherein controlling one or more environmental parameters of the first well is performed without modifying a corresponding parameter for any of the other wells of the plurality of wells.

201. A microfluidic-enabled cell-culture device for dynamic evolution of living cells, comprising:
 a pneumatic layer for directing flow of fluid to a plurality of individually addressable wells,
 wherein the device is configured to:
  seed a first well of the plurality of wells by causing, by the pneumatic layer, a cell suspension to flow to the first well; and
  culture a population of cells in a first well.

202. A non-transitory computer-readable storage medium for dynamic evolution of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
 seed a first well of the plurality of wells by causing, by the pneumatic layer, a cell suspension to flow to the first well; and
 culture a population of cells in a first well.

203. A method for dynamic evolution of living cells, comprising:
 at a microfluidic-enabled cell-culture device comprising pneumatic layer for directing flow of fluid to a plurality of individually addressable wells:
 perturbing one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

204. The method of embodiment 203, wherein introducing the fluid into the first well comprises pumping less than 1000 nL per pump stroke of a pump controlled by the pneumatic layer.

205. The method of any one of embodiments 203-204, wherein the fluid comprises a small molecule mixture.

206. The method of any one of embodiments 203-205, wherein the fluid comprises one or more of an antibody mixture and a reagent enabling genetic perturbations to a cell in the population of cells.

207. A method for dynamic evolution of living cells, comprising:
 at a microfluidic-enabled cell-culture device comprising pneumatic layer for controlling flow of fluid to a plurality of individually addressable wells:
 perturbing one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

208. The method of any one of embodiments 203-207, wherein perturbing one or more characteristics of the environment in the first well is performed without perturbing a corresponding characteristics of any of the other wells of the plurality of wells.

209. The method of any one of embodiments 203-208, wherein perturbing one or more characteristics of the environment in the first well comprises automatically performing a first perturbation at a first time, waiting for a predefined period, and then performing a second perturbation at a second time.

210. The method of embodiment 209, wherein perturbing one or more characteristics of the environment in the first well comprises, after performing the first perturbation and before performing the second perturbation, causing a fluid media in the first well to be removed from the first well.

211. A microfluidic-enabled cell-culture device for dynamic evolution of living cells, comprising:
 a pneumatic layer for directing flow of fluid to a plurality of individually addressable wells,
 wherein the device is configured to perturb one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

212. A non-transitory computer-readable storage medium for dynamic evolution of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
 perturb one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

213. A microfluidic-enabled cell-culture device for dynamic evolution of living cells, comprising:
 a pneumatic layer for directing flow of fluid to a plurality of individually addressable wells,
 wherein the device is configured to perturb one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

214. A non-transitory computer-readable storage medium for dynamic evolution of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
perturb one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, CO2 level, O2 level, confluency, fluid flow, alkalinity, acidity, basicity, input fluid temperature, output fluid temperature, ambient light intensity, electrical potential, impedance, or resistance of the environment in the first well.

215. A method for dynamic evolution and monitoring of one or more characteristics of in living cells, comprising:
at a microfluidic-enabled cell-culture device comprising pneumatic layer for controlling flow of fluid to a plurality of individually addressable wells, and one or more sensors configured to detect data regarding environments inside one or more of the plurality of wells:
monitoring, by the one or more sensors, one or more characteristics of a population of cells as it evolves in a first well of the plurality of wells.

216. The method of embodiment 215, wherein monitoring one or more characteristics of the population of cells comprises monitoring one or more phenotypes of the population of cells as it evolves in the first well.

217. The method of any one of embodiments 215-216, wherein monitoring one or more characteristics of the population of cells comprises performing microscopy on the cell population in first well.

218. The method of embodiment 217, wherein performing microscopy comprises performing one or more of fluorescent microscopy, bright-field microscopy, phase contrast microscopy, and differential interference contrast microscopy on the cell population in first well.

219. The method of any one of embodiments 215-218, wherein monitoring one or more characteristics of the population of cells comprises performing one or more of absorbance-based measurements and luminescence-based measurements on the cell population in first well.

220. The method of any one of embodiments 215-219, wherein monitoring one or more characteristics of the population of cells comprises monitoring activity of signaling networks of the cell population in first well using fluorescently tagged reporters.

221. The method of any one of embodiments 215-220, wherein monitoring one or more characteristics of the population of cells comprises monitoring subcellular localization and structure of the cell population in first well using fluorescently tagged reporters.

222. The method of any one of embodiments 215-221, wherein monitoring one or more characteristics of the population of cells comprises using one or more of dye and genetically-encoded fluorescent proteins to perform a viability assay on the cell population in first well.

223. The method of any one of embodiments 215-222, wherein monitoring one or more characteristics of the population of cells comprises performing one or more of a functional assay and a structural assay on the cell population in first well.

224. The method of any one of embodiments 215-223, wherein the monitoring is performed during perturbation of the population of cells.

225. The method of any one of embodiments 215-224, wherein the monitoring is performed following cessation of perturbation of the population of cells.

226. A microfluidic-enabled cell-culture device for dynamic evolution and monitoring of one or more characteristics of in living cells, comprising:
a pneumatic layer for controlling flow of fluid to a plurality of individually addressable wells; and
one or more sensors configured to detect data regarding environments inside one or more of the plurality of wells;
wherein the device is configured to:
monitor, by the one or more sensors, one or more characteristics of a population of cells as it evolves in a first well of the plurality of wells.

227. A non-transitory computer-readable storage medium for dynamic evolution and monitoring of one or more characteristics of in living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:
monitor, by the one or more sensors, one or more characteristics of a population of cells as it evolves in a first well of the plurality of wells 228. A method for dynamic evolution and harvesting of living cells, comprising:
at a microfluidic-enabled cell-culture device comprising pneumatic layer for controlling flow of fluid to a plurality of individually addressable wells, and one or more sensors configured to detect data regarding environments inside one or more of the plurality of wells:
automatically removing all or part of an evolved population of cells from a first well of the plurality of wells, without removing cells from any of the other wells of the plurality of wells.

229. The method of embodiment 228, comprising:
after removing all or part of the evolved population of cells from the first well, using the all or part of the evolved population of cells to seed a second well, separate from the first well;
culturing a second population of cells in a second well;
perturbing one or more characteristics of an environment in the second well following the culturing of the second population of cells; and
monitoring, by the one or more sensors, one or more characteristics of the second population of cells as it evolves in the second well.

230. The method of any one of embodiments 228-229, comprising collecting supernatant from the first well.

231. The method of any one of embodiments 228-230, wherein collecting the supernatant from the first well is performed without collecting or removing supernatant from any of the other wells of the plurality of wells.

232. The method of any one of embodiments 228-231, wherein the supernatant comprises secreted proteome and metabolites.

233. The method of any one of embodiments 228-232, comprising, after removing all or part of the evolved population of cells from the first well, performing analysis on the removed evolved population of cells comprising one or more of genomic analysis, transcriptomic analysis, proteomic analysis, epigenetic analysis, and metabolomic analysis.

234. A microfluidic-enabled cell-culture device for dynamic evolution and harvesting of living cells, comprising:

a pneumatic layer for controlling flow of fluid to a plurality of individually addressable wells; and one or more sensors configured to detect data regarding environments inside one or more of the plurality of wells;

wherein the device is configured to:

automatically remove all or part of an evolved population of cells from a first well of the plurality of wells, without removing cells from any of the other wells of the plurality of wells.

235. A non-transitory computer-readable storage medium for dynamic evolution and harvesting of living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:

automatically remove all or part of an evolved population of cells from a first well of the plurality of wells, without removing cells from any of the other wells of the plurality of wells.

236. The microfluidic-enabled multiwell device of any one of embodiments 44-50, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance adaptation.

237. The microfluidic-enabled multiwell device of any one of embodiments 44-50 or 236, wherein the assay comprises microscopy measurements.

238. The microfluidic-enabled multiwell device of any one of embodiments 44-50 or 236-237, wherein cells of the assay comprise one or more of immortalized cells, primary cells, pluripotent cells, pluripotent-derived cells, adherent cells, or suspension cells.

239. The microfluidic-enabled multiwell device of any one of embodiments 44-50 or 236-238, wherein cells of the assay are derived from a clinical sample.

240. The microfluidic-enabled multiwell device of any one of embodiments 44-50 or 236-239, wherein cells subject to the assay comprise one or more of a 3D culture model, an organoid model, and a coculture model.

241. The microfluidic-enabled multiwell device of any one of embodiments 44-50 or 236-240, wherein cells subject to the assay comprise reporter cells.

242. The microfluidic-enabled multiwell device of any one of embodiments 44-50 or 236-241, wherein cells subject to the assay comprise a library of cells arrayed in the device.

243. The microfluidic-enabled multiwell device of any one of embodiments 44-50 or 236-242, wherein the assay and protocol is conducted without tissue culture incubators.

244. The microfluidic-enabled multiwell device of any one of embodiments 44-50 or 236-243, wherein the assay and protocol is conducted in a laboratory environment.

245. The microfluidic-enabled multiwell device of any one of embodiments 44-50 or 236-244, wherein assay and protocol is conducted in one of a field location, a point-of-care location, and a pharmacy.

246. The microfluidic-enabled multiwell device of any one of embodiments 1-50 or 236-245, wherein the cell culture is conducted without tissue culture incubators.

247. The microfluidic-enabled multiwell device of any one of embodiments 1-50 or 236-246, wherein at the cell culture is conducted in a laboratory environment.

248. The microfluidic-enabled multiwell device of any one of embodiments 1-50 or 236-247, wherein at the cell culture is conducted in one or more of a field location, a point-of-care, and a pharmacy.

249. The microfluidic-enabled multiwell device of any one of embodiments 1-50 or 236-248, wherein at the well layer contains cryopreserved cells that are thawed during the cell culture.

250. The microfluidic-enabled multiwell device of any one of embodiments 1-50 or 236-249, wherein the instructions are configured to be executed by the one or more processors to cause the device to:

in accordance with receiving the data collected from the one or more sensors regarding the environment inside the microfluidic module, control one or more parameters of an environment inside the microfluidics module, wherein the one or more parameters includes one or more of temperature, pressure, pH, humidity, $CO_2$, $O_2$, confluency, fluid flow, alkalinity, input fluid temperature, output fluid temperature, ambient light intensity, electrical potential, impedance, or resistance.

251. The microfluidic-enabled multiwell device of any one of embodiments 1-50 or 236-250, wherein the instructions are configured to be executed by the one or more processors to cause the device to:

monitor, by the sensor module, one or more parameters of an environment surrounding the multiwell device;

store data regarding the monitoring of the parameters of the environment surrounding the multiwell device on a computer storage of the device; and wirelessly transmit the stored data regarding the monitoring of the parameters of the environment surrounding the multiwell device to a user.

252. The microfluidic-enabled multiwell device of any one of embodiments 1-50 or 236-251, wherein the instructions are configured to be executed by the one or more processors to cause the device to:

monitor, by the sensor module, one or more parameters of an environment surrounding the multiwell device;

in accordance with monitoring one or more environmental parameters, adjust one or more parameters of the environment inside the microfluidics module.

253. The microfluidic-enabled multiwell device of any one of embodiments 1-50 or 236-252, wherein:

the well layer comprises a first plurality of wells arranged into a plurality of rows;

the fluid channels layer comprises a first input channel and a first output channel both corresponding to a first row of the plurality of rows;

the fluidic channels layer comprises a second input channel and a second output channel both corresponding to a second row of the plurality of rows;

two wells in the first row are individually fluidly connectible to the first input channel by a first plurality of respective input valves;

the two in the first row are individually fluidly connectible to the first output channel by a first plurality of respective output valves;

two wells in the second row are individually fluidly connectible to the second input channel by a second plurality of respective input valves;

the two wells in the second row are individually fluidly connectible to the second output channel by a second plurality of respective output valves.

254. The microfluidic-enabled multiwell device of embodiment 253, wherein:
- the first input channel is fluidly connectible to a common input channel via a first channel input valve;
- the first output channel is fluidly connectible to a common output channel via a first channel output valve;
- the second input channel is fluidly connectible to the common input channel via a second channel input valve;
- the second output channel is fluidly connectible to the common output channel via a second channel output valve.

255. The microfluidic-enabled multiwell device of embodiment 254, wherein causing fluid to flow to an individually addressable well in the multiwell device comprises:
- opening the first channel input valve and the first channel output to allow flow into and out of the first output channel;
- opening one of the first plurality of input valves and a corresponding one of the first plurality of output valves to allow flow into and out of the individually addressable well.

256. The microfluidic-enabled multiwell device of any one of embodiments 253-255, wherein a micropump is configured to provide vacuum force to selectively cause flow through any individual well of the two wells in the first row and the two wells in the second row.

257. The microfluidic-enabled multiwell device of embodiment 256, wherein the micropump is downstream from the common output channel.

258. The microfluidic-enabled multiwell device of any one of embodiments 1-50 or 236-257, wherein the device is configured to be received by a docking component.

259. The microfluidic-enabled multiwell device of embodiment 258, wherein the device is configured to be fluidly coupled to the docking component.

260. The microfluidic-enabled multiwell device of any one of embodiments 258-259, wherein the device is configured to be pneumatically coupled to the docking component.

261. The microfluidic-enabled multiwell device of any one of embodiments 258-260, wherein the device is configured to be electronically communicatively coupled to the docking component.

262. The methods of any of any one of embodiments 133-138, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance adaptation.

263. The method of any of any one of embodiments 133-138 or 262, wherein the assay comprises microscopy measurements.

264. The method of any of any one of embodiments 133-138 or 262-263, wherein the cells comprise one or more of immortalized cells, primary cells, pluripotent cells, pluripotent-derived cells, adherent cells, suspension cells.

265. The method of any of any one of embodiments 133-138 or 262-264, wherein the cells are derived from a clinical sample.

266. The method of any of any one of embodiments 133-138 or 262-265, wherein the assayed cells comprise one or more of a 3D culture model, an organoid model, and a coculture model.

267. The method of any of any one of embodiments 133-138 or 262-266, wherein the assayed cells are reporter cells.

268. The method of any of any one of embodiments 133-138 or 262-267, wherein the assayed cells are a library of cells arrayed in the device.

269. The method of any of any one of embodiments 122-138 or 262-268, wherein at least one of the cell culture, assays, and protocols is conducted without tissue culture incubators.

270. The method of any of any one of embodiments 122-138 or 262-269, wherein at least one of the cell culture, assays, or protocols is conducted in a standard laboratory environment.

271. The method of any of any one of embodiments 122-138 or 262-270, wherein at least one of the cell culture, assays, or protocols is conducted in one or more of a field location, a point-of-care, and a pharmacy.

272. A method for dynamic adaptation and monitoring of characteristics in living cells, comprising:
- at a microfluidic-enabled cell-culture device comprising a pneumatic layer for directing flow of fluid to a plurality of individually addressable wells, and one or more sensors configured to detect data regarding environments inside one or more of the plurality of wells:
- culturing a population of cells in a first well of the plurality of wells;
- perturbing one or more characteristics of an environment in the first well following the culturing of the population of cells;
- monitoring one or more characteristics of the population of cells in the first well;
- removing all or part of the adapted population of cells from the first well.

273. The method of embodiment 272, comprising, before culturing the population of cells in the first well, seeding the first well by causing a cell suspension to flow to the first well.

274. The method of embodiment 273, wherein causing the cell suspension to flow to the first well comprises causing one or more valves to be actuated in association with displacement of a portion of a pneumatic layer of the cell-culture device.

275. The method of any one of embodiments 273-274, wherein causing the cell suspension to flow to the first well comprises causing one or more valves be actuated in association with displacement of a portion of a pneumatic layer of the cell-culture device such that the cell suspension does not flow to any of the other wells of the plurality of wells.

276. The method of any one of embodiments 273-275, comprising, after seeding the first well and before culturing the population of cells in the first well, co-culture seeding the first well by causing a second cell suspension to flow to the first well.

277. The method of any one of embodiments 273-276, comprising causing a plurality of cells in the cell suspension to be retained in the first well by one or more geometrical confinements in the first well.

278. The method of any one of embodiments 272-277, wherein culturing the population of cells in the first well comprises automatically monitoring and controlling one or more environmental parameters of the first well.

279. The method of embodiment 278, wherein controlling one or more environmental parameters of the first well is performed without modifying a corresponding parameter for any of the other wells of the plurality of wells.

280. The method of any one of embodiments 272-279, comprising, before culturing the population of cells in the first well, selecting and attaching a well layer of a microfluidics module to the microfluidic-enabled cell-culture device, the well layer comprising the plurality of individually addressable wells.

281. The method of any one of embodiments 272-280, wherein:
the well layer comprises cells loaded into the first well before attaching the well layer to the cell-culture device; and
culturing the population of cells comprises culturing the population of cells from the cells loaded into the first well.

282. The method of embodiment 281, wherein selecting the well layer comprises selecting a well layer having one or more of a material, micropatterning, coating, and geometrical configuration configured for the culturing of the population of cells.

283. The method of any one of embodiments 281-282, wherein selecting the well layer comprises selecting a well layer having one or more of a material, micropatterning, coating, and geometrical configuration configured for the perturbation of the population of cells.

284. The method of any one of embodiments 272-283, wherein perturbing one or more characteristics of the environment in the first well comprises introducing small molecules into the first well by causing a small molecule mixture to flow to the first well.

285. The method of any one of embodiments 272-284, wherein perturbing one or more characteristics of the environment in the first well comprises introducing antibodies into the first well by causing an antibody mixture to flow to the first well.

286. The method of any one of embodiments 272-285, wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

287. The method of any one of embodiments 272-286, wherein perturbing one or more characteristics of the environment in the first well is performed without perturbing a corresponding characteristics of any of the other wells of the plurality of wells.

288. The method of any one of embodiments 272-287, wherein perturbing one or more characteristics of the environment in the first well comprises introducing fluid into the first well by pumping less than 1000 nL per pump stroke of a pump controlled by the pneumatic layer.

289. The method of any one of embodiments 272-288, wherein perturbing one or more characteristics of the environment in the first well comprises automatically performing a first perturbation at a first time, waiting for a predefined period, and then performing a second perturbation at a second time.

290. The method of embodiment 289, wherein perturbing one or more characteristics of the environment in the first well comprises, after performing the first perturbation and before performing the second perturbation, causing a fluid media in the first well to be exchanged from the first well.

291. The method of any one of embodiments 272-290, wherein monitoring one or more characteristics of the population of cells comprises monitoring one or more characteristics of the population of cells as it adapts in the first well.

292. The method of any one of embodiments 272-291, wherein monitoring one or more characteristics of the population of cells comprises monitoring the cell population in the first well by one or more of the sensors of the cell-culture device.

293. The method of embodiment 292, wherein monitoring one or more characteristics of the population of cells comprises performing one or more of fluorescent microscopy, bright-field microscopy, phase contrast microscopy, and differential interference contrast microscopy on the cell population in first well.

294. The method of any one of embodiments 272-293, wherein monitoring one or more characteristics of the population of cells comprises performing one or more of absorbance-based measurements and luminescence-based measurements on the cell population in first well.

295. The method of any one of embodiments 272-294, wherein monitoring one or more characteristics of the population of cells comprises monitoring activity of signaling networks of the cell population in first well using fluorescently tagged reporters.

296. The method of any one of embodiments 272-295, wherein monitoring one or more characteristics of the population of cells comprises monitoring subcellular localization and structure of the cell population in first well using fluorescently tagged reporters.

297. The method of any one of embodiments 272-296, wherein monitoring one or more characteristics of the population of cells comprises using one or more of dye and genetically-encoded fluorescent proteins to perform a viability assay on the cell population in first well.

298. The method of any one of embodiments 272-297, wherein monitoring one or more characteristics of the population of cells comprises performing one or more of a functional assay and a structural assay on the cell population in first well.

299. The method of any one of embodiments 272-298, wherein the monitoring is performed during perturbation of the population of cells.

300. The method of any one of embodiments 272-299, wherein the monitoring is performed following cessation of perturbation of the population of cells.

301. The method of any one of embodiments 272-300, wherein removing all or part of the adapted population of cells from the first well comprises causing a portion of the population of cells to remain in the first well by controlling an amount of fluid caused to flow from the well.

302. The method of any one of embodiments 272-301, wherein removing all or part of the adapted population of cells from the first well comprises causing a portion of the population of cells to remain in the first well by one or more geometrical confinement in the well.

303. The method of any one of embodiments 272-302, wherein removing all or part of the adapted population of cells from the first well comprises automated addition of one or more reagents to dissociate attachment-dependent cell lines of the cell population in first well.

304. The method of any one of embodiments 272-303, wherein removing all or part of the adapted population of cells from the first well comprises automatically causing cells of the cell population to flow out of the first well.

305. The method of any one of embodiments 272-304, comprising: after removing all or part of the adapted population of cells from the first well, using the all or part of the adapted population of cells to seed a second well, separate from the first well;
culturing a second population of cells in a second well;
perturbing one or more characteristics of an environment in the second well following the culturing of the second population of cells; and
monitoring one or more characteristics of the second population of cells as it adapts in the second well.

306. The method of any one of embodiments 272-305, comprising collecting supernatant from the first well.

307. The method of embodiment 306, wherein collecting the supernatant from the first well is performed without collecting or removing supernatant from any of the other wells of the plurality of wells.

308. The method of any one of embodiments 306-307, wherein the supernatant comprises secreted proteome and metabolites.

309. The method of any one of embodiments 272-308, comprising, after removing all or part of the adapted population of cells from the first well, performing analysis on the removed adapted population of cells comprising one or more of genomic analysis, transcriptomic analysis, proteomic analysis, epigenetic analysis, and metabolomic analysis.

310. The method of any one of embodiments 272-309, wherein the population of cells comprises one or more of mammalian cells, human cells, primate cells, rodent cells, insect cells, marsupial cells, fish cells, biofilms, microorganisms, bacteria cells, reporter cells, immortalized cells, hiPSC lines, hiPSC derived tissue specific lineages (e.g. cardiac, neural), co-cultured iPSC derived tissue specific lineages expressing fluorescent reporters including a fluorescent lineage identifier (e.g. co-cultured iPSC derived neural or cardiac lineages expressing fluorescent reporters including a fluorescent lineage identifier), co-cultured immortalized cells expressing fluorescent reporters including a fluorescent reporter cell line identifier that enables identification of a given reporter cell line in a mixed population, dissociated biopsies, patient-derived cell lines, and cells with an adapted characteristic.

311. A microfluidic-enabled cell-culture device for dynamic adaptation and monitoring of characteristics in living cells, comprising:
a pneumatic layer for directing flow of fluid to a plurality of individually addressable wells;
one or more sensors configured to detect data regarding environments inside one or more of the plurality of wells;
wherein the device is configured to:
culture a population of cells in a first well of the plurality of wells;
perturb one or more characteristics of an environment in the first well following the culturing of the population of cells;
monitor one or more characteristics of the population of cells in the first well;
remove all or part of the adapted population of cells from the first well.

312. A non-transitory computer-readable storage medium for dynamic adaptation and monitoring of characteristics in living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:
culture a population of cells in a first well of the plurality of wells;
perturb one or more characteristics of an environment in the first well following the culturing of the population of cells;
monitor one or more characteristics of the population of cells in the first well;
remove all or part of the adapted population of cells from the first well.

313. A method for dynamic adaptation of living cells, comprising:
at a microfluidic-enabled cell-culture device comprising pneumatic layer for directing flow of fluid to a plurality of individually addressable wells:
seeding a first well of the plurality of wells by causing, by the pneumatic layer, a cell suspension to flow to the first well; and
culturing a population of cells in a first well.

314. The method of embodiment 313, wherein causing the cell suspension to flow to the first well comprises causing one or more valves to be actuated in association with displacement of a portion of a pneumatic layer of the cell-culture device.

315. The method of any one of embodiments 313-314, wherein causing the cell suspension to flow to the first well is performed without causing the cell suspension to flow to any of the other wells of the plurality of wells.

316. The method of any one of embodiments 313-315, comprising causing a plurality of cells in the cell suspension to be retained in the first well by one or more geometrical confinements in the first well.

317. The method of any one of embodiments 313-316, wherein culturing the population of cells in the first well comprises automatically monitoring and controlling one or more environmental parameters of the first well.

318. The method of embodiment 317, wherein controlling one or more environmental parameters of the first well is performed without modifying a corresponding parameter for any of the other wells of the plurality of wells.

319. A microfluidic-enabled cell-culture device for dynamic adaptation of living cells, comprising:
a pneumatic layer for directing flow of fluid to a plurality of individually addressable wells,
wherein the device is configured to:
seed a first well of the plurality of wells by causing, by the pneumatic layer, a cell suspension to flow to the first well; and
culture a population of cells in a first well.

320. A non-transitory computer-readable storage medium for dynamic adaptation of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
seed a first well of the plurality of wells by causing, by the pneumatic layer, a cell suspension to flow to the first well; and
culture a population of cells in a first well.

321. A method for dynamic adaptation of living cells, comprising:
at a microfluidic-enabled cell-culture device comprising pneumatic layer for directing flow of fluid to a plurality of individually addressable wells:
perturbing one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

322. The method of embodiment 321, wherein introducing the fluid into the first well comprises pumping less than 1000 nL per pump stroke of a pump controlled by the pneumatic layer.

323. The method of any one of embodiments 321-322, wherein the fluid comprises a small molecule mixture.

324. The method of any one of embodiments 321-323, wherein the fluid comprises one or more of an antibody mixture and a reagent enabling genetic perturbations to a cell in the population of cells.

325. A method for dynamic adaptation of living cells, comprising:
at a microfluidic-enabled cell-culture device comprising pneumatic layer for controlling flow of fluid to a plurality of individually addressable wells:
perturbing one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

326. The method of any one of embodiments 321-325, wherein perturbing one or more characteristics of the environment in the first well is performed without perturbing a corresponding characteristics of any of the other wells of the plurality of wells.

327. The method of any one of embodiments 321-326, wherein perturbing one or more characteristics of the environment in the first well comprises automatically performing a first perturbation at a first time, waiting for a predefined period, and then performing a second perturbation at a second time.

328. The method of embodiment 327, wherein perturbing one or more characteristics of the environment in the first well comprises, after performing the first perturbation and before performing the second perturbation, causing a fluid media in the first well to be removed from the first well.

329. A microfluidic-enabled cell-culture device for dynamic adaptation of living cells, comprising:
a pneumatic layer for directing flow of fluid to a plurality of individually addressable wells,
wherein the device is configured to perturb one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

330. A non-transitory computer-readable storage medium for dynamic adaptation of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
perturb one or more characteristics of an environment in a first well of the plurality of wells, wherein the first well contains a population of cells, and wherein perturbing one or more characteristics of the environment in the first well comprises introducing a fluid into the first well by causing the fluid to flow to the first well.

331. A microfluidic-enabled cell-culture device for dynamic adaptation of living cells, comprising:
a pneumatic layer for directing flow of fluid to a plurality of individually addressable wells,
wherein the device is configured to perturb one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

332. A non-transitory computer-readable storage medium for dynamic adaptation of living cells, the non-transitory computer-readable storage medium comprising instructions configured to be executed by one or more processors of a microfluidic-enabled cell-culture device comprising a pneumatic layer for directing flow of fluid to a plurality of individually addressable wells to cause the device to:
perturb one or more characteristics of an environment in a first well of the plurality of wells, wherein the first well contains a population of cells, and wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, or resistance of the environment in the first well.

333. A method for dynamic adaptation and monitoring of one or more characteristics of in living cells, comprising:
at a microfluidic-enabled cell-culture device comprising pneumatic layer for controlling flow of fluid to a plurality of individually addressable wells, and one or more sensors configured to detect data regarding environments inside one or more of the plurality of wells:
monitoring, by the one or more sensors, one or more characteristics of a population of cells as it adapts in a first well of the plurality of wells.

334. The method of embodiment 333, wherein monitoring one or more characteristics of the population of cells comprises monitoring one or more characteristics of the population of cells as it adapts in the first well.

335. The method of any one of embodiments 333-334, wherein monitoring one or more characteristics of the population of cells comprises performing microscopy on the cell population in first well.

336. The method of embodiment 335, wherein performing microscopy comprises performing one or more of fluorescent microscopy, bright-field microscopy, phase contrast microscopy, and differential interference contrast microscopy on the cell population in first well.

337. The method of any one of embodiments 333-336, wherein monitoring one or more characteristics of the population of cells comprises performing one or more of absorbance-based measurements and luminescence-based measurements on the cell population in first well.

338. The method of any one of embodiments 333-337, wherein monitoring one or more characteristics of the population of cells comprises monitoring activity of signaling networks of the cell population in first well using fluorescently tagged reporters.

339. The method of any one of embodiments 333-338, wherein monitoring one or more characteristics of the population of cells comprises monitoring subcellular localization and structure of the cell population in first well using fluorescently tagged reporters.

340. The method of any one of embodiments 333-339, wherein monitoring one or more characteristics of the population of cells comprises using one or more of dye and genetically-encoded fluorescent proteins to perform a viability assay on the cell population in first well.

341. The method of any one of embodiments 333-340, wherein monitoring one or more characteristics of the population of cells comprises performing one or more of a functional assay and a structural assay on the cell population in first well.

342. The method of any one of embodiments 333-341, wherein the monitoring is performed during perturbation of the population of cells.

343. The method of any one of embodiments 333-342, wherein the monitoring is performed following cessation of perturbation of the population of cells.

344. A microfluidic-enabled cell-culture device for dynamic adaptation and monitoring of one or more characteristics of in living cells, comprising:
a pneumatic layer for controlling flow of fluid to a plurality of individually addressable wells; and
one or more sensors configured to detect data regarding environments inside one or more of the plurality of wells;
wherein the device is configured to:
monitor, by the one or more sensors, one or more characteristics of a population of cells as it adapts in a first well of the plurality of wells.

345. A non-transitory computer-readable storage medium for dynamic adaptation and monitoring of one or more characteristics of in living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:
monitor, by the one or more sensors, one or more characteristics of a population of cells as it adapts in a first well of the plurality of wells 346. A method for dynamic adaptation and harvesting of living cells, comprising:
at a microfluidic-enabled cell-culture device comprising pneumatic layer for controlling flow of fluid to a plurality of individually addressable wells, and one or more sensors configured to detect data regarding environments inside one or more of the plurality of wells:
automatically removing all or part of an adapted population of cells from a first well of the plurality of wells, without removing cells from any of the other wells of the plurality of wells.

347. The method of embodiment 346, comprising:
after removing all or part of the adapted population of cells from the first well, using the all or part of the adapted population of cells to seed a second well, separate from the first well;
culturing a second population of cells in a second well;
perturbing one or more characteristics of an environment in the second well following the culturing of the second population of cells; and
monitoring, by the one or more sensors, one or more characteristics of the second population of cells as it adapts in the second well.

348. The method of any one of embodiments 346-347, comprising collecting supernatant from the first well.

349. The method of any one of embodiments 346-348, wherein collecting the supernatant from the first well is performed without collecting or removing supernatant from any of the other wells of the plurality of wells.

350. The method of any one of embodiments 346-349, wherein the supernatant comprises secreted proteome and metabolites.

351. The method of any one of embodiments 346-350, comprising, after removing all or part of the adapted population of cells from the first well, performing analysis on the removed adapted population of cells comprising one or more of genomic analysis, transcriptomic analysis, proteomic analysis, epigenetic analysis, and metabolomic analysis.

352. A microfluidic-enabled cell-culture device for dynamic adaptation and harvesting of living cells, comprising:
a pneumatic layer for controlling flow of fluid to a plurality of individually addressable wells; and
one or more sensors configured to detect data regarding environments inside one or more of the plurality of wells;
wherein the device is configured to:
automatically remove all or part of an adapted population of cells from a first well of the plurality of wells, without removing cells from any of the other wells of the plurality of wells.

353. A non-transitory computer-readable storage medium for dynamic adaptation and harvesting of living cells, the non-transitory computer-readable storage medium comprising instructions configured to be executed by one or more processors of a microfluidic-enabled cell-culture device comprising a pneumatic layer for directing flow of fluid to a plurality of individually addressable wells and one or more sensors configured to detect data regarding environments inside one or more of the plurality of wells to cause the device to:
automatically remove all or part of an adapted population of cells from a first well of the plurality of wells, without removing cells from any of the other wells of the plurality of wells.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of any and all patents and publications referred to in this application are hereby incorporated herein by reference. All references, citations, projects, documents, or other publications mentioned anywhere herein are hereby incorporated by reference in their entirety.

The invention claimed is:

1. A method for dynamic evolution and monitoring of characteristics in living cells, comprising:
in a microfluidic-enabled cell-culture device comprising a pneumatic layer for directing flow of fluid to a plurality of individually addressable wells, and one or more sensors configured to detect data regarding environments inside one or more of the plurality of wells:
culturing a population of cells in a first well of the plurality of wells;
perturbing one or more characteristics of an environment in the first well following the culturing of the population of cells;
monitoring one or more characteristics of the population of cells in the first well;
removing all or part of the evolved population of cells from the first well;
seeding a second well, separate from the first well, with the all or part of the evolved population of cells;
culturing a second population of cells, comprising all or part of the evolved population cells, in the second well;
perturbing one or more characteristics of an environment in the second well following the culturing of the second population of cells; and
monitoring one or more characteristics of the second population of cells as it evolves in the second well.

2. The method of claim 1, comprising, before culturing the population of cells in the first well, seeding the first well by causing a cell suspension to flow to the first well.

3. The method of claim 2, wherein causing the cell suspension to flow to the first well comprises causing one or more valves to be actuated in association with displacement of a portion of a pneumatic layer of the cell-culture device.

4. The method of claim 2, wherein causing the cell suspension to flow to the first well comprises causing one or more valves be actuated in association with displacement of a portion of a pneumatic layer of the cell-culture device such that the cell suspension does not flow to any of the other wells of the plurality of wells.

5. The method of claim 2, comprising, after seeding the first well and before culturing the population of cells in the first well, co-culture seeding the first well by causing a second cell suspension to flow to the first well.

6. The method of claim 2, comprising causing a plurality of cells in the cell suspension to be retained in the first well by one or more geometrical confinements in the first well.

7. The method of claim 1, wherein culturing the population of cells in the first well comprises automatically monitoring and controlling one or more environmental parameters of the first well.

8. The method of claim 7, wherein controlling one or more environmental parameters of the first well is performed without modifying a corresponding parameter for any of the other wells of the plurality of wells.

9. The method of claim 1, comprising, before culturing the population of cells in the first well, selecting and attaching a well layer of a microfluidics module to the microfluidic-enabled cell-culture device, the well layer comprising the plurality of individually addressable wells.

10. The method of claim 9, wherein:
the well layer comprises cells loaded into the first well before attaching the well layer to the cell-culture device; and
culturing the population of cells comprises culturing the population of cells from the cells loaded into the first well.

11. The method of claim 9, wherein selecting the well layer comprises selecting a well layer having one or more of a material, micropatterning, coating, and geometrical configuration configured for the culturing of the population of cells.

12. The method of claim 9, wherein selecting the well layer comprises selecting a well layer having one or more of a material, micropatterning, coating, and geometrical configuration configured for the perturbation of the population of cells.

13. The method of claim 1, wherein perturbing one or more characteristics of the environment in the first well comprises introducing small molecules into the first well by causing a small molecule mixture to flow to the first well.

14. The method of claim 1, wherein perturbing one or more characteristics of the environment in the first well comprises introducing antibodies into the first well by causing an antibody mixture to flow to the first well.

15. The method of claim 1, wherein perturbing one or more characteristics of the environment in the first well comprises altering one or more microenvironmental parameters including one or more of temperature, pressure, pH, humidity, $CO_2$ level, $O_2$ level, confluency, fluid flow, alkalinity, acidity, basicity, input fluid temperature, output fluid temperature, ambient light intensity, electrical potential, impedance, and resistance of the environment in the first well.

16. The method of claim 1, wherein perturbing one or more characteristics of the environment in the first well is performed without perturbing a corresponding characteristics of any of the other wells of the plurality of wells.

17. The method of claim 1, wherein perturbing one or more characteristics of the environment in the first well comprises introducing fluid into the first well by pumping less than 1000 nL per pump stroke of a pump controlled by the pneumatic layer.

18. The method of claim 1, wherein perturbing one or more characteristics of the environment in the first well comprises automatically performing a first perturbation at a first time, waiting for a predefined period, and then performing a second perturbation at a second time.

19. The method of claim 18, wherein perturbing one or more characteristics of the environment in the first well comprises, after performing the first perturbation and before performing the second perturbation, causing a fluid media in the first well to be exchanged from the first well.

20. The method of claim 1, wherein monitoring one or more characteristics of the population of cells comprises monitoring one or more phenotypes of the population of cells as it evolves in the first well.

21. The method of claim 1, wherein monitoring one or more characteristics of the population of cells comprises monitoring the cell population in the first well by one or more of the sensors of the cell-culture device.

22. The method of claim 21, wherein monitoring one or more characteristics of the population of cells comprises performing one or more of fluorescent microscopy, brightfield microscopy, phase contrast microscopy, and differential interference contrast microscopy on the cell population in the first well.

23. The method of claim 1, wherein monitoring one or more characteristics of the population of cells comprises performing one or more of absorbance-based measurements and luminescence-based measurements on the cell population in the first well.

24. The method of claim 1, wherein monitoring one or more characteristics of the population of cells comprises monitoring activity of signaling networks of the cell population in the first well using fluorescently tagged reporters.

25. The method of claim 1, wherein monitoring one or more characteristics of the population of cells comprises monitoring subcellular localization and structure of the cell population in the first well using fluorescently tagged reporters.

26. The method of claim 1, wherein monitoring one or more characteristics of the population of cells comprises using one or more of dye and genetically-encoded fluorescent proteins to perform a viability assay on the cell population in the first well.

27. The method of claim 1, wherein monitoring one or more characteristics of the population of cells comprises performing one or more of a functional assay and a structural assay on the cell population in the first well.

28. The method of claim 1, wherein the monitoring is performed during perturbation of the population of cells.

29. The method of claim 1, wherein the monitoring is performed following cessation of perturbation of the population of cells.

30. The method of claim 1, wherein removing all or part of the evolved population of cells from the first well comprises causing a portion of the population of cells to remain in the first well by controlling an amount of fluid caused to flow from the well.

31. The method of claim 1, wherein removing all or part of the evolved population of cells from the first well comprises causing a portion of the population of cells to remain in the first well by one or more geometrical confinement in the well.

32. The method of claim 1, wherein removing all or part of the evolved population of cells from the first well comprises automated addition of one or more reagents to dissociate attachment-dependent cell lines of the cell population in the first well.

33. The method of claim 1, wherein removing all or part of the evolved population of cells from the first well comprises automatically causing cells of the cell population to flow out of the first well.

34. The method of claim 1, comprising collecting supernatant from the first well.

35. The method of claim 34, wherein collecting the supernatant from the first well is performed without collecting or removing supernatant from any of the other wells of the plurality of wells.

36. The method of claim 34, wherein the supernatant comprises secreted proteome and metabolites.

37. The method of claim 1, comprising, after removing all or part of the evolved population of cells from the first well, performing an analysis on the removed evolved population of cells comprising one or more of genomic analysis, transcriptomic analysis, proteomic analysis, epigenetic analysis, and metabolomic analysis.

38. The method of claim 1, wherein the population of cells comprises one or more of mammalian cells, human cells, primate cells, rodent cells, insect cells, marsupial cells, fish cells, biofilms, microorganisms, bacteria cells, reporter cells, immortalized cells, hiPSC lines, hiPSC derived tissue specific lineages, co-cultured iPSC derived tissue specific lineages expressing fluorescent reporters including a fluorescent lineage identifier, co-cultured immortalized cells expressing fluorescent reporters including a fluorescent reporter cell line identifier that enables identification of a given reporter cell line in a mixed population, dissociated biopsies, patient-derived cell lines, and cells with an evolved phenotype.

* * * * *